United States Patent
Buettelmann et al.

(10) Patent No.: US 9,604,977 B2
(45) Date of Patent: Mar. 28, 2017

(54) BICYCLIC THIOPHENYLAMIDE COMPOUNDS

(71) Applicant: Hoffmann-La Roche Inc., Little Falls, NJ (US)

(72) Inventors: Bernd Buettelmann, Schopfheim (DE); Simona M. Ceccarelli, Basel (CH); Holger Kuehne, Loerrach (DE); Bernd Kuhn, Reinach BL (CH); Werner Neidhart, Hagenthal-le-Bas (FR); Ulrike Obst Sander, Reinach BL (CH); Hans Richter, Grenzach-Wyhlen (DE)

(73) Assignee: Hoffman-La Roche Inc., Little Falls, NJ (US)

( * ) Notice: Subject to any disclaimer, the term of this patent is extended or adjusted under 35 U.S.C. 154(b) by 0 days.

(21) Appl. No.: 14/574,950

(22) Filed: Dec. 18, 2014

(65) Prior Publication Data

US 2015/0175594 A1 Jun. 25, 2015

Related U.S. Application Data

(63) Continuation of application No. PCT/EP2013/062314, filed on Jun. 14, 2013.

(30) Foreign Application Priority Data

Jun. 19, 2012 (EP) .................................... 12172528

(51) Int. Cl.

| | | |
|---|---|---|
| *C07D 333/50* | (2006.01) | |
| *C07D 333/66* | (2006.01) | |
| *C07D 417/04* | (2006.01) | |
| *C07D 413/14* | (2006.01) | |
| *C07D 409/04* | (2006.01) | |
| *C07D 409/14* | (2006.01) | |
| *C07D 417/14* | (2006.01) | |
| *C07D 495/04* | (2006.01) | |
| *C07D 495/10* | (2006.01) | |
| *C07D 413/04* | (2006.01) | |

(52) U.S. Cl.
CPC ......... *C07D 417/04* (2013.01); *C07D 333/50* (2013.01); *C07D 333/66* (2013.01); *C07D 409/04* (2013.01); *C07D 409/14* (2013.01); *C07D 413/04* (2013.01); *C07D 413/14* (2013.01); *C07D 417/14* (2013.01); *C07D 495/04* (2013.01); *C07D 495/10* (2013.01)

(58) Field of Classification Search
CPC .. C07D 333/50; C07D 333/66; C07D 409/04; C07D 409/14; C07D 413/04; C07D 413/14; C07D 417/04; C07D 417/14; C07D 495/04; C07D 495/10
See application file for complete search history.

(56) References Cited

U.S. PATENT DOCUMENTS

2011/0053915 A1* 3/2011 Ivaschenko .......... A61K 9/0019
514/217.04

FOREIGN PATENT DOCUMENTS

| WO | 2005/023818 A2 | 3/2005 |
| WO | 2005/033102 A2 | 4/2005 |
| WO | 2007/036730 A1 | 4/2007 |
| WO | 2008/000407 A1 | 1/2008 |

OTHER PUBLICATIONS

Chemcats p. 2-3, 2001 and 2002.*
International Search Report and Written Opinion on patentability for International Patent Application No. PCT/EP2013/062314.

* cited by examiner

*Primary Examiner* — Valerie Rodriguez-Garcia
(74) *Attorney, Agent, or Firm* — Robert C. Hall

(57) ABSTRACT

Compounds having the formula (I)

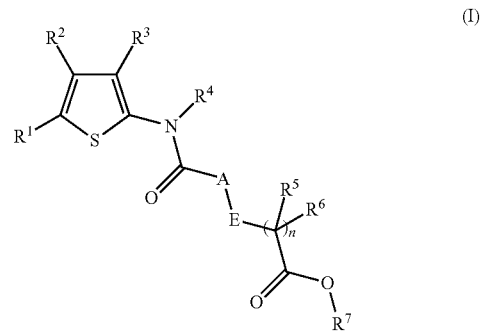

wherein $R^1$, $R^2$, $R^3$, $R^4$, $R^5$, $R^6$, $R^7$, A, E and n are as described herein, compositions including the compounds and methods of using the compounds as fatty-acid binding protein (FABP) 4 and/or 5 inhibitors for the treatment or prophylaxis of type 2 diabetes, atherosclerosis, chronic kidney diseases, non-alcoholic steatohepatitis and cancer.

21 Claims, No Drawings

BICYCLIC THIOPHENYLAMIDE COMPOUNDS

CROSS REFERENCE TO RELATED APPLICATIONS

This application is a Continuation of International Application No. PCT/EP2012/062314 filed on Jun. 14, 2013, which is entitled to the priority of EP Application No. 12172528.7 filed on Jun. 19, 2012, the disclosures of which are incorporated herein by reference in their entirety.

FIELD OF THE INVENTION

The present invention relates to organic compounds useful for therapy or prophylaxis in a mammal, and in particular to fatty-acid binding protein (FABP) 4 and/or 5 inhibitors, more particularly dual FABP 4/5 inhibitors for the treatment or prophylaxis of e.g. type 2 diabetes, atherosclerosis, chronic kidney diseases, non-alcoholic steatohepatitis and cancer.

BACKGROUND OF THE INVENTION

FABP4 (aP2) and FABP5 (mal1) are members of the fatty acid binding protein family. FABPs are proteins of 14-15 KDa that act as chaperones for fatty acids in the aqueous cytosolic environment and facilitate their movement between cellular compartments. So far at least nine members of this family have been identified with a tissue-specific pattern of expression. FABP4 is mainly expressed in adipose and macrophages, but also in other cell types, whereas FABP5 is expressed in a wide range of tissues and organs. FABPs are responsible for the transfer of fatty acids to different cell compartments and are thus implicated in key cellular functions such as lipid storage in adipocytes, fatty acid oxidation in mitochondria, ER signaling, fatty-acid-dependent gene expression, regulation of cytosolic enzymes activity, modulation of inflammatory response and leukotrienes synthesis. Plasma FABP4 is secreted by adipose tissue in mice and secretion is de-regulated in obesity and blocking of plasma FABP4 in vivo by antibodies improves insulin sensitivity.

Several genetic evidences in human support a role of FABP4 and FABP5 in metabolic diseases. A mutation in the FABP4 promoter (SNP T-87C) leading to 50% reduction in gene expression is associated to reduced cardiovascular diseases (CVDs) and type 2 diabetes (T2D) risk and to reduced plasma triglycerides (TGs). Two mutations in FABP5 gene, one in the 5'UTR (rs454550), one in the promoter (nSNP), are associated, respectively to increased (OR 4.24) and decreased risk (OR 0.48) of T2D. In addition, it was shown that FABP4 protein and mRNA levels in atherosclerotic plaque macrophages are associated to plaques instability and CV death. Finally, a large number of publications report the association between FABP4 and FABP5 plasma levels and severity of metabolic diseases. Elevated FABP4 plasma levels are associated with atherogenic dyslipidemia, reduced endothelial function, increased intima-media (IM) thickness, metabolic syndrome, obesity and insulin resistance IR. Elevated FABP5 plasma levels are associated to metabolic syndrome.

Genetic and pharmacological studies in mice largely confirm the human evidences. It was demonstrated that loss-of-function in FABP4 and FABP5 improves insulin sensitivity, lowers glucose, and protects against atherosclerosis. FABP4 knockout mice on high fat diet showed metabolic improvement that was tempered by compensatory upregulation of FABP5 in adipose. Mice with a deletion of FABP5 gene on high fat (HF) diet showed body weight reduction and improved glucose and insulin tolerance. The FABP4/FABP5 double-knockout mice were strongly protected from hyperglycemia, insulin resistance, and hepatic steatosis. In addition, in an ApoE deficient background, FABP4 and FABP5 deletion was highly protective against the development of atherosclerosis and increased longevity. A specific FABP4 inhibitor (BMS309403), showed in a clamp study in ob/ob mice a reduction of hepatic glucose production, increased glucose uptake in muscle and adipose and reduction in hepatic steatosis, but no change in body weight and energy consumption. Also, it showed a decrease in atherosclerotic plaques formation in ApoE KO mice. A dual FABP45 inhibitor Compound 3 described in Journal of Lipid Research 2011, 52, 646 showed in mice under HF diet a reduction in plasma triglyceride and free fatty acid, but no improvement in insulin and glucose tolerance.

SUMMARY OF THE INVENTION

The present invention provides novel compounds of formula (I)

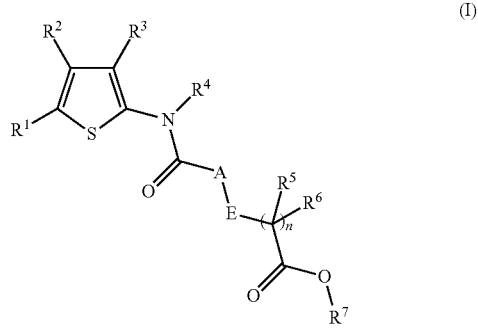

$R^1$ and $R^2$ together form $-CR^{14}=CR^{15}-CR^{16}=CR^{17}-$, $-CR^{14}R^{15}-O-(CR^{16}R^{17})_m-CR^{18}R^{19}-$, $-CR^{14}R^{15}-(CR^{16}R^{17})_m-O-CR^{18}R^{19}-$, $-O-CR^{14}R^{15}-(CR^{16}R^{17})_m-CR^{18}R^{19}-$, $-CR^{14}R^{15}-NR^{22}-CR^{16}R^{17}-CR^{18}R^{19}-$, $-CR^{14}R^{15}-S(O)_2-CR^{16}R^{17}-CR^{18}R^{19}-$, $-CR^{14}R^{15}-CR^{20}R^{21}-$ or $-CR^{14}R^{15}-CR^{16}R^{17}-(CR^{18}R^{19})_p-CR^{20}R^{21}-$;

$R^3$ is a substituted aryl, substituted heterocycloalkyl or substituted heteroaryl, wherein substituted aryl, substituted heterocycloalkyl and substituted heteroaryl are substituted with $R^{23}$ and can be further substituted with $R^{24}$ and/or $R^{25}$;

$R^4$ is H or alkyl;

$R^5$ and $R^6$ are independently selected from H, alkyl and cycloalkyl;

$R^7$ is H, alkyl or cycloalkyl;

A is $NR^8$ or $CR^9R^{10}$;

E is $NR^{11}$ or $CR^{12}R^{13}$;

$R^8$ and $R^{11}$ are independently selected from H, alkyl or cycloalkyl;

$R^9$, $R^{10}$, $R^{12}$ and $R^{13}$ are independently selected from H, halogen, alkyl, haloalkyl or cycloalkyl;

or $R^5$ and $R^{12}$ together with the carbon atoms to which they are attached form a substituted cycloalkyl, substituted aryl, substituted heterocycloalkyl or substituted heteroaryl, wherein substituted cycloalkyl, substituted aryl, substituted heterocycloalkyl and substituted heteroaryl are substituted with $R^{26}$ and can be further substituted with $R^{27}$ and/or $R^{28}$, wherein in case $R^5$ and $R^{12}$ together with the carbon atoms to which they are attached form a substituted aryl or substituted heteroaryl, then $R^6$ and $R^{13}$ are absent;

or $R^8$ and $R^{12}$ together with the nitrogen and carbon atoms to which they are attached form a substituted heterocycloalkyl or substituted heteroaryl, wherein substituted heterocycloalkyl and substituted heteroaryl are substituted with $R^{26}$ and can be further substituted with $R^{27}$ and/or $R^{28}$, wherein in case $R^8$ and $R^{12}$ together with the carbon atoms to which they are attached form a substituted heteroaryl, then $R^{13}$ is absent;

or $R^9$ and $R^{11}$ together with the nitrogen and carbon atoms to which they are attached form a substituted heterocycloalkyl or substituted heteroaryl, wherein substituted heterocycloalkyl and substituted heteroaryl are substituted with $R^{26}$ and can be further substituted with $R^{27}$ and/or $R^{28}$, wherein in case $R^9$ and $R^{11}$ together with the carbon atoms to which they are attached form a substituted heteroaryl, then $R^{10}$ is absent;

or $R^9$ and $R^{12}$ together with the carbon atoms to which they are attached form a substituted cycloalkyl, substituted aryl, substituted heterocycloalkyl or substituted heteroaryl, wherein substituted cycloalkyl, substituted aryl, substituted heterocycloalkyl and substituted heteroaryl are substituted with $R^{26}$ and can be further substituted with $R^{27}$ and/or $R^{28}$, wherein in case $R^9$ and $R^{12}$ together with the carbon atoms to which they are attached form a substituted aryl or substituted heteroaryl, then $R^{10}$ and $R^{13}$ are absent;

or $R^{10}$ and $R^{13}$ together with the carbon atoms to which they are attached form a substituted cycloalkyl, substituted aryl, substituted heterocycloalkyl or substituted heteroaryl, wherein substituted cycloalkyl, substituted aryl, substituted heterocycloalkyl and substituted heteroaryl are substituted with $R^{29}$ and can be further substituted with $R^{30}$ and/or $R^{31}$, wherein in case $R^{10}$ and $R^{13}$ together with the carbon atoms to which they are attached form a substituted aryl or substituted heteroaryl, then $R^9$ and $R^{12}$ are absent;

or $R^{10}$ and $R^{13}$ together with the carbon atoms to which they are attached form a double bond;

$R^{14}, R^{15}, R^{16}, R^{17}, R^{18}, R^{19}, R^{20}, R^{21}, R^{23}, R^{24}, R^{25}, R^{26}, R^{27}, R^{28}, R^{29}, R^{30}$ and $R^{31}$ are independently selected from H, oxo, hydroxy, halogen, alkyl, cycloalkyl, haloalkyl, alkoxy, alkoxyalkyl, alkoxycarbonyl or carboxy;

or $R^{16}$ and $R^{17}$ together with the carbon atoms to which they are attached form a cycloalkyl or heterocycloalkyl;

or $R^{14}$ and $R^{20}$ together with the carbon atoms to which they are attached form —$CH_2$— or —$CH_2$—$CH_2$—;

$R^{22}$ is H, alkyl, cycloalkyl or alkoxycarbonyl;

m is zero or 1;

n is zero or 1;

p is zero, 1 or 2;

or pharmaceutically acceptable salts.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of illnesses, especially in the treatment or prophylaxis of type 2 diabetes, metabolic syndrome, atherosclerosis, dyslipidemia, liver diseases involving inflammation, steatosis and/or fibrosis, such as non-alcoholic fatty liver disease, in particular non-alcoholic steatohepatitis, obesity, lipodystrophy, such as genetic and iatrogenic lipodystrophy, cancer, eye diseases supported by endothelial proliferation and angiogenesis, such as macular degeneration and retinopathy, lung diseases, such as asthma, bronchopulmonary dysplasia and chronic obstructive pulmonary disease, sarcoidosis, chronic renal diseases, such as vasculitis, focal segmental glomerulosclerosis, diabetic nephropathy, lupus nephritis, polycystic kidney disease and drug or toxin-induced chronic tubulointerstitial nephritis, chronic inflammatory and autoimmune inflammatory diseases, preeclampsia and polycystic ovary syndrome, and the use of the said compounds, salts or esters for the production of medicaments for the treatment or prophylaxis of of type 2 diabetes, metabolic syndrome, atherosclerosis, dyslipidemia, liver diseases involving inflammation, steatosis and/or fibrosis, such as non-alcoholic fatty liver disease, in particular non-alcoholic steatohepatitis, obesity, lipodystrophy, such as genetic and iatrogenic lipodystrophy, cancer, eye diseases supported by endothelial proliferation and angiogenesis, such as macular degeneration and retinopathy, lung diseases, such as asthma, bronchopulmonary dysplasia and chronic obstructive pulmonary disease, sarcoidosis, chronic renal diseases, such as vasculitis, focal segmental glomerulosclerosis, diabetic nephropathy, lupus nephritis, polycystic kidney disease and drug or toxin-induced chronic tubulointerstitial nephritis, chronic inflammatory and autoimmune inflammatory diseases, preeclampsia and polycystic ovary syndrome.

Compounds of the present invention are FABP 4 and/or 5 inhibitors, more particularly dual FABP 4 and 5 inhibitors. Some particular compounds of formula (I) of the present invention are also selective FABP 4 and/or 5 inhibitors compared to FABP 3 and/or 1.

DETAILED DESCRIPTION OF THE INVENTION

The term "alkoxy" denotes a group of the formula —O—R', wherein R' is an alkyl group.

Examples of alkoxy group include methoxy, ethoxy, n-propoxy, isopropoxy, n-butoxy, isobutoxy and tert-butoxy. Particular alkoxy group include methoxy, ethoxy and isopropoxy. More particular alkoxy group is methoxy.

The term "alkoxyalkyl" denotes an alkyl group wherein at least one of the hydrogen atoms of the alkyl group has been replaced by an alkoxy group. Exemplary alkoxyalkyl groups include methoxymethyl, ethoxymethyl, methoxyethyl, ethoxyethyl, methoxypropyl and ethoxypropyl. Particular alkoxyalkyl group include methoxymethyl and methoxyethyl. More particular alkoxyalkyl group is methoxyethyl.

The term "alkoxycarbonyl" denotes a group of the formula —C(O)—R', wherein R' is an alkoxy group. Examples of alkoxycarbonyl group include group wherein R' is methoxy, ethoxycarbonyl, n-propoxycarbonyl, isopropoxy, n-butoxy, isobutoxy and tert-butoxy. Particular alkoxycarbonyl group include group wherein R' is methoxy, ethoxy, isopropoxy and tert-butoxy. More particular alkoxycarbonyl group wherein R' is group is tert-butoxy.

The term "alkyl" denotes a monovalent linear or branched saturated hydrocarbon group of 1 to 12 carbon atoms, in particular of 1 to 7 carbon atoms, more particular of 1 to 4 carbon atoms, for example, methyl, ethyl, propyl, isopropyl, n-butyl, iso-butyl, sec-butyl, and tert-butyl. Particular alkyl groups include methyl, isopropyl and tert-butyl.

The term "aryl" denotes a monovalent aromatic carbocyclic mono- or bicyclic ring system comprising 6 to 10 carbon ring atoms. Examples of aryl moieties include phenyl and naphthyl. Particular aryl group is phenyl.

The term "carbonyl" denotes a —C(O)— group.

The term "carboxy" denotes a —C(O)OH group.

The term "cycloalkyl" denotes a monovalent saturated monocyclic or bicyclic hydrocarbon group of 3 to 10 ring carbon atoms, particularly a monovalent saturated monocyclic hydrocarbon group of 3 to 8 ring carbon atoms. Bicyclic means consisting of two saturated or partially saturated carbocycles having two carbon atoms in common. Particular cycloalkyl groups are cyclopropyl, cyclobutyl, cyclopentyl, cyclohexyl, cycloheptenyl, bicyclo[2.2.2]heptanyl, bicyclo[2.2.2]octanyl, cyclohexenyl, substituted bycyclo[2.2.2]heptanyl and substituted bicyclo[2.2.2]octenyl.

The term "haloalkyl" denotes an alkyl group wherein at least one of the hydrogen atoms of the alkyl group has been replaced by same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl groups are trifluoromethyl.

The term "halogen" and "halo" are used interchangeably herein and denote fluoro, chloro, bromo, or iodo. Particular halogens are chloro and fluoro. More particular halogen is fluoro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl. Particular heteroaryl groups are oxadiazolyl, oxazolyl, thiazolyl, pyridinyl or pyrimidinyl.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having two ring atoms in common, i.e. the bridge separating the two rings is either a single bond or a chain of one or two ring atoms. Examples for monocyclic saturated heterocycloalkyl are 4,5-dihydro-oxazolyl, oxetanyl, azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydropyridinyl, or dihydropyranyl. Further particular examples of heterocycloalkyl group are 4,5-dihydro-oxazolyl and pyrrolidinyl.

The term "oxo" denotes a =O group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn). Further particular protecting groups are the tert-butoxycarbonyl (Boc) and the fluorenylmethoxycarbonyl (Fmoc). More particular protecting group is the tert-butoxycarbonyl (Boc).

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

An embodiment of the present invention are compounds according to formula (I) as described herein, wherein
$R^1$ and $R^2$ together form —$CR^{14}$=$CR^{15}$—$CR^{16}$=$CR^{17}$—, —$CR^{14}R^{15}$—O—$(CR^{16}R^{17})_m$—$CR^{18}R^{19}$—, —O—$CR^{14}R^{15}$—$(CR^{16}R^{17})_m$—$CR^{18}R^{19}$—, —$CR^{14}R^{15}$—$NR^{22}$—$CR^{16}R^{17}$—$CR^{18}R^{19}$—, —$CR^{14}R^{18}$—$S(O)_2$—$CR^{16}R^{17}$—$CR^{18}R^{19}$— or —$CR^{14}R^{15}$—$CR^{16}R^{17}$—$(CR^{18}R^{19})_p$—$CR^{20}R^{21}$—;

$R^3$ is a substituted aryl, substituted heterocycloalkyl or substituted heteroaryl, wherein substituted aryl, substituted heterocycloalkyl and substituted heteroaryl are substituted with $R^{23}$ and can be further substituted with $R^{24}$ and/or $R^{25}$;

$R^4$ is H or alkyl;

$R^5$ and $R^6$ are independently selected from H, alkyl and cycloalkyl;

$R^7$ is H, alkyl or cycloalkyl;

A is $NR^8$ or $CR^9R^{10}$;

E is $NR^{11}$ or $CR^{12}R^{13}$;

$R^8$ and $R^{11}$ are independently selected from H, alkyl or cycloalkyl;

$R^9$, $R^{10}$, $R^{12}$ and $R^{13}$ are independently selected from H, halogen, alkyl, haloalkyl or cycloalkyl;

or $R^5$ and $R^{12}$ together with the carbon atoms to which they are attached form a substituted cycloalkyl, substituted aryl, substituted heterocycloalkyl or substituted heteroaryl, wherein substituted cycloalkyl, substituted aryl, substituted heterocycloalkyl and substituted heteroaryl are substituted with $R^{26}$ and can be further substituted with $R^{27}$ and/or $R^{28}$, wherein in case $R^5$ and $R^{12}$ together with the carbon atoms to which they are attached form a substituted aryl or substituted heteroaryl, then $R^6$ and $R^{13}$ are absent;

or $R^8$ and $R^{12}$ together with the nitrogen and carbon atoms to which they are attached form a substituted heterocycloalkyl or substituted heteroaryl, wherein substituted heterocycloalkyl and substituted heteroaryl are substituted with $R^{26}$ and can be further substituted with $R^{27}$ and/or $R^{28}$, wherein in case $R^8$ and $R^{12}$ together with the carbon atoms to which they are attached form a substituted heteroaryl, then $R^{13}$ is absent;

or $R^9$ and $R^{11}$ together with the nitrogen and carbon atoms to which they are attached form a substituted heterocycloalkyl or substituted heteroaryl, wherein substituted heterocycloalkyl and substituted heteroaryl are substituted with $R^{26}$ and can be further substituted with $R^{27}$ and/or $R^{28}$, wherein in case $R^9$ and $R^{11}$ together with the carbon atoms to which they are attached form a substituted heteroaryl, then $R^{10}$ is absent;

or $R^9$ and $R^{12}$ together with the carbon atoms to which they are attached form a substituted cycloalkyl, substituted aryl, substituted heterocycloalkyl or substituted heteroaryl, wherein substituted cycloalkyl, substituted aryl, substituted heterocycloalkyl and substituted heteroaryl are substituted with $R^{26}$ and can be further substituted with $R^{27}$ and/or $R^{28}$, wherein in case $R^9$ and $R^{12}$ together with the carbon atoms to which they are attached form a substituted aryl or substituted heteroaryl, then $R^{10}$ and $R^{13}$ are absent;

or $R^{10}$ and $R^{13}$ together with the carbon atoms to which they are attached form a substituted cycloalkyl, substituted aryl, substituted heterocycloalkyl or substituted heteroaryl, wherein substituted cycloalkyl, substituted aryl, substituted heterocycloalkyl and substituted heteroaryl are substituted with $R^{29}$ and can be further substituted with $R^{30}$ and/or $R^{31}$, wherein in case $R^{10}$ and $R^{13}$ together with the carbon atoms to which they are attached form a substituted aryl or substituted heteroaryl, then $R^9$ and $R^{12}$ are absent;

or $R^{10}$ and $R^{13}$ together with the carbon atoms to which they are attached form a double bond;

$R^{14}$, $R^{15}$, $R^{16}$, $R^{17}$, $R^{18}$, $R^{19}$, $R^{20}$, $R^{21}$, $R^{23}$, $R^{24}$, $R^{25}$, $R^{26}$, $R^{27}$, $R^{28}$, $R^{29}$, $R^{30}$ and $R^{31}$ are independently selected from H, oxo, halogen, alkyl, cycloalkyl, haloalkyl, alkoxy, alkoxyalkyl, alkoxycarbonyl or carboxy;

or $R^{16}$ and $R^{17}$ together with the carbon atoms to which they are attached form a cycloalkyl or heterocycloalkyl;

or $R^{14}$ and $R^{20}$ together with the carbon atoms to which they are attached form —$CH_2$— or —$CH_2$—$CH_2$—;

$R^{22}$ is H, alkyl, cycloalkyl or alkoxycarbonyl;

m is zero or 1;

n is zero or 1;

p is zero, 1 or 2;

or pharmaceutically acceptable salts.

A further embodiment of the present invention are compounds according to formula (I) as described herein, wherein $R^1$ and $R^2$ together form —$CR^{14}R^{15}$—O—$(CR^{16}R^{17})_m$—$CR^{18}R^{19}$—, —$CR^{14}R^{15}$—O—$(CR^{16}R^{17})_m$$CR^{18}R^{19}$— or —$CR^{14}R^{15}$— $CR^{16}R^{17}$—$(CR^{18}R^{19})_p$—$CR^{20}R^{21}$—.

A further embodiment of the present invention are compounds according to formula (I) as described herein, wherein $R^1$ and $R^2$ together form —$CR^{14}R^{15}$—O—$(CR^{16}R^{17})_m$$CR^{18}R^{19}$— or —$CR^{14}R^{15}$—$CR^{16}R^{17}$—$(CR^{18}R^{19})_p$—$CR^{20}R^{21}$—.

A particular embodiment of the present invention are compounds according to formula (I) as described herein, wherein $R^1$ and $R^2$ together form —$CR^{14}R^{15}$—O—$(CR^{16}R^{17})_m$—$CR^{18}R^{19}$—.

A particular embodiment of the present invention are compounds according to formula (I) as described herein, wherein $R^1$ and $R^2$ together form —$CR^{14}R^{15}$—O—$(CR^{16}R^{17})_m$—$CR^{18}R^{19}$— and of formula (III).

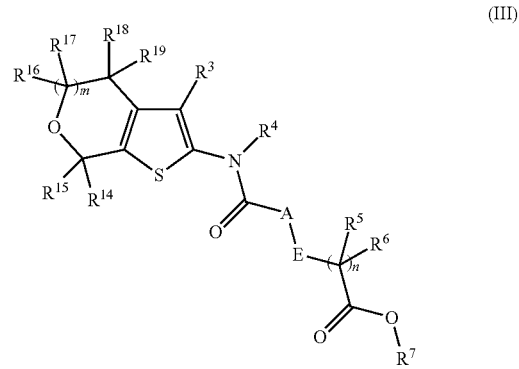

(III)

In a further embodiment of the present invention are compounds according to formula (I) as described herein, wherein $R^1$ and $R^2$ together form —$CR^{14}R^{15}$—$CR^{16}R^{17}$—$CR^{18}R^{19})_p$—$CR^{20}R^{21}$—.

A particular embodiment of the present invention are compounds according to formula (I) as described herein, wherein $R^1$ and $R^2$ together form —$CR^{14}R^{15}$—$CR^{16}R^{17}$—$(CR^{18}R^{19})_p$—$CR^{20}R^{21}$— and of formula (IV).

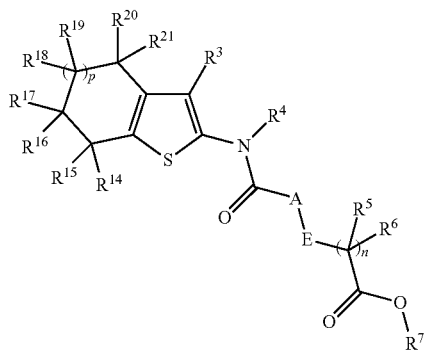
(IV)

Another further embodiment of the present invention are compounds according to formula (I) as described herein, wherein $R^3$ is a substituted phenyl, substituted 4,5-dihydro-oxazolyl, pyrrolidinyl, substituted [1,2,4]-oxadiazolyl, oxazolyl, substituted [1,2,4]-thiadiazolyl, thiazolyl, pyridinyl or pyrimidinyl, wherein substituted phenyl, substituted 4,5-dihydro-oxazolyl, substituted [1,2,4]-thiadiazolyl, and substituted [1,2,4]-oxadiazolyl are substituted with $R^{23}$ and can be further substituted with $R^{24}$ and/or $R^{25}$.

Another further embodiment of the present invention are compounds according to formula (I) as described herein, wherein $R^3$ is a substituted phenyl, substituted 4,5-dihydro-oxazolyl, pyrrolidinyl, substituted [1,2,4]-oxadiazolyl, oxazolyl, thiazolyl or pyrimidinyl, wherein substituted phenyl, substituted 4,5-dihydro-oxazolyl and substituted [1,2,4]-oxadiazolyl are substituted with $R^{23}$ and can be further substituted with $R^{24}$ and/or $R^{25}$.

Another embodiment of the present invention are compounds according to formula (I) as described herein, wherein $R^3$ is substituted [1,2,4]-oxadiazolyl, oxazolyl, substituted [1,2,4]-thiadiazolyl or thiazolyl, wherein substituted [1,2,4]-oxadiazolyl and substituted [1,2,4]-thiadiazolyl are substituted with $R^{23}$ and can be further substituted with $R^{24}$ and/or $R^{25}$.

Another embodiment of the present invention are compounds according to formula (I) as described herein, wherein $R^3$ is substituted [1,2,4]-oxadiazolyl, oxazolyl, thiazolyl or pyrimidinyl, wherein substituted [1,2,4]-oxadiazolyl is substituted with $R^{23}$ and can be further substituted with $R^{24}$ and/or $R^{25}$.

Another particular embodiment of the present invention are compounds according to formula (I) as described herein, wherein $R^4$ is H.

The present invention also relates to compounds according to formula (I) as described herein, wherein $R^5$ and $R^6$ are H.

A further particular embodiment of the present invention are compounds according to formula (I) as described herein, wherein $R^7$ is H or alkyl.

A more particular embodiment of the present invention are compounds according to formula (I) as described herein, wherein $R^7$ is H.

Also an embodiment of the present invention are compounds according to formula (I) as described herein, wherein A is $NR^8$.

The present invention also relates to compounds according to formula (I) as described herein, wherein $R^8$ is H.

Another embodiment of the present invention are compounds according to formula (I) as described herein, wherein A is $CR^9R^{10}$.

A further particular embodiment of the present invention are compounds according to formula (I) as described herein, wherein is E is $NR^{11}$.

A particular embodiment of the present invention are compounds according to formula (I) as described herein, wherein $R^{11}$ is H.

Also an embodiment of the present invention are compounds according to formula (I) as described herein, wherein E is $CR^{12}R^{13}$.

A further particular embodiment of the present invention are compounds according to formula (I) as described herein, wherein in case A is $NR^8$ then E is $CR^{12}R^{13}$.

The present invention also relates to compounds according to formula (I) as described herein, wherein $R^9$, $R^{10}$, $R^{12}$ and $R^{13}$ are independently selected from H, halogen or alkyl.

Another embodiment of the present invention are compounds according to formula (I) as described herein, wherein $R^9$ is H or halogen.

The present invention also relates to compounds according to formula (I) as described herein, wherein $R^{10}$ is H or halogen.

Also an embodiment of the present invention are compounds according to formula (I) as described herein, wherein $R^{12}$ is H, halogen or alkyl.

Also an embodiment of the present invention are compounds according to formula (I) as described herein, wherein $R^{13}$ is H, halogen or alkyl.

Another embodiment of the present invention are compounds according to formula (I) as described herein, wherein $R^{10}$ and $R^{13}$ together with the carbon atoms to which they are attached form a double bond.

A particular embodiment of the present invention are compounds according to formula (I) as described herein, wherein $R^5$ and $R^{12}$ together with the carbon atoms to which they are attached form a heteroaryl which is substituted with $R^{26}$ and can be further substituted with $R^{27}$ and/or $R^{28}$, and $R^6$ and $R^{13}$ are absent.

A further particular embodiment of the present invention are compounds according to formula (I) as described herein, wherein $R^5$ and $R^{12}$ together with the carbon atoms to which they are attached form substituted pyridinyl or substituted pyrazolyl, wherein substituted pyridinyl and substituted pyrazolyl are substituted with $R^{26}$ and can be further substituted with $R^{27}$ and/or $R^{28}$, and $R^6$ and $R^{13}$ are absent.

A more particular embodiment of the present invention are compounds according to formula (I) as described herein, wherein $R^8$ and $R^{12}$ together with the nitrogen and carbon atoms to which they are attached form a heterocycloalkyl which is substituted with $R^{26}$ and can be further substituted with $R^{27}$ and/or $R^{28}$.

Also a particular embodiment of the present invention are compounds according to formula (I) as described herein, wherein $R^8$ and $R^{12}$ together with the nitrogen and carbon atoms to which they are attached form substituted azetidinyl, substituted pyrrolidinyl or substituted piperidinyl, wherein substituted azetidinyl, substituted pyrrolidinyl and substituted piperidinyl are substituted with $R^{26}$ and can be further substituted with $R^{27}$ and/or $R^{28}$.

Also a particular embodiment of the present invention are compounds according to formula (I) as described herein, wherein $R^9$ and $R^{11}$ together with the nitrogen and carbon atoms to which they are attached form a heterocycloalkyl which is substituted with $R^{26}$ and can be further substituted with $R^{27}$ and/or $R^{28}$.

Another embodiment of the present invention are compounds according to formula (I) as described herein, wherein $R^9$ and $R^{11}$ together with the nitrogen and carbon atoms to which they are attached form pyrrolidinyl which is substituted with $R^{26}$ and can be further substituted with $R^{27}$ and/or $R^{28}$.

Another embodiment of the present invention are compounds according to formula (I) as described herein, wherein $R^9$ and $R^{12}$ together with the carbon atoms to which they are attached form a substituted cycloalkyl, substituted aryl or substituted heteroaryl, wherein substituted cycloalkyl, substituted aryl and substituted heteroaryl are substituted with $R^{26}$ and can be further substituted with $R^{27}$ and/or $R^{28}$, wherein in case $R^9$ and $R^{12}$ together with the carbon atoms to which they are attached form a substituted aryl or substituted heteroaryl, then $R^{10}$ and $R^{13}$ are absent.

Also an embodiment of the present invention are compounds according to formula (I) as described herein, wherein $R^9$ and $R^{12}$ together with the carbon atoms to which they are attached form a substituted cycloalkyl or substituted heterocycloalkyl, wherein substituted cycloalkyl and substituted heterocycloalkyl are substituted with $R^{26}$ and can be further substituted with $R^{27}$ and/or $R^{28}$.

Also an embodiment of the present invention are compounds according to formula (I) as described herein, wherein $R^9$ and $R^{12}$ together with the carbon atoms to which they are attached form a cycloalkyl which is substituted with $R^{26}$ and can be further substituted with $R^{27}$ and/or $R^{28}$.

Also an embodiment of the present invention are compounds according to formula (I) as described herein, wherein $R^9$ and $R^{12}$ together with the carbon atoms to which they are attached form substituted cyclopropyl, substituted cyclobutyl, substituted cyclopentyl, substituted cyclohexyl, substituted cycloheptenyl, substituted bicyclo[2.2.2]heptanyl, substituted bicyclo[2.2.2]octanyl, substituted cyclohexenyl, substituted bycyclo[2.2.2]heptanyl or substituted bicyclo[2.2.2]octenyl, wherein substituted cyclopropyl, substituted cyclobutyl, substituted cyclopentyl, substituted cyclohexyl, substituted cycloheptenyl, substituted bicyclo[2.2.2]heptanyl, substituted bicyclo[2.2.2]octanyl, substituted cyclohexenyl, substituted bycyclo[2.2.2]heptanyl and substituted bycyclo[2.2.2]octenyl are substituted with $R^{26}$ and can be further substituted with $R^{27}$ and/or $R^{28}$.

A further embodiment of the present invention are compounds according to formula (I) as described herein, wherein $R^9$ and $R^{12}$ together with the carbon atoms to which they are attached form substituted cyclopentyl, substituted cyclohexyl or substituted bicyclo[2.2.2]octanyl, wherein substituted cyclopentyl, substituted cyclohexyl or substituted bicyclo[2.2.2]octanyl are substituted with $R^{26}$ and can be further substituted with $R^{27}$ and/or $R^{28}$.

Another embodiment of the present invention are compounds according to formula (I) as described herein, wherein $R^9$ and $R^{12}$ together with the carbon atoms to which they are attached form cyclohexyl substituted with $R^{26}$ and can be further substituted with $R^{27}$ and/or $R^{28}$.

A further embodiment of the present invention are compounds according to formula (I) as described herein, wherein $R^9$ and $R^{12}$ together with the carbon atoms to which they are attached form a substituted aryl or substituted heteroaryl, wherein substituted aryl and substituted heteroaryl are substituted with $R^{26}$ and can be further substituted with $R^{27}$ and/or $R^{28}$, and $R^{10}$ and $R^{13}$ are absent.

A particular embodiment of the present invention are compounds according to formula (I) as described herein, wherein $R^9$ and $R^{12}$ together with the carbon atoms to which they are attached form a substituted phenyl, substituted pyridinyl, substituted pyrazolyl or substituted pyrazinyl, wherein substituted phenyl, substituted pyridinyl, substituted pyrazolyl and substituted pyrazinyl are substituted with $R^{26}$ and can be further substituted with $R^{27}$ and/or $R^{28}$, and $R^{10}$ and $R^{13}$ are absent.

A particular embodiment of the present invention are compounds according to formula (I) as described herein, wherein $R^9$ and $R^{12}$ together with the carbon atoms to which they are attached form a substituted phenyl or substituted pyrazinyl, wherein substituted phenyl or substituted pyrazinyl are substituted with $R^{26}$ and can be further substituted with $R^{27}$ and/or $R^{28}$, and $R^{10}$ and $R^{13}$ are absent.

A further particular embodiment of the present invention are compounds according to formula (I) as described herein, wherein $R^{10}$ and $R^{13}$ together with the carbon atoms to which they are attached form cyclopropyl which is substituted with $R^{29}$ and can be further substituted with $R^{30}$ and/or $R^{31}$.

A more particular embodiment of the present invention are compounds according to formula (I) as described herein wherein $R^{14}$, $R^{15}$, $R^{16}$, $R^{17}$, $R^{18}$, $R^{19}$, $R^{20}$, $R^{21}$, $R^{23}$, $R^{24}$, $R^{25}$, $R^{26}$, $R^{27}$, $R^{28}$, $R^{29}$, $R^{30}$ and $R^{31}$ are independently selected from H, halogen, alkyl, cycloalkyl, haloalkyl, alkoxy or alkoxyalkyl.

Another embodiment of the present invention are compounds according to formula (I) as described herein, wherein $R^{14}$, $R^{15}$, $R^{18}$, $R^{19}$, $R^{20}$ and $R^{21}$ are independently selected from H and alkyl.

A further particular embodiment of the present invention are compounds according to formula (I) as described herein, wherein $R^{14}$, $R^{15}$, $R^{18}$, $R^{19}$, $R^{20}$ and $R^{21}$ are H.

A more particular embodiment of the present invention are compounds according to formula (I) as described herein, wherein $R^{14}$ and $R^{20}$ together with the carbon atoms to which they are attached form —$CH_2$—.

Also a particular embodiment of the present invention are compounds according to formula (I) as described herein, wherein $R^{16}$ is H, halogen, alkyl, haloalkyl or alkoxy.

Also a particular embodiment of the present invention are compounds according to formula (I) as described herein, wherein $R^{16}$ is H, halogen or alkyl.

Another embodiment of the present invention are compounds according to formula (I) as described herein, wherein $R^{17}$ is H, halogen or alkyl.

Another embodiment of the present invention are compounds according to formula (I) as described herein, wherein $R^{17}$ is H or halogen.

Also an embodiment of the present invention are compounds according to formula (I) as described herein, wherein $R^{16}$ and $R^{17}$ are halogen.

Also an embodiment of the present invention are compounds according to formula (I) as described herein, wherein $R^{16}$ and $R^{17}$ together with the carbon atoms to which they are attached form a cyclopropyl or oxetanyl.

A further embodiment of the present invention are compounds according to formula (I) as described herein, wherein $R^{23}$ is H, alkyl, cycloalkyl, haloalkyl or alkoxyalkyl.

Another embodiment of the present invention are compounds according to formula (I) as described herein, wherein $R^{23}$ is alkyl, cycloalkyl, or haloalkyl.

A further embodiment of the present invention are compounds according to formula (I) as described herein, wherein $R^{23}$ is alkyl.

A particular embodiment of the present invention are compounds according to formula (I) as described herein, wherein $R^{24}$ is alkyl.

A further embodiment of the present invention are compounds according to formula (I) as described herein, wherein $R^{26}$, $R^{27}$, $R^{28}$, $R^{29}$, $R^{30}$ and $R^{31}$ are H.

Another embodiment of the present invention are compounds according to formula (I) as described herein, wherein $R^{22}$ is alkoxycarbonyl.

A further embodiment of the present invention are compounds according to formula (I) as described herein, wherein n is 0.

A particular embodiment of the present invention are compounds according to formula (I) as described herein, wherein n is 1.

A further particular embodiment of the present invention are compounds according to formula (I) as described herein, wherein m is 1.

Particular examples of compounds of formula (I) as described herein are selected from 2-(3-Phenyl-benzo[b]thiophen-2-ylcarbamoyl)-cyclopent-1-enecarboxylic acid;

2-[3-(3-Methyl-[1,2,4]oxadiazol-5-yl)-4,5,6,7-tetrahydro-benzo[b]thiophen-2-ylcarbamoyl]-cyclopent-1-enecarboxylic acid;

2-[3-(3-Methyl-[1,2,4]oxadiazol-5-yl)-4,5,6,7-tetrahydro-benzo[b]thiophen-2-ylcarbamoyl]-cyclohex-1-enecarboxylic acid;

(Z)-3-[3-(3-Methyl-[1,2,4]oxadiazol-5-yl)-4,5,6,7-tetrahydro-benzo[b]thiophen-2-ylcarbamoyl]-acrylic acid;

2-[3-(3-Cyclopropyl-[1,2,4]oxadiazol-5-yl)-4,5,6,7-tetrahydro-benzo[b]thiophen-2-ylcarbamoyl]-cyclopent-1-enecarboxylic acid;

2-[3-(3-Cyclopropyl-[1,2,4]oxadiazol-5-yl)-benzo[b]thiophen-2-ylcarbamoyl]-cyclopent-1-enecarboxylic acid;

(1RS,2SR)-2-[3-(3-Methyl-[1,2,4]oxadiazol-5-yl)-4,5,6,7-tetrahydro-benzo[b]thiophen-2-ylcarbamoyl]-cyclopentanecarboxylic acid;

2-[3-(4-Methyl-thiazol-2-yl)-4,5,6,7-tetrahydro-benzo[b]thiophen-2-ylcarbamoyl]-cyclopent-1-enecarboxylic acid;

3-[3-(3-Methyl-[1,2,4]oxadiazol-5-yl)-4,5,6,7-tetrahydro-benzo[b]thiophen-2-ylcarbamoyl]-pyrazine-2-carboxylic acid;

(1RS,3SR)-2,2-Dimethyl-3-[3-(3-methyl-[1,2,4]oxadiazol-5-yl)-4,5,6,7-tetrahydro-benzo[b]thiophen-2-ylcarbamoyl]-cyclopropanecarboxylic acid;

3-[3-(3-Methyl-[1,2,4]oxadiazol-5-yl)-4,5,6,7-tetrahydro-benzo[b]thiophen-2-ylcarbamoyl]-bicyclo[2.2.2]oct-2-ene-2-carboxylic acid;

(1RS,2SR)-2-[3-(3-Methyl-[1,2,4]oxadiazol-5-yl)-4,5,6,7-tetrahydro-benzo[b]thiophen-2-ylcarbamoyl]-cyclohexanecarboxylic acid;

2-[3-(4,4-Dimethyl-4,5-dihydro-oxazol-2-yl)-4,5,6,7-tetrahydro-benzo[b]thiophen-2-ylcarbamoyl]-cyclopent-1-enecarboxylic acid;

2-(3-Pyrimidin-2-yl-4,5,6,7-tetrahydro-benzo[b]thiophen-2-ylcarbamoyl)-cyclopent-1-enecarboxylic acid;

2-(3-[1,2,4]Oxadiazol-3-yl-4,5,6,7-tetrahydro-benzo[b]thiophen-2-ylcarbamoyl)-cyclopent-1-enecarboxylic acid;

2-(3-Pyrimidin-2-yl-4,5,6,7-tetrahydro-benzo[b]thiophen-2-ylcarbamoyl)-cyclohex-1-enecarboxylic acid;

3-(3-Pyrimidin-2-yl-4,5,6,7-tetrahydro-benzo[b]thiophen-2-ylcarbamoyl)-pyrazine-2-carboxylic acid, (1RS,6SR)-6-[3-(3-Methyl-[1,2,4]oxadiazol-5-yl)-4,5,6,7-tetrahydro-benzo[b]thiophen-2-ylcarbamoyl]-cyclohex-3-enecarboxylic acid;

3-(3-Pyrimidin-2-yl-4,5,6,7-tetrahydro-benzo[b]thiophen-2-ylcarbamoyl)-bicyclo[2.2.2]oct-2-ene-2-carboxylic acid;

3-(3-[1,2,4]Oxadiazol-3-yl-4,5,6,7-tetrahydro-benzo[b]thiophen-2-ylcarbamoyl)-bicyclo[2.2.2]oct-2-ene-2-carboxylic acid;

2,2,3,3-Tetrafluoro-N-[3-(3-methyl-[1,2,4]oxadiazol-5-yl)-4,5,6,7-tetrahydro-benzo[b]thiophen-2-yl]-succinamic acid;

(R)-1-[3-(3-Methyl-[1,2,4]oxadiazol-5-yl)-4,5,6,7-tetrahydro-benzo[b]thiophen-2-ylcarbamoyl]-pyrrolidine-2-carboxylic acid;

3-[3-(5-tert-Butyl-[1,2,4]oxadiazol-3-yl)-4,5,6,7-tetrahydro-benzo[b]thiophen-2-ylcarbamoyl]-bicyclo[2.2.2]oct-2-ene-2-carboxylic acid;

2-[3-(5-tert-Butyl-[1,2,4]oxadiazol-3-yl)-4,5,6,7-tetrahydro-benzo[b]thiophen-2-ylcarbamoyl]-cyclopent-1-enecarboxylic acid;

2-(5,5-Dimethyl-3-pyrimidin-2-yl-4,5,6,7-tetrahydro-benzo[b]thiophen-2-ylcarbamoyl)-cyclopent-1-enecarboxylic acid;

2-[5,5-Dimethyl-3-(4-methyl-thiazol-2-yl)-4,5,6,7-tetrahydro-benzo[b]thiophen-2-ylcarbamoyl]-cyclopent-1-enecarboxylic acid;

(R)-1-[3-(3-Cyclopropyl-[1,2,4]oxadiazol-5-yl)-4,5,6,7-tetrahydro-benzo[b]thiophen-2-ylcarbamoyl]-pyrrolidine-2-carboxylic acid;

(1RS,6SR)-6-[6,6-Dimethyl-3-(4-methyl-thiazol-2-yl)-4,5,6,7-tetrahydro-benzo[b]thiophen-2-ylcarbamoyl]-cyclohex-3-enecarboxylic acid;

2-[6,6-Dimethyl-3-(4-methyl-thiazol-2-yl)-4,5,6,7-tetrahydro-benzo[b]thiophen-2-ylcarbamoyl]-cyclopent-1-enecarboxylic acid;

{1-[3-(3-Cyclopropyl-[1,2,4]oxadiazol-5-yl)-4,5,6,7-tetrahydro-benzo[b]thiophen-2-ylcarbamoyl]-pyrrolidin-2-yl}-acetic acid;

(R)-1-[3-(3-Cyclopropyl-[1,2,4]oxadiazol-5-yl)-4,5,6,7-tetrahydro-benzo[b]thiophen-2-ylcarbamoyl]-piperidine-2-carboxylic acid;

(R)-1-[3-(3-Cyclopropyl-[1,2,4]oxadiazol-5-yl)-4,5,6,7-tetrahydro-benzo[b]thiophen-2-ylcarbamoyl]-azetidine-2-carboxylic acid;

3-[3-(3-Cyclopropyl-[1,2,4]oxadiazol-5-yl)-4,5,6,7-tetrahydro-benzo[b]thiophen-2-ylcarbamoyl]-bicyclo[2.2.2]oct-2-ene-2-carboxylic acid;

(1RS,2SR)-2-[3-(3-Cyclopropyl-[1,2,4]oxadiazol-5-yl)-4,5,6,7-tetrahydro-benzo[b]thiophen-2-ylcarbamoyl]-cyclohexanecarboxylic acid;

3-[6,6-Dimethyl-3-(4-methyl-thiazol-2-yl)-4,5,6,7-tetrahydro-benzo[b]thiophen-2-ylcarbamoyl]-bicyclo[2.2.2]oct-5-ene-2-carboxylic acid;

(1SR,2SR)-2-[6,6-Dimethyl-3-(4-methyl-thiazol-2-yl)-4,5,6,7-tetrahydro-benzo[b]thiophen-2-ylcarbamoyl]-cyclohexanecarboxylic acid;

(1SR,2SR)-2-[3-(3-Methyl-[1,2,4]oxadiazol-5-yl)-4,5,6,7-tetrahydro-benzo[b]thiophen-2-ylcarbamoyl]-cyclohexanecarboxylic acid;

N-[3-(3-Methyl-[1,2,4]oxadiazol-5-yl)-4,5,6,7-tetrahydro-benzo[b]thiophen-2-yl]-phthalamic acid;

(1RS,6SR)-6-[6-Methoxy-3-(4-methyl-thiazol-2-yl)-4,5,6,7-tetrahydro-benzo[b]thiophen-2-ylcarbamoyl]-cyclohex-3-enecarboxylic acid;

2-[3-(4-Methyl-thiazol-2-yl)-5,6,7,8-tetrahydro-4H-cyclohepta[b]thiophen-2-ylcarbamoyl]-cyclopent-1-enecarboxylic acid;

3-[3-(3-Methyl-[1,2,4]oxadiazol-5-yl)-4,5,6,7-tetrahydro-benzo[b]thiophen-2-ylcarbamoyl]-bicyclo[2.2.2]oct-5-ene-2-carboxylic acid;

2-[3-(3-Ethyl-[1,2,4]oxadiazol-5-yl)-4,5,6,7-tetrahydro-benzo[b]thiophen-2-ylcarbamoyl]-cyclopent-1-enecarboxylic acid;

N-[6,6-Dimethyl-3-(4-methyl-thiazol-2-yl)-4,5,6,7-tetrahydro-benzo[b]thiophen-2-yl]-phthalamic acid;

2-{3-[3-(3-Cyclopropyl-[1,2,4]oxadiazol-5-yl)-4,5,6,7-tetrahydro-benzo[b]thiophen-2-yl]-ureido}-nicotinic acid;

4-{3-[3-(3-Cyclopropyl-[1,2,4]oxadiazol-5-yl)-4,5,6,7-tetrahydro-benzo[b]thiophen-2-yl]-ureido}-2-methyl-2H-pyrazole-3-carboxylic acid;

(1RS,6SR)-6-[3-(4-Methyl-thiazol-2-yl)-5,6,7,8-tetrahydro-4H-cyclohepta[b]thiophen-2-ylcarbamoyl]-cyclohex-3-enecarboxylic acid;

3-[6,6-Dimethyl-3-(4-methyl-thiazol-2-yl)-4,5,6,7-tetrahydro-benzo[b]thiophen-2-ylcarbamoyl]-bicyclo[2.2.2]oct-2-ene-2-carboxylic acid;

(1SR,2SR)-2-[3-(4-Methyl-thiazol-2-yl)-4,5,6,7-tetrahydro-benzo[b]thiophen-2-ylcarbamoyl]-cyclohexanecarboxylic acid;

3-[3-(4-Methyl-thiazol-2-yl)-4,5,6,7-tetrahydro-benzo[b]thiophen-2-ylcarbamoyl]-bicyclo[2.2.2]oct-2-ene-2-carboxylic acid;

2-[6-Methoxy-3-(4-methyl-thiazol-2-yl)-4,5,6,7-tetrahydro-benzo[b]thiophen-2-ylcarbamoyl]-cyclohexanecarboxylic acid;

3-[3-(4-Methyl-thiazol-2-yl)-5,6,7,8-tetrahydro-4H-cyclohepta[b]thiophen-2-ylcarbamoyl]-bicyclo[2.2.2]oct-2-ene-2-carboxylic acid;

(1SR,2SR)-2-{[3-(4-methyl-1,3-thiazol-2-yl)-4,7-dihydro-5H-spiro[1-benzothiophene-6,1'-cyclopropan]-2-yl]carbamoyl}cyclohexanecarboxylic acid;

(S)-1-[3-(3-Cyclopropyl-[1,2,4]oxadiazol-5-yl)-4,5,6,7-tetrahydro-benzo[b]thiophen-2-ylcarbamoyl]-pyrrolidine-2-carboxylic acid;

(1SR,2SR)-2-[3-(4-Methyl-thiazol-2-yl)-5,6,7,8-tetrahydro-4H-cyclohepta[b]thiophen-2-ylcarbamoyl]-cyclohexanecarboxylic acid;

2-[3-(3-Cyclopropyl-[1,2,4]oxadiazol-5-yl)-4,7-dihydro-5H-thieno[2,3-c]pyran-2-ylcarbamoyl]-cyclopent-1-enecarboxylic acid;

3-[3-(4-Methyl-thiazol-2-yl)-4,7-dihydro-5H-thieno[2,3-c]pyran-2-ylcarbamoyl]-bicyclo[2.2.2]oct-2-ene-2-carboxylic acid;

2-[3-(4,5-Dimethyl-oxazol-2-yl)-4,7-dihydro-5H-thieno[2,3-c]pyran-2-ylcarbamoyl]-cyclopent-1-enecarboxylic acid;

2-[3-(3-Cyclopropyl-[1,2,4]oxadiazol-5-yl)-4,4,6,6-tetramethyl-4,6-dihydro-thieno[2,3-c]furan-2-ylcarbamoyl]-cyclopent-1-enecarboxylic acid;

2-[3-(4-Methyl-thiazol-2-yl)-4,7-dihydro-5H-thieno[2,3-c]pyran-2-ylcarbamoyl]-cyclopent-1-enecarboxylic acid;

2-[(2-Carboxy-cyclopent-1-enecarbonyl)-amino]-3-(4-methyl-thiazol-2-yl)-4,7-dihydro-5H-thieno[2,3-c]pyridine-6-carboxylic acid tert-butyl ester;

2-[3-(3-Trifluoromethyl-[1,2,4]oxadiazol-5-yl)-4,5,6,7-tetrahydro-benzo[b]thiophen-2-ylcarbamoyl]-cyclopent-1-enecarboxylic acid;

3-[3-(3-Trifluoromethyl-[1,2,4]oxadiazol-5-yl)-4,5,6,7-tetrahydro-benzo[b]thiophen-2-ylcarbamoyl]-bicyclo[2.2.2]oct-2-ene-2-carboxylic acid;

(RS)-{2-[3-(4-Methyl-thiazol-2-yl)-4,5,6,7-tetrahydro-benzo[b]thiophen-2-ylcarbamoyl]-pyrrolidin-1-yl}-acetic acid;

3-[3-(3-Cyclopropyl-[1,2,4]oxadiazol-5-yl)-4,7-dihydro-5H-thieno[2,3-c]pyran-2-ylcarbamoyl]-bicyclo[2.2.2]oct-2-ene-2-carboxylic acid;

2-[3-(4-Methyl-thiazol-2-yl)-6,6-dioxo-4,5,6,7-tetrahydro-6λ6-thieno[2,3-c]thiopyran-2-ylcarbamoyl]-cyclopent-1-enecarboxylic acid;

2-[3-(4-Methyl-thiazol-2-yl)-4,7-dihydro-5H-thieno[2,3-c]pyran-2-ylcarbamoyl]-cyclohex-1-enecarboxylic acid;

2-[3-(3-Isopropyl-[1,2,4]oxadiazol-5-yl)-4,5,6,7-tetrahydro-benzo[b]thiophen-2-ylcarbamoyl]-cyclopent-1-enecarboxylic acid;

3-[3-(3-Isopropyl-[1,2,4]oxadiazol-5-yl)-4,5,6,7-tetrahydro-benzo[b]thiophen-2-ylcarbamoyl]-bicyclo[2.2.2]oct-2-ene-2-carboxylic acid;

2-[3-(3-Isopropyl-[1,2,4]oxadiazol-5-yl)-4,7-dihydro-5H-thieno[2,3-c]pyran-2-ylcarbamoyl]-cyclopent-1-enecarboxylic acid;

3-[3-(3-Isopropyl-[1,2,4]oxadiazol-5-yl)-4,7-dihydro-5H-thieno[2,3-c]pyran-2-ylcarbamoyl]-bicyclo[2.2.2]oct-2-ene-2-carboxylic acid;

2-[3-(3-Trifluoromethyl-[1,2,4]oxadiazol-5-yl)-4,7-dihydro-5H-thieno[2,3-c]pyran-2-ylcarbamoyl]-cyclopent-1-enecarboxylic acid;

2-(3-(3-Methyl-1,2,4-oxadiazol-5-yl)-5,7-dihydro-4H-spiro[benzo[b]thiophene-6,3'-oxetane]-2-ylcarbamoyl)cyclopent-1-enecarboxylic acid;

3-(3-(3-methyl-1,2,4-oxadiazol-5-yl)-5,7-dihydro-4H-spiro[benzo[b]thiophene-6,3'-oxetane]-2-ylcarbamoyl)bicyclo[2.2.2]oct-2-ene-2-carboxylic acid;

2-(3-(4-methylthiazol-2-yl)-5,7-dihydro-4H-spiro[benzo[b]thiophene-6,3'-oxetane]-2-ylcarbamoyl)cyclopent-1-enecarboxylic acid;

(1SR,2SR)-2-[3-(3-Isopropyl-[1,2,4]oxadiazol-5-yl)-4,7-dihydro-5H-thieno[2,3-c]pyran-2-ylcarbamoyl]-cyclohexanecarboxylic acid;

(1RS,2SR)-2-[3-(3-Isopropyl-[1,2,4]oxadiazol-5-yl)-4,7-dihydro-5H-thieno[2,3-c]pyran-2-ylcarbamoyl]-cyclohexanecarboxylic acid;

2-[4,4-Dimethyl-3-(3-methyl-[1,2,4]oxadiazol-5-yl)-5,6-dihydro-4H-cyclopenta[b]thiophen-2-ylcarbamoyl]-cyclopent-1-enecarboxylic acid;

2-[3-(4-Methyl-oxazol-2-yl)-4,7-dihydro-5H-thieno[2,3-c]pyran-2-ylcarbamoyl]-cyclopent-1-enecarboxylic acid;

3-[3-(4-Methyl-oxazol-2-yl)-4,7-dihydro-5H-thieno[2,3-c]pyran-2-ylcarbamoyl]-bicyclo[2.2.2]oct-2-ene-2-carboxylic acid;

3-[3-(3-Cyclopropyl-[1,2,4]oxadiazol-5-yl)-benzo[b]thiophen-2-ylcarbamoyl]-bicyclo[2.2.2]oct-2-ene-2-carboxylic acid;

2-[6,6-Dioxo-3-(3-trifluoromethyl-[1,2,4]oxadiazol-5-yl)-4,5,6,7-tetrahydro-6λ6-thieno[2,3-c]thiopyran-2-ylcarbamoyl]-cyclopent-1-enecarboxylic acid;

2,2-Dimethyl-N-[3-(3-methyl-[1,2,4]oxadiazol-5-yl)-4,5,6,7-tetrahydro-benzo[b]thiophen-2-yl]-succinamic acid;

2-[3-(3-Cyclopropyl-[1,2,4]oxadiazol-5-yl)-5,5-dimethyl-4,7-dihydro-5H-thieno[2,3-c]pyran-2-ylcarbamoyl]-cyclopent-1-enecarboxylic acid;

2-[3-(3-Cyclopropyl-[1,2,4]oxadiazol-5-yl)-5,5-dimethyl-4,7-dihydro-5H-thieno[2,3-c]pyran-2-ylcarbamoyl]-cyclohex-1-enecarboxylic acid;

2-[3-(4-Trifluoromethyl-thiazol-2-yl)-4,5,6,7-tetrahydro-benzo[b]thiophen-2-ylcarbamoyl]-cyclopent-1-enecarboxylic acid;

2-[3-(4-Trifluoromethyl-thiazol-2-yl)-4,5,6,7-tetrahydro-benzo[b]thiophen-2-ylcarbamoyl]-cyclohex-1-enecarboxylic acid;

3-[3-(4-Trifluoromethyl-thiazol-2-yl)-4,5,6,7-tetrahydro-benzo[b]thiophen-2-ylcarbamoyl]-bicyclo[2.2.2]oct-2-ene-2-carboxylic acid;

(RS)-2-[3-(3-Cyclopropyl-[1,2,4]oxadiazol-5-yl)-6-methyl-4,5,6,7-tetrahydro-benzo[b]thiophen-2-ylcarbamoyl]-cyclopent-1-enecarboxylic acid;
2-[3-(4-Trifluoromethyl-thiazol-2-yl)-4,7-dihydro-5H-thieno[2,3-c]pyran-2-ylcarbamoyl]-cyclopent-1-enecarboxylic acid;
2-[3-(4-Trifluoromethyl-thiazol-2-yl)-4,7-dihydro-5H-thieno[2,3-c]pyran-2-ylcarbamoyl]-cyclohex-1-enecarboxylic acid;
3-[3-(4-Trifluoromethyl-thiazol-2-yl)-4,7-dihydro-5H-thieno[2,3-c]pyran-2-ylcarbamoyl]-bicyclo[2.2.2]oct-2-ene-2-carboxylic acid;
(RS)-2-[3-(3-Cyclopropyl-[1,2,4]oxadiazol-5-yl)-6-methyl-4,5,6,7-tetrahydro-benzo[b]thiophen-2-ylcarbamoyl]-cyclohex-1-enecarboxylic acid;
(RS)-3-[3-(3-Cyclopropyl-[1,2,4]oxadiazol-5-yl)-6-methyl-4,5,6,7-tetrahydro-benzo[b]thiophen-2-ylcarbamoyl]-bicyclo[2.2.2]oct-2-ene-2-carboxylic acid;
2-[4,4-Dimethyl-3-(3-methyl-[1,2,4]oxadiazol-5-yl)-5,6-dihydro-4H-cyclopenta[b]thiophen-2-ylcarbamoyl]-cyclohex-1-enecarboxylic acid;
3-[4,4-Dimethyl-3-(3-methyl-[1,2,4]oxadiazol-5-yl)-5,6-dihydro-4H-cyclopenta[b]thiophen-2-ylcarbamoyl]-bicyclo[2.2.2]oct-2-ene-2-carboxylic acid;
2-[3-(4-Cyclopropyl-thiazol-2-yl)-4,7-dihydro-5H-thieno[2,3-c]pyran-2-ylcarbamoyl]-cyclopent-1-enecarboxylic acid;
3-[3-(4-Cyclopropyl-thiazol-2-yl)-4,7-dihydro-5H-thieno[2,3-c]pyran-2-ylcarbamoyl]-bicyclo[2.2.2]oct-2-ene-2-carboxylic acid;
3-[3-(3-Cyclopropyl-[1,2,4]oxadiazol-5-yl)-5,5-dimethyl-4,7-dihydro-5H-thieno[2,3-c]pyran-2-ylcarbamoyl]-bicyclo[2.2.2]oct-2-ene-2-carboxylic acid;
3,3-Dimethyl-4-[3-(3-methyl-[1,2,4]oxadiazol-5-yl)-4,5,6,7-tetrahydro-benzo[b]thiophen-2-ylcarbamoyl]-butyric acid;
2-[3-(3-Methyl-[1,2,4]oxadiazol-5-yl)-4,7-dihydro-5H-thieno[2,3-c]pyran-2-ylcarbamoyl]-cyclohex-1-enecarboxylic acid;
2-[3-(4,5-Dimethyl-thiazol-2-yl)-4,7-dihydro-5H-thieno[2,3-c]pyran-2-ylcarbamoyl]-cyclopent-1-enecarboxylic acid;
2-[3-(3-Cyclopropyl-[1,2,4]oxadiazol-5-yl)-4,4-dimethyl-4,5,6,7-tetrahydro-benzo[b]thiophen-2-ylcarbamoyl]-cyclopent-1-enecarboxylic acid;
3-[3-(3-Cyclopropyl-[1,2,4]oxadiazol-5-yl)-4,4-dimethyl-4,5,6,7-tetrahydro-benzo[b]thiophen-2-ylcarbamoyl]-bicyclo[2.2.2]oct-2-ene-2-carboxylic acid;
3-[3-(3-Methyl-[1,2,4]oxadiazol-5-yl)-4,7-dihydro-5H-thieno[2,3-c]pyran-2-ylcarbamoyl]-bicyclo[2.2.2]oct-2-ene-2-carboxylic acid;
2-[3-(3-Methyl-[1,2,4]oxadiazol-5-yl)-4,7-dihydro-5H-thieno[2,3-c]pyran-2-ylcarbamoyl]-cyclopent-1-enecarboxylic acid;
(1RS,2SR)-2-[3-(3-Trifluoromethyl-[1,2,4]oxadiazol-5-yl)-4,7-dihydro-5H-thieno[2,3-c]pyran-2-ylcarbamoyl]-cyclohexanecarboxylic acid;
2-[3-(4-Cyclopropyl-thiazol-2-yl)-4,7-dihydro-5H-thieno[2,3-c]pyran-2-ylcarbamoyl]-cyclohex-1-enecarboxylic acid;
(+)-2-[3-(3-Cyclopropyl-[1,2,4]oxadiazol-5-yl)-6-methyl-4,5,6,7-tetrahydro-benzo[b]thiophen-2-ylcarbamoyl]-cyclohex-1-enecarboxylic acid;
(−)-2-[3-(3-Cyclopropyl-[1,2,4]oxadiazol-5-yl)-6-methyl-4,5,6,7-tetrahydro-benzo[b]thiophen-2-ylcarbamoyl]-cyclohex-1-enecarboxylic acid;
2-{3-[3-(2-Methoxy-ethyl)-[1,2,4]oxadiazol-5-yl]-4,7-dihydro-5H-thieno[2,3-c]pyran-2-ylcarbamoyl}-cyclohex-1-enecarboxylic acid;
3-{3-[3-(2-Methoxy-ethyl)-[1,2,4]oxadiazol-5-yl]-4,7-dihydro-5H-thieno[2,3-c]pyran-2-ylcarbamoyl}-bicyclo[2.2.2]oct-2-ene-2-carboxylic acid;
(1RS,5SR)-5-[3-(3-Methyl-[1,2,4]oxadiazol-5-yl)-4,5,6,7-tetrahydro-benzo[b]thiophen-2-ylcarbamoyl]-bicyclo[3.1.0]hexane-1-carboxylic acid methyl ester;
(1RS,5SR)-5-[3-(3-Methyl-[1,2,4]oxadiazol-5-yl)-4,5,6,7-tetrahydro-benzo[b]thiophen-2-ylcarbamoyl]-bicyclo[3.1.0]hexane-1-carboxylic acid;
(1SR,2SR)-2-[3-(3-Trifluoromethyl-[1,2,4]oxadiazol-5-yl)-4,7-dihydro-5H-thieno[2,3-c]pyran-2-ylcarbamoyl]-cyclohexanecarboxylic acid;
(1SR,2SR)-2-[3-(3-Trifluoromethyl-[1,2,4]oxadiazol-5-yl)-4,7-dihydro-5H-thieno[2,3-c]pyran-2-ylcarbamoyl]-cyclohexanecarboxylic acid;
(1RS,2SR)-2-[3-(3-Trifluoromethyl-[1,2,4]oxadiazol-5-yl)-4,7-dihydro-5H-thieno[2,3-c]pyran-2-ylcarbamoyl]-cyclohexanecarboxylic acid;
(1RS,2SR)-2-[3-(3-Trifluoromethyl-[1,2,4]oxadiazol-5-yl)-4,7-dihydro-5H-thieno[2,3-c]pyran-2-ylcarbamoyl]-cyclohexanecarboxylic acid;
2-[5-(3-Cyclopropyl-[1,2,4]oxadiazol-5-yl)-3-thia-tricyclo[5.2.1.0²,⁶]deca-2(6),4-dien-4-ylcarbamoyl]-cyclopent-1-enecarboxylic acid;
2-{3-[3-(2-Methoxy-ethyl)-[1,2,4]oxadiazol-5-yl]-4,7-dihydro-5H-thieno[2,3-c]pyran-2-ylcarbamoyl}-cyclopent-1-enecarboxylic acid;
2-[3-(3-Methyl-[1,2,4]oxadiazol-5-yl)-5,6,7,8-tetrahydro-4H-cyclohepta[b]thiophen-2-ylcarbamoyl]-cyclopent-1-enecarboxylic acid;
2-[3-(3-Methyl-[1,2,4]oxadiazol-5-yl)-5,6,7,8-tetrahydro-4H-cyclohepta[b]thiophen-2-ylcarbamoyl]-cyclohex-1-enecarboxylic acid;
3-[3-(3-Methyl-[1,2,4]oxadiazol-5-yl)-5,6,7,8-tetrahydro-4H-cyclohepta[b]thiophen-2-ylcarbamoyl]-bicyclo[2.2.2]oct-2-ene-2-carboxylic acid;
2-[3-(3-Cyclopropyl-[1,2,4]oxadiazol-5-yl)-5,6,7,8-tetrahydro-4H-cyclohepta[b]thiophen-2-ylcarbamoyl]-cyclopent-1-enecarboxylic acid;
2-[3-(3-Cyclopropyl-[1,2,4]oxadiazol-5-yl)-5,6,7,8-tetrahydro-4H-cyclohepta[b]thiophen-2-ylcarbamoyl]-cyclohex-1-enecarboxylic acid;
3-[3-(3-Cyclopropyl-[1,2,4]oxadiazol-5-yl)-5,6,7,8-tetrahydro-4H-cyclohepta[b]thiophen-2-ylcarbamoyl]-bicyclo[2.2.2]oct-2-ene-2-carboxylic acid;
2-[3-(3-Trifluoromethyl-[1,2,4]oxadiazol-5-yl)-5,6,7,8-tetrahydro-4H-cyclohepta[b]thiophen-2-ylcarbamoyl]-cyclopent-1-enecarboxylic acid;
2-[3-(3-Trifluoromethyl-[1,2,4]oxadiazol-5-yl)-5,6,7,8-tetrahydro-4H-cyclohepta[b]thiophen-2-ylcarbamoyl]-cyclohex-1-enecarboxylic acid;
3-[3-(3-Trifluoromethyl-[1,2,4]oxadiazol-5-yl)-5,6,7,8-tetrahydro-4H-cyclohepta[b]thiophen-2-ylcarbamoyl]-bicyclo[2.2.2]oct-2-ene-2-carboxylic acid;
2-[3-(3-Methyl-[1,2,4]oxadiazol-5-yl)-5,6-dihydro-4H-cyclopenta[b]thiophen-2-ylcarbamoyl]-cyclopent-1-enecarboxylic acid;
2-[3-(3-Methyl-[1,2,4]oxadiazol-5-yl)-5,6-dihydro-4H-cyclopenta[b]thiophen-2-ylcarbamoyl]-cyclohex-1-enecarboxylic acid;
3-[3-(3-Methyl-[1,2,4]oxadiazol-5-yl)-5,6-dihydro-4H-cyclopenta[b]thiophen-2-ylcarbamoyl]-bicyclo[2.2.2]oct-2-ene-2-carboxylic acid;

2-[3-(3-Cyclopropyl-[1,2,4]oxadiazol-5-yl)-5,6-dihydro-4H-cyclopenta[b]thiophen-2-ylcarbamoyl]-cyclopent-1-enecarboxylic acid;
2-[3-(3-Cyclopropyl-[1,2,4]oxadiazol-5-yl)-5,6-dihydro-4H-cyclopenta[b]thiophen-2-ylcarbamoyl]-cyclohex-1-enecarboxylic acid;
3-[3-(3-Cyclopropyl-[1,2,4]oxadiazol-5-yl)-5,6-dihydro-4H-cyclopenta[b]thiophen-2-ylcarbamoyl]-bicyclo[2.2.2]oct-2-ene-2-carboxylic acid;
2-[3-(3-Trifluoromethyl-[1,2,4]oxadiazol-5-yl)-5,6-dihydro-4H-cyclopenta[b]thiophen-2-ylcarbamoyl]-cyclopent-1-enecarboxylic acid;
2-[3-(3-Trifluoromethyl-[1,2,4]oxadiazol-5-yl)-5,6-dihydro-4H-cyclopenta[b]thiophen-2-ylcarbamoyl]-cyclohex-1-enecarboxylic acid;
3-[3-(3-Trifluoromethyl-[1,2,4]oxadiazol-5-yl)-5,6-dihydro-4H-cyclopenta[b]thiophen-2-ylcarbamoyl]-bicyclo[2.2.2]oct-2-ene-2-carboxylic acid;
2-[3-(4-Methyl-thiazol-2-yl)-5,6-dihydro-4H-cyclopenta[b]thiophen-2-ylcarbamoyl]-cyclopent-1-enecarboxylic acid;
2-[3-(4-Methyl-thiazol-2-yl)-5,6-dihydro-4H-cyclopenta[b]thiophen-2-ylcarbamoyl]-cyclohex-1-enecarboxylic acid;
3-[3-(4-Methyl-thiazol-2-yl)-5,6-dihydro-4H-cyclopenta[b]thiophen-2-ylcarbamoyl]-bicyclo[2.2.2]oct-2-ene-2-carboxylic acid;
2-[6,6-Difluoro-3-(3-methyl-[1,2,4]oxadiazol-5-yl)-4,5,6,7-tetrahydro-benzo[b]thiophen-2-ylcarbamoyl]-cyclopent-1-enecarboxylic acid;
2-[6,6-Difluoro-3-(3-methyl-[1,2,4]oxadiazol-5-yl)-4,5,6,7-tetrahydro-benzo[b]thiophen-2-ylcarbamoyl]-cyclohex-1-enecarboxylic acid;
3-[6,6-Difluoro-3-(3-methyl-[1,2,4]oxadiazol-5-yl)-4,5,6,7-tetrahydro-benzo[b]thiophen-2-ylcarbamoyl]-bicyclo[2.2.2]oct-2-ene-2-carboxylic acid;
2-[3-(3-Cyclopropyl-[1,2,4]oxadiazol-5-yl)-6,6-difluoro-4,5,6,7-tetrahydro-benzo[b]thiophen-2-ylcarbamoyl]-cyclopent-1-enecarboxylic acid;
2-[3-(3-Cyclopropyl-[1,2,4]oxadiazol-5-yl)-6,6-difluoro-4,5,6,7-tetrahydro-benzo[b]thiophen-2-ylcarbamoyl]-cyclohex-1-enecarboxylic acid;
3-[3-(3-Cyclopropyl-[1,2,4]oxadiazol-5-yl)-6,6-difluoro-4,5,6,7-tetrahydro-benzo[b]thiophen-2-ylcarbamoyl]-bicyclo[2.2.2]oct-2-ene-2-carboxylic acid;
2-[6,6-Difluoro-3-(3-trifluoromethyl-[1,2,4]oxadiazol-5-yl)-4,5,6,7-tetrahydro-benzo[b]thiophen-2-ylcarbamoyl]-cyclopent-1-enecarboxylic acid;
2-[6,6-Difluoro-3-(3-trifluoromethyl-[1,2,4]oxadiazol-5-yl)-4,5,6,7-tetrahydro-benzo[b]thiophen-2-ylcarbamoyl]-cyclohex-1-enecarboxylic acid;
3-[6,6-Difluoro-3-(3-trifluoromethyl-[1,2,4]oxadiazol-5-yl)-4,5,6,7-tetrahydro-benzo[b]thiophen-2-ylcarbamoyl]-bicyclo[2.2.2]oct-2-ene-2-carboxylic acid;
2-[6,6-Difluoro-3-(4-methyl-thiazol-2-yl)-4,5,6,7-tetrahydro-benzo[b]thiophen-2-ylcarbamoyl]-cyclopent-1-enecarboxylic acid;
2-[6,6-Difluoro-3-(4-methyl-thiazol-2-yl)-4,5,6,7-tetrahydro-benzo[b]thiophen-2-ylcarbamoyl]-cyclohex-1-enecarboxylic acid;
3-[6,6-Difluoro-3-(4-methyl-thiazol-2-yl)-4,5,6,7-tetrahydro-benzo[b]thiophen-2-ylcarbamoyl]-bicyclo[2.2.2]oct-2-ene-2-carboxylic acid,
(1RS,2SR)-2-[3-(3-Cyclopropyl-[1,2,4]oxadiazol-5-yl)-6,6-difluoro-4,5,6,7-tetrahydro-benzo[b]thiophen-2-ylcarbamoyl]-cyclohexanecarboxylic acid;
(1SR,2SR)-2-[3-(3-Cyclopropyl-[1,2,4]oxadiazol-5-yl)-6,6-difluoro-4,5,6,7-tetrahydro-benzo[b]thiophen-2-ylcarbamoyl]-cyclohexanecarboxylic acid;
(1RS,2SR)-2-[6,6-Difluoro-3-(4-methyl-thiazol-2-yl)-4,5,6,7-tetrahydro-benzo[b]thiophen-2-ylcarbamoyl]-cyclohexanecarboxylic acid;
(1SR,2SR)-2-[6,6-Difluoro-3-(4-methyl-thiazol-2-yl)-4,5,6,7-tetrahydro-benzo[b]thiophen-2-ylcarbamoyl]-cyclohexanecarboxylic acid;
(1RS,2SR)-2-[3-(3-Cyclopropyl-[1,2,4]oxadiazol-5-yl)-5,6,7,8-tetrahydro-4H-cyclohepta[b]thiophen-2-ylcarbamoyl]-cyclohexanecarboxylic acid;
(1SR,2SR)-2-[3-(3-Cyclopropyl-[1,2,4]oxadiazol-5-yl)-5,6,7,8-tetrahydro-4H-cyclohepta[b]thiophen-2-ylcarbamoyl]-cyclohexanecarboxylic acid;
(1RS,2SR)-2-[3-(4-Methyl-thiazol-2-yl)-5,6,7,8-tetrahydro-4H-cyclohepta[b]thiophen-2-ylcarbamoyl]-cyclohexanecarboxylic acid;
(1SR,2SR)-2-[3-(4-Methyl-thiazol-2-yl)-5,6,7,8-tetrahydro-4H-cyclohepta[b]thiophen-2-ylcarbamoyl]-cyclohexanecarboxylic acid;
(1RS,2SR)-2-[3-(3-Cyclopropyl-[1,2,4]oxadiazol-5-yl)-5,6-dihydro-4H-cyclopenta[b]thiophen-2-ylcarbamoyl]-cyclohexanecarboxylic acid;
(1SR,2SR)-2-[3-(3-Cyclopropyl-[1,2,4]oxadiazol-5-yl)-5,6-dihydro-4H-cyclopenta[b]thiophen-2-ylcarbamoyl]-cyclohexanecarboxylic acid;
(1RS,2SR)-2-[3-(4-Methyl-thiazol-2-yl)-5,6-dihydro-4H-cyclopenta[b]thiophen-2-ylcarbamoyl]-cyclohexanecarboxylic acid;
(1SR,2SR)-2-[3-(4-Methyl-thiazol-2-yl)-5,6-dihydro-4H-cyclopenta[b]thiophen-2-ylcarbamoyl]-cyclohexanecarboxylic acid;
and pharmaceutically acceptable salts thereof.

Particular examples of compounds of formula (I) as described herein are selected from
(1RS,2SR)-2-[3-(3-Cyclopropyl-[1,2,4]oxadiazol-5-yl)-5,6,7,8-tetrahydro-4H-cyclohepta[b]thiophen-2-ylcarbamoyl]-cyclohexanecarboxylic acid;
2-[3-(3-Cyclopropyl-[1,2,4]oxadiazol-5-yl)-6-ethyl-4,5,6,7-tetrahydro-benzo[b]thiophen-2-ylcarbamoyl]-cyclopent-1-enecarboxylic acid;
2-[(S)-3-(3-Cyclopropyl-[1,2,4]oxadiazol-5-yl)-6-ethyl-4,5,6,7-tetrahydro-benzo[b]thiophen-2-ylcarbamoyl]-cyclopent-1-enecarboxylic acid;
2-[(R)-3-(3-Cyclopropyl-[1,2,4]oxadiazol-5-yl)-6-ethyl-4,5,6,7-tetrahydro-benzo[b]thiophen-2-ylcarbamoyl]-cyclopent-1-enecarboxylic acid;
3-[3-(3-Cyclopropyl-[1,2,4]oxadiazol-5-yl)-6-ethyl-4,5,6,7-tetrahydro-benzo[b]thiophen-2-ylcarbamoyl]-bicyclo[2.2.2]oct-2-ene-2-carboxylic acid;
3-[(S)-3-(3-Cyclopropyl-[1,2,4]oxadiazol-5-yl)-6-ethyl-4,5,6,7-tetrahydro-benzo[b]thiophen-2-ylcarbamoyl]-bicyclo[2.2.2]oct-2-ene-2-carboxylic acid;
3-[(R)-3-(3-Cyclopropyl-[1,2,4]oxadiazol-5-yl)-6-ethyl-4,5,6,7-tetrahydro-benzo[b]thiophen-2-ylcarbamoyl]-bicyclo[2.2.2]oct-2-ene-2-carboxylic acid;
2-[3-(3-Cyclopropyl-[1,2,4]oxadiazol-5-yl)-6-trifluoromethyl-4,5,6,7-tetrahydro-benzo[b]thiophen-2-ylcarbamoyl]-cyclopent-1-enecarboxylic acid;
2-[(S)-3-(3-Cyclopropyl-[1,2,4]oxadiazol-5-yl)-6-trifluoromethyl-4,5,6,7-tetrahydro-benzo[b]thiophen-2-ylcarbamoyl]-cyclopent-1-enecarboxylic acid;
2-[(R)-3-(3-Cyclopropyl-[1,2,4]oxadiazol-5-yl)-6-trifluoromethyl-4,5,6,7-tetrahydro-benzo[b]thiophen-2-ylcarbamoyl]-cyclopent-1-enecarboxylic acid;

2-[3-(3-Cyclopropyl-[1,2,4]oxadiazol-5-yl)-6-trifluoromethyl-4,5,6,7-tetrahydro-benzo[b]thiophen-2-ylcarbamoyl]-cyclohex-1-enecarboxylic acid;

3-[3-(3-Cyclopropyl-[1,2,4]oxadiazol-5-yl)-6-trifluoromethyl-4,5,6,7-tetrahydro-benzo[b]thiophen-2-ylcarbamoyl]-bicyclo[2.2.2]oct-2-ene-2-carboxylic acid;

3-[(S)-3-(3-Cyclopropyl-[1,2,4]oxadiazol-5-yl)-6-trifluoromethyl-4,5,6,7-tetrahydro-benzo[b]thiophen-2-ylcarbamoyl]-bicyclo[2.2.2]oct-2-ene-2-carboxylic acid;

3-[(R)-3-(3-Cyclopropyl-[1,2,4]oxadiazol-5-yl)-6-trifluoromethyl-4,5,6,7-tetrahydro-benzo[b]thiophen-2-ylcarbamoyl]-bicyclo[2.2.2]oct-2-ene-2-carboxylic acid;

3-[6-Ethyl-3-(4-methyl-thiazol-2-yl)-4,5,6,7-tetrahydro-benzo[b]thiophen-2-ylcarbamoyl]-bicyclo[2.2.2]oct-2-ene-2-carboxylic acid;

3-[(S)-6-Ethyl-3-(4-methyl-thiazol-2-yl)-4,5,6,7-tetrahydro-benzo[b]thiophen-2-ylcarbamoyl]-bicyclo[2.2.2]oct-2-ene-2-carboxylic acid;

3-[(R)-6-Ethyl-3-(4-methyl-thiazol-2-yl)-4,5,6,7-tetrahydro-benzo[b]thiophen-2-ylcarbamoyl]-bicyclo[2.2.2]oct-2-ene-2-carboxylic acid;

2-[6-Ethyl-3-(4-methyl-thiazol-2-yl)-4,5,6,7-tetrahydro-benzo[b]thiophen-2-ylcarbamoyl]-cyclopent-1-enecarboxylic acid;

2-[(S)-6-Ethyl-3-(4-methyl-thiazol-2-yl)-4,5,6,7-tetrahydro-benzo[b]thiophen-2-ylcarbamoyl]-cyclopent-1-enecarboxylic acid;

2-[(R)-6-Ethyl-3-(4-methyl-thiazol-2-yl)-4,5,6,7-tetrahydro-benzo[b]thiophen-2-ylcarbamoyl]-cyclopent-1-enecarboxylic acid;

3-[3-(4-Methyl-thiazol-2-yl)-6-trifluoromethyl-4,5,6,7-tetrahydro-benzo[b]thiophen-2-ylcarbamoyl]-bicyclo[2.2.2]oct-2-ene-2-carboxylic acid;

3-[(S)-3-(4-Methyl-thiazol-2-yl)-6-trifluoromethyl-4,5,6,7-tetrahydro-benzo[b]thiophen-2-ylcarbamoyl]-bicyclo[2.2.2]oct-2-ene-2-carboxylic acid;

3-[(R)-3-(4-Methyl-thiazol-2-yl)-6-trifluoromethyl-4,5,6,7-tetrahydro-benzo[b]thiophen-2-ylcarbamoyl]-bicyclo[2.2.2]oct-2-ene-2-carboxylic acid;

2-[3-(4-Methyl-thiazol-2-yl)-6-trifluoromethyl-4,5,6,7-tetrahydro-benzo[b]thiophen-2-ylcarbamoyl]-cyclopent-1-enecarboxylic acid;

2-[(S)-3-(4-Methyl-thiazol-2-yl)-6-trifluoromethyl-4,5,6,7-tetrahydro-benzo[b]thiophen-2-ylcarbamoyl]-cyclopent-1-enecarboxylic acid;

2-[(R)-3-(4-Methyl-thiazol-2-yl)-6-trifluoromethyl-4,5,6,7-tetrahydro-benzo[b]thiophen-2-ylcarbamoyl]-cyclopent-1-enecarboxylic acid;

2-[3-(4-Methyl-thiazol-2-yl)-6-trifluoromethyl-4,5,6,7-tetrahydro-benzo[b]thiophen-2-ylcarbamoyl]-cyclohex-1-enecarboxylic acid;

2-[3-(3-Cyclopropyl-[1,2,4]oxadiazol-5-yl)-6-ethyl-4,5,6,7-tetrahydro-benzo[b]thiophen-2-ylcarbamoyl]-cyclohex-1-enecarboxylic acid;

2-[6-Ethyl-3-(4-methyl-thiazol-2-yl)-4,5,6,7-tetrahydro-benzo[b]thiophen-2-ylcarbamoyl]-cyclohex-1-enecarboxylic acid;

3-[3-(3-Cyclopropyl-[1,2,4]oxadiazol-5-yl)-4,7-dihydro-5H-thieno[2,3-c]pyran-2-ylcarbamoyl]-isonicotinic acid;

3-[3-(3-Cyclopropyl-[1,2,4]oxadiazol-5-yl)-4,5,6,7-tetrahydro-benzo[b]thiophen-2-ylcarbamoyl]-isonicotinic acid;

2-[6,6-Difluoro-3-(3-methyl-[1,2,4]thiadiazol-5-yl)-4,5,6,7-tetrahydro-benzo[b]thiophen-2-ylcarbamoyl]-cyclopent-1-enecarboxylic acid;

2-[6,6-Difluoro-3-(3-methyl-[1,2,4]thiadiazol-5-yl)-4,5,6,7-tetrahydro-benzo[b]thiophen-2-ylcarbamoyl]-cyclohex-1-enecarboxylic acid;

2-[3-(3-Cyclopropyl-[1,2,4]thiadiazol-5-yl)-6,6-difluoro-4,5,6,7-tetrahydro-benzo[b]thiophen-2-ylcarbamoyl]-cyclopent-1-enecarboxylic acid;

2-[3-(3-Cyclopropyl-[1,2,4]thiadiazol-5-yl)-6,6-difluoro-4,5,6,7-tetrahydro-benzo[b]thiophen-2-ylcarbamoyl]-cyclohex-1-enecarboxylic acid;

2-[3-(3-Cyclopropyl-[1,2,4]oxadiazol-5-yl)-6-fluoro-4,5,6,7-tetrahydro-benzo[b]thiophen-2-ylcarbamoyl]-cyclopent-1-enecarboxylic acid;

2-[3-(3-Methyl-[1,2,4]thiadiazol-5-yl)-4,5,6,7-tetrahydro-benzo[b]thiophen-2-ylcarbamoyl]-cyclopent-1-enecarboxylic acid;

2-[3-(3-Methyl-[1,2,4]thiadiazol-5-yl)-4,5,6,7-tetrahydro-benzo[b]thiophen-2-ylcarbamoyl]-cyclohex-1-enecarboxylic acid;

2-[3-(3-Cyclopropyl-[1,2,4]oxadiazol-5-yl)-6-fluoro-4,5,6,7-tetrahydro-benzo[b]thiophen-2-ylcarbamoyl]-cyclohex-1-enecarboxylic acid;

3-[3-(3-Methyl-[1,2,4]thiadiazol-5-yl)-4,5,6,7-tetrahydro-benzo[b]thiophen-2-ylcarbamoyl]-bicyclo[2.2.2]oct-2-ene-2-carboxylic acid;

3-[6,6-Difluoro-3-(3-methyl-[1,2,4]thiadiazol-5-yl)-4,5,6,7-tetrahydro-benzo[b]thiophen-2-ylcarbamoyl]-bicyclo[2.2.2]oct-2-ene-2-carboxylic acid;

2-[3-(3-Cyclopropyl-[1,2,4]thiadiazol-5-yl)-4,5,6,7-tetrahydro-benzo[b]thiophen-2-ylcarbamoyl]-cyclopent-1-enecarboxylic acid;

2-[3-(3-Cyclopropyl-[1,2,4]thiadiazol-5-yl)-4,5,6,7-tetrahydro-benzo[b]thiophen-2-ylcarbamoyl]-cyclohex-1-enecarboxylic acid;

(R)-1-[3-(3-Cyclopropyl-[1,2,4]oxadiazol-5-yl)-6,6-difluoro-4,5,6,7-tetrahydro-benzo[b]thiophen-2-ylcarbamoyl]-pyrrolidine-2-carboxylic acid;

(R)-1-[3-(3-Cyclopropyl-[1,2,4]oxadiazol-5-yl)-5,6-dihydro-4H-cyclopenta[b]thiophen-2-ylcarbamoyl]-pyrrolidine-2-carboxylic acid;

2-[4-(3-Cyclopropyl-[1,2,4]oxadiazol-5-yl)-2-thia-bicyclo[3.2.0]hepta-1(5),3-dien-3-ylcarbamoyl]-cyclopent-1-enecarboxylic acid;

3-[3-(3-Cyclopropyl-[1,2,4]thiadiazol-5-yl)-4,5,6,7-tetrahydro-benzo[b]thiophen-2-ylcarbamoyl]-bicyclo[2.2.2]oct-2-ene-2-carboxylic acid;

3-[3-(3-Cyclopropyl-[1,2,4]thiadiazol-5-yl)-6,6-difluoro-4,5,6,7-tetrahydro-benzo[b]thiophen-2-ylcarbamoyl]-bicyclo[2.2.2]oct-2-ene-2-carboxylic acid;

(R)-1-[3-(3-Cyclopropyl-[1,2,4]oxadiazol-5-yl)-5,6,7,8-tetrahydro-4H-cyclohepta[b]thiophen-2-ylcarbamoyl]-pyrrolidine-2-carboxylic acid;

(2R,4S)-1-[3-(3-Cyclopropyl-[1,2,4]oxadiazol-5-yl)-4,5,6,7-tetrahydro-benzo[b]thiophen-2-ylcarbamoyl]-4-hydroxy-pyrrolidine-2-carboxylic acid;

(2R,4R)-1-[3-(3-Cyclopropyl-[1,2,4]oxadiazol-5-yl)-4,5,6,7-tetrahydro-benzo[b]thiophen-2-ylcarbamoyl]-4-hydroxy-pyrrolidine-2-carboxylic acid;

2-[5-(3-Cyclopropyl-[1,2,4]oxadiazol-5-yl)-3,4-dihydro-2H-thieno[2,3-b]pyran-6-ylcarbamoyl]-cyclohex-1-enecarboxylic acid;

2-[5-(3-Cyclopropyl-[1,2,4]oxadiazol-5-yl)-3,4-dihydro-2H-thieno[2,3-b]pyran-6-ylcarbamoyl]-cyclopent-1-enecarboxylic acid;

2-[3-(3-Cyclopropyl-[1,2,4]oxadiazol-5-yl)-4,5,6,7-tetrahydro-benzo[b]thiophen-2-ylcarbamoyl]-4,4-dimethyl-cyclopent-1-enecarboxylic acid;

2-[3-(3-Cyclopropyl-[1,2,4]oxadiazol-5-yl)-6,7-dihydro-4H-thieno[3,2-c]pyran-2-ylcarbamoyl]-cyclopent-1-enecarboxylic acid;
2-[3-(3-Cyclopropyl-[1,2,4]oxadiazol-5-yl)-6,7-dihydro-4H-thieno[3,2-c]pyran-2-ylcarbamoyl]-cyclohex-1-enecarboxylic acid;
3-[3-(3-Cyclopropyl-[1,2,4]oxadiazol-5-yl)-4,7-dihydro-5H-thieno[2,3-c]pyran-2-ylcarbamoyl]-5-methyl-1H-pyrazole-4-carboxylic acid;
2-[3-(3-Cyclopropyl-[1,2,4]oxadiazol-5-yl)-6-hydroxy-6-methyl-4,5,6,7-tetrahydro-benzo[b]thiophen-2-ylcarbamoyl]-cyclopent-1-enecarboxylic acid;
3-[3-(3-Cyclopropyl-[1,2,4]oxadiazol-5-yl)-6-hydroxy-6-methyl-4,5,6,7-tetrahydro-benzo[b]thiophen-2-ylcarbamoyl]-bicyclo[2.2.2]oct-2-ene-2-carboxylic acid;
2-[3-(3-Cyclopropyl-[1,2,4]oxadiazol-5-yl)-6-hydroxy-6-methyl-4,5,6,7-tetrahydro-benzo[b]thiophen-2-ylcarbamoyl]-cyclohex-1-enecarboxylic acid;
3-[3-(3-Cyclopropyl-[1,2,4]oxadiazol-5-yl)-4,7-dihydro-5H-thieno[2,3-c]pyran-2-ylcarbamoyl]-pyridine-2-carboxylic acid;
2-[3-(3-Cyclopropyl-[1,2,4]oxadiazol-5-yl)-4,7-dihydro-5H-thieno[2,3-c]pyran-2-ylcarbamoyl]-nicotinic acid;
(1S,5R)-5-[3-(3-Cyclopropyl-[1,2,4]oxadiazol-5-yl)-4,7-dihydro-5H-thieno[2,3-c]pyran-2-ylcarbamoyl]-bicyclo[3.1.0]hexane-1-carboxylic acid;
3-[3-(3-Cyclopropyl-[1,2,4]oxadiazol-5-yl)-4,7-dihydro-5H-thieno[2,3-c]pyran-2-ylcarbamoyl]-1,5-dimethyl-1H-pyrazole-4-carboxylic acid;
2-[3-(6-Chloro-pyridin-2-yl)-4,5,6,7-tetrahydro-benzo[b]thiophen-2-ylcarbamoyl]-cyclopent-1-enecarboxylic acid;
2-[3-(5-Chloro-pyridin-2-yl)-4,5,6,7-tetrahydro-benzo[b]thiophen-2-ylcarbamoyl]-cyclopent-1-enecarboxylic acid;
2-[6,6-Difluoro-3-(4-isopropyl-thiazol-2-yl)-4,5,6,7-tetrahydro-benzo[b]thiophen-2-ylcarbamoyl]-cyclopent-1-enecarboxylic acid;
3-[6,6-Difluoro-3-(4-isopropyl-thiazol-2-yl)-4,5,6,7-tetrahydro-benzo[b]thiophen-2-ylcarbamoyl]-bicyclo[2.2.2]oct-2-ene-2-carboxylic acid;
2-[6,6-Difluoro-3-(4-isopropyl-thiazol-2-yl)-4,5,6,7-tetrahydro-benzo[b]thiophen-2-ylcarbamoyl]-cyclohex-1-enecarboxylic acid;
2-[3-(4-Methyl-thiazol-2-yl)-4,5,6,7-tetrahydro-benzo[b]thiophen-2-ylcarbamoyl]-nicotinic acid;
2-[6,6-Difluoro-3-(4-methyl-thiazol-2-yl)-4,5,6,7-tetrahydro-benzo[b]thiophen-2-ylcarbamoyl]-nicotinic acid;
2-[3-(3-Cyclopropyl-[1,2,4]oxadiazol-5-yl)-5,5-dimethyl-4,5,6,7-tetrahydro-benzo[b]thiophen-2-ylcarbamoyl]-cyclopent-1-enecarboxylic acid;
2-[3-(3-Cyclopropyl-[1,2,4]oxadiazol-5-yl)-5,5-dimethyl-4,5,6,7-tetrahydro-benzo[b]thiophen-2-ylcarbamoyl]-cyclohex-1-enecarboxylic acid;
3-[3-(3-Cyclopropyl-[1,2,4]oxadiazol-5-yl)-5,5-dimethyl-4,5,6,7-tetrahydro-benzo[b]thiophen-2-ylcarbamoyl]-bicyclo[2.2.2]oct-2-ene-2-carboxylic acid;
2-[3-(3-Cyclopropyl-[1,2,4]oxadiazol-5-yl)-4,5,6,7-tetrahydro-benzo[b]thiophen-2-ylcarbamoyl]-cyclohex-1-enecarboxylic acid;
2-[3-(3-Cyclopropyl-[1,2,4]oxadiazol-5-yl)-6-methoxy-6-methyl-4,5,6,7-tetrahydro-benzo[b]thiophen-2-ylcarbamoyl]-cyclohex-1-enecarboxylic acid;
2-[6,6-Difluoro-3-(3-trifluoromethyl-[1,2,4]oxadiazol-5-yl)-4,5,6,7-tetrahydro-benzo[b]thiophen-2-ylcarbamoyl]-nicotinic acid;
2-[3-(3-Trifluoromethyl-[1,2,4]oxadiazol-5-yl)-4,5,6,7-tetrahydro-benzo[b]thiophen-2-ylcarbamoyl]-nicotinic acid;
2-[(R)-3-(3-Cyclopropyl-[1,2,4]oxadiazol-5-yl)-6-methoxy-6-methyl-4,5,6,7-tetrahydro-benzo[b]thiophen-2-ylcarbamoyl]-cyclopent-1-enecarboxylic acid;
2-[(S)-3-(3-Cyclopropyl-[1,2,4]oxadiazol-5-yl)-6-methoxy-6-methyl-4,5,6,7-tetrahydro-benzo[b]thiophen-2-ylcarbamoyl]-cyclopent-1-enecarboxylic acid;
5-[3-(3-Cyclopropyl-[1,2,4]oxadiazol-5-yl)-4,5,6,7-tetrahydro-benzo[b]thiophen-2-ylcarbamoyl]-3,6-dihydro-2H-pyran-4-carboxylic acid;
4-[3-(3-Cyclopropyl-[1,2,4]oxadiazol-5-yl)-4,5,6,7-tetrahydro-benzo[b]thiophen-2-ylcarbamoyl]-5,6-dihydro-2H-pyran-3-carboxylic acid;
2-[3-(3-Cyclopropyl-[1,2,4]oxadiazol-5-yl)-6,6-dioxo-4,5,6,7-tetrahydro-6λ6-thieno[2,3-c]thiopyran-2-ylcarbamoyl]-cyclopent-1-enecarboxylic acid;
2-{2-[(2-Carboxy-cyclopent-1-enecarbonyl)-amino]-6,6-difluoro-4,5,6,7-tetrahydro-benzo[b]thiophen-3-yl}-thiazole-4-carboxylic acid ethyl ester;
2-[(S)-3-(3-Cyclopropyl-[1,2,4]oxadiazol-5-yl)-6-fluoro-4,5,6,7-tetrahydro-benzo[b]thiophen-2-ylcarbamoyl]-cyclohex-1-enecarboxylic acid;
2-[(R)-3-(3-Cyclopropyl-[1,2,4]oxadiazol-5-yl)-6-fluoro-4,5,6,7-tetrahydro-benzo[b]thiophen-2-ylcarbamoyl]-cyclohex-1-enecarboxylic acid;
5-[3-(3-Cyclopropyl-[1,2,4]oxadiazol-5-yl)-6,6-difluoro-4,5,6,7-tetrahydro-benzo[b]thiophen-2-ylcarbamoyl]-3,6-dihydro-2H-pyran-4-carboxylic acid;
4-[3-(3-Cyclopropyl-[1,2,4]oxadiazol-5-yl)-6,6-difluoro-4,5,6,7-tetrahydro-benzo[b]thiophen-2-ylcarbamoyl]-5,6-dihydro-2H-pyran-3-carboxylic acid;
4-[6,6-Difluoro-3-(4-methyl-thiazol-2-yl)-4,5,6,7-tetrahydro-benzo[b]thiophen-2-ylcarbamoyl]-5,6-dihydro-2H-pyran-3-carboxylic acid;
5-[6,6-Difluoro-3-(4-methyl-thiazol-2-yl)-4,5,6,7-tetrahydro-benzo[b]thiophen-2-ylcarbamoyl]-3,6-dihydro-2H-pyran-4-carboxylic acid;
(2R)-1-[[3-(3-methyl-1,2,4-oxadiazol-5-yl)-5,6,7,8-tetrahydro-4H-cyclohepta[b]thiophen-2-yl]carbamoyl]pyrrolidine-2-carboxylic acid;
(2R)-1-[[3-[3-(trifluoromethyl)-1,2,4-oxadiazol-5-yl]-5,6,7,8-tetrahydro-4H-cyclohepta[b]thiophen-2-yl]carbamoyl]pyrrolidine-2-carboxylic acid;
(2R)-1-[[3-[3-(trifluoromethyl)-1,2,4-oxadiazol-5-yl]-4,5,6,7-tetrahydrobenzothiophen-2-yl]carbamoyl]pyrrolidine-2-carboxylic acid;
(2S)-1-[[3-(3-cyclopropyl-1,2,4-oxadiazol-5-yl)-5,6,7,8-tetrahydro-4H-cyclohepta[b]thiophen-2-yl]carbamoyl]pyrrolidine-2-carboxylic acid;
and pharmaceutically acceptable salts thereof.
Further particular examples of compounds of formula (I) as described herein are selected from
2-[3-(3-Methyl-[1,2,4]oxadiazol-5-yl)-4,5,6,7-tetrahydro-benzo[b]thiophen-2-ylcarbamoyl]-cyclopent-1-enecarboxylic acid;
2-[3-(3-Methyl-[1,2,4]oxadiazol-5-yl)-4,5,6,7-tetrahydro-benzo[b]thiophen-2-ylcarbamoyl]-cyclohex-1-enecarboxylic acid;
2-[3-(3-Cyclopropyl-[1,2,4]oxadiazol-5-yl)-4,7-dihydro-5H-thieno[2,3-c]pyran-2-ylcarbamoyl]-cyclopent-1-enecarboxylic acid;
3-[3-(3-Trifluoromethyl-[1,2,4]oxadiazol-5-yl)-4,5,6,7-tetrahydro-benzo[b]thiophen-2-ylcarbamoyl]-bicyclo[2.2.2]oct-2-ene-2-carboxylic acid;

3-[3-(3-Cyclopropyl-[1,2,4]oxadiazol-5-yl)-4,7-dihydro-5H-thieno[2,3-c]pyran-2-ylcarbamoyl]-bicyclo[2.2.2]oct-2-ene-2-carboxylic acid;
2-[3-(3-Isopropyl-[1,2,4]oxadiazol-5-yl)-4,5,6,7-tetrahydro-benzo[b]thiophen-2-ylcarbamoyl]-cyclopent-1-enecarboxylic acid;
3-[3-(3-Isopropyl-[1,2,4]oxadiazol-5-yl)-4,5,6,7-tetrahydro-benzo[b]thiophen-2-ylcarbamoyl]-bicyclo[2.2.2]oct-2-ene-2-carboxylic acid;
2-[3-(4-Methyl-oxazol-2-yl)-4,7-dihydro-5H-thieno[2,3-c]pyran-2-ylcarbamoyl]-cyclopent-1-enecarboxylic acid;
2-[3-(4-Trifluoromethyl-thiazol-2-yl)-4,7-dihydro-5H-thieno[2,3-c]pyran-2-ylcarbamoyl]-cyclohex-1-enecarboxylic acid;
(+)-2-[3-(3-Cyclopropyl-[1,2,4]oxadiazol-5-yl)-6-methyl-4,5,6,7-tetrahydro-benzo[b]thiophen-2-ylcarbamoyl]-cyclohex-1-enecarboxylic acid;
2-[3-(3-Cyclopropyl-[1,2,4]oxadiazol-5-yl)-5,6,7,8-tetrahydro-4H-cyclohepta[b]thiophen-2-ylcarbamoyl]-cyclohex-1-enecarboxylic acid;
3-[3-(3-Cyclopropyl-[1,2,4]oxadiazol-5-yl)-5,6,7,8-tetrahydro-4H-cyclohepta[b]thiophen-2-ylcarbamoyl]-bicyclo[2.2.2]oct-2-ene-2-carboxylic acid;
3-[3-(3-Trifluoromethyl-[1,2,4]oxadiazol-5-yl)-5,6,7,8-tetrahydro-4H-cyclohepta[b]thiophen-2-ylcarbamoyl]-bicyclo[2.2.2]oct-2-ene-2-carboxylic acid;
3-[3-(3-Cyclopropyl-[1,2,4]oxadiazol-5-yl)-5,6-dihydro-4H-cyclopenta[b]thiophen-2-ylcarbamoyl]-bicyclo[2.2.2]oct-2-ene-2-carboxylic acid;
2-[3-(3-Cyclopropyl-[1,2,4]oxadiazol-5-yl)-6,6-difluoro-4,5,6,7-tetrahydro-benzo[b]thiophen-2-ylcarbamoyl]-cyclopent-1-enecarboxylic acid;
2-[6,6-Difluoro-3-(3-trifluoromethyl-[1,2,4]oxadiazol-5-yl)-4,5,6,7-tetrahydro-benzo[b]thiophen-2-ylcarbamoyl]-cyclopent-1-enecarboxylic acid;
3-[6,6-Difluoro-3-(3-trifluoromethyl-[1,2,4]oxadiazol-5-yl)-4,5,6,7-tetrahydro-benzo[b]thiophen-2-ylcarbamoyl]-bicyclo[2.2.2]oct-2-ene-2-carboxylic acid;
2-[6,6-Difluoro-3-(4-methyl-thiazol-2-yl)-4,5,6,7-tetrahydro-benzo[b]thiophen-2-ylcarbamoyl]-cyclohex-1-enecarboxylic acid;
and pharmaceutically acceptable salts thereof.

Also further particular examples of compounds of formula (I) as described herein are selected from
2-[3-(3-Cyclopropyl-[1,2,4]thiadiazol-5-yl)-6,6-difluoro-4,5,6,7-tetrahydro-benzo[b]thiophen-2-ylcarbamoyl]-cyclopent-1-enecarboxylic acid;
2-[3-(3-Cyclopropyl-[1,2,4]thiadiazol-5-yl)-6,6-difluoro-4,5,6,7-tetrahydro-benzo[b]thiophen-2-ylcarbamoyl]-cyclohex-1-enecarboxylic acid;
2-[3-(3-Cyclopropyl-[1,2,4]oxadiazol-5-yl)-6-fluoro-4,5,6,7-tetrahydro-benzo[b]thiophen-2-ylcarbamoyl]-cyclopent-1-enecarboxylic acid;
(R)-1-[3-(3-Cyclopropyl-[1,2,4]oxadiazol-5-yl)-5,6,7,8-tetrahydro-4H-cyclohepta[b]thiophen-2-ylcarbamoyl]-pyrrolidine-2-carboxylic acid;
2-[3-(3-Cyclopropyl-[1,2,4]oxadiazol-5-yl)-6,7-dihydro-4H-thieno[3,2-c]pyran-2-ylcarbamoyl]-cyclohex-1-enecarboxylic acid;
2-[3-(3-Cyclopropyl-[1,2,4]oxadiazol-5-yl)-4,7-dihydro-5H-thieno[2,3-c]pyran-2-ylcarbamoyl]-nicotinic acid;
2-[3-(3-Cyclopropyl-[1,2,4]oxadiazol-5-yl)-4,5,6,7-tetrahydro-benzo[b]thiophen-2-ylcarbamoyl]-cyclohex-1-enecarboxylic acid;
5-[3-(3-Cyclopropyl-[1,2,4]oxadiazol-5-yl)-4,5,6,7-tetrahydro-benzo[b]thiophen-2-ylcarbamoyl]-3,6-dihydro-2H-pyran-4-carboxylic acid;
4-[3-(3-Cyclopropyl-[1,2,4]oxadiazol-5-yl)-4,5,6,7-tetrahydro-benzo[b]thiophen-2-ylcarbamoyl]-5,6-dihydro-2H-pyran-3-carboxylic acid;
4-[3-(3-Cyclopropyl-[1,2,4]oxadiazol-5-yl)-6,6-difluoro-4,5,6,7-tetrahydro-benzo[b]thiophen-2-ylcarbamoyl]-5,6-dihydro-2H-pyran-3-carboxylic acid;
5-[6,6-Difluoro-3-(4-methyl-thiazol-2-yl)-4,5,6,7-tetrahydro-benzo[b]thiophen-2-ylcarbamoyl]-3,6-dihydro-2H-pyran-4-carboxylic acid;
(2R)-1-[[3-[3-(trifluoromethyl)-1,2,4-oxadiazol-5-yl]-5,6,7,8-tetrahydro-4H-cyclohepta[b]thiophen-2-yl]carbamoyl]pyrrolidine-2-carboxylic acid;
(2R)-1-[[3-[3-(trifluoromethyl)-1,2,4-oxadiazol-5-yl]-4,5,6,7-tetrahydrobenzothiophen-2-yl]carbamoyl]pyrrolidine-2-carboxylic acid;
and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the person skilled in the art such as e.g. chiral chromatography or crystallization. In case one of the starting materials or compounds of formula (I) contain one or more functional groups which are not stable or are reactive under the reaction conditions of one or more reaction steps, appropriate protecting groups can be introduced before the critical step applying methods well known in the art. Such protecting groups can be removed at a later stage of the synthesis using standard methods described in the literature. The substituents and indices used in the following description of the processes have the significance given herein.

The following abbreviations are used in the present text: AcCl=Acetyl chloride, tert-BuOH=tert-butyl alcohol, CDI=N,N'-carbonyldiimidazole, CHCl$_3$=chloroform, CH$_2$Cl$_2$=dichloromethane, CH$_3$CN=acetonitrile, CsCO$_3$=cesium carbonate, DBU=1,8-diazabicyclo[5.4.0]undec-7-ene, DCC=N,N'-dicyclohexylcarbodiimide, DIPEA=diisopropylethylamine (Huenig's base), DMAP=4-dimethylaminopyridine, DMA=N,N-dimethylacetamide, DME=1,2-dimethoxyethane, DMF=N,N-dimethylformamide, DMSO=dimethylsulfoxide, EDCI=1-(3-dimethylaminopropyl)-3-ethylcarbodiimide hydrochloride, ESI=electrospray inonisation, EtOAc=ethyl acetate, EtOH=ethanol, Et$_2$O=diethyl ether, h=hour(s), HATU=O-(7-Azabenzotriazol-1-yl)-N,N,N',N'-tetramethyluronium hexafluorophosphate, HCl=hydrochloric acid, H$_2$O=water, HOBt=1-hydroxy-1,2,3-benzotriazole, HPLC=high-performance liquid chromatography, K$_2$CO$_3$=potassium carbonate, KF=potassium fluoride, KHCO$_3$=potassium bicarbonate, LiOH=lithium hydroxide, MeOH=methanol, MgSO$_4$=magnesium sulfate, min.=minute(s), MPLC=medium pressure liquid chromatography, MS=mass spectrum, Mukaiyama reagent=2-chloro- or 2-bromo-1-methylpyridinium iodide, Na$_2$SO$_4$=sodium sulfate, NaClO$_2$=sodium chlorite; NaH=sodium hydride, NaHCO$_3$=sodium bicarbonate, NaH$_2$PO$_4$=sodium dihydrogen phosphate, NaOH=sodium hydroxide, NaOMe=sodium methoxide, NEt$_3$=triethylamine, NH$_4$Cl=ammonium chloride, NH$_4$OAc=ammonium acetate, Pd(Ph$_3$P)$_4$=tetrakis(triphenylphosphine)palladium(0), RT=room temperature, TBAF=tetrabutylammonium fluoride, TBTU=O-benzotriazol-1-yl-N,N,N',N'-tetramethyluronium tetrafluoroborate, THF=tetrahydrofuran, TBME=tert-butyl methyl ether, TFA=trifluoroacetic acid, TLC=thin layer chromatography.

Compounds of the general formula IA, wherein $R^4$ is H, $R^7$ is alkyl or cycloalkyl, A is $CR^9R^{10}$, E is $CR^{12}R^{13}$ and n is zero, IB, wherein $R^4$ is alkyl, $R^7$ is alkyl or cycloalkyl, A is $CR^9R^{10}$, E is $CR^{12}R^{13}$ and n is zero, IC, wherein $R^4$ and $R^7$ are H, A is $CR^9R^{10}$, E is $CR^{12}R^{13}$ and n is zero and ID, wherein $R^4$ is alkyl, $R^7$ is H, A is $CR^9R^{10}$, E is $CR^{12}R^{13}$ and n is zero can be prepared for example as outlined in Scheme 1.

Acylation of 2-aminothiophenes II (either commercially available or prepared according to literature procedures or as described in Schemes 4-6) with dicarboxylic acid mono esters 1, either commercially available or prepared according to literature procedures, furnishes compounds IA and IB, respectively (step a). Amide couplings of this type are widely described in the literature and can be accomplished by the usage of coupling reagents such as, e.g., CDI, DCC, HATU, HOBT, TBTU or Mukaiyama reagent in a suitable solvent, e.g., DMF, DMA, $CH_2Cl_2$ or dioxane, optionally in the presence of a base (e.g., $NEt_3$, DIPEA (Huenig's base) or DMAP). Alternatively, the carboxylic acids 1 can be converted into their acid chlorides by treatment with, e.g. thionyl chloride, neat or optionally in a solvent such as $CH_2Cl_2$. Reaction of the acid chloride with 2-aminothiophenes II in an appropriate solvent such as $CH_2Cl_2$ or DMF and a base, e.g. $NEt_3$, Huenig's base, pyridine, DMAP or lithium bis(trimethylsilyl)amide at temperatures ranging from 0° C. to the reflux temperature of the solvent or solvent mixture yields compounds IA and IB, respectively (step a).

Compounds IB can alternatively be prepared through alkylation of compounds IA with compounds of the type $R^4X$, in which X is a suitable leaving group such as chlorine, bromine, iodine, $-OSO_2$alkyl (e.g. mesylate (methanesulfonate), $-OSO_2$fluoroalkyl (e.g. triflate (trifluoromethanesulfonate) or $-OSO_2$aryl (e.g. tosylate (p-toluenesulfonate) using a suitable base in an appropriate solvent (e.g. sodium hydride in DMF) at temperatures between 0° C. and the boiling temperature of the solvent (step b).

Acylation of 2-aminothiophenes II with carboxylic acid anhydrides 2 (either commercially available or accessible by methods known in the art) in appropriate solvents (e.g. $Et_2O$, THF, dioxane, DMF or $CH_3CN$) furnishes compounds IC and ID. The reaction can be carried out in the presence of a suitable base such as $NEt_3$, Huenig's base, DMAP, DBU or lithium bis(trimethylsilyl)amide (step c).

Compounds IC may be also prepared from compounds IA (step d) for those cases, in which the substituent $R^7$ in compounds of formula IA is a cleavable alkyl group. Cleavage of the ester functionality in IA under basic (e.g. methyl or ethyl esters with lithium or sodium hydroxide in polar solvents such as methanol, $H_2O$ or THF or mixtures of said solvents) or under acidic conditions (e.g. a tert-butyl ester using concentrated hydrochloric acid in tetrahydrofuran or formic acid in an appropriate solvent such as alcohols like isopropanol) furnishes compounds IC (step d). Further esters include, but are not limited to, e.g. allyl or benzyl esters that can be cleaved by methods known to those skilled in the art.

Compounds IB can also be prepared from compounds ID through alkylation of ID with compounds $R^7X$ in which X is a suitable leaving group such as chlorine, bromine, iodine, $-OSO_2$alkyl (e.g. mesylate (methanesulfonate), $-OSO_2$fluoroalkyl (e.g. triflate (trifluoromethanesulfonate) or $-OSO_2$aryl (e.g. tosylate (p-toluenesulfonate) using a suitable base in an appropriate solvent (e.g. sodium hydride in DMF) at temperatures between 0° C. and the boiling temperature of the solvent (step e).

Compounds IC may also be prepared from intermediates 3 by cleavage of the imide applying procedures described in literature (e.g. L. Aurelio et al., J. Med. Chem. 2010, 53(18), 6550-6559), for example by using a suitable base and solvent such as NaOH in THF or $H_2O$ and EtOH (step g).

Compounds ID may be also prepared from compounds IB for those cases, in which the substituent $R^7$ in compounds of formula IB is a cleavable alkyl group, using the methods described before (step h).

Intermediates 3 in turn can be obtained by acylation of 2-aminothiophenes II in which $R^4$ is hydrogen through acylation with carboxylic acid anhydrides 2 under the conditions described above (step f).

Scheme 1

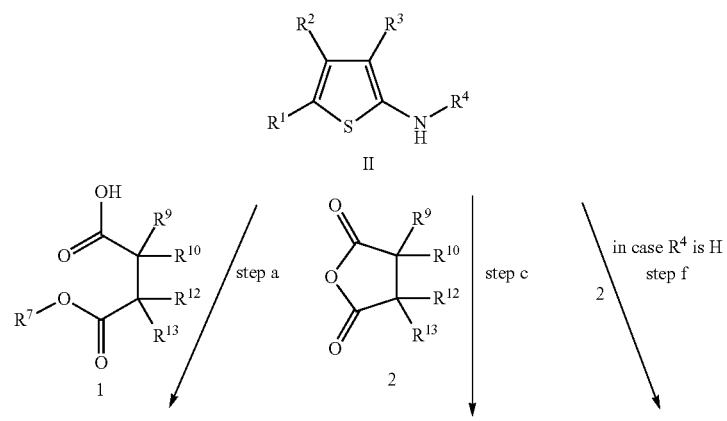

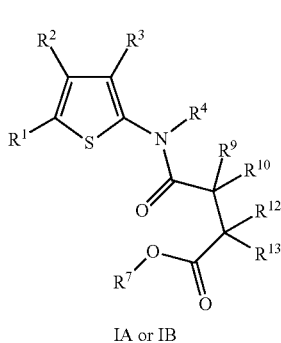 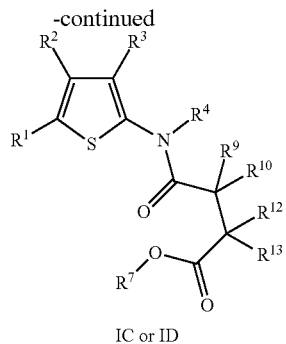 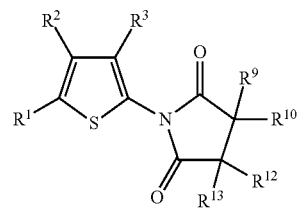

IA or IB    IC or ID    3

$$IA \xrightarrow{\text{step b}} IB \xleftarrow{\text{step e}} ID$$
$$\text{step d} \downarrow \quad \uparrow \text{step h}$$
$$IC \xleftarrow{\text{step g}} 3$$

An alternative synthesis of compounds IA-ID is shown in Scheme 2. Persons skilled in the art will acknowledge that the transformations are only applicable for those compounds that carry substituents, in particular $R^7$, that are stable and not reactive under the applied reaction conditions.

Gewald reaction using α-cyanoesters 4 in which $R^a$ is a cleavable alkyl group such as, e.g. a methyl, ethyl or tert-butyl group, cyclic ketones 5 and elemental sulfur in the presence of a base such as morpholine in a suitable solvent like EtOH furnishes thiophene intermediates 6 (step a).

Protection of the amine functionality with a suitable protective group such as an acetyl group and subsequent cleavage of the ester applying methods known in the art and as described in literature (e.g. Y. Huang et al. *Chem Biol. Drug Des.* 2010, 76, 116-129) gives acid intermediates 7 (steps b, c).

Intermediates 7 can be decarboxylated according to literature procedures (e.g. K. Gewald et al., *Z. Chem.* 1967, 7(5), 186-187; H. Luetjens et al., *J. Med. Chem.* 2003, 46(10), 1870-1877; S. Takada, *J. Med. Chem.* 1988, 31(9), 1738-1745; WO2005044008), for example using copper and quinoline at elevated temperatures to give intermediates 8 (step d).

Removal of the protective group in 8 applying methods known to those skilled in the art and as described in literature yields 2-aminothiophenes 9 (step e).

Acylation of intermediates 9 using the conditions outlined under Scheme 1, with dicarboxylic acid mono esters 1, either commercially available or prepared according to literature procedures, gives intermediates 10 (step f).

Iodination of intermediates 10 using literature procedures (e.g. WO2005/044008) for example using iodine in THF or iodine monochloride in acetic acid yields intermediates 11 (step g).

Cross-coupling reactions of 11 with, e.g. organoboron, -tin or -zinc reagents $R^3M$ furnishes compounds IA (step h). Reactions of this type are widely described in literature (e.g. N. Miyaura (ed.), "Cross-coupling reactions: A practical guide", *Curr. Topics Chem.* 219). For example, reaction of 11 with (substituted) aryl- or heteroaryl-boronic acids $R^3$—$B(OH)_2$ or boronic esters $R^3$—$B(OR')_2$ (e.g. pinacol or trimethylene glycol ester, either commercially available or prepared using literature procedures as described for example in "Boronic Acids—Preparation and Applications in Organic Synthesis and Medicine" by Dennis G. Hall (ed.) 1$^{st}$ Ed., 2005, John Wiley & Sons, New York) using a suitable catalyst (e.g. dichloro[1,1-bis(diphenylphosphino)-ferrocene] palladium(II) $CH_2Cl_2$ adduct, tetrakis(triphenylphosphine)palladium(0) or palladium (II) acetate with triphenylphosphine) in an appropriate solvent (e.g. dioxane, DME, $H_2O$, toluene, DMF or mixtures thereof) and a suitable base (e.g. $Na_2CO_3$, $NaHCO_3$, KF, potassium carbonate or $NEt_3$) at temperatures between room temperature and the boiling point of the solvent or solvent mixture yields compounds IA (step h). Suzuki reactions of this type are broadly described in literature (e.g. A. Suzuki, N. Miyaura, *Chem. Rev.* 1979, 95, 2457-2483; A. Suzuki, *J. Organomet. Chem.* 1999, 576, 147-168; V. Polshettiwar et al., *Chem. Sus. Chem.* 2010, 3, 502-522) and are well known to those skilled in the art. Alternatively, aryl- or heteroaryl-trifluoroborates $R^3BF_3K$ can be used in the cross-coupling reaction applying a palladium catalyst such as tetrakis-(triphenylphosphine) palladium(0), palladium(II) acetate or dichloro[1,1'-bis(diphenyl-phosphino)ferrocene]palladium(II) $CH_2Cl_2$ adduct in the presence of a suitable base such as cesium carbonate or potassium phosphate in solvents such as toluene, THF, dioxane, $H_2O$ or mixtures thereof, at temperatures between room temperature and the boiling point of the solvent or solvent mixture.

Compounds IA can be also synthesized by reacting 11 with (substituted) aryl- or heteroaryl tin reagents $R^3$—$SnR_3$ (R=e.g. Me or n-Bu; either commercially available or prepared according to literature procedures) in the presence of a suitable catalyst (e.g. tetrakis(triphenylphosphine)-palladium(0), benzylbis(triphenyl-phosphine)palladium(II) chloride, bis(triphenylphosphine)-palladium(II) dichloride or dichloro[1,1'-bis(diphenylphosphino)ferrocene]palladium (II) $CH_2Cl_2$ adduct) in an appropriate solvent (e.g. THF, dioxane, DMF or HMPA or mixtures thereof) at temperatures between room temperature and the boiling point of the solvent or solvent mixture, optionally in the presence of lithium chloride. Stille couplings of this type are broadly described in literature (e.g. J. K. Stille, *Angew. Chem. Int. Ed. Engl.* 1986, 25, 508-524) and well known to those skilled in the art (step h).

Alternatively, compounds IA can be synthesized from reaction of 11 with (substituted) aryl- or heteroaryl zinc halides $R^3$—ZnX (X=Cl, Br or I) (either commercially available or synthesized by methods described in literature) using a nickel (e.g. tetrakis(triphenylphosphine)nickel(0)) or palladium catalyst (e.g. tetrakis(triphenyl-phosphine)palladium(0)) in an appropriate solvent such as THF or DMA in a temperature range between room temperature and boiling point of the solvent. Negishi couplings of this type are broadly described in literature (e.g. "Name Reactions for Homologations—Part I: Negishi cross-coupling reaction", Li, J. J., Corey, E. J., Eds.; Wiley & Sons, Hoboken, N.J., 2009, 70-99; G. Organ, *Eur. J. Org. Chem.* 2010, 4343-4354) and well known to those skilled in the art (step h).

Compounds IA may then be further converted into compounds IB-ID as described under Scheme 1 (steps i, j, k).

Compounds IB may be also prepared by cross-coupling reactions of intermediates 12 with organoboron, -tin or -zinc reagents $R^3M$ using the coupling conditions described above (step m).

Intermediates 12 are available for example through alkylation of intermediates 11 with an alkylating agent $R^4$—X in which X signifies a suitable leaving group such as chlorine, bromine, iodine, —OSO2alkyl (e.g. mesylate (methanesulfonate), —OSO2fluoroalkyl (e.g. triflate (trifluoromethanesulfonate) or —OSO2aryl (e.g. tosylate (p-toluenesulfonate) using a suitable base, e.g. sodium hydride in an appropriate solvent such as THF or DMF (step l).

Scheme 2

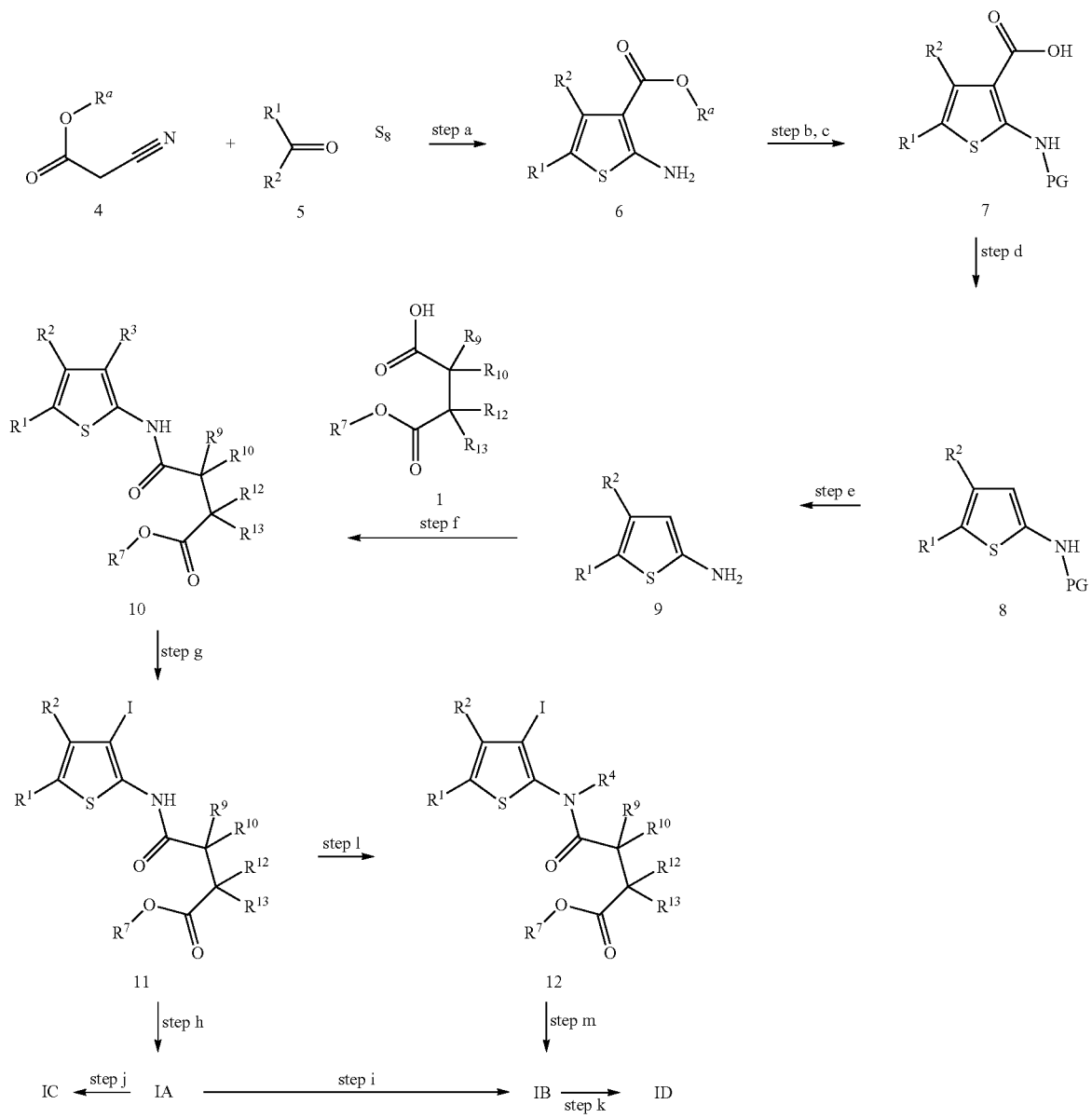

$R^a$ is alkyl, e.g. Me, Et and tBu
PG = Protective group

An alternative synthesis of compounds IC from intermediates 9 is shown in Scheme 3.

Acylation of 2-aminothiophene intermediates 9, prepared as described under Scheme 2, with carboxylic acid anhydrides 2 (either commercially available or accessible by methods described in references or by methods known in the art) in appropriate solvents (e.g. Et$_2$O, THF, dioxane, DMF or CH$_3$CN) furnishes intermediates 13. The reaction can be carried out in the presence of a suitable base such as NEt$_3$, Huenig's base, DMAP, DBU or lithium bis(trimethylsilyl) amide (step a).

Iodination of intermediates 13 according to literature procedures (e.g. WO2005/044008) for example using iodine in THF or iodine monochloride in acetic acid, yields intermediates 14 (step b).

Cross-coupling reactions of intermediates 14 with organoboron, -tin or zinc reagents R$^3$M using the coupling conditions described under Scheme 2 gives intermediates 3 (step c) which can be further converted into compounds IC using the reaction conditions described under Scheme 1.

Chem. 1988, 119, 985-992, H. Zhang et al., Synthesis 2004, 18, 3055-3059; M. Sridhar et al., Tetrahedron Lett., 2007, 48(18), 3171-3172; Z. Puterová et al., Arkivoc 2010(i), 209-246; T. Wang et al., Synlett 2010, 1351-1354; DE2627935; WO2005/044008; WO2009/033581).

Gewald reaction as described above using commercially available and appropriately substituted acetonitriles 16, cyclic ketones 5 and elemental sulfur in the presence of a base such as morpholine yields 2-aminothiophenes IIa (step a).

In cases where the acetonitrile derivatives 16 are commercially not available they may be prepared from compounds 15 in which X is a suitable leaving group such as chlorine, bromine, —OSO$_2$alkyl (e.g. mesylate (methanesulfonate), —OSO$_2$fluoroalkyl (e.g. triflate (trifluoromethanesulfonate) or —OSO$_2$aryl (e.g. tosylate (p-toluenesulfonate) by nucleophilic substitution with sodium or potassium cyanide in an appropriate solvent such as DMSO or DMF at temperatures between 0° C. and the boiling temperature of the solvent (step f). Reactions of this type are Scheme 3

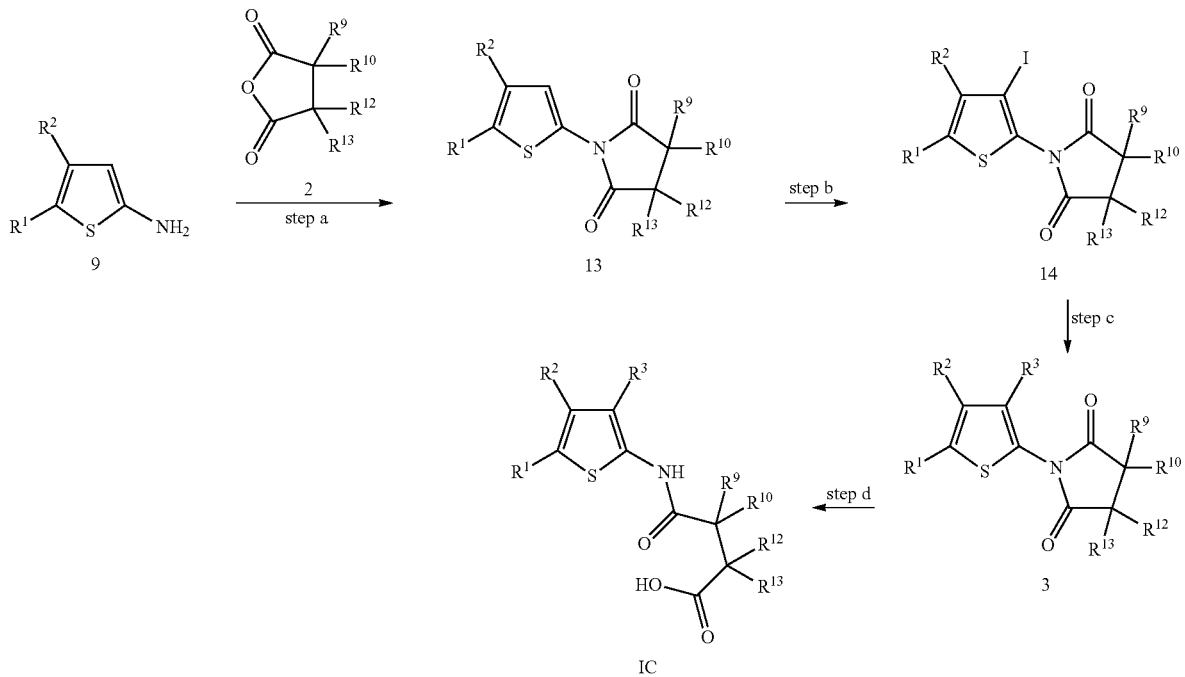

An example for the construction of 2-aminothiophenes IIa, wherein R$^4$ is H, IIb, wherein R$^4$ is methyl and IIc, wherein R$^4$ is alkyl or cycloalkyl, is shown in Scheme 4.

The synthesis of substituted 2-aminothiophenes IIa is broadly described in literature. In particular, the Gewald reaction, a one-pot multi-component condensation between an α-methylene carbonyl compound (cyclic or acyclic ketone or aldehyde), elemental sulfur, a base (e.g. NEt$_3$, morpholine) and an α-activated nitrile (e.g. α-cyanoesters leading to compounds with R$^3$ being an ester group, malonitrile giving compounds in which R$^3$ is cyano, or aryl- or heteroarylacetonitriles leading to compounds with R$^3$ being aryl or heteroaryl) is often applied for the synthesis of poly-substituted 2-amino-thiophenes (e.g. K. Gewald et al., Angew. Chem. 1961, 73(3), 114-114; K. Gewald et al., Chem. Ber. 1965, 98, 3571-3577; K. Gewald et al., Monatsh.

known to those skilled in the art and have been described in literature (e.g. M. Katkevics; Synlett 2011, 17, 2525-2528; R. Gomez et al., Bioorg. Med. Chem. Lett. 2011, 21(24), 7344-7350; F. Fache et al., Eur. J. Org. Chem. 2011, 30, 6039-6055; US2012/0015999). In case R$^3$ is an 1,2,4-oxadiazole ring bearing, e.g. an alkyl, cycloalkyl, chloroalkyl or optionally substituted aryl substituent in the 3-position (R$^b$), the acetonitrile derivatives 16 may be prepared from amidoximes 17 (either commercially available or prepared for example by reaction of alkyl, cycloalkyl, chloroalkyl or aryl nitriles with hydroxylamine in analogy to literature procedures, e.g. WO2005082859; WO20050076347; WO2008093960) and commercially available 1-cyanoacetyl-3,5-dimethylpyrazole 18 according to literature procedures (e.g. I. O. Zhuravel et al., Synthetic Commun. 2008, 38(21), 3778-3784; A. V. Borisov et al., J. Comb. Chem. 2009, (6), 1023-1029) (step g).

Alkylation of 2-aminothiophenes IIa with methyliodide or dimethylsulfate using a suitable base and solvent such as potassium carbonate (optionally in the presence of potassium iodide) in CH₃CN or CsCO₃ in DMF furnishes compounds IIb in which $R^4$ is a methyl group (step b). Microwave irradiation may be applied to accelerate the reaction. Alternatively, compounds IIa can be converted into compounds IIb by reaction of IIa with triethyl orthoformate and subsequent reduction of the resulting ethoxymethyl-enamino-thiophene intermediate with a suitable reducing (p-toluenesulfonate) using a suitable base, e.g. sodium hydride in an appropriate solvent such as THF or DMF furnishes intermediates 20 (step d).

Removal of the protective group in intermediates 20 applying methods known to those skilled in the art and as described in literature gives 2-aminothiophenes IIb and IIc, respectively. Reactions of this type have also been published in literature (e.g. WO2005044008; P. J. Scammels et al., *Org. Biomol. Chem.* 2011, 9(13), 4886-4902) (step e).

Scheme 4

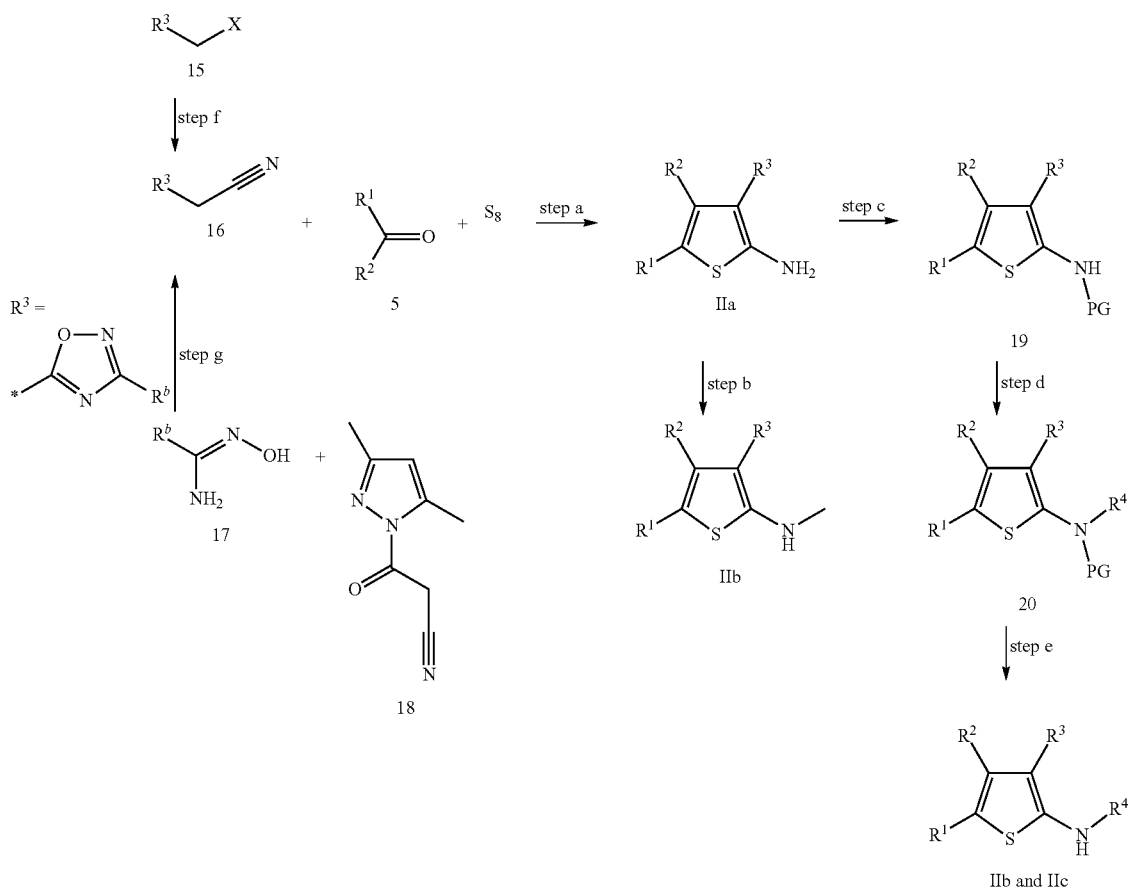

$R^b$ = e.g. alkyl, cycloalkyl chloroalkyl, (substituted) aryl
PG = Protective group agent such as NaBH₄ in an appropriate solvent such as EtOH. Reactions of both types are described in literature (e.g. WO2008/154221; WO2011/100838; I. C. Gonzalez et al., *Bioorg. Med. Chem. Lett.* 2004, 14(15), 4037-4043) and are known to those skilled in the art (step b).

2-Aminothiophenes IIb and IIc can be prepared from IIa, for example by first protecting the amine function in IIa with a suitable protective group such as an acetyl or a tert-butoxycarbonyl (Boc) group by methods known in the art and as described in literature to give intermediates 19 (step c).

Alkylation of intermediates 19 with an alkylating agent $R^4$—X in which X signifies a suitable leaving group such as chlorine, bromine, iodine, —OSO₂alkyl (e.g. mesylate (methanesulfonate), —OSO₂fluoroalkyl (e.g. triflate (trifluoromethanesulfonate) or —OSO₂aryl (e.g. tosylate 2-Aminothiophenes IIa-IIc may alternatively also be prepared from intermediates 8 according to Scheme 5.

Iodination of intermediates 8 according to literature procedures (e.g. WO2005044008), for example using iodine in THF or iodine monochloride in acetic acid, yields intermediates 21 (step a).

Cross-coupling reactions of intermediates 21 with organoboron, -tin or zinc reagents $R^3M$ using the coupling conditions described under Scheme 2 furnishes intermediates 19 (step b).

Removal of the protective group in 19 applying methods known to those skilled in the art yields 2-aminothiophenes IIa (step c) which can be further converted into compounds IIb according to the procedures described under Scheme 4 (step d).

Intermediates 19 can be transferred into intermediates 20 by reaction with an alkylating agent R⁴—X in which X signifies a suitable leaving group such as chlorine, bromine, iodine, —OSO₂alkyl (e.g. mesylate (methanesulfonate), —OSO₂fluoroalkyl (e.g. triflate (trifluoromethanesulfonate) or —OSO₂aryl (e.g. tosylate (p-toluenesulfonate) using a suitable base, e.g. sodium hydride in an appropriate solvent such as THF or DMF (step e).

Removal of the protective group in intermediates 20 applying methods known to those skilled in the art and as described in literature gives 2-aminothiophenes IIb and IIc, respectively.

Cleavage of the protective group in intermediates 24 using literature methods known by those skilled in the art yields intermediates 25 (step c).

Alkylation of the intermediates 24 by reaction with an alkylating agent R⁴—X in which X signifies a suitable leaving group such as chlorine, bromine, iodine, —OSO₂alkyl (e.g. mesylate (methanesulfonate), —OSO₂fluoroalkyl (e.g. triflate (trifluoromethanesulfonate) or —OSO₂aryl (e.g. tosylate (p-toluenesulfonate) using a suitable base, e.g. sodium hydride in an appropriate solvent such as THF or DMF yields intermediates 26 (step d).

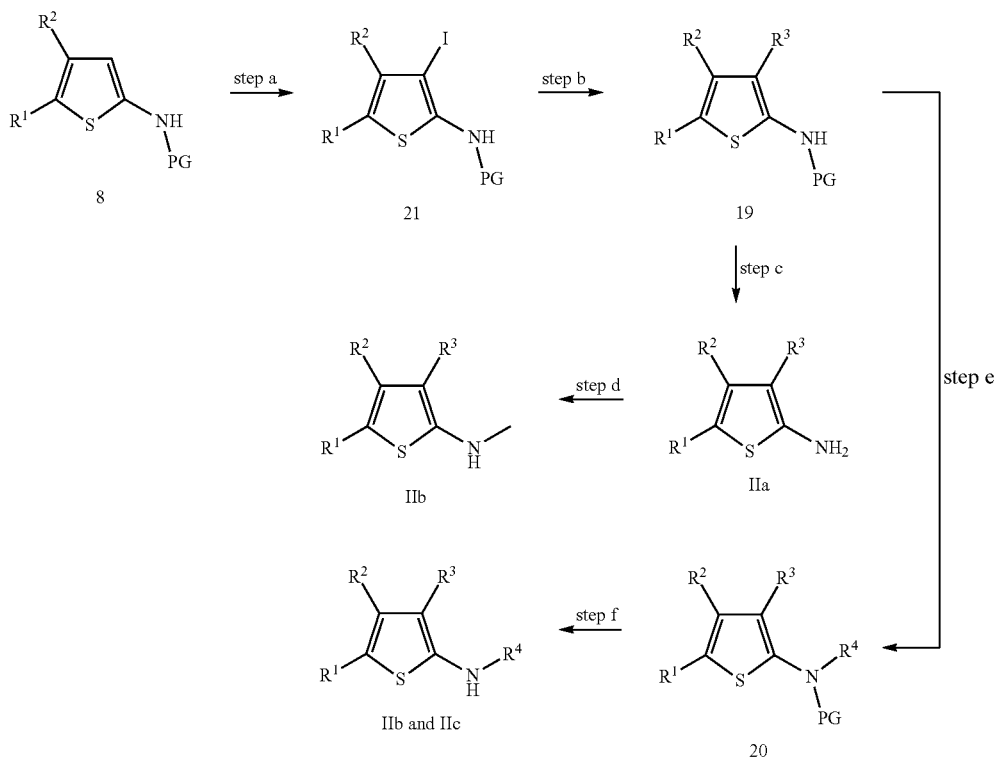

Scheme 5

2-Aminothiophenes wherein $R^3$ is heterocycloalkyl or heteroaryl which can be built up from aryl carboxylic acid precursors can also be prepared from thiophene carboxylic acid intermediates such as 7 which in turn can be synthesized for example by the methods described under Scheme 2. The synthesis of heterocyclic ring systems from carboxylic acids is widely described in the literature and well known by those skilled in the art. One example in which $R^3$ is a 3-substituted 1,2,4-oxadiazole ring is shown in Scheme 6.

Reaction of 7 with substituted N-hydroxycarboximidamides 22 (either commercially available or prepared for example by reaction of nitriles of the type $R^{23}CN$ with hydroxylamine in analogy to literature procedures, e.g. WO2005/082859; WO2005/076347; WO2008/093960) applying standard coupling conditions using for example EDCI together with HOBT or HATU in a suitable solvent such as DMF (step a) and cyclization of the resulting intermediates 23 using for example TBAF in THF yields intermediates 24 (step b).

Intermediates 27 may be prepared from intermediates 26 through removal of the protective group using literature procedures (step f). Alternatively, alkylation of intermediates 25 using the methods for example described under Scheme 4 gives intermediates 27 (step e).

Scheme 6

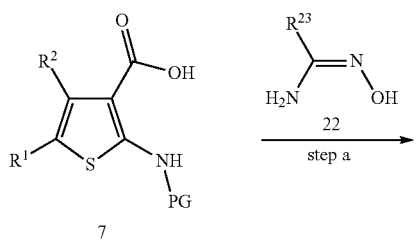

-continued

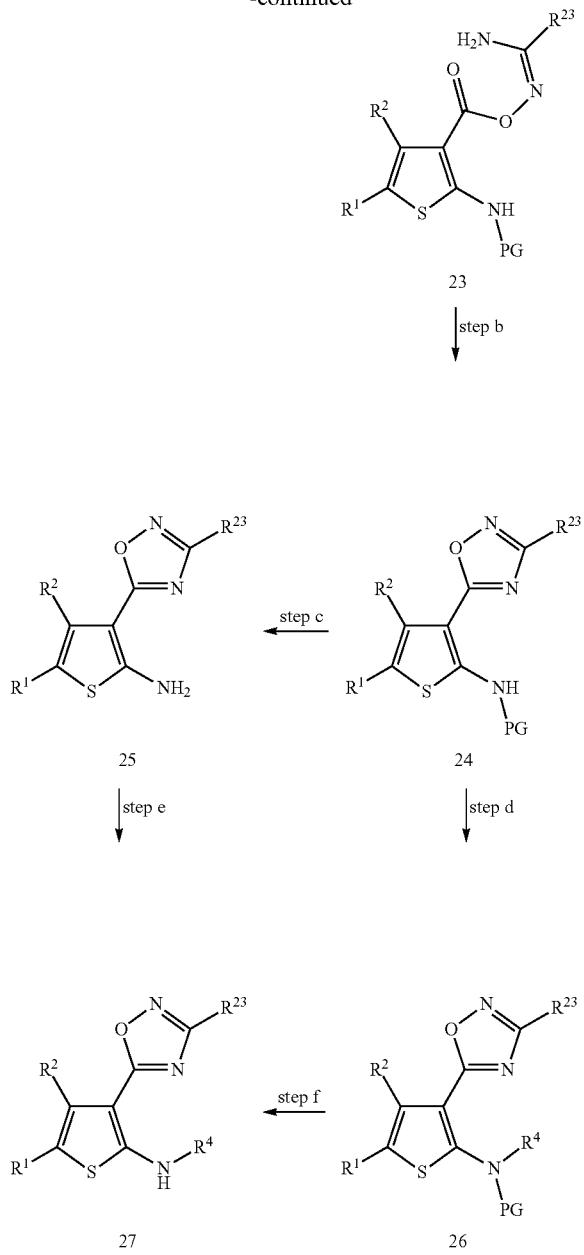

$R^a$ = cleavable alkyl group (e.g. Me, Et, tBu)
$R^b$ = e.g. alkyl, cycloalkyl chloroalkyl, (substituted) aryl
PG - Protective group Compounds of the general formula I, wherein A is $NR^8$, E is $CR^{12}R^{13}$ and n is zero or 1 can be prepared for example according to Scheme 7. Particularly, compounds of formula IE, wherein $R^4$ is H and $R^7$ is alkyl or cycloalkyl, IF, wherein $R^4$ and $R^7$ are H, IG, wherein $R^4$ is H, $R^7$ is alkyl or cycloalkyl and $R^8$ is H, IH, wherein $R^4$ is alkyl, $R^7$ is alkyl or cycloalkyl and $R^8$ is H, LI, wherein $R^4$, $R^7$ and $R^8$ are H, IK, wherein $R^4$ is alkyl and $R^7$ and $R^8$ are H, IL, wherein $R^4$ is H or alkyl, $R^7$ is alkyl or cycloalkyl and $R^8$ is alkyl, and IM, wherein $R^4$ and $R^7$ are H and $R^8$ is alkyl.

The amino group in 2-aminothiophenes IIa, wherein $R^4$ is H, can be converted into an isocyanate functionality for example by reacting IIa with phosgene or a substitute thereof (e.g. trichloromethyl chloroformate ("diphosgene") or bis(trichloromethyl) carbonate ("triphosgene")) in an appropriate solvent such as THF or $CH_2Cl_2$, optionally in the presence of a base such as pyridine or $NEt_3$ to yield intermediates 28 (step a). Transformation of this type are well known in the art and broadly described in literature (e.g. G. N. Anilkumar et al., *Bioorg. Med. Chem. Lett.* 2011, 21(18), 5336-5341; DE3529247; WO2011/140527; WO2011/123937).

Reaction of the isocyanates 28 with appropriately substituted α- or β-amino acids ($R^7$ is H) or esters ($R^7$ is alkyl or cycloalkyl) 29 (n is zero and 1, commercially available or synthesized by methods known in the art) in an appropriate solvent such as toluene, DMF or $CH_2Cl_2$ optionally in the presence of a suitable base such as $NEt_3$ or Huenig's base gives compounds IE and IF, respectively (step b). Additions of primary or secondary amines to isocyanates are described in literature (e.g. W. J. McClellan et al., *Bioorg. Med. Chem. Lett.* 2011, 21(18), 5620-5624; J. Regan et al., *J. Med. Chem.* 2002, 45(14), 2994-3008; U.S. Pat. No. 4,314,842; WO2006/067385) and are well known to those skilled in the art.

Compounds IF can alternatively be synthesized from compounds IE for those cases, in which the substituent $R^7$ in compounds of formula IE is a cleavable alkyl group, using the methods described under Scheme 1 (step c).

2-Aminothiophenes II can be reacted with isocyanates 30 (either commercially available or synthesized by methods known in the art) in an appropriate solvent such as toluene, DMF or $CH_2Cl_2$ optionally in the presence of a suitable base such as $NEt_3$ or Huenig's base to give compounds IG and IH, respectively (step d).

In case $R^7$ in compounds IG and IH is a cleavable ester group, it can be cleaved applying procedures known in the art and as published to yield compounds LI and IK, respectively (step e).

Compounds IL may be synthesized through alkylation of compounds IH with compounds of the type $R^8X$, in which X is a suitable leaving group such as chlorine, bromine, iodine, —$OSO_2$alkyl (e.g. mesylate (methanesulfonate), —$OSO_2$fluoroalkyl (e.g. triflate (trifluoromethanesulfonate) or —$OSO_2$aryl (e.g. tosylate (p-toluenesulfonate) using a suitable base in an appropriate solvent (e.g. sodium hydride in DMF) at temperatures between 0° C. and the boiling temperature of the solvent (step f).

In case $R^7$ in compounds IL is a cleavable ester group, it can be cleaved applying procedures known by those skilled in the art and as described in literature to yield compounds IM (step g).

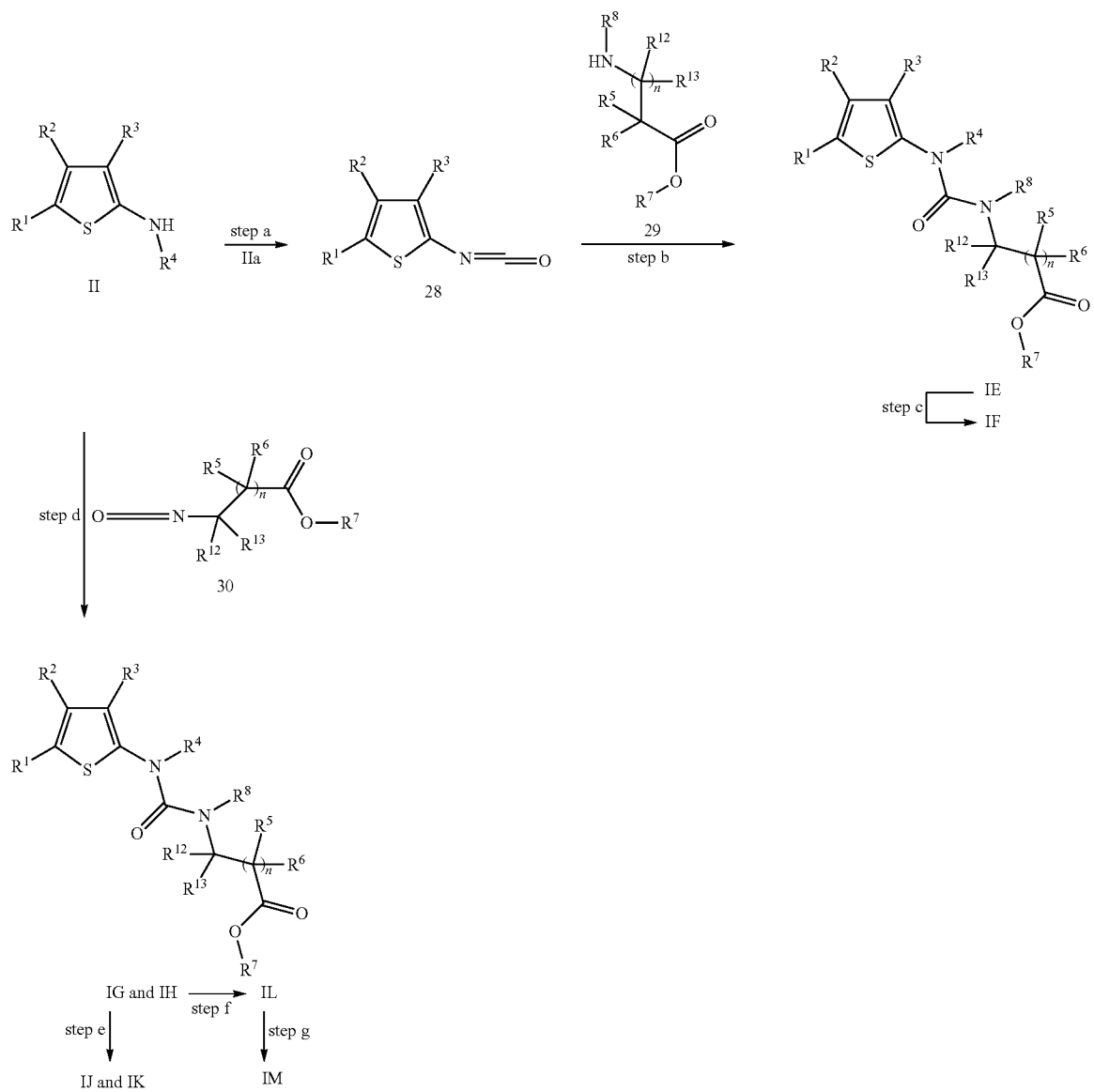

Compounds IN, wherein A is $CR^8R^9$, E is $NR^{11}$, n is 1 and $R^7$ is alkyl or cycloalkyl, and IO, wherein A is $CR^8R^9$, E is $NR^{11}$, n is 1 and $R^7$ is H can be prepared for example as shown in Scheme 8.

Compounds IN can be synthesized for example through acylation of 2-aminothiophenes II with appropriately substituted (alkoxycarbonylmethyl-amino)-acetic acid or (cycloalkoxycarbonylmethyl-amino)-acetic acid derivatives 31 (either commercially available or synthesized by methods known in the art), using literature procedures and the methods described under Scheme 1.

If $R^7$ is compounds IN is a cleavable ester group it can be cleaved applying procedures known by those skilled in the art and as described in literature to yield compounds IO (step b).

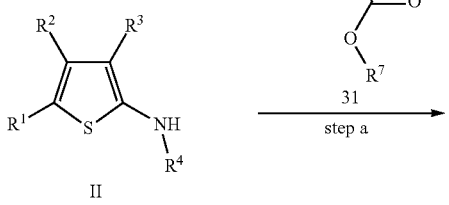

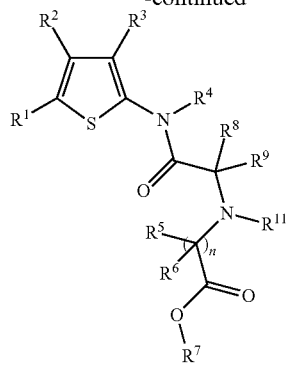

IN

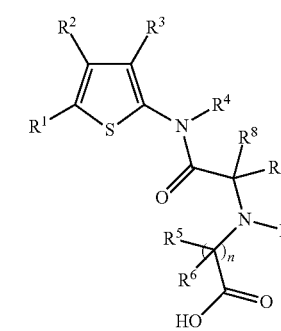

IO

Also an embodiment of the present invention is a process to prepare a compound of formula (I) as defined above comprising the reaction of a) a compound of formula (II) in the presence of a compound of formula (V);

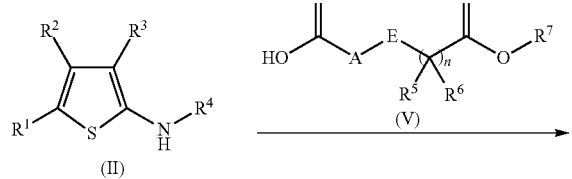

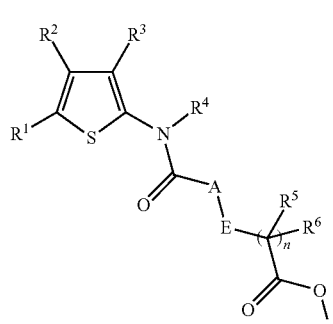

b) a compound of formula (II) in the presence of a compound of formula (VI);

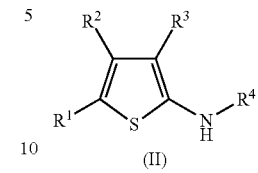

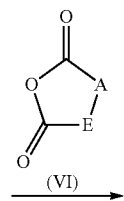

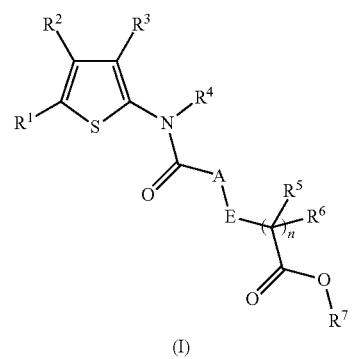

c) a compound of formula (VII) in the presence of a compound of formula (VIII);

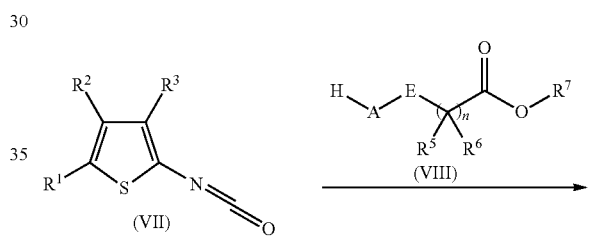

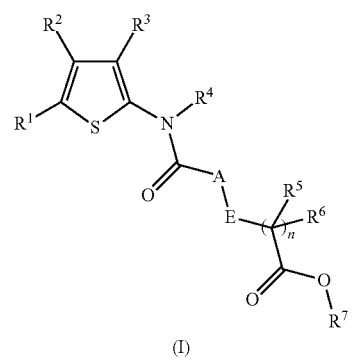

or d) a compound of formula (II) in the presence of a compound of formula (IX);

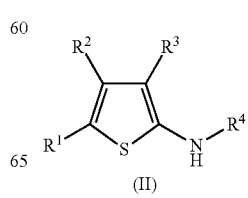

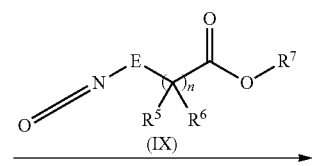

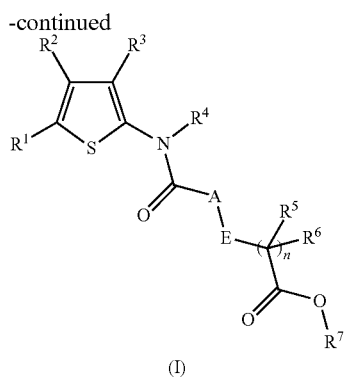

(I)

wherein $R^1$, $R^2$, $R^3$, $R^4$, $R^5$, $R^6$ are as defined above and wherein $R^7$ is alkyl or cycloalkyl and A is $CR^9R^{10}$ in step a), A is $CR^9R^{10}$, E is $CR^{12}R^{13}$ and n is zero in step b), $R^4$ is H, A is $NR^8$ in step c) and d).

Also a further preferred embodiment of the present invention is a process to prepare a compound of formula (I) as defined above comprising the reaction of a compound of formula (II) in the presence of a compound of formula (VI).

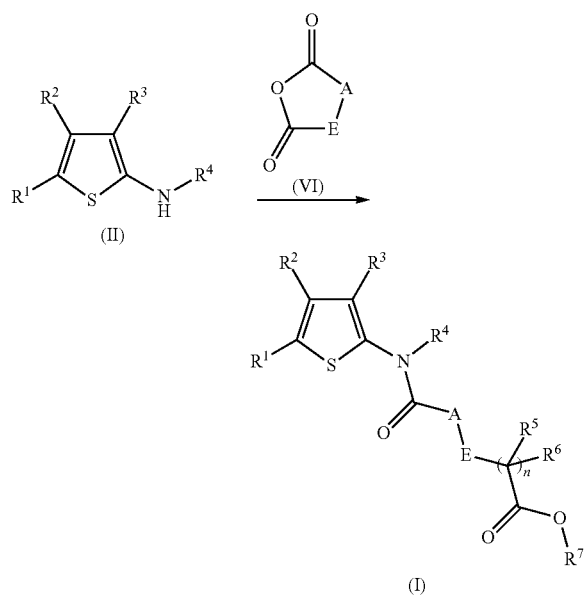

wherein $R^1$, $R^2$, $R^3$, $R^4$, $R^5$, $R^6$, $R^7$ and n are as defined above and wherein A is $CR^9R^{10}$ and E is $CR^{12}R^{13}$. In particular in the presence of a solvent, particularly acetonitrile, THF or $Et_2O$, in the presence or not of a base, particularly in the presence of DMAP, DIEPA or DBU, at a temperature comprised between 0° C. and reflux, particularly between RT and reflux.

Also an object of the present invention is a compound according to formula (I) as described herein for use as therapeutically active substance.

Likewise an object of the present invention is a pharmaceutical composition comprising a compound according to formula (I) as described herein and a therapeutically inert carrier.

In accordance with the invention, the compounds of formula (I) or their pharmaceutically acceptable salts and esters can be used for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome.

Particular liver diseases are liver diseases involving inflammation, steatosis and/or fibrosis, such non-alcoholic fatty liver disease, more particularly non-alcoholic steatohepatitis.

Particular lipodystrophy are genetic and iatrogenic lipodystrophy.

Particular eye diseases are eye diseases supported by endothelial proliferation and angiogenesis, particularly macular degeneration and retinopathy.

Particular lung diseases are asthma, bronchopulmonary dysplasia and chronic obstructive pulmonary disease.

Particular chronic renal diseases are vasculitis, focal segmental glomerulosclerosis, diabetic nephropathy, lupus nephritis, polycystic kidney disease and drug or toxin-induced chronic tubulointerstitial nephritis.

The present invention also relates to the use of a compound according to formula (I) as described herein for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome.

The present invention particularly relates to the use of a compound according to formula (I) as described herein for the treatment or prophylaxis of type 2 diabetes, atherosclerosis, cancer, chronic renal disease and non-alcoholic steatohepatitis.

The present invention also relates to the use of a compound according to formula (I) as described herein for the treatment or prophylaxis of non-alcoholic steatohepatitis.

A particular embodiment of the present invention is a compound according to formula (I) as described herein for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome.

Another particular embodiment of the present invention is a compound according to formula (I) as described herein for the treatment or prophylaxis of type 2 diabetes, atherosclerosis, cancer, chronic renal disease and non-alcoholic steatohepatitis.

Also a particular embodiment of the present invention is a compound according to formula (I) as described herein for the treatment or prophylaxis of non-alcoholic steatohepatitis.

The present invention also relates to the use of a compound according to formula (I) as described herein for the preparation of a medicament for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome.

The present invention particularly relates to the use of a compound according to formula (I) as described herein for the preparation of a medicament for the treatment or prophylaxis of type 2 diabetes, atherosclerosis, cancer, chronic renal disease and non-alcoholic steatohepatitis.

Also an embodiment of the present invention is the use of a compound according to formula (I) as described herein for the preparation of a medicament for the treatment or prophylaxis of non-alcoholic steatohepatitis.

Also an object of the invention is a method for the treatment or prophylaxis of type 2 diabetes, metabolic syndrome, atherosclerosis, dyslipidemia, liver diseases, obesity, lipodystrophy, cancer, eye diseases, lung diseases, sarcoidosis, chronic renal diseases, chronic inflammatory and autoimmune inflammatory diseases, preeclampsia and polycystic ovary syndrome, which method comprises administering an effective amount of a compound according to formula (I) as described herein.

Another object of the invention is a method for the treatment or prophylaxis of type 2 diabetes, atherosclerosis, cancer, chronic renal disease and non-alcoholic steatohepatitis, which method comprises administering an effective amount of a compound according to formula (I) as described herein.

Also an embodiment of the present invention is a method for the treatment or prophylaxis of non-alcoholic steatohepatitis, which method comprises administering an effective amount of a compound according to formula (I) as described herein.

Also an embodiment of the present invention is a method for the treatment or prophylaxis of lipodystrophy, which method comprises administering an effective amount of a compound according to formula (I) as described herein.

Also a particular embodiment of the present invention is a compound according to formula (I) as described herein, when manufactured according to any one of the described processes.

Assay Procedures

Compounds were profiled for activity against human FABP4 (huFABP4) and/or human FABP5 (huFABP5) in Terbium (Tb) time resolved-fluorescence energy transfer (TR-FRET) assays monitoring the direct binding of Bodipy labeled fatty acid to His6 tagged FABP proteins (huFABP4 was expressed in house in *E. Coli* and purified, huFABP5 was purchased from Cayman Chemical Co., cat.no. 10010364), bound to Terbium labeled anti His6 tag antibody. Assay read-outs reflected energy transfer, upon binding of the ligand to the FABP protein, from the Terbium donor molecule to the acceptor Bodipy moiety. Final ligand concentration (125 nM) approximated the Kd for each protein.

Stock DMSO solutions (1.8 mM) of compounds were serially diluted 3-fold for ten concentrations with 100% DMSO (50 µM to 0.003 µM final compound concentration). 1 µl of these compound dilutions and 1 µl of Bodipy labeled fatty acid 4.5 µM in 100% DMSO (Bodipy FL C11, cat. no. D3862, Invitrogen) were sequentially pipetted in wells of 384-well black polypropylene plates (Thermo Matrix cat. no. 4344). FABP4 or FABP5 protein was then added (28 µl of 64 nM protein in 25 mM Tris pH 7.5, 0.4 mg/ml γ-globulin, 1 mM DTT, 0.012% NP40, final protein concentration: 50 nM). Assay blanks contained ligand, but no protein. Neutral controls contained ligand, but no compound. After adding the detection reagent (Tb antiHis6 antibody, Columbia Biosciences, TB-110, 6 µl of a 24 nM Ab solution in 25 mM Tris pH 7.5, 0.4 mg/ml γ-globulin, final Tb antiHis6 Ab concentration: 4 nM), plates were spun one minute at 1000 rpm. Following an incubation at room temperature with shaking for 30 minutes, plates were read using an Envision reader (Perkin Elmer, Extinction wavelength: 340 nm, Emission: 490 nm and 520 nm, time delay: 100 µs; time window: 200 µs, 50 flashes).

Final assay conditions were: 50 nM FABP protein, 125 nM Bodipy labeled fatty acid, 0.009% (vol/vol) NP40, 5.5% (vol/vol) DMSO in a total final assay volume of 36 µl. The assay was performed in triplicate.

The relative fluorescence units (RFU) ratio (520 nm*10000488 nm) were used to calculate the percent inhibition: 100−(RFU ratio compound blank)/neutral control−blank)*100. These percent inhibition values were then fit to dose response curves using a 4 parameter logistic model (Hill sigmoidal dose-response model). $IC_{50}$s reflected compound concentrations associated with 50% inhibition of protein activity compared to that of neutral controls.

| Example | IC50 h-fabp4-ecoli-r µM | IC50 h-fabp5-ecoli-r µM |
|---|---|---|
| 1 | 0.06 | 1.32 |
| 2 | 0.08 | 0.2 |
| 3 | 0.03 | 0.11 |
| 4 | 1.01 | 15.13 |
| 5 | 0.16 | 0.14 |
| 6 | 0.61 | 0.67 |
| 7 | 3.38 | 19.48 |
| 8 | 0.15 | 0.15 |
| 9 | 0.15 | 9.37 |
| 10 | 0.37 | 6.34 |
| 11 | 0.07 | 0.36 |
| 12 | 0.36 | 1.03 |
| 13 | 0.22 | 0.57 |
| 14 | 2.69 | 4.25 |
| 15 | 1.59 | 4.54 |
| 16 | 5.02 | 10.2 |
| 17 | 5.17 | 50 |
| 18 | 0.61 | 0.54 |
| 19 | 5.88 | 16.16 |
| 20 | 4.98 | 16.7 |
| 21 | 5.5 | 33.27 |
| 22 | 0.81 | 3.44 |
| 23 | 0.59 | 5.95 |
| 24 | 0.77 | 1.46 |
| 25 | 2.07 | 1.69 |
| 26 | 0.11 | 0.15 |
| 27 | 0.12 | 0.89 |
| 28 | 1.9 | 0.25 |
| 29 | 0.2 | 0.06 |
| 30 | 2.01 | 6.56 |
| 31 | 0.96 | 0.7 |
| 32 | 3.21 | 14.12 |
| 33 | 0.05 | 0.06 |
| 34 | 0.15 | 0.27 |
| 35 | 4.56 | 2.37 |
| 36 | 1.17 | 0.22 |
| 37 | 0.22 | 0.56 |
| 38 | 0.71 | 14 |
| 39 | 0.87 | 0.64 |
| 40 | 0.12 | 0.11 |
| 41 | 0.6 | 9.28 |
| 42 | 0.06 | 0.1 |
| 43 | 8.3 | 4.62 |
| 44 | 0.28 | 25.07 |
| 45 | 0.48 | 30.87 |
| 46 | 1.09 | 0.4 |
| 47 | 0.63 | 0.18 |
| 48 | 0.55 | 0.16 |
| 49 | 0.12 | 0.11 |
| 50 | 9.54 | 2.48 |
| 51 | 0.17 | 0.16 |
| 52 | 1.05 | 1.05 |
| 53 | 0.97 | 5.96 |
| 54 | 0.82 | 0.3 |
| 55 | 0.03 | 0.15 |
| 56 | 0.14 | 0.39 |
| 57 | 4.4 | 1.14 |
| 58 | 1.25 | 0.07 |

| Example | IC50 h-fabp4-ecoli-r µM | IC50 h-fabp5-ecoli-r µM |
|---|---|---|
| 59 | 0.09 | 0.12 |
| 60 | 7.15 | 0.34 |
| 61 | 0.01 | 0.02 |
| 62 | 0.01 | 0.03 |
| 63 | 6.1 | 8.91 |
| 64 | 0.03 | 0.21 |
| 65 | 1.11 | 1.27 |
| 66 | 0.13 | 0.21 |
| 67 | 0.02 | 0.05 |
| 68 | 0.02 | 0.07 |
| 69 | 0.05 | 0.58 |
| 70 | 0.07 | 0.85 |
| 71 | 0.16 | 1.18 |
| 72 | 0.4 | 0.98 |
| 73 | 1.89 | 4.03 |
| 74 | 0.49 | 0.15 |
| 75 | 4.26 | 23.02 |
| 76 | 3.6 | 15.28 |
| 77 | 0.15 | 0.02 |
| 78 | 0.02 | 0.55 |
| 79 | 0.82 | 1.06 |
| 80 | 0.07 | 0.03 |
| 81 | 0.41 | 1.13 |
| 82 | 1.04 | 8.08 |
| 83 | 0.17 | 0.12 |
| 84 | 0.31 | 0.64 |
| 85 | 0.02 | 0.02 |
| 86 | 0.01 | 0.02 |
| 87 | 0.03 | 0.03 |
| 88 | 0.02 | 0.01 |
| 89 | 0.02 | 0.08 |
| 90 | 0.01 | 0.07 |
| 91 | 0.06 | 0.2 |
| 92 | 0.02 | 0.02 |
| 93 | 0.03 | 0.01 |
| 94 | 3.98 | 0.28 |
| 95 | 3.04 | 0.09 |
| 96 | 0.01 | 0.05 |
| 97 | 0.04 | 0.13 |
| 98 | 0.14 | 0.31 |
| 99 | 2.13 | 7.76 |
| 100 | 0.96 | 5.39 |
| 101 | 8.17 | 2.51 |
| 102 | 0.05 | 0.01 |
| 103 | 0.4 | 0.03 |
| 104 | 0.61 | 1.51 |
| 105 | 0.16 | 0.55 |
| 106 | 0.81 | 3.94 |
| 107 | 0.09 | 0.05 |
| 108 | 0.04 | 0.06 |
| 109 | 0.14 | 0.02 |
| 110 | 3.13 | 37.35 |
| 111 | 2.12 | 31.36 |
| 112 | 9.14 | 27.32 |
| 113 | 0.1 | 0.1 |
| 114 | 9.54 | 19.15 |
| 115 | 2.18 | 5.77 |
| 116 | 1.29 | 2.56 |
| 117 | 0.79 | 9.66 |
| 118 | 0.03 | 0.03 |
| 119 | 0.56 | 4.92 |
| 120 | 0.03 | 0.06 |
| 121 | 0.04 | 0.1 |
| 122 | 0.04 | 0.12 |
| 123 | 0.04 | 0.04 |
| 124 | 0.02 | 0.03 |
| 125 | 0.02 | 0.05 |
| 126 | 0.01 | 0.03 |
| 127 | 1.32 | 1.39 |
| 128 | 0.01 | 0.03 |
| 129 | 0.02 | 0.11 |
| 130 | 0.46 | 1.58 |
| 131 | 0.08 | 0.56 |
| 132 | 0.02 | 0.03 |
| 133 | 0.4 | 0.41 |
| 134 | 0.02 | 0.08 |
| 135 | 0.01 | 0.04 |
| 136 | 4.53 | 7.93 |
| 137 | 0.02 | 0.07 |
| 138 | 0.44 | 0.29 |
| 139 | 0.06 | 0.04 |
| 140 | 0.24 | 0.09 |
| 141 | 0.07 | 0.18 |
| 142 | 2.23 | 7.79 |
| 143 | 0.09 | 0.39 |
| 144 | 0.03 | 0.03 |
| 145 | 1.04 | 1.55 |
| 146 | 0.07 | 0.06 |
| 147 | 0.01 | 0.02 |
| 148 | 8.49 | 12.74 |
| 149 | 0.04 | 0.05 |
| 150 | 0.02 | 0.03 |
| 151 | 0.03 | 0.02 |
| 152 | 0.42 | 0.08 |
| 153 | 0.91 | 1.13 |
| 154 | 1.08 | 1.24 |
| 155 | 1.78 | 0.54 |
| 156 | 1.5 | 0.76 |
| 157 | 0.4 | 0.49 |
| 158 | 0.38 | 0.42 |
| 159 | 0.28 | 0.08 |
| 160 | 1.02 | 0.47 |
| 161 | 0.36 | 1.05 |
| 162 | 0.2 | 1.45 |
| 163 | 0.47 | 0.2 |
| 164 | 1.78 | 0.31 |
| 165 | 0.402 | 0.494 |
| 166 | 0.024 | 0.013 |
| 167 | 0.042 | 0.013 |
| 168 | 0.116 | 0.018 |
| 169 | 0.136 | 0.032 |
| 170 | 0.096 | 0.039 |
| 171 | 0.05 | 0.054 |
| 172 | 0.57 | 0.151 |
| 173 | 0.096 | 0.22 |
| 174 | 0.151 | 0.048 |
| 175 | 1.32 | 1.04 |
| 176 | 0.563 | 0.133 |
| 177 | 0.348 | 0.067 |
| 178 | 0.731 | 0.156 |
| 179 | 0.388 | 0.15 |
| 180 | 0.137 | 0.032 |
| 181 | 0.218 | 0.055 |
| 182 | 0.25 | 0.057 |
| 183 | 0.243 | 0.054 |
| 184 | 0.70 | 0.074 |
| 185 | 2.53 | 0.08 |
| 186 | 1.14 | 0.157 |
| 187 | 1.21 | 0.227 |
| 188 | 0.272 | 0.022 |
| 189 | 0.806 | 0.282 |
| 190 | 0.956 | 0.137 |
| 191 | 0.20 | 0.075 |
| 192 | 0.315 | 0.048 |
| 193 | 0.088 | 0.01 |
| 194 | 1.27 | 44.5 |
| 195 | 0.22 | 1.21 |
| 196 | 0.022 | 0.068 |
| 197 | 0.047 | 0.085 |
| 198 | 0.026 | 0.05 |
| 199 | 0.01 | 0.033 |
| 200 | 0.018 | 0.043 |
| 201 | 0.023 | 0.043 |
| 202 | 0.024 | 0.041 |
| 203 | 0.104 | 0.203 |
| 204 | 0.033 | 0.067 |
| 205 | 0.047 | 0.11 |
| 206 | 0.016 | 0.030 |
| 207 | 0.025 | 0.06 |
| 208 | 0.303 | 2.26 |

| Example | IC50 h-fabp4-ecoli-r μM | IC50 h-fabp5-ecoli-r μM |
| --- | --- | --- |
| 209 | 0.24 | 2.29 |
| 210 | 0.521 | 1.18 |
| 211 | 0.012 | 0.034 |
| 212 | 0.049 | 0.15 |
| 213 | 0.084 | 0.414 |
| 214 | 2.16 | 13.23 |
| 215 | 0.43 | 0.607 |
| 216 | 0.069 | 0.145 |
| 217 | 0.009 | 0.034 |
| 218 | 0.013 | 0.019 |
| 219 | 0.018 | 0.057 |
| 220 | 0.311 | 0.515 |
| 221 | 0.476 | 2.52 |
| 222 | 0.236 | 0.203 |
| 223 | 0.54 | 0.148 |
| 224 | 0.436 | 0.257 |
| 225 | 1.14 | >50 |
| 226 | 0.033 | 0.781 |
| 227 | 0.23 | 0.604 |
| 228 | 0.47 | 1.80 |
| 229 | 0.84 | 0.62 |
| 230 | 2.07 | 21.5 |
| 231 | 0.02 | 0.03 |
| 232 | 0.04 | 0.08 |
| 233 | 0.05 | 0.071 |
| 234 | 0.82 | 12.9 |
| 235 | 3.41 | >50 |
| 236 | 0.01 | 0.038 |
| 237 | 0.026 | 0.092 |
| 238 | 0.022 | 0.077 |
| 239 | 0.011 | 0.063 |
| 240 | 0.138 | 0.113 |
| 241 | 0.30 | 34.2 |
| 242 | 0.112 | 8.75 |
| 243 | 0.27 | 0.14 |
| 244 | 0.87 | 1.04 |
| 245 | 0.045 | 0.49 |
| 246 | 0.017 | 0.12 |
| 247 | 0.22 | 2.12 |
| 248 | 0.261 | 1.93 |
| 249 | 0.359 | 0.603 |
| 250 | 0.36 | 0.64 |
| 251 | 0.183 | 1.1 |
| 252 | 0.045 | 0.26 |
| 253 | 0.485 | 0.522 |
| 254 | 0.115 | 0.238 |
| 255 | 0.379 | 0.509 |
| 256 | 0.012 | 0.245 |
| 257 | 0.034 | 0.38 |
| 258 | 0.109 | 1.0 |

Compounds of formula (I) and their pharmaceutically acceptable salts or esters thereof as described herein have $IC_{50}$ (FABP4 inhibition) values between 0.000001 μM and 1000 μM, particular compounds have $IC_{50}$ values between 0.000005 μM and 500 μM, further particular compounds have $IC_{50}$ values between 0.00005 μM and 5 μM.

Compounds of formula (I) and their pharmaceutically acceptable salts or esters thereof as described herein have $IC_{50}$ (FABP5 inhibition) values between 0.000001 μM and 1000 μM, particular compounds have $IC_{50}$ values between 0.000005 μM and 500 μM, further particular compounds have $IC_{50}$ values between 0.00005 μM and 50 μM.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions).

The compounds of formula (I) and their pharmaceutically acceptable salts can be processed with pharmaceutically inert, inorganic or organic adjuvants for the production of tablets, coated tablets, dragées and hard gelatin capsules. Lactose, corn starch or derivatives thereof, talc, stearic acid or its salts etc. can be used, for example, as such adjuvants for tablets, dragées and hard gelatin capsules.

Suitable adjuvants for soft gelatin capsules are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

In accordance with the invention, the compounds of formula (I) or their pharmaceutically acceptable salts and esters can be used for the treatment or prophylaxis of type 2 diabetes related microvascular complications (such as, but not limited to diabetic retinopathy, diabetic neuropathy and diabetic nephropathy), coronary artery disease, obesity and underlying inflammatory diseases, chronic inflammatory and autoimmune/inflammatory diseases The invention is illustrated hereinafter by Examples, which have no limiting character.

In case the preparative examples are obtained as a mixture of enantiomers, the pure enantiomers can be separated by methods described herein or by methods known to the person skilled in the art, such as e.g. chiral chromatography or crystallization.

EXAMPLES

All examples and intermediates were prepared under argon atmosphere if not specified otherwise.

Example 1

2-(3-Phenyl-benzo[b]thiophen-2-ylcarbamoyl)-cyclopent-1-enecarboxylic acid

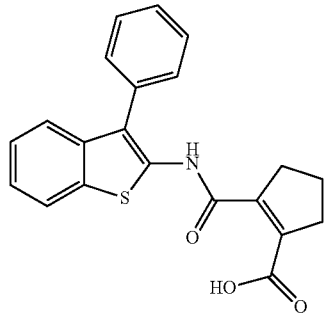 [SMILES: O=C(O)C1=C(C(=O)Nc2sc3ccccc3c2-c2ccccc2)CCC1]

3-Phenyl-benzo[b]thiophen-2-ylamine (17 mg, 75.5 μmol) and 1-cyclopentene-1,2-dicarboxylic anhydride (20.8 mg, 0.15 mmol) were dissolved in THF (1 mL) and the yellow solution was stirred at RT overnight. The reaction mixture was heated to 60° C. for 4 h and then another batch of 1-cyclopentene-1,2-dicarboxylic anhydride (5.2 mg, 0.038 mmol) was added. After stirring at 60° C. for 2 h the crude reaction mixture was kept in a fridge for 66 h. After evaporation of the solvent the residue was triturated in Et$_2$O and filtered off to give the title compound as a yellow solid (5 mg, 18%). MS (ESI): m/z=362.3 [M−H]$^-$.

Intermediates a) 3-Phenyl-benzo[b]thiophen-2-ylamine

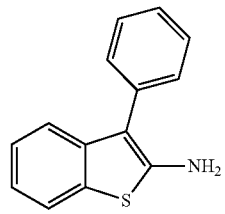 [SMILES: Nc1sc2ccccc2c1-c1ccccc1]

(3-Phenyl-benzo[b]thiophen-2-yl)-carbamic acid tert-butyl ester (30 mg, 92.2 μmol) and 4M HCl in dioxane (500 μL, 2.0 mmol) were combined with dioxane (500 μL). The yellow solution was stirred overnight. The formed precipitate was filtered, washed with dioxane and dried under high vacuum to give the title compound as a light yellow solid (17 mg, 82%). LC-MS (ESI): m/z=226.0 [M+H]$^+$.

b) (3-Phenyl-benzo[b]thiophen-2-yl)-carbamic acid tert-butyl ester

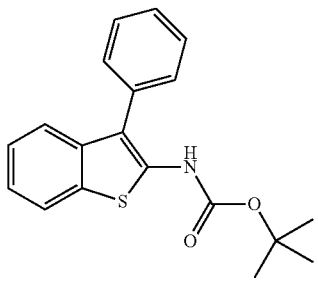 [SMILES: CC(C)(C)OC(=O)Nc1sc2ccccc2c1-c1ccccc1]

3-Phenyl-benzo[b]thiophene-2-carboxylic acid (72.6 mg, 285 μmol), NEt$_3$ (28.9 mg, 39.7 μL, 285 μmol) and diphenylphosphoryl azide (80.1 mg, 62.8 μL, 291 μmol, CAS RN 26386-88-9) were dissolved in tert-BuOH (1 mL). The reaction mixture was stirred for 5 h at 85° C. and finally at RT overnight. The suspension was filtered and the solid washed twice with a small amount of tert-BuOH. The filtrate was diluted with EtOAc, washed twice with H$_2$O and once with brine. The combined organic phases were dried over Na$_2$SO$_4$, filtered and evaporated. The crude residue was purified by flash chromatography on silica gel (0% to 10% EtOAc in n-heptane) to give the title compound as a yellow solid (30 mg, 32%). MS (ESI): m/z=326.3 [M+H]$^+$.

c) 3-Phenyl-benzo[b]thiophene-2-carboxylic acid

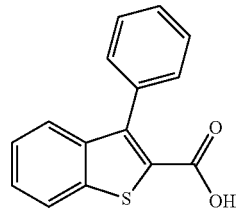 [SMILES: O=C(O)c1sc2ccccc2c1-c1ccccc1]

3-Phenyl-benzo[b]thiophene-2-carbaldehyde (0.312 g, 1.31 mmol) was diluted in CH$_3$CN (6.8 mL) and the solution was cooled to 10° C. To the solution H$_2$O (0.536 mL), NaH$_2$PO$_4$ (47 mg, 0.392 mmol) and hydrogen peroxide (636 mg, 561 μL, 6.55 mmol, 35% wt solution in H$_2$O) were added. Then a solution of NaClO$_2$ (0.166 g, 1.83 mmol) in H$_2$O (1.89 mL) was added dropwise over 5 min. and the two phase-system was vigorously stirred at 10° C. After 4.5 h another batch of NaH$_2$PO$_4$ (23.6 mg, 0.197 mmol) in H$_2$O (0.268 mL) followed by a further batch of NaClO$_2$ (83 mg, 0.918 mmol) in H$_2$O (0.945 mL) were added. The reaction was stirred for 2 h and then quenched by addition of Na$_2$SO$_3$. Finally, the reaction mixture was dropped into an aqueous solution of Na$_2$SO$_3$. The two phases became a solution by adding some H$_2$O. After acidification to pH 1 with 2M HCl the solid was filtered off and washed with H$_2$O. The solid was dried under high vacuum to give the title compound as a white solid (0.289 g, 87%). MS (ESI): m/z=253.1 [M−H]$^-$.

d) 3-Phenyl-benzo[b]thiophene-2-carbaldehyde

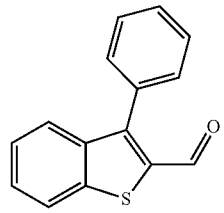 [SMILES: O=Cc1sc2ccccc2c1-c1ccccc1]

3-Bromobenzothiophene-2-carboxaldehyde (1.0 g, 3.94 mmol, CAS RN 10135-00-9) was dissolved in DME (180 mL). The reaction flask was evacuated and purged with argon three times. Pd(Ph$_3$P)$_4$ (137 mg, 118 μmol) was added and then 2M aqueous Na$_2$CO$_3$ solution (3.94 mL, 7.88 mmol) and phenylboronic acid (0.528 g, 4.33 mmol) were added. The reaction mixture was heated to 80° C. and stirred overnight. After evaporation of the solvent, the residue was taken up in Et₂O and H₂O and the layers were separated. The organic phase was dried over Na₂SO₄, filtered and evaporated. The crude residue was taken up in CHCl₃Et₂On-heptane and filtered. The filtrate was kept and purified by flash chromatography on silica gel (gradient of EtOAc in n-heptane, 0% to 8%). The product-containing fractions were further purified by preparative HPLC to give the title compound as a light yellow oil (0.372 g, 40%). MS (ESI): m/z=239.1 [M+H]⁺.

Example 2

2-[3-(3-Methyl-[1,2,4]oxadiazol-5-yl)-4,5,6,7-tetrahydro-benzo[b]thiophen-2-ylcarbamoyl]-cyclopent-1-enecarboxylic acid

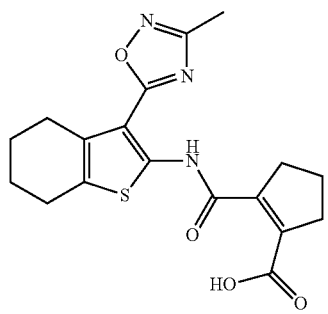 [SMILES: Cc1noc(-c2c(NC(=O)C3=C(C(=O)O)CCC3)sc3c2CCCC3)n1]

3-(3-Methyl-[1,2,4]oxadiazol-5-yl)-4,5,6,7-tetrahydro-benzo[b]thiophen-2-ylamine (92 mg) was dissolved in CH₃CN (5 mL) at RT under argon, treated with DMAP (52.5 mg) and cyclopentene-1,2-dicarboxylic anhydride (66.8 mg) and then heated at 60° C. for 12 h. The mixture was then cooled to RT and then partitioned between EtOAc and aqueous HCl. The layers were separated, the organic layers dried over Na₂SO₄ and concentrated in vacuo. The residue was purified by flash chromatography (EtOAc/n-heptane, gradient from 0 to 40%) to give the desired compound as a yellow solid (37 mg). MS (ESI): m/z=374.1 [M+H]⁺.

Intermediates a) 3-(3-Methyl-[1,2,4]oxadiazol-5-yl)-4,5,6,7-tetrahydro-benzo[b]thiophen-2-ylamine

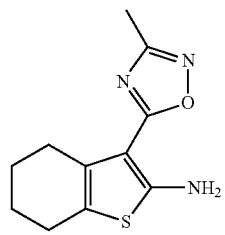 [SMILES: Cc1noc(-c2c(N)sc3c2CCCC3)n1]

N-(3-(3-methyl-1,2,4-oxadiazol-5-yl)-4,5,6,7-tetrahydrobenzo[b]thiophen-2-yl)acetamide (1.4 g) was suspended in EtOH (45 mL) at RT under argon, treated with a solution of NaOMe in MeOH (5.4M, 1.87 mL) and heated at reflux for 3 h. The mixture was cooled to RT and partitioned between EtOAc and aqueous NaHCO₃ solution. The layers were separated and the organic layers were dried and concentrated in vacuo. The residue was purified by flash chromatography (EtOAc/n-heptane, gradient from 0 to 40%) to give the desired compound as a light brown solid (564 mg). MS (ESI): m/z=236.1 [M+H]⁺.

b) N-(3-(3-methyl-1,2,4-oxadiazol-5-yl)-4,5,6,7-tetrahydrobenzo[b]thiophen-2-yl)acetamide

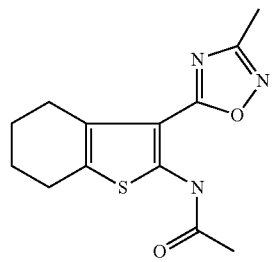 [SMILES: CC(=O)Nc1sc2c(c1-c1nc(C)no1)CCCC2]

2-Amino-4,5,6,7-tetrahydro-benzo[b]thiophene-3-carboxylic acid amide (7 g, CAS RN 4815-28-5) was treated at RT with N,N-dimethylacetamide dimethyl acetal (15.8 g) and then heated at 120° C. for 1.5 h under an argon atmosphere. The reaction mixture was cooled to RT, concentrated in vacuo, treated with hydroxylamine hydrochloride (2.23 g) in 1N aqueous NaOH (53.5 mL) and then diluted with dioxane (49 mL) followed by acetic acid (70 mL). After stirring for 30 min. at RT the mixture was heated at 90° C. for 1 h. The reaction was then cooled to RT, concentrated in vacuo, diluted with H₂O and aqueous Na₂CO₃. After extraction with CH₂Cl₂ the dried organic layers were concentrated in vacuo and the residue was purified by flash chromatography (EtOAc/n-heptane, gradient from 0-40%) to give the desired N-(3-(3-methyl-1,2,4-oxadiazol-5-yl)-4,5,6,7-tetrahydrobenzo[b]thiophen-2-yl)acetamide (5.8 g) as an off-white solid. MS (ESI): m/z=278.09 [M+H]⁺.

Example 3

2-[3-(3-Methyl-[1,2,4]oxadiazol-5-yl)-4,5,6,7-tetrahydro-benzo[b]thiophen-2-ylcarbamoyl]-cyclohex-1-enecarboxylic acid

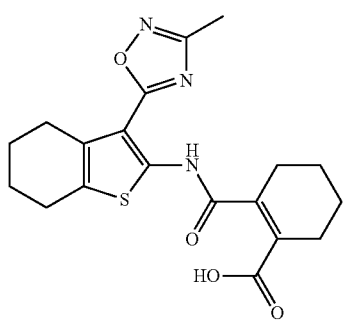 [SMILES: Cc1noc(-c2c(NC(=O)C3=C(C(=O)O)CCCC3)sc3c2CCCC3)n1]

2-(3-(3-Methyl-1,2,4-oxadiazol-5-yl)-4,5,6,7-tetrahydrobenzo[b]thiophen-2-yl)-4,5,6,7-tetrahydro-1H-isoindole-1,3(2H)-dione (50 mg) in a mixture of THF (2 mL) and 1M NaOH (271 μL) was stirred for 2.5 h at RT under argon. The reaction was then diluted with H₂O and extracted with EtOAc. The combined organic layers were washed with 2M KHCO₃, dried over Na₂SO₄ and concentrated in vacuo. The residue was washed with n-heptane and tried under high vacuum to give the title compound as a yellow solid. MS (ESI): m/z=388.1 [M+H]⁺.

Intermediate a) 2-(3-(3-Methyl-1,2,4-oxadiazol-5-yl)-4,5,6,7-tetrahydrobenzo[b]thiophen-2-yl)-4,5,6,7-tetrahydro-1H-isoindole-1,3(2H)-dione

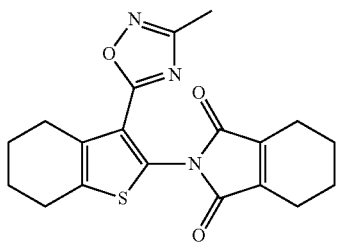 [SMILES: Cc1noc(-c2c(N3C(=O)C4=C(CCCC4)C3=O)sc3c2CCCC3)n1]

3-(3-Methyl-[1,2,4]oxadiazol-5-yl)-4,5,6,7-tetrahydro-benzo[b]thiophen-2-ylamine (100 mg, example 2, intermediate a) in CH₃CN (5 mL) was treated under argon with DIPEA (84.8 mg) and 3,4,5,6-tetrahydrophthalic anhydride (95.5 mg) and the mixture was heated to reflux for 17 h. More 3,4,5,6-tetrahydrophthalic anhydride (95.5 mg) was added and the mixture was heated to reflux for further 19 h. The mixture was then cooled to RT, and partitioned between EtOAc and aqueous diluted HCl (pH 1). The layers were separated, the organic layers were dried over Na₂SO₄ and concentrated in vacuo. The residue was purified by flash chromatography (EtOAc/n-heptane, gradient from 0 to 20%) to give the desired compound as a light yellow solid (63 mg). MS (EI): m/z=369 [M]⁺.

Example 4

(Z)-3-[3-(3-Methyl-[1,2,4]oxadiazol-5-yl)-4,5,6,7-tetrahydro-benzo[b]thiophen-2-ylcarbamoyl]-acrylic acid

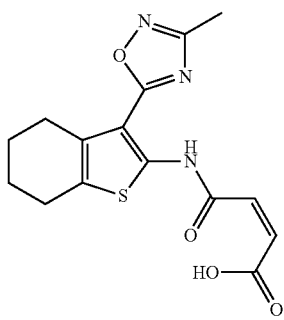 [SMILES: Cc1noc(-c2c(NC(=O)/C=C\C(=O)O)sc3c2CCCC3)n1]

The title compound was obtained in analogy to example 2, from 3-(3-methyl-[1,2,4]oxadiazol-5-yl)-4,5,6,7-tetrahydro-benzo[b]thiophen-2-ylamine (example 2, intermediate a) and maleic anhydride as a yellow solid. MS (ESI): m/z=334.08 [M+H]⁺.

Example 5

2-[3-(3-Cyclopropyl-[1,2,4]oxadiazol-5-yl)-4,5,6,7-tetrahydro-benzo[b]thiophen-2-ylcarbamoyl]-cyclopent-1-enecarboxylic acid

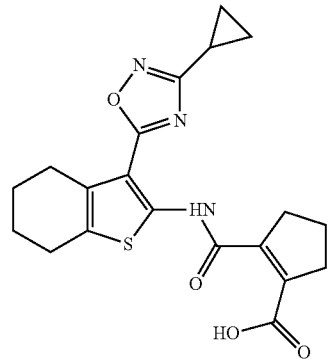 [SMILES: O=C(O)C1=C(C(=O)Nc2sc3c(c2-c2nc(C4CC4)no2)CCCC3)CCC1]

For tert-butoxy carbonyl cleavage prior to coupling, tert-butyl 3-(3-cyclopropyl-1,2,4-oxadiazol-5-yl)-4,5,6,7-tetrahydrobenzo[b]thiophen-2-ylcarbamate (30 mg) in CH₂Cl₂ ((830 μl) was treated at RT under argon with TFA (946 mg, 639 μL). The mixture was stirred at RT for 20 min. and then concentrated in vacuo to give the crude amine salt. For the subsequent coupling, the crude salt was dissolved in CH₃CN (4 mL) at RT under argon, treated with DMAP (18.9 mg, 152 μmol) and cyclopentene-1,2-dicarboxylic anhydride (13.0 mg, 91.3 μmol). The reaction solution was then heated at 60° C. for 18.5 h and at 80° C. for further 1.5 h. The reaction was then cooled to RT and partitioned between EtOAc and aqueous HCl (pH 1). The layers were separated and the organic layers were dried over Na₂SO₄ and concentrated in vacuo. The residue was purified by flash chromatography (EtOAc/n-heptane, gradient from 0 to 60%) to give the desired compound as a yellow solid (4.3 mg). MS (EI): m/z=400.2 [M+H]⁺.

Intermediates a) tert-Butyl 3-(3-cyclopropyl-1,2,4-oxadiazol-5-yl)-4,5,6,7-tetrahydrobenzo[b]thiophen-2-ylcarbamate

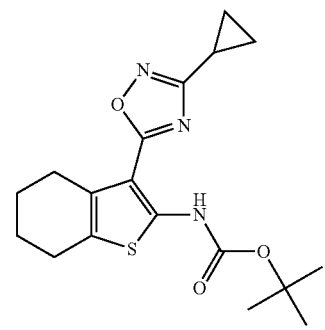 [SMILES: CC(C)(C)OC(=O)Nc1sc2c(c1-c1nc(C3CC3)no1)CCCC2]

tert-Butyl {3-[({[cyclopropyl(imino)methyl]amino}oxy)carbonyl]-4,5,6,7-tetrahydro-1-benzothiophen-2-yl}carbamate (793 mg) was dissolved in THF (20.9 mL) at RT under argon, TBAF in THF (20.9 mL, 1M solution) was added and the reaction solution was then heated to reflux for 1 h until TLC (n-heptan/EtOAc: 1/1) indicated completion of the reaction. The reaction mixture was diluted with $H_2O$ and extracted with EtOAc. The combined organic layers were washed with 2M aqueous $KHCO_3$ solution, dried over $Na_2SO_4$ and concentrated in vacuo. The residue was purified by flash chromatography (EtOAc/n-heptane, gradient from 0 to 10%) to give the desired compound as a white solid (614 mg). MS (ESI): m/z=362.1 $[M+H]^+$.

b) tert-Butyl {3-[({[cyclopropyl(imino)methyl]amino}oxy)carbonyl]-4,5,6,7-tetrahydro-1-benzothiophen-2-yl}carbamate

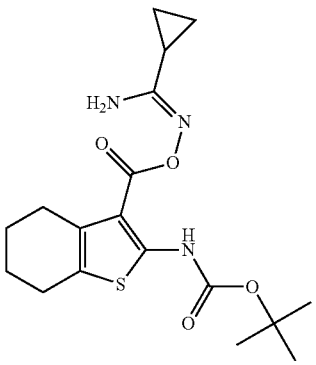 [SMILES: CC(C)(C)OC(=O)Nc1sc2c(c1C(=O)O/N=C(\N)C1CC1)CCCC2]

2-tert-Butoxycarbonylamino-4,5,6,7-tetrahydro-benzo[b]thiophene-3-carboxylic acid (1 g; prepared according to Y. Huang et al., *Chem. Biol. Drug Des.* 2010, 76, 116-129) was dissolved in DMF (33.6 mL) at RT under argon. Then HATU (1.29 g), DIPEA (443 mg) and (Z)—N'-hydroxycyclopropanecarboximidamide (374 mg) were added and the reaction solution was stirred at RT for 16 h until TLC (n-heptane/EtOAc: 1/1v/v) indicated completion of the reaction. The reaction mixture was diluted with $H_2O$ and extracted with EtOAc. The combined organic layers were washed with 2M $KHCO_3$, dried over $Na_2SO_4$ and concentrated in vacuo. The residue was purified by flash chromatography (EtOAc/n-heptane, gradient from 0 to 25%) to give the desired compound as a light yellow solid (1.28 g). MS (ESI): m/z=380.1 $[M+H]^+$.

Example 6

2-[3-(3-Cyclopropyl-[1,2,4]oxadiazol-5-yl)-benzo[b]thiophen-2-ylcarbamoyl]-cyclopent-1-enecarboxylic acid

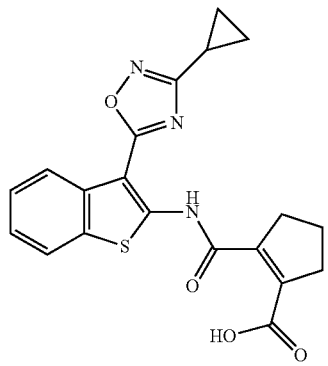 [SMILES: O=C(O)C1=C(C(=O)Nc2sc3ccccc3c2-c2nc(C3CC3)no2)CCC1]

The title compound was obtained in analogy to example 5, from tert-butyl 3-(3-cyclopropyl-1,2,4-oxadiazol-5-yl)benzo[b]thiophen-2-ylcarbamate and cyclopentene-1,2-dicarboxylic anhydride as a brown solid. MS (EI): m/z=395 $[M]^+$.

Intermediates a) tert-Butyl 3-(3-cyclopropyl-1,2,4-oxadiazol-5-yl)benzo[b]thiophen-2-ylcarbamate

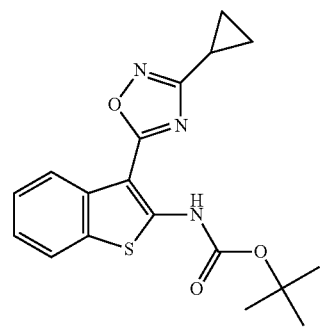 [SMILES: CC(C)(C)OC(=O)Nc1sc2ccccc2c1-c1nc(C2CC2)no1]

The title compound was prepared in analogy to example 5, intermediate a, from tert-butyl 3-((amino(cyclopropyl)methyleneaminooxy)carbonyl)benzo[b]thiophen-2-ylcarbamate with TBAF in THF. Light brown solid. MS (ESI): m/z=356.1 $[M-H]^-$.

b) tert-Butyl 3-((amino(cyclopropyl)methyleneaminooxy)carbonyl)benzo[b]thiophen-2-ylcarbamate

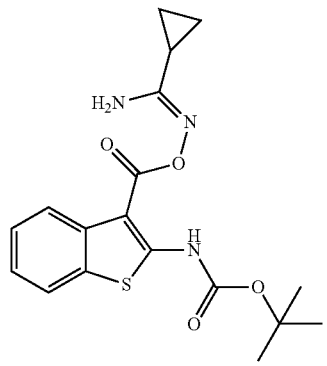 [SMILES: CC(C)(C)OC(=O)Nc1sc2ccccc2c1C(=O)O/N=C(\N)C1CC1]

The title compound was prepared in analogy to example 5, intermediate b, from 2-(tert-butoxycarbonylamino)benzo[b]thiophene-3-carboxylic acid (prepared in analogy to M. Kamata, WO2007013691) and (Z)—N'-hydroxycyclopropanecarboximidamide. Light brown solid. MS (ESI): m/z=376.1 $[M+H]^+$.

Example 7

(1RS,2SR)-2-[3-(3-Methyl-[1,2,4]oxadiazol-5-yl)-4,5,6,7-tetrahydro-benzo[b]thiophen-2-ylcarbamoyl]-cyclopentanecarboxylic acid

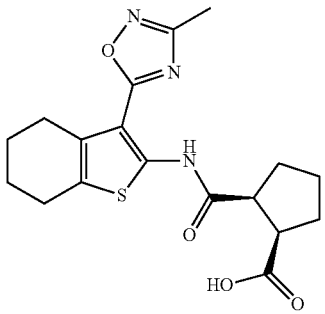 [SMILES: Cc1noc(-c2c(NC(=O)[C@H]3CCC[C@H]3C(=O)O)sc3c2CCCC3)n1]

The title compound was obtained in analogy to example 2, from 3-(3-methyl-[1,2,4]oxadiazol-5-yl)-4,5,6,7-tetrahydro-benzo[b]thiophen-2-ylamine (example 2, intermediate a) and cis-1,2-cyclopentanedicarboxylic anhydride as a light brown solid. MS (ESI): m/z=376.3 [M+H]$^+$.

Example 8

2-[3-(4-Methyl-thiazol-2-yl)-4,5,6,7-tetrahydro-benzo[b]thiophen-2-ylcarbamoyl]-cyclopent-1-enecarboxylic acid

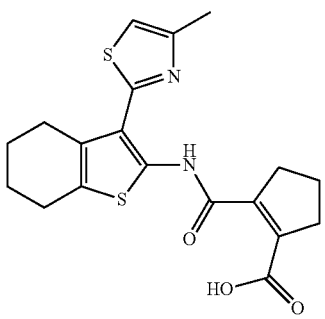 [SMILES: Cc1csc(-c2c(NC(=O)C3=C(C(=O)O)CCC3)sc3c2CCCC3)n1]

The title compound was obtained in analogy to example 2, from 3-(4-methyl-thiazol-2-yl)-4,5,6,7-tetrahydro-benzo[b]thiophen-2-ylamine and cyclopentene-1,2-dicarboxylic anhydride. Yellow solid. MS (ESI): m/z=389.09 [M+H]$^+$.

Intermediates a) 3-(4-Methyl-thiazol-2-yl)-4,5,6,7-tetrahydro-benzo[b]thiophen-2-ylamine

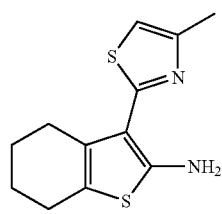 [SMILES: Cc1csc(-c2c(N)sc3c2CCCC3)n1]

To a solution of 2-cyclohexylidene-2-(4-methylthiazol-2-yl)acetonitrile (218 mg) in EtOH (12 mL) was added DBU (331 mg, 324 uL) and sulfur (32 mg) and the reaction mixture heated at 65° C. for 2 h. The reaction solution was cooled to RT and then partitioned between EtOAc and half saturated aqueous NH$_4$Cl solution. The layers were separated, the aqueous layer extracted with EtOAc. The combined organic layers were washed with brine, dried over MgSO$_4$ and concentrated in vacuo. The residue was purified by flash chromatography (EtOAc/n-heptane, gradient from 0 to 5%) to give the desired compound as a dark brown viscous oil (165 mg). MS (ESI): m/z=251.06 [M+H]$^+$.

b) 2-Cyclohexylidene-2-(4-methylthiazol-2-yl)acetonitrile

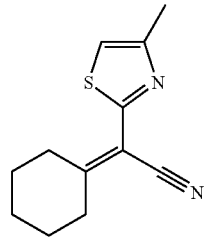

A suspension of cyclohexanone (0.981 g), 2-(4-methylthiazol-2-yl)acetonitrile (1.38 g) and NH$_4$OAc (1.54 g) in toluene (30 mL) was heated at reflux for 4.5 h until completion of reaction according to TLC. The reaction mixture was cooled to RT and partitioned between 2M aqueous KHCO$_3$ solution and EtOAc. The layers were separated, the aqueous layer extracted EtOAc. The combined organic layers were washed with brine, dried over MgSO$_4$, filtered and concentrated in vacuo. The residue was purified by flash chromatography (EtOAc/n-heptane, gradient from 0 to 15%) to give the desired compound as a light brown solid (1.92 g). MS (ESI): m/z=219.09 [M+H]$^+$.

Example 9

3-[3-(3-Methyl-[1,2,4]oxadiazol-5-yl)-4,5,6,7-tetrahydro-benzo[b]thiophen-2-ylcarbamoyl]-pyrazine-2-carboxylic acid

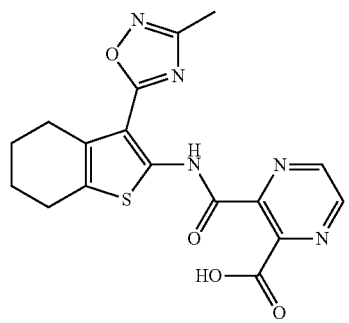 [SMILES: Cc1noc(-c2c(NC(=O)c3nccnc3C(=O)O)sc3c2CCCC3)n1]

The title compound was obtained in analogy to example 2, from 3-(3-methyl-[1,2,4]oxadiazol-5-yl)-4,5,6,7-tetrahydro-benzo[b]thiophen-2-ylamine (example 2, intermedi-

Example 10

(1RS,3SR)-2,2-Dimethyl-3-[3-(3-methyl-[1,2,4]oxadiazol-5-yl)-4,5,6,7-tetrahydro-benzo[b]thiophen-2-ylcarbamoyl]-cyclopropanecarboxylic acid

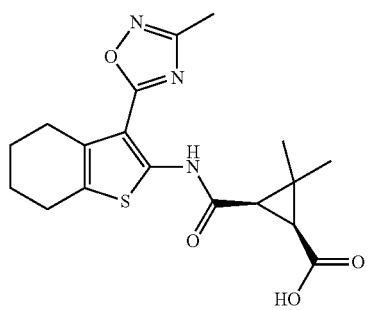 [SMILES: Cc1noc(-c2c(NC(=O)[C@@H]3[C@H](C(=O)O)C3(C)C)sc3c2CCCC3)n1]

The title compound was obtained in analogy to example 2, from 3-(3-methyl-[1,2,4]oxadiazol-5-yl)-4,5,6,7-tetrahydro-benzo[b]thiophen-2-ylamine (example 2, intermediate a) and carbonic anhydride as an off-white solid. MS (ESI): m/z=376.1 [M+H]+.

Example 11

3-[3-(3-Methyl-[1,2,4]oxadiazol-5-yl)-4,5,6,7-tetrahydro-benzo[b]thiophen-2-ylcarbamoyl]-bicyclo[2.2.2]oct-2-ene-2-carboxylic acid

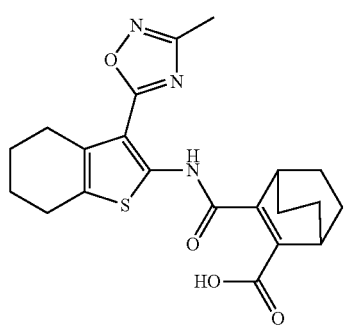 [SMILES: Cc1noc(-c2c(NC(=O)C3=C(C(=O)O)C4CCC3CC4)sc3c2CCCC3)n1]

The title compound was obtained in analogy to example 2, from 3-(3-methyl-[1,2,4]oxadiazol-5-yl)-4,5,6,7-tetrahydro-benzo[b]thiophen-2-ylamine (example 2, intermediate a) and bicyclo[2.2.2]oct-2-ene-2,3-dicarboxylic anhydride as a yellow solid. MS (ESI): m/z=414.1 [M+H]+.

Example 12

(1RS,2SR)-2-[3-(3-Methyl-[1,2,4]oxadiazol-5-yl)-4,5,6,7-tetrahydro-benzo[b]thiophen-2-ylcarbamoyl]-cyclohexanecarboxylic acid

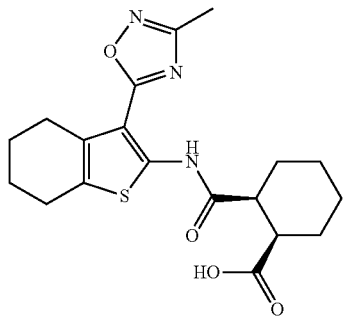 [SMILES: Cc1noc(-c2c(NC(=O)[C@H]3CCCC[C@H]3C(=O)O)sc3c2CCCC3)n1]

The title compound was obtained in analogy to example 2, from 3-(3-methyl-[1,2,4]oxadiazol-5-yl)-4,5,6,7-tetrahydro-benzo[b]thiophen-2-ylamine (example 2, intermediate a) and cis-1,2-cyclohexanedicarboxylic anhydride (CAS RN 13149-00-3). Light brown solid. MS (ESI): m/z=390.1 [M+H]+.

Example 13

2-[3-(4,4-Dimethyl-4,5-dihydro-oxazol-2-yl)-4,5,6,7-tetrahydro-benzo[b]thiophen-2-ylcarbamoyl]-cyclopent-1-enecarboxylic acid

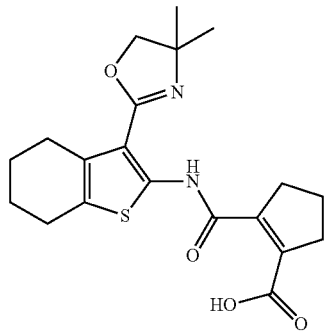 [SMILES: CC1(C)COC(c2c(NC(=O)C3=C(C(=O)O)CCC3)sc3c2CCCC3)=N1]

The title compound was obtained in analogy to example 5, from tert-butyl 3-(4,4-dimethyl-4,5-dihydrooxazol-2-yl)-4,5,6,7-tetrahydrobenzo[b]thiophen-2-ylcarbamate and cyclopentene-1,2-dicarboxylic anhydride as a yellow solid. MS (ESI): m/z=389.1 [M+H]+.

Intermediates a) tert-Butyl 3-(4,4-dimethyl-4,5-dihydrooxazol-2-yl)-4,5,6,7-tetrahydrobenzo[b]thiophen-2-ylcarbamate

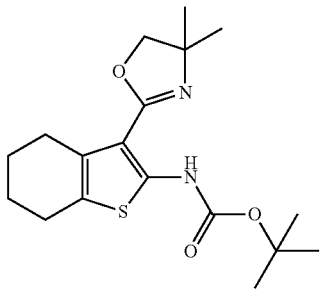 [SMILES: CC1(C)COC(c2c(NC(=O)OC(C)(C)C)sc3c2CCCC3)=N1]

tert-Butyl 3-(1-hydroxy-2-methylpropan-2-ylcarbamoyl)-4,5,6,7-tetrahydrobenzo[b]thiophen-2-ylcarbamate (180 mg) and Burgess reagent (120 mg) were dissolved in THF (4.88 mL) under argon and stirred at RT for 1 h until TLC (n-heptane/EtOAc: 1/1 v/v) indicated completion of the reaction. The reaction mixture was diluted with H$_2$O and extracted with EtOAc. The combined organic layers were washed with 2M aqueous KHCO$_3$ solution, dried over Na$_2$SO$_4$ and concentrated in vacuo. The residue was purified by flash chromatography (EtOAc/n-heptane, gradient from 0 to 25%) to give the desired product tert-butyl 3-(4,4-dimethyl-4,5-dihydrooxazol-2-yl)-4,5,6,7-tetrahydrobenzo[b]thiophen-2-ylcarbamate as white solid. MS (ESI): m/z=351.1 [M+H]$^+$.

b) tert-Butyl 3-(1-hydroxy-2-methylpropan-2-ylcarbamoyl)-4,5,6,7-tetrahydrobenzo[b]thiophen-2-ylcarbamate

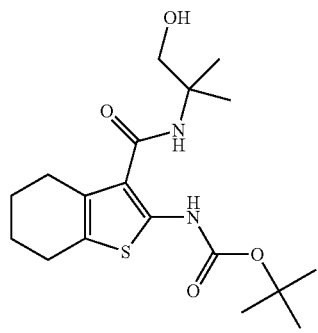 [SMILES: CC(C)(CO)NC(=O)c1c(NC(=O)OC(C)(C)C)sc2c1CCCC2]

2-tert-Butoxycarbonylamino-4,5,6,7-tetrahydro-benzo[b]thiophene-3-carboxylic acid (200 mg, prepared according Y. Huang et al., *Chem. Biol. Drug Des.* 2010, 76, 116-129) was dissolved in DMF (5 mL) at RT under argon. Then HATU (264 mg), DIPEA (88.7 mg) and 2-amino-2-methylpropan-1-ol (63.1 mg) were added and the reaction solution was stirred at RT for 4 h until TLC (n-heptane/EtOAc: 11) indicated completion of the reaction. The reaction mixture was diluted with H$_2$O and extracted with EtOAc. The combined organic layers were washed with 2M aqueous KHCO$_3$ solution, dried over Na$_2$SO$_4$ and concentrated in vacuo. The residue was purified by flash chromatography (EtOAc/n-heptane, gradient from 0 to 25%) to give the desired compound as a colorless solid (197 mg). MS (ESI): m/z=369.1 [M+H]$^+$.

Example 14

2-(3-Pyrimidin-2-yl-4,5,6,7-tetrahydro-benzo[b]thiophen-2-ylcarbamoyl)-cyclopent-1-enecarboxylic acid

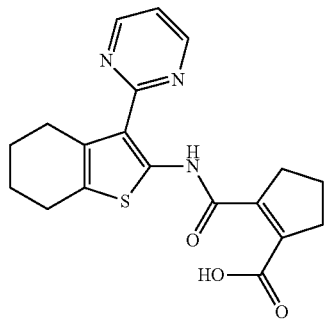 [SMILES: O=C(O)C1=C(C(=O)Nc2sc3c(c2-c2ncccn2)CCCC3)CCC1]

The title compound was obtained in analogy to example 2, from 3-(pyrimidin-2-yl)-4,5,6,7-tetrahydrobenzo[b]thiophen-2-amine and cyclopentene-1,2-dicarboxylic anhydride. Yellow solid. MS (ESI): m/z=370.1 [M+H]$^+$.

Intermediate 3-(Pyrimidin-2-yl)-4,5,6,7-tetrahydrobenzo[b]thiophen-2-amine

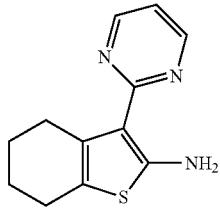 [SMILES: Nc1sc2c(c1-c1ncccn1)CCCC2]

Cyclohexanone (491 mg), dissolved in ethanol (15 mL) at RT under argon was treated with 2-(pyrimidin-2-yl)acetonitrile (596 mg), morpholine (1.09 g), sulfur (176 mg) and the mixture was then heated at 65° C. for 16 h until TLC indicated completion of the reaction. The reaction mixture was cooled to RT and partitioned between half saturated aqueous NH$_4$Cl solution and EtOAc. The layers were separated and the aqueous layer extracted with EtOAc. The combined organic layers were dried over Na$_2$SO$_4$ and then evaporated in vacuo. The residue was purified by flash chromatography (EtOAc/n-heptane, gradient from 0 to 20%) to give the desired compound as a brown solid (512 mg). MS (ESI): m/z=232.09 [M+H]$^+$.

Example 15

2-(3-[1,2,4]Oxadiazol-3-yl-4,5,6,7-tetrahydro-benzo[b]thiophen-2-ylcarbamoyl)-cyclopent-1-enecarboxylic acid

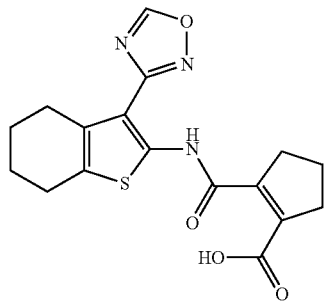 [SMILES: O=C(O)C1=C(C(=O)Nc2sc3c(c2-c2ncon2)CCCC3)CCC1]

The title compound was obtained in analogy to example 2, from 3-(1,2,4-oxadiazol-3-yl)-4,5,6,7-tetrahydrobenzo[b]thiophen-2-amine and cyclopentene-1,2-dicarboxylic anhydride as a yellow solid. MS (ESI): m/z=360.1 [M+H]$^+$.

Intermediates a) 3-(1,2,4-Oxadiazol-3-yl)-4,5,6,7-tetrahydrobenzo[b]thiophen-2-amine

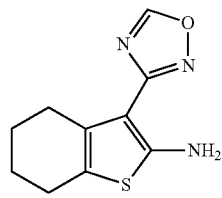 [SMILES: Nc1sc2c(c1-c1ncon1)CCCC2]

The title compound was obtained in analogy to example 14, intermediate a, from cyclohexanone and 2-(1,2,4-oxadiazol-3-yl)acetonitrile as a yellow solid. MS (ESI): m/z=222.06 [M+H]$^+$.

b) 2-(1,2,4-Oxadiazol-3-yl)acetonitrile

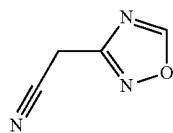

3-(Chloromethyl)-1,2,4-oxadiazole (1.46 g) was dissolved in DMSO (40 mL) at RT under argon, treated with sodium cyanide (755 mg) and the reaction mixture was stirred at RT for 4.5 h. The reaction mixture was then partitioned between H$_2$O and EtOAc, the organic layer was extracted with EtOAc, the combined organic layers were dried over Na$_2$SO$_4$ and then evaporated in vacuo to give the desired compound as a yellow liquid (0.949 g), which was used without further purification in the next reaction step. MS (EI): m/z=109 [M]$^+$.

Example 16

2-(3-Pyrimidin-2-yl-4,5,6,7-tetrahydro-benzo[b]thiophen-2-ylcarbamoyl)-cyclohex-1-enecarboxylic acid

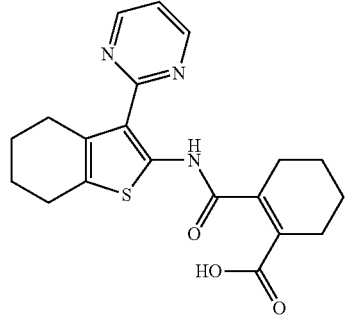 [SMILES: O=C(O)C1=C(C(=O)Nc2sc3c(c2-c2ncccn2)CCCC3)CCCC1]

The title compound was obtained in analogy to example 3, from 2-(3-(pyrimidin-2-yl)-4,5,6,7-tetrahydrobenzo[b]thiophen-2-yl)-4,5,6,7-tetrahydro-1H-isoindole-1,3(2H)-dione and sodium hydroxide as a light yellow solid. MS (ESI): m/z=384.1 [M+H]$^+$.

Intermediate 2-(3-(Pyrimidin-2-yl)-4,5,6,7-tetrahydrobenzo[b]thiophen-2-yl)-4,5,6,7-tetrahydro-1H-isoindole-1,3(2H)-dione

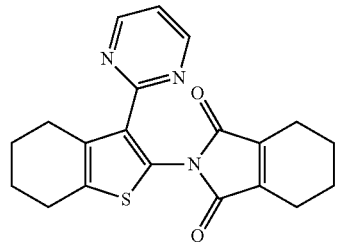 [SMILES: O=C1C2=C(CCCC2)C(=O)N1c1sc2c(c1-c1ncccn1)CCCC2]

The title compound was obtained in analogy to example 3, from 3-(pyrimidin-2-yl)-4,5,6,7-tetrahydrobenzo[b]thiophen-2-amine (example 14, intermediate) and 3,4,5,6-tetrahydrophthalic anhydride as a brown solid. MS (ESI): m/z=366.1 [M+H]$^+$.

Example 17

3-(3-Pyrimidin-2-yl-4,5,6,7-tetrahydro-benzo[b]thiophen-2-ylcarbamoyl)-pyrazine-2-carboxylic acid

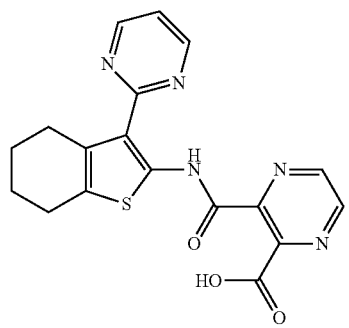 [SMILES: O=C(O)c1nccnc1C(=O)Nc1sc2c(c1-c1ncccn1)CCCC2]

The title compound was obtained in analogy to example 2, from 3-(pyrimidin-2-yl)-4,5,6,7-tetrahydrobenzo[b]thiophen-2-amine (example 14, intermediate) and 2,3-pyridazinedicarboxylic anhydride as a yellow solid. MS (ESI): m/z=382.09 [M+H]+.

Example 18

(1RS,6SR)-6-[3-(3-Methyl-[1,2,4]oxadiazol-5-yl)-4,5,6,7-tetrahydro-benzo[b]thiophen-2-ylcarbamoyl]-cyclohex-3-enecarboxylic acid

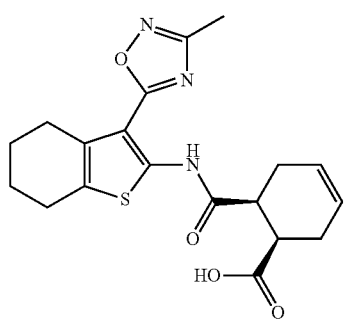 [SMILES: Cc1noc(-c2c(NC(=O)[C@H]3CC=CC[C@H]3C(=O)O)sc3c2CCCC3)n1]

The title compound was obtained in analogy to example 2, from 3-(3-methyl-[1,2,4]oxadiazol-5-yl)-4,5,6,7-tetrahydro-benzo[b]thiophen-2-ylamine (example 2, intermediate a) and cis-1,2,3,6-tetrahydrophthalic anhydride as an off-white solid. MS (ESI): m/z=388.1 [M+H]+.

Example 19

3-(3-Pyrimidin-2-yl-4,5,6,7-tetrahydro-benzo[b]thiophen-2-ylcarbamoyl)-bicyclo[2.2.2]oct-2-ene-2-carboxylic acid

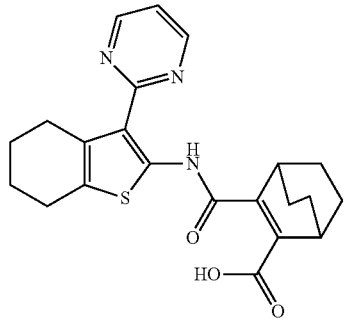 [SMILES: O=C(O)C1=C(C(=O)Nc2sc3c(c2-c2ncccn2)CCCC3)C2CCC1CC2]

The title compound was obtained in analogy to example 2, from 3-(pyrimidin-2-yl)-4,5,6,7-tetrahydrobenzo[b]thiophen-2-amine (example 14, intermediate) and bicyclo[2.2.2]oct-2-ene-2,3-dicarboxylic anhydride (CAS RN 151813-29-5) as a yellow solid. MS (ESI): m/z=410.1 [M+H]+.

Example 20

3-(3-[1,2,4]Oxadiazol-3-yl-4,5,6,7-tetrahydro-benzo[b]thiophen-2-ylcarbamoyl)-bicyclo[2.2.2]oct-2-ene-2-carboxylic acid

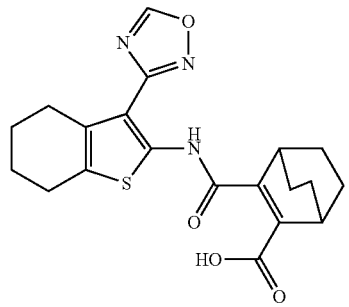 [SMILES: O=C(O)C1=C(C(=O)Nc2sc3c(c2-c2ncon2)CCCC3)C2CCC1CC2]

The title compound was obtained in analogy to example 2, from 3-(1,2,4-oxadiazol-3-yl)-4,5,6,7-tetrahydrobenzo[b]thiophen-2-amine (example 15, intermediate a) and bicyclo[2.2.2]oct-2-ene-2,3-dicarboxylic anhydride (CAS RN 151813-29-5) as a yellow solid. MS (ESI): m/z=400.1 [M+H]+.

Example 21

2,2,3,3-Tetrafluoro-N-[3-(3-methyl-[1,2,4]oxadiazol-5-yl)-4,5,6,7-tetrahydro-benzo[b]thiophen-2-yl]-succinamic acid

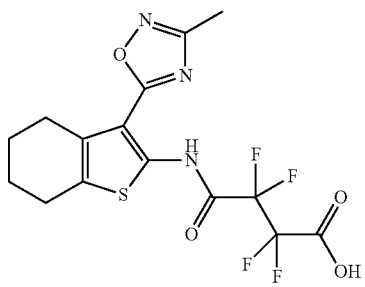 [SMILES: Cc1noc(-c2c(NC(=O)C(F)(F)C(F)(F)C(=O)O)sc3c2CCCC3)n1]

The title compound was obtained in analogy to example 2, from 3-(3-methyl-[1,2,4]oxadiazol-5-yl)-4,5,6,7-tetrahydro-benzo[b]thiophen-2-ylamine (example 2, intermediate a) and tetrafluorosuccinic anhydride as an off-white solid. MS (ESI): m/z=406.0 [M−H]−.

Example 22

(R)-1-[3-(3-Methyl-[1,2,4]oxadiazol-5-yl)-4,5,6,7-tetrahydro-benzo[b]thiophen-2-ylcarbamoyl]-pyrrolidine-2-carboxylic acid

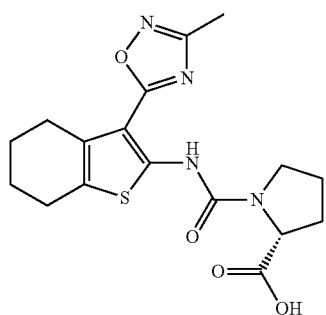 [SMILES: Cc1noc(-c2c(NC(=O)N3CCC[C@@H]3C(=O)O)sc3c2CCCC3)n1]

5-(2-Isocyanato-4,5,6,7-tetrahydrobenzo[b]thiophen-3-yl)-3-methyl-1,2,4-oxadiazole (111 mg) was suspended in $CH_2Cl_2$ (4 mL) at RT under argon, $NEt_3$ (43 mg, 58.9 μL) was added followed by (R)-pyrrolidine-2-carboxylic acid (48.9 mg) and the mixture was stirred for 22 h at RT. The reaction mixture was then partitioned between 3M aqueous HCl and $CH_2Cl_2$, the layers were separated and the aqueous layer was extracted with $CH_2Cl_2$. The combined organic layers were dried over $Na_2SO_4$ and then concentrated in vacuo. The residue was purified by flash chromatography (MeOH/$CH_2Cl_2$, gradient from 0 to 5%) to give the desired compound as a light brown solid (84 mg). MS (ESI): m/z=377.1 [M+H]$^+$.

Intermediate 5-(2-Isocyanato-4,5,6,7-tetrahydrobenzo[b]thiophen-3-yl)-3-methyl-1,2,4-oxadiazole

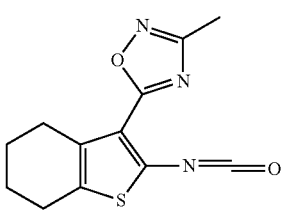 [SMILES: Cc1noc(-c2c(N=C=O)sc3c2CCCC3)n1]

3-(3-Methyl-[1,2,4]oxadiazol-5-yl)-4,5,6,7-tetrahydro-benzo[b]thiophen-2-ylamine (example 2, intermediate a; 100 mg) was dissolved in THF (4 mL) at RT under argon and then treated with bis(trichloromethyl) carbonate (101 mg). The suspension was then heated at 70° C. for 2 h until TLC indicated completion of the reaction. The mixture was then cooled to RT and the solvent was removed in vacuo to give the desired compound as a light brown solid. MS (ESI): m/z=262.1 [M+H]$^+$.

Example 23

3-[3-(5-tert-Butyl-[1,2,4]oxadiazol-3-yl)-4,5,6,7-tetrahydro-benzo[b]thiophen-2-ylcarbamoyl]-bicyclo[2.2.2]oct-2-ene-2-carboxylic acid

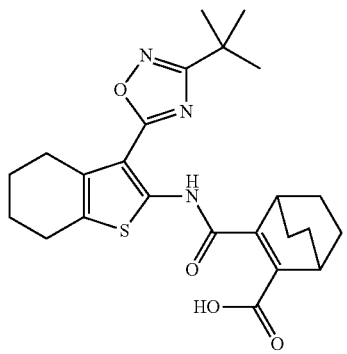 [SMILES: CC(C)(C)c1noc(-c2c(NC(=O)C3=C(C(=O)O)C4CCC3CC4)sc3c2CCCC3)n1]

The title compound was obtained in analogy to example 2, from 3-(5-tert-butyl-1,2,4-oxadiazol-3-yl)-4,5,6,7-tetrahydrobenzo[b]thiophen-2-amine and bicyclo[2.2.2]oct-2-ene-2,3-dicarboxylic anhydride as a yellow solid. MS (ESI): m/z=456.19 [M+H]$^+$.

Intermediates a) 3-(5-tert-Butyl-1,2,4-oxadiazol-3-yl)-4,5,6,7-tetrahydrobenzo[b]thiophen-2-amine

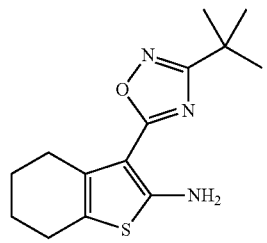 [SMILES: CC(C)(C)c1noc(-c2c(N)sc3c2CCCC3)n1]

The title compound was obtained in analogy to example 14, intermediate a, from cyclohexanone and 2-(5-tert-butyl-1,2,4-oxadiazol-3-yl)acetonitrile as a yellow solid. MS (ESI): m/z=278.3 [M+H]$^+$.

b) 2-(5-tert-Butyl-1,2,4-oxadiazol-3-yl)acetonitrile

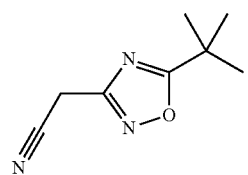

The title compound was obtained in analogy to example 15, intermediate b, from 5-tert-butyl-3-(chloromethyl)-1,2,4-oxadiazole and sodium cyanide as a colorless liquid. MS (EI): m/z=165 [M]$^+$.

Example 24

2-[3-(5-tert-Butyl-[1,2,4]oxadiazol-3-yl)-4,5,6,7-tetrahydro-benzo[b]thiophen-2-ylcarbamoyl]-cyclopent-1-enecarboxylic acid

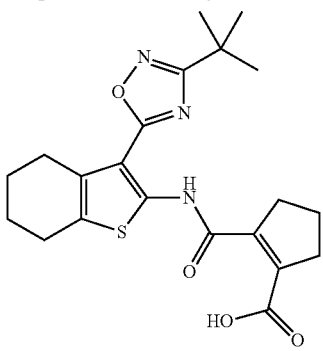 [SMILES: CC(C)(C)c1noc(-c2c(NC(=O)C3=C(C(=O)O)CCC3)sc3c2CCCC3)n1]

The title compound was obtained in analogy to example 2, from 3-(5-tert-butyl-1,2,4-oxadiazol-3-yl)-4,5,6,7-tetrahydrobenzo[b]thiophen-2-amine (example 23, intermediate a) and cyclopentene-1,2-dicarboxylic anhydride as a yellow solid. MS (ESI): m/z=416.1 [MH]$^+$.

Example 25

2-(5,5-Dimethyl-3-pyrimidin-2-yl-4,5,6,7-tetrahydro-benzo[b]thiophen-2-ylcarbamoyl)-cyclopent-1-enecarboxylic acid

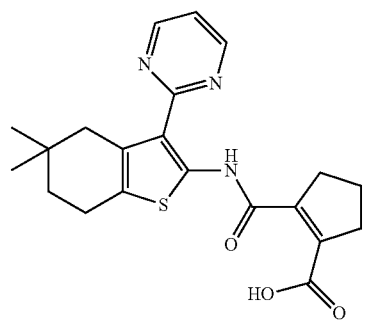 [SMILES: CC1(C)CCc2sc(NC(=O)C3=C(C(=O)O)CCC3)c(-c3ncccn3)c2C1]

The title compound was obtained in analogy to example 2, from 5,5-dimethyl-3-(pyrimidin-2-yl)-4,5,6,7-tetrahydrobenzo[b]thiophen-2-amine and cyclopentene-1,2-dicarboxylic anhydride as a yellow solid. MS (ESI): m/z=398.1 [M+H]$^+$.

Intermediate 5,5-Dimethyl-3-(pyrimidin-2-yl)-4,5,6,7-tetrahydrobenzo[b]thiophen-2-amine

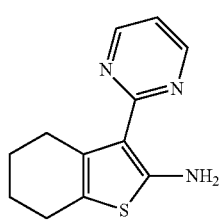 [SMILES: Nc1sc2c(c1-c1ncccn1)CCCC2]

The title compound was obtained in analogy to example 14, intermediate, from 3,3-dimethylcyclohexanone and 2-(pyrimidin-2-yl)acetonitrile and sulfur as a viscous oil. MS (EI): m/z=259 [M]$^+$.

Example 26

2-[5,5-Dimethyl-3-(4-methyl-thiazol-2-yl)-4,5,6,7-tetrahydro-benzo[b]thiophen-2-ylcarbamoyl]-cyclopent-1-enecarboxylic acid

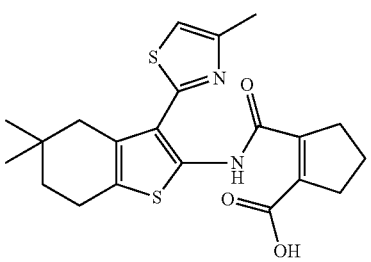 [SMILES: Cc1csc(-c2c(NC(=O)C3=C(C(=O)O)CCC3)sc3c2CC(C)(C)CC3)n1]

The title compound was obtained in analogy to example 2, from 5,5-dimethyl-3-(4-methylthiazol-2-yl)-4,5,6,7-tetrahydrobenzo[b]thiophen-2-amine and cyclopentene-1,2-dicarboxylic anhydride as a yellow solid. MS (ESI): m/z=417.1 [MH]$^+$.

Intermediate 5,5-Dimethyl-3-(4-methylthiazol-2-yl)-4,5,6,7-tetrahydrobenzo[b]thiophen-2-amine

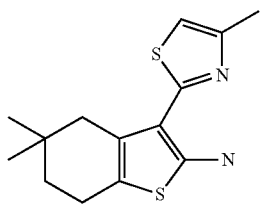

The title compound was obtained in analogy to example 14, intermediate, from 3,3-dimethylcyclohexanone and 2-(4-methylthiazol-2-yl)acetonitrile and sulfur as an orange viscous oil. MS (ESI): m/z=279.1 [M+H]$^+$.

Example 27

(R)-1-[3-(3-Cyclopropyl-[1,2,4]oxadiazol-5-yl)-4,5,6,7-tetrahydro-benzo[b]thiophen-2-ylcarbamoyl]-pyrrolidine-2-carboxylic acid

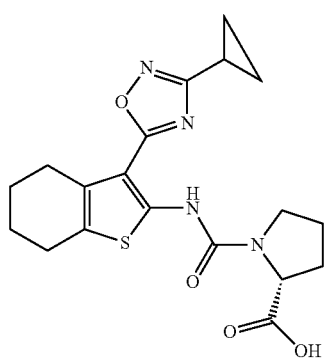 [SMILES: O=C(O)[C@H]1CCCN1C(=O)Nc1sc2c(c1-c1nc(C3CC3)no1)CCCC2]

3-Cyclopropyl-5-(2-isocyanato-4,5,6,7-tetrahydrobenzo[b]thiophen-3-yl)-1,2,4-oxadiazole (101 mg) was suspended in CH$_2$Cl$_2$ (3.52 mL) at RT under argon, NEt$_3$ (35.6 mg, 48.7 µl) was added followed by (R)-pyrrolidine-2-carboxylic acid (40.5 mg, 352 µmol) and the mixture was then stirred at RT for 16 h. The reaction mixture was then partitioned between 3M aqueous HCl and CH$_2$Cl$_2$, the layers were separated and the aqueous layer was extracted with CH$_2$Cl$_2$. The combined organic layers were dried over Na$_2$SO$_4$ and then concentrated in vacuo. The residue was purified by flash chromatography (MeOH/CH$_2$Cl$_2$, gradient from 0 to 5%) to give the desired product as a light yellow solid (68 mg). MS (ESI): m/z=403.1 [M+H]$^+$.

Intermediates a) 3-Cyclopropyl-5-(2-isocyanato-4,5,6,7-tetrahydrobenzo[b]thiophen-3-yl)-1,2,4-oxadiazole

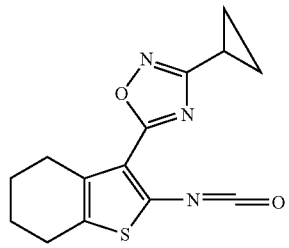 [SMILES: O=C=Nc1sc2c(c1-c1nc(C3CC3)no1)CCCC2]

3-(3-Cyclopropyl-1,2,4-oxadiazol-5-yl)-4,5,6,7-tetrahydrobenzo[b]thiophen-2-amine (294 mg) was dissolved in THF (11.2 mL) at RT under argon and then treated with bis(trichloromethyl) carbonate (267 mg, 900 µmol). The suspension was then heated at reflux for 90 min. until TLC indicated completion of the reaction. The mixture was then cooled to RT and the solvent was removed in vacuo to give the desired compound as an off-white solid. MS (ESI): m/z=288.1 [M+H]$^+$.

b) 3-(3-Cyclopropyl-1,2,4-oxadiazol-5-yl)-4,5,6,7-tetrahydrobenzo[b]thiophen-2-amine

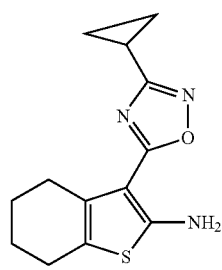 [SMILES: Nc1sc2c(c1-c1nc(C3CC3)no1)CCCC2]

tert-Butyl 3-(3-cyclopropyl-1,2,4-oxadiazol-5-yl)-4,5,6,7-tetrahydrobenzo[b]thiophen-2-ylcarbamate (459 mg, example 5, intermediate a) was dissolved in CH$_2$Cl$_2$ (10 mL) at RT under argon, treated with TFA (14.5 g, 9.78 mL) and the solution was then stirred at RT for 40 min. until TLC indicated completion of reaction (n-heptane/EtOAc 1/1 v/v). The reaction was then concentrated in vacuo, the residue taken up in EtOAc which was then washed with 2M KHCO$_3$ solution and dried over Na$_2$SO$_4$. The solvent was removed in vacuo and the residue purified by flash chromatography (EtOAc/n-heptane gradient from 0 to 10%) to give the title compound as light brown solid (300 mg). MS (ESI): m/z=262.1 [M+H]$^+$.

Example 28

(1RS,6SR)-6-[6,6-Dimethyl-3-(4-methyl-thiazol-2-yl)-4,5,6,7-tetrahydro-benzo[b]thiophen-2-ylcarbamoyl]-cyclohex-3-enecarboxylic acid

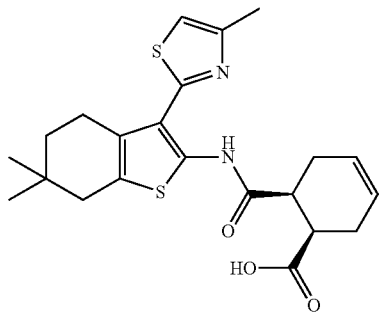 [SMILES: Cc1csc(-c2c(NC(=O)[C@H]3CC=CC[C@H]3C(=O)O)sc3c2CCC(C)(C)C3)n1]

The title compound was obtained in analogy to example 2, from 6,6-dimethyl-3-(4-methylthiazol-2-yl)-4,5,6,7-tetrahydrobenzo[b]thiophen-2-amine and cis-1,2,3,6-tetrahydrophthalic anhydride as an off-white solid. MS (ESI): m/z=431.1 [M+H]$^+$.

Intermediate 6,6-Dimethyl-3-(4-methylthiazol-2-yl)-4,5,6,7-tetrahydrobenzo[b]thiophen-2-amine

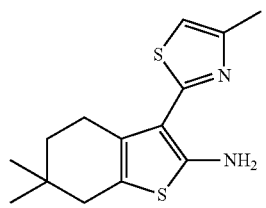

The title compound was obtained in analogy to example 14, intermediate, from 4,4-dimethylcyclohexanone and 2-(4-methylthiazol-2-yl)acetonitrile and sulfur as a viscous orange oil. MS (ESI): m/z=279.09 [M+H]$^+$.

Example 29

2-[6,6-Dimethyl-3-(4-methyl-thiazol-2-yl)-4,5,6,7-tetrahydro-benzo[b]thiophen-2-ylcarbamoyl]-cyclopent-1-enecarboxylic acid

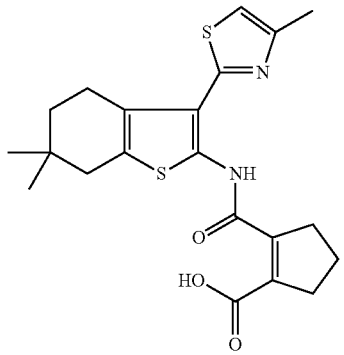 [SMILES: Cc1csc(-c2c(NC(=O)C3=C(C(=O)O)CCC3)sc3c2CCC(C)(C)C3)n1]

The title compound was obtained in analogy to example 2, from 6,6-dimethyl-3-(4-methylthiazol-2-yl)-4,5,6,7-tetrahydrobenzo[b]thiophen-2-amine (example 28, intermediate) and cyclopentene-1,2-dicarboxylic anhydride as a yellow solid. MS (ESI): m/z=417.1 [M+H]$^+$.

Example 30

{1-[3-(3-Cyclopropyl-[1,2,4]oxadiazol-5-yl)-4,5,6,7-tetrahydro-benzo[b]thiophen-2-ylcarbamoyl]-pyrrolidin-2-yl}-acetic acid

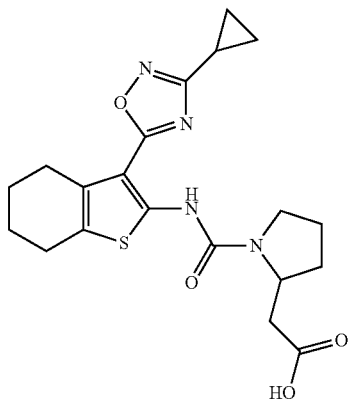 [SMILES: O=C(O)CC1CCCN1C(=O)Nc1sc2c(c1-c1nc(C3CC3)no1)CCCC2]

{1-[3-(3-Cyclopropyl-[1,2,4]oxadiazol-5-yl)-4,5,6,7-tetrahydro-benzo[b]thiophen-2-ylcarbamoyl]-pyrrolidin-2-yl}-acetic acid ethyl ester (280 mg, 630 μmol) in EtOH (9 mL) was treated at RT under argon with 3M NaOH (840 μl) and the reaction mixture was heated at 70° C. for 16 h until TLC indicated completion of reaction. The reaction mixture was then cooled to RT and concentrated in vacuo. The residue was partitioned between diluted aqueous HCl (pH 1) and CH$_2$Cl$_2$. The layers were separated, the organic layer extracted with CH$_2$Cl$_2$. The combined organic layers were dried over Na$_2$SO$_4$, and then concentrated in vacuo. The residue was purified by flash chromatography (MeOH/CH$_2$Cl$_2$, gradient from 0 to 5%) to give the desired compound as an amorphous brown solid (178 mg). MS (ESI): m/z=417.3 [M+H]$^+$.

Intermediate a) {1-[3-(3-Cyclopropyl-[1,2,4]oxadiazol-5-yl)-4,5,6,7-tetrahydro-benzo[b]thiophen-2-ylcarbamoyl]-pyrrolidin-2-yl}-acetic acid ethyl ester

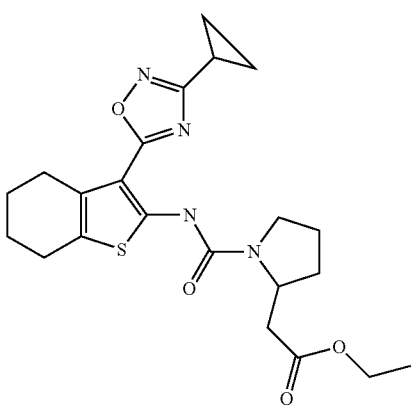 [SMILES: CCOC(=O)CC1CCCN1C(=O)Nc1sc2c(c1-c1nc(C3CC3)no1)CCCC2]

The title compound was obtained in analogy to example 27, from 3-cyclopropyl-5-(2-isocyanato-4,5,6,7-tetrahydrobenzo[b]thiophen-3-yl)-1,2,4-oxadiazole (example 27, intermediate a) and ethyl pyrrolidin-2-ylacetate hydrochloride as a light brown solid. MS (ESI): m/z=445.41 [M+H]$^+$.

Example 31

(R)-1-[3-(3-Cyclopropyl-[1,2,4]oxadiazol-5-yl)-4,5,6,7-tetrahydro-benzo[b]thiophen-2-ylcarbamoyl]-piperidine-2-carboxylic acid

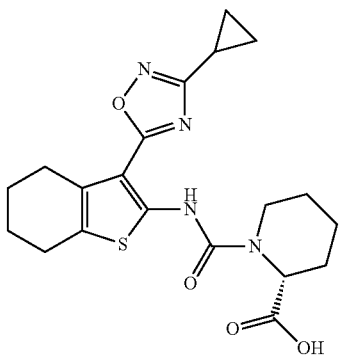 [SMILES: O=C(O)[C@H]1CCCCN1C(=O)Nc1sc2c(c1-c1nc(C3CC3)no1)CCCC2]

The title compound was obtained in analogy to example 27, from 3-cyclopropyl-5-(2-isocyanato-4,5,6,7-tetrahydrobenzo[b]thiophen-3-yl)-1,2,4-oxadiazole (example 27, intermediate a) and (R)-piperidine-2-carboxylic acid as an off-white solid. MS (ESI): m/z=417.3 [M+H]$^+$.

Example 32

(R)-1-[3-(3-Cyclopropyl-[1,2,4]oxadiazol-5-yl)-4,5,6,7-tetrahydro-benzo[b]thiophen-2-ylcarbamoyl]-azetidine-2-carboxylic acid

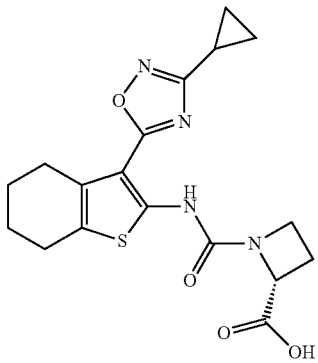 [SMILES: O=C(O)[C@H]1CCN1C(=O)Nc1sc2c(c1-c1nc(C3CC3)no1)CCCC2]

The title compound was obtained in analogy to example 27, from 3-cyclopropyl-5-(2-isocyanato-4,5,6,7-tetrahydrobenzo[b]thiophen-3-yl)-1,2,4-oxadiazole (example 27, intermediate a) and (R)-azetidine-2-carboxylic acid as an off-white solid. MS (ESI): m/z=389.2 [M+H]+.

Example 33

3-[3-(3-Cyclopropyl-[1,2,4]oxadiazol-5-yl)-4,5,6,7-tetrahydro-benzo[b]thiophen-2-ylcarbamoyl]-bicyclo[2.2.2]oct-2-ene-2-carboxylic acid

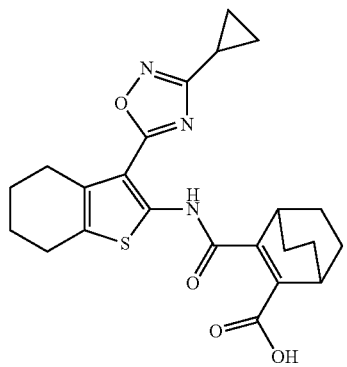 [SMILES: O=C(O)C1=C(C(=O)Nc2sc3c(c2-c2nc(C4CC4)no2)CCCC3)C2CCC1CC2]

The title compound was obtained in analogy to example 2, from 3-(3-cyclopropyl-1,2,4-oxadiazol-5-yl)-4,5,6,7-tetrahydrobenzo[b]thiophen-2-amine (example 27, intermediate b) and bicyclo[2.2.2]oct-2-ene-2,3 dicarboxylic anhydride as a yellow solid. MS (ESI): m/z=440.3 [M+H]+.

Example 34

(1RS,2SR)-2-[3-(3-Cyclopropyl-[1,2,4]oxadiazol-5-yl)-4,5,6,7-tetrahydro-benzo[b]thiophen-2-ylcarbamoyl]-cyclohexanecarboxylic acid

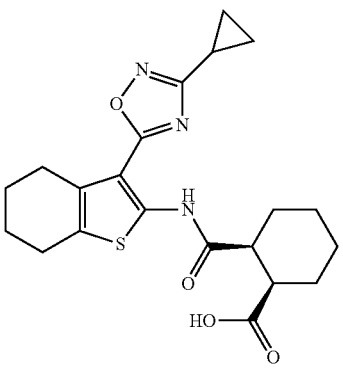 [SMILES: O=C(Nc1sc2c(c1-c1nc(C3CC3)no1)CCCC2)[C@H]1CCCC[C@H]1C(=O)O]

The title compound was obtained in analogy to example 2, from 3-(3-cyclopropyl-1,2,4-oxadiazol-5-yl)-4,5,6,7-tetrahydrobenzo[b]thiophen-2-amine (example 27, intermediate b) and cis-1,2-cyclohexanedicarboxylic anhydride as a white solid. MS (ESI): m/z=416.3 [M+H]+.

Example 35

3-[6,6-Dimethyl-3-(4-methyl-thiazol-2-yl)-4,5,6,7-tetrahydro-benzo[b]thiophen-2-ylcarbamoyl]-bicyclo[2.2.2]oct-5-ene-2-carboxylic acid

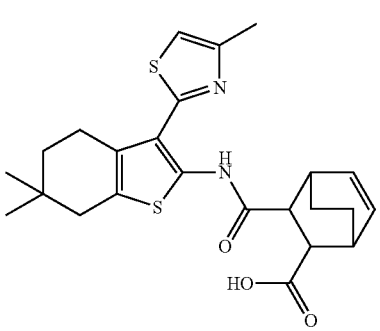 [SMILES: Cc1csc(-c2c(NC(=O)C3C4C=CC(CC4)C3C(=O)O)sc3c2CCC(C)(C)C3)n1]

The title compound was obtained in analogy to example 2, from 6,6-dimethyl-3-(4-methylthiazol-2-yl)-4,5,6,7-tetrahydrobenzo[b]thiophen-2-amine (example 28, intermediate b) and endo-bicyclo[2.2.2]oct-5-ene-2,3-dicarboxylic anhydride as an off-white solid MS (ESI): m/z=457.1 [M+H]+.

Example 36

(1SR,2SR)-2-[6,6-Dimethyl-3-(4-methyl-thiazol-2-yl)-4,5,6,7-tetrahydro-benzo[b]thiophen-2-ylcarbamoyl]-cyclohexanecarboxylic acid

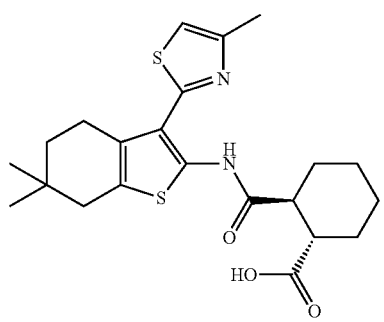 [SMILES: Cc1csc(-c2c(NC(=O)[C@H]3CCCC[C@@H]3C(=O)O)sc3c2CCC(C)(C)C3)n1]

The title compound was obtained in analogy to example 2, from 6,6-dimethyl-3-(4-methylthiazol-2-yl)-4,5,6,7-tetrahydrobenzo[b]thiophen-2-amine (example 28, intermediate) and trans1,2-cyclohexanedicarboxylic anhydride (CAS RN 14166-21-3) as an off-white solid. MS (ESI): m/z=433.1 [M+H]$^+$.

Example 37

(1SR,2SR)-2-[3-(3-Methyl-[1,2,4]oxadiazol-5-yl)-4,5,6,7-tetrahydro-benzo[b]thiophen-2-ylcarbamoyl]-cyclohexanecarboxylic acid

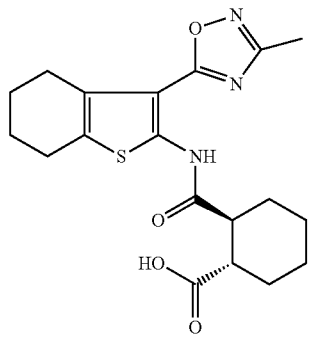 [SMILES: Cc1noc(-c2c(NC(=O)[C@H]3CCCC[C@@H]3C(=O)O)sc3c2CCCC3)n1]

The title compound was obtained in analogy to example 2, from 3-(3-methyl-[1,2,4]oxadiazol-5-yl)-4,5,6,7-tetrahydro-benzo[b]thiophen-2-ylamine (example 2, intermediate a) and trans1,2-cyclohexanedicarboxylic anhydride as a white solid. MS (ESI): m/z=390.1 [M+H$^+$].

Example 38

N-[3-(3-Methyl-[1,2,4]oxadiazol-5-yl)-4,5,6,7-tetrahydro-benzo[b]thiophen-2-yl]-phthalamic acid

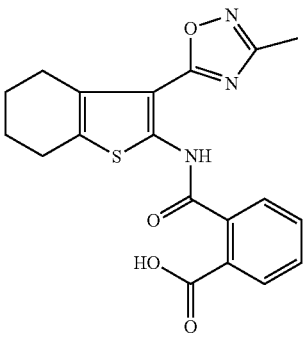 [SMILES: Cc1noc(-c2c(NC(=O)c3ccccc3C(=O)O)sc3c2CCCC3)n1]

The title compound was obtained in analogy to example 2, from 3-(3-methyl-[1,2,4]oxadiazol-5-yl)-4,5,6,7-tetrahydro-benzo[b]thiophen-2-ylamine (example 2, intermediate a) and phthalic anhydride as a light yellow solid. MS (ESI): m/z=384.1 [M+H]$^+$.

Example 39

6-[6-Methoxy-3-(4-methyl-thiazol-2-yl)-4,5,6,7-tetrahydro-benzo[b]thiophen-2-ylcarbamoyl]-cyclohex-3-enecarboxylic acid

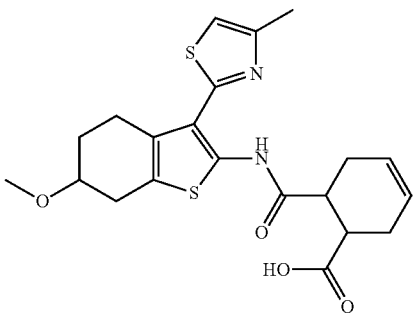 [SMILES: COC1CCc2c(sc(NC(=O)C3CC=CCC3C(=O)O)c2-c2nc(C)cs2)C1]

The title compound was obtained in analogy to example 2, from 6-methoxy-3-(4-methylthiazol-2-yl)-4,5,6,7-tetrahydrobenzo[b]thiophen-2-amine and cis-1,2,3,6-tetrahydrophthalic anhydride as a light brown solid. MS (ESI): m/z=433.1 [M+H]$^+$.

Intermediate

6-Methoxy-3-(4-methylthiazol-2-yl)-4,5,6,7-tetrahydrobenzo[b]thiophen-2-amine

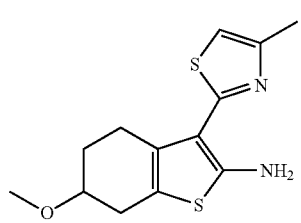

The title compound was obtained in analogy to example 14, intermediate, from 4-methoxycyclohexanone, 2-(4-methylthiazol-2-yl)acetonitrile and sulfur as a viscous brown oil. MS (ESI): m/z=281.2 [M+H]+.

Example 40

2-[3-(4-Methyl-thiazol-2-yl)-5,6,7,8-tetrahydro-4H-cyclohepta[b]thiophen-2-ylcarbamoyl]-cyclopent-1-enecarboxylic acid

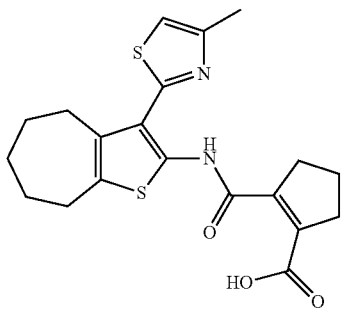 [SMILES: Cc1csc(-c2c(NC(=O)C3=C(C(=O)O)CCC3)sc3c2CCCCC3)n1]

The title compound was obtained in analogy to example 2, from 3-(4-methylthiazol-2-yl)-5,6,7,8-tetrahydro-4H-cyclohepta[b]thiophen-2-amine and 1-cyclopentene-1,2-dicarboxylic anhydride as a yellow solid. MS (ESI): m/z=403.1 [M+H]+.

Intermediates a) 3-(4-Methylthiazol-2-yl)-5,6,7,8-tetrahydro-4H-cyclohepta[b]thiophen-2-amine

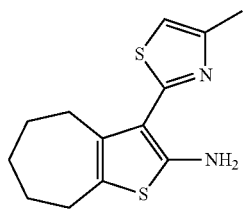 [SMILES: Cc1csc(-c2c(N)sc3c2CCCCC3)n1]

The title compound was obtained in analogy to example 8, intermediate a, from 2-cycloheptylidene-2-(4-methylthiazol-2-yl)acetonitrile and sulfur as a yellow solid. MS (ESI): m/z=265.1 [M+H]+.

b) 2-Cycloheptylidene-2-(4-methylthiazol-2-yl)acetonitrile

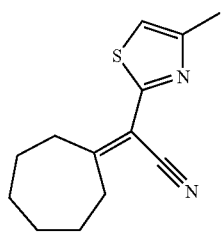 [SMILES: Cc1csc(C(C#N)=C2CCCCCC2)n1]

The title compound was obtained in analogy to example 8, intermediate b, from cycloheptanone and 2-(4-methylthiazol-2-yl)acetonitrile as a viscous oil. MS (ESI): m/z=233.1 [M+H]+.

Example 41

(3-[3-(3-Methyl-[1,2,4]oxadiazol-5-yl)-4,5,6,7-tetrahydro-benzo[b]thiophen-2-ylcarbamoyl]-bicyclo[2.2.2]oct-5-ene-2-carboxylic acid

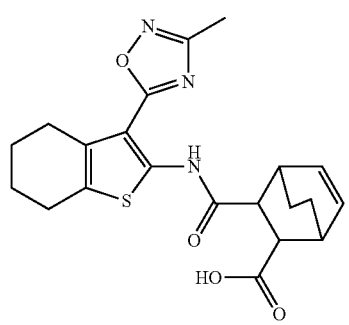 [SMILES: Cc1noc(-c2c(NC(=O)C3C4C=CC(CC4)C3C(=O)O)sc3c2CCCC3)n1]

The title compound was obtained in analogy to example 2, from 3-(3-methyl-[1,2,4]oxadiazol-5-yl)-4,5,6,7-tetrahydro-benzo[b]thiophen-2-ylamine (example 2, intermediate a) and endo-bicyclo[2.2.2]oct-5-ene-2,3-dicarboxylic anhydride as a light brown solid. MS (ESI): m/z=412.2 [M−H]−.

Example 42

2-[3-(3-Ethyl-[1,2,4]oxadiazol-5-yl)-4,5,6,7-tetrahydro-benzo[b]thiophen-2-ylcarbamoyl]-cyclopent-1-enecarboxylic acid

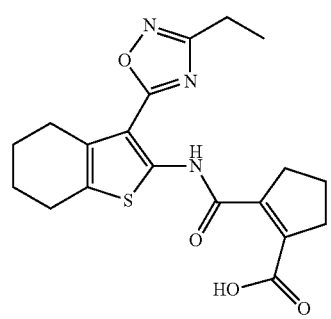 [SMILES: CCc1noc(-c2c(NC(=O)C3=C(C(=O)O)CCC3)sc3c2CCCC3)n1]

The title compound was obtained in analogy to example 2, from 3-(3-ethyl-1,2,4-oxadiazol-5-yl)-4,5,6,7-tetrahydrobenzo[b]thiophen-2-amine and 1-cyclopentene-1,2-dicarboxylic anhydride as a yellow solid. MS (ESI): m/z=388.1 [M+H]+.

Intermediates a) 3-(3-Ethyl-1,2,4-oxadiazol-5-yl)-4,5,6,7-tetrahydrobenzo[b]thiophen-2-amine

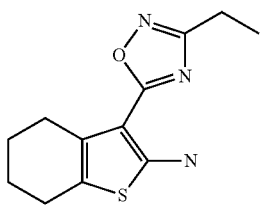 [SMILES: CCc1noc(-c2c(N)sc3c2CCCC3)n1]

The title compound was obtained in analogy to example 14, intermediate, from cyclohexanone, 2-(3-ethyl-1,2,4-oxadiazol-5-yl)acetonitrile and sulfur as a light brown solid. MS (ESI): m/z=250.1 [M+H]$^+$.

b) 2-(3-Ethyl-1,2,4-oxadiazol-5-yl)acetonitrile

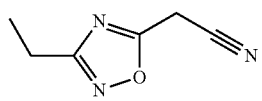

The title compound was obtained in analogy to example 15, intermediate b, from 5-(chloromethyl)-3-ethyl-1,2,4-oxadiazole and sodium cyanide as an orange liquid. MS (EI): m/z=137 [M]$^+$.

Example 43

N-[6,6-Dimethyl-3-(4-methyl-thiazol-2-yl)-4,5,6,7-tetrahydro-benzo[b]thiophen-2-yl]-phthalamic acid

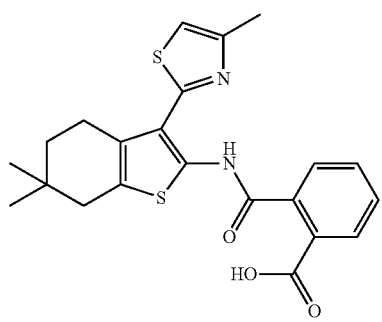 [SMILES: Cc1csc(-c2c(NC(=O)c3ccccc3C(=O)O)sc3c2CCC(C)(C)C3)n1]

The title compound was obtained in analogy to example 2, from 6,6-dimethyl-3-(4-methylthiazol-2-yl)-4,5,6,7-tetrahydrobenzo[b]thiophen-2-amine (example 28, intermediate) and phthalic anhydride as a light yellow solid. MS (ESI): m/z=427.1 [M+H]$^+$.

Example 44

2-{3-[3-(3-Cyclopropyl-[1,2,4]oxadiazol-5-yl)-4,5,6,7-tetrahydro-benzo[b]thiophen-2-yl]-ureido}-nicotinic acid

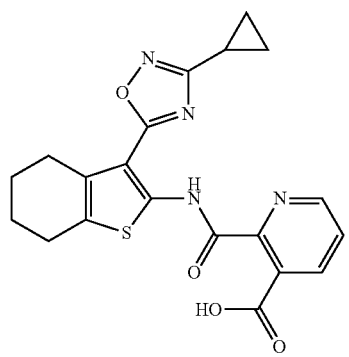

The title compound was obtained in analogy to example 27, from 3-cyclopropyl-5-(2-isocyanato-4,5,6,7-tetrahydrobenzo[b]thiophen-3-yl)-1,2,4-oxadiazole (example 27, intermediate a) and 2-aminonicotinic acid as an off-white solid. MS (ESI): m/z=426.1 [M+H]$^+$.

Example 45

4-{3-[3-(3-Cyclopropyl-[1,2,4]oxadiazol-5-yl)-4,5,6,7-tetrahydro-benzo[b]thiophen-2-yl]-ureido}-2-methyl-2H-pyrazole-3-carboxylic acid

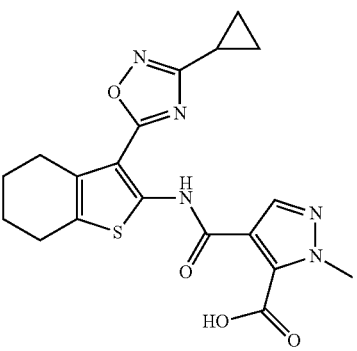 [SMILES: Cn1ncc(C(=O)Nc2sc3c(c2-c2nc(C4CC4)no2)CCCC3)c1C(=O)O]

The title compound was obtained in analogy to example 27, from 3-cyclopropyl-5-(2-isocyanato-4,5,6,7-tetrahydrobenzo[b]thiophen-3-yl)-1,2,4-oxadiazole (example 27, intermediate a) and 4-amino-1-methyl-1H-pyrazole-5-carboxylic acid as an off-white solid. MS (ESI): m/z=429.1 [M+H]$^+$.

Example 46

(1RS,6SR)-6-[3-(4-Methyl-thiazol-2-yl)-5,6,7,8-tetra-hydro-4H-cyclohepta[b]thiophen-2-ylcarbamoyl]-cyclohex-3-enecarboxylic acid

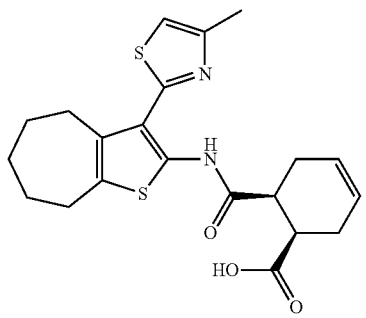 [SMILES: Cc1csc(-c2c(NC(=O)[C@H]3CC=CC[C@H]3C(=O)O)sc3c2CCCCC3)n1]

The title compound was obtained in analogy to example 2, from 3-(4-methylthiazol-2-yl)-5,6,7,8-tetrahydro-4H-cyclohepta[b]thiophen-2-amine (example 40, intermediate a) and cis-1,2,3,6-tetrahydrophthalic anhydride as a dark brown solid. MS (ESI): m/z=417.1 [M+H]$^+$.

Example 47

3-[6,6-Dimethyl-3-(4-methyl-thiazol-2-yl)-4,5,6,7-tetrahydro-benzo[b]thiophen-2-ylcarbamoyl]-bicyclo[2.2.2]oct-2-ene-2-carboxylic acid

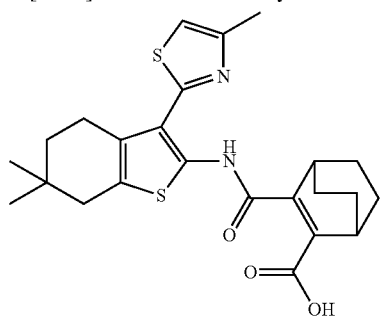

The title compound was obtained in analogy to example 2, from 6,6-dimethyl-3-(4-methylthiazol-2-yl)-4,5,6,7-tetrahydrobenzo[b]thiophen-2-amine (example 28, intermediate) and bicyclo[2.2.2]oct-2-ene-2,3-dicarboxylic anhydride as a yellow solid. MS (ESI): m/z=457.1 [M+H]$^+$.

Example 48

(1SR,2SR)-2-[3-(4-Methyl-thiazol-2-yl)-4,5,6,7-tetrahydro-benzo[b]thiophen-2-ylcarbamoyl]-cyclohexanecarboxylic acid

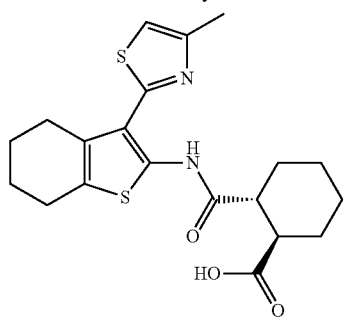

The title compound was obtained in analogy to example 2, from 3-(4-methyl-thiazol-2-yl)-4,5,6,7-tetrahydro-benzo[b]thiophen-2-ylamine (example 8, intermediate a) and trans-1,2-cyclohexanedicarboxylic anhydride as a light brown solid. MS (ESI): m/z=405.1 [M+H]$^+$.

Example 49

3-[3-(4-Methyl-thiazol-2-yl)-4,5,6,7-tetrahydro-benzo[b]thiophen-2-ylcarbamoyl]-bicyclo[2.2.2]oct-2-ene-2-carboxylic acid

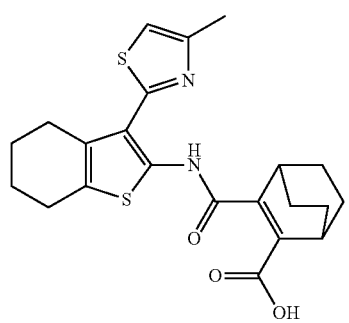 [SMILES: Cc1csc(-c2c(NC(=O)C3=C(C(=O)O)C4CCC3CC4)sc3c2CCCC3)n1]

The title compound was obtained in analogy to example 2, from 3-(4-methyl-thiazol-2-yl)-4,5,6,7-tetrahydro-benzo[b]thiophen-2-ylamine (example 8, intermediate a) and bicyclo[2.2.2]oct-2-ene-2,3-dicarboxylic anhydride as a yellow solid. MS (ESI): m/z=429.1 [M+H]$^+$].

Example 50

2-[6-Methoxy-3-(4-methyl-thiazol-2-yl)-4,5,6,7-tetrahydro-benzo[b]thiophen-2-ylcarbamoyl]-cyclohexanecarboxylic acid

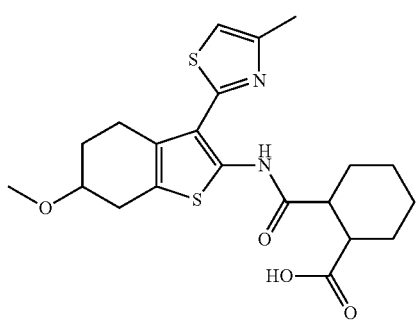 [SMILES: COC1CCc2c(sc(NC(=O)C3CCCCC3C(=O)O)c2-c2nc(C)cs2)C1]

The title compound was obtained in analogy to example 2, from 6-methoxy-3-(4-methylthiazol-2-yl)-4,5,6,7-tetrahydrobenzo[b]thiophen-2-amine (example 39, intermediate) and trans-1,2-cyclohexanedicarboxylic anhydride as a brown solid. MS (ESI): m/z=435.1 [M+H]$^+$].

Example 51

3-[3-(4-Methyl-thiazol-2-yl)-5,6,7,8-tetrahydro-4H-cyclohepta[b]thiophen-2-ylcarbamoyl]-bicyclo[2.2.2]oct-2-ene-2-carboxylic acid

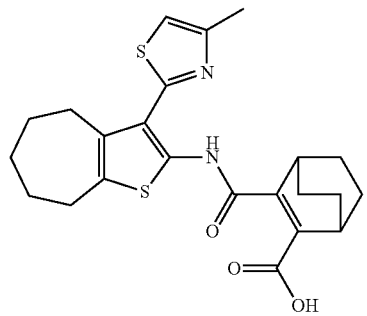 [SMILES: Cc1csc(-c2c(NC(=O)C3=C(C(=O)O)C4CCC3CC4)sc3c2CCCCC3)n1]

The title compound was obtained in analogy to example 2, from 3-(4-methylthiazol-2-yl)-5,6,7,8-tetrahydro-4H-cyclohepta[b]thiophen-2-amine (example 40, intermediate a) and bicyclo[2.2.2]oct-2-ene-2,3-dicarboxylic anhydride as a light brown solid. MS (ESI): m/z=443.3 [M+H]$^+$.

Example 52

(1SR,2SR)-2-{[3-(4-methyl-1,3-thiazol-2-yl)-4,7-dihydro-5H-spiro[1-benzothiophene-6,1'-cyclopropan]-2-yl]carbamoyl}cyclohexanecarboxylic acid

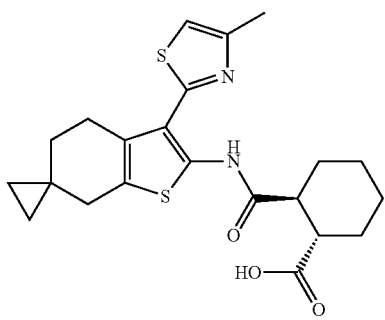 [SMILES: Cc1csc(-c2c(NC(=O)[C@H]3CCCC[C@@H]3C(=O)O)sc3c2CCC2(CC2)C3)n1]

The title compound was obtained in analogy to example 2, from 3-(4-methylthiazol-2-yl)-5,7-dihydro-4H-spiro[benzo[b]thiophene-6,1'-cyclopropan]-2-amine and trans1,2-cyclohexanedicarboxylic anhydride as a light brown solid. MS (ESI): m/z=431.3 [M+H]$^+$.

Intermediates a) 2-(4-Methylthiazol-2-yl)-2-(spiro[2.5]octan-6-ylidene)acetonitrile

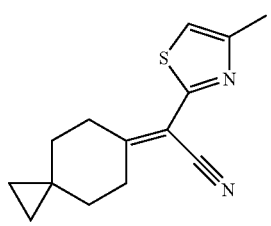 [SMILES: Cc1csc(C(C#N)=C2CCC3(CC2)CC3)n1]

The title compound was obtained in analogy to example 8, intermediate b, from spiro[2.5]octan-6-one and 2-(4-methylthiazol-2-yl)acetonitrile as a light yellow solid. MS (ESI): m/z=245.2 [M+H]$^+$.

b) 3-(4-Methylthiazol-2-yl)-5,7-dihydro-4H-spiro[benzo[b]thiophene-6,1'-cyclopropan]-2-amine

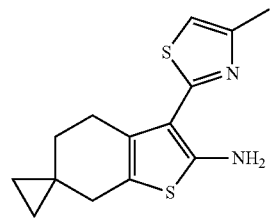 [SMILES: Cc1csc(-c2c(N)sc3c2CCC2(CC2)C3)n1]

The title compound was obtained in analogy to example 8, intermediate a, from 2-(4-methylthiazol-2-yl)-2-(spiro[2.5]octan-6-ylidene)acetonitrile and sulfur as a dark brown gum. MS (ESI): m/z=277.0 [M+H]$^+$.

Example 53

(S)-1-[3-(3-Cyclopropyl-[1,2,4]oxadiazol-5-yl)-4,5,6,7-tetrahydro-benzo[b]thiophen-2-ylcarbamoyl]-pyrrolidine-2-carboxylic acid

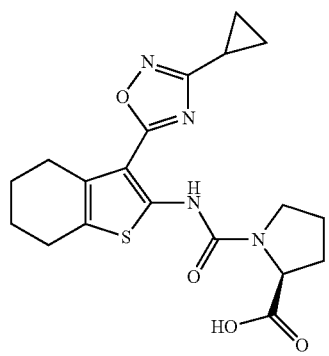 [SMILES: O=C(O)[C@@H]1CCCN1C(=O)Nc1sc2c(c1-c1nc(C3CC3)no1)CCCC2]

The title compound was obtained in analogy to example 27, from 3-cyclopropyl-5-(2-isocyanato-4,5,6,7-tetrahydrobenzo[b]thiophen-3-yl)-1,2,4-oxadiazole (example 27, intermediate a) and (S)-proline as an off-white solid. MS (ESI): m/z=403.1 [M+H]$^+$.

Example 54

(1SR,2SR)-2-[3-(4-Methyl-thiazol-2-yl)-5,6,7,8-tetrahydro-4H-cyclohepta[b]thiophen-2-ylcarbamoyl]-cyclohexanecarboxylic acid

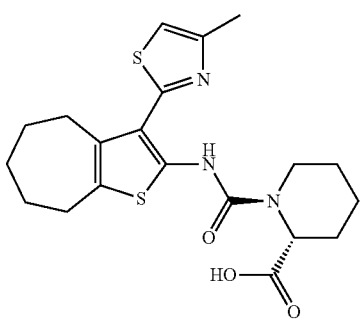

The title compound was obtained in analogy to example 2, from 3-(4-methylthiazol-2-yl)-5,6,7,8-tetrahydro-4H-cyclohepta[b]thiophen-2-amine (example 40, intermediate a) and trans-1,2-cyclohexanedicarboxylic anhydride as a light brown solid. MS (ESI): m/z=417.1 [M+H]$^+$.

Example 55

2-[3-(3-Cyclopropyl-[1,2,4]oxadiazol-5-yl)-4,7-dihydro-5H-thieno[2,3-c]pyran-2-ylcarbamoyl]-cyclopent-1-enecarboxylic acid

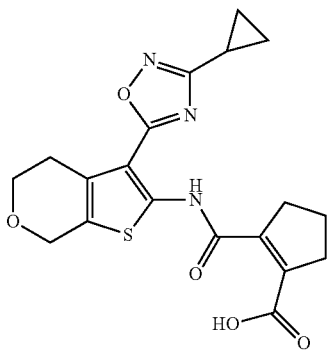 [SMILES: O=C(O)C1=C(C(=O)Nc2sc3c(c2-c2nc(C4CC4)no2)CCOC3)CCC1]

To a solution of 3-(3-cyclopropyl-1,2,4-oxadiazol-5-yl)-5,7-dihydro-4H-thieno[2,3-c]pyran-2-amine (0.1 g, 380 µmol) in CH$_3$CN (8 mL) were added DBU (116 mg, 114 µL, 760 µmol) and 1-cyclopentene-1,2-dicarboxylic anhydride (57.7 mg, 418 µmol, CAS RN 3205-94-5) and the yellow solution was stirred at 65° C. for 2.75 h. The reaction mixture was poured on 1M aqueous HCl solution and EtOAc and the layers were separated. The aqueous layer was extracted twice with EtOAc. The organic layers were washed once with brine, dried over MgSO$_4$, filtered and evaporated. The product was purified by preparative HPLC (Gemini NX column) using a gradient of MeOH:H$_2$O (containing 0.1% formic acid) (20:80 to 98:2). Yellow solid (0.09 g; 59%). MS (ESI): m/z=402.11 [M+H]$^+$.

Intermediate 3-(3-Cyclopropyl-[1,2,4]oxadiazol-5-yl)-4,7-dihydro-5H-thieno[2,3-c]pyran-2-ylamine

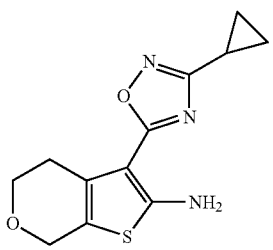 [SMILES: Nc1sc2c(c1-c1nc(C3CC3)no1)CCOC2]

To a solution of (3-cyclopropyl-[1,2,4]oxadiazol-5-yl)-acetonitrile (1 g, 6.7 mmol, Princeton BioMolecular Research, Inc.) in EtOH (33 mL) were added dihydro-2H-pyran-4(3H)-one (671 mg, 6.7 mmol, CAS RN 23462-75-1) and sulfur (215 mg, 6.7 mmol) and the light yellow suspension was stirred at 50° C. for 30 min. To this mixture was added dropwise morpholine (39.2 g, 39.2 mL, 450 mmol) over 10 min. to give a brown solution which was stirred at 50° C. for 50 min. The reaction mixture was poured on H$_2$O (250 mL) and EtOAc (200 mL) and the layers were separated. The aqueous layer was extracted three times with EtOAc (3×100 mL) and the organic layers were washed with brine (150 mL), dried over MgSO$_4$, filtered, treated with silica gel and evaporated. The compound was purified by silica gel chromatography on a 50 g column using an MPLC system eluting with a gradient of n-heptane:EtOAc (100:0 to 40:60). Yellow solid (1.42 g; 80%). MS (ESI): m/z=264.1 [M+H]$^+$.

Example 56

3-[3-(4-Methyl-thiazol-2-yl)-4,7-dihydro-5H-thieno[2,3-c]pyran-2-ylcarbamoyl]-bicyclo[2.2.2]oct-2-ene-2-carboxylic acid

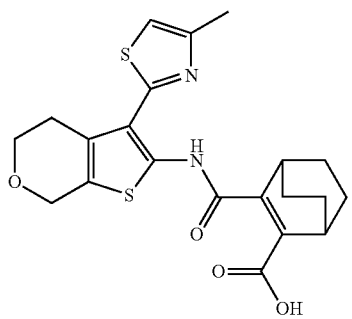 [SMILES: Cc1csc(-c2c(NC(=O)C3=C(C(=O)O)C4CCC3CC4)sc3c2CCOC3)n1]

To a solution of 3-(4-methylthiazol-2-yl)-5,7-dihydro-4H-thieno[2,3-c]pyran-2-amine (0.1 g, 396 µmol) in Et$_2$O (5 mL) was added bicyclo[2.2.2]oct-2-ene-2,3-dicarboxylic anhydride (77.7 mg, 436 µmol) and the reaction mixture was stirred at RT for 26 h. The suspension was filtered and washed with Et$_2$O. Brown solid (0.1 g; 58%). MS (ESI): m/z=431.11 [M+H]$^+$.

Intermediates a) 3-(4-Methyl-thiazol-2-yl)-4,7-dihydro-5H-thieno[2,3-c]pyran-2-ylamine

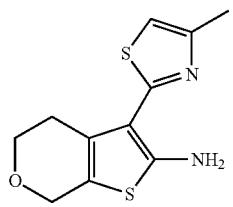 [SMILES: Cc1csc(-c2c(N)sc3c2CCOC3)n1]

To a solution of 2-(4-methylthiazol-2-yl)-2-(2H-pyran-4(3H,5H,6H)-ylidene)acetonitrile (329 mg, 1.49 mmol) in EtOH (15 mL) was added DBU (568 mg, 558 µL, 3.73 mmol) and sulfur (47.8 mg, 1.49 mmol). The reaction mixture was stirred at 65° C. for 2 h. The dark solution was poured on 30 mL 10% aqueous NaHCO$_3$ solution and 30 mL EtOAc and the layers were separated. The aqueous layer was extracted a second time with 30 mL EtOAc. The organic layers were washed with 30 mL brine, dried over MgSO$_4$, filtered and concentrated under vacuum. The compound was purified by silica gel chromatography on a 20 g column using an MPLC (Flashmaster) system eluting with a gradient of n-heptane:EtOAc (100:0 to 60:40). Yellow solid (294 mg, 78%). MS (ESI): m/z=253.046 [M+H]+.

b) (4-Methyl-thiazol-2-yl)-(tetrahydro-pyran-4-ylidene)-acetonitrile

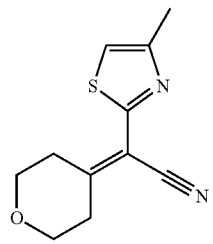

To a solution of tetrahydro-4H-pyran-4-one (200 mg, 2.0 mmol, CAS RN 143562-54-3) in toluene (8 mL) was added 2-(4-methylthiazol-2-yl)acetonitrile (276 mg, 2.0 mmol, CAS RN 19785-39-8) and NH₄OAc (308 mg, 4.0 mmol). The reaction mixture was stirred at 100° C. for 18 h, poured on 30 mL 10% aqueous NaHCO₃ and 30 mL EtOAc and the layers were separated. The aqueous layer was extracted a second time with 30 mL EtOAc. The organic layers were washed with 30 mL brine, dried over MgSO₄, filtered and concentrated under vacuum. The compound was purified by silica gel chromatography on a 50 g column using an MPLC (Flashmaster) system eluting with a gradient of n-heptane: EtOAc (100:0 to 40:60). Light yellow solid (351 mg, 79.8%). MS (ESI): m/z=221.074 [M+H]+.

Example 57

2-[3-(4,5-Dimethyl-oxazol-2-yl)-4,7-dihydro-5H-thieno[2,3-c]pyran-2-ylcarbamoyl]-cyclopent-1-enecarboxylic acid

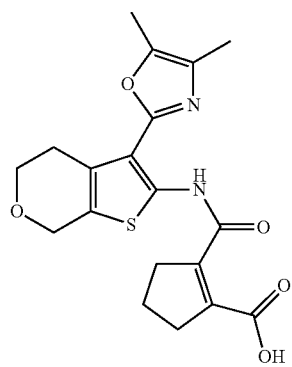 [SMILES: Cc1nc(-c2c(NC(=O)C3=C(C(=O)O)CCC3)sc3c2CCOC3)oc1C]

To a solution of 3-(4,5-dimethyl-oxazol-2-yl)-4,7-dihydro-5H-thieno[2,3-c]pyran-2-ylamine (72 mg, 288 μmol) in Et₂O (3 mL) was added 1-cyclopentene-1,2-dicarboxylic anhydride (43.7 mg, 316 μmol, CAS RN 3205-94-5) and DMAP (1.76 mg, 14.4 μmol). The reaction mixture was stirred at RT for 18 h and then concentrated under vacuum. The remaining yellow residue was purified by preparative HPLC (Gemini NX column) with a gradient of MeOH:H₂O (containing 0.1% formic acid) (80:20 to 98:2). Yellow solid (58 mg, 52%). MS (ESI): m/z=389.117 [M+H]+.

Intermediates a) 3-(4,5-Dimethyl-oxazol-2-yl)-4,7-dihydro-5H-thieno[2,3-c]pyran-2-ylamine

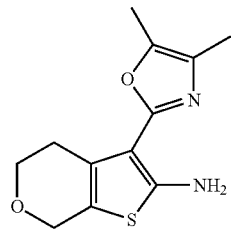 [SMILES: Cc1nc(-c2c(N)sc3c2CCOC3)oc1C]

The title compound was prepared in analogy to example 56, intermediate a, from (4,5-dimethyl-oxazol-2-yl)-(tetrahydro-pyran-4-ylidene)-acetonitrile and using a gradient of n-heptane:EtOAc (100:0 to 50:50) for the chromatographic purification. Yellow solid (60%). MS (ESI): m/z=251.086 [M+H]+.

b) (4,5-Dimethyl-oxazol-2-yl)-(tetrahydro-pyran-4-ylidene)-acetonitrile

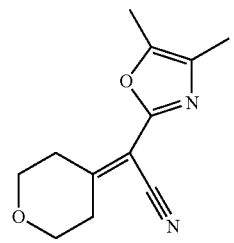 [SMILES: Cc1nc(C(C#N)=C2CCOCC2)oc1C]

The title compound was prepared in analogy to example 56, intermediate b, from dihydro-2H-pyran-4(3H)-one and (4,5-dimethyl-oxazol-2-yl)-acetonitrile and using a gradient of n-heptane:EtOAc (100:0 to 70:30) for the chromatographic purification. Light yellow solid (55%). MS (ESI): m/z=219.113 [M+H]+.

c) (4,5-Dimethyl-oxazol-2-yl)-acetonitrile

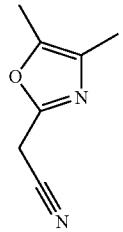

To a suspension of sodium cyanide (404 mg, 8.24 mmol) in CH₃CN (4.8 mL) was added 15-crown-5 (908 mg, 816 μL, 4.12 mmol, CAS RN 33100-27-5) and the suspension was stirred at RT for 45 minutes. To this mixture was added dropwise a solution of 2-(chloromethyl)-4,5-dimethyloxazole (300 mg, 2.06 mmol, Enamine Ltd.) in CH₃CN (2.4 mL) over 30 minutes. The light yellow suspension was stirred at RT for 18 h. The reaction mixture was poured on 30 mL H₂O and 30 mL EtOAc and the layers were separated. The aqueous layer was extracted a second time with 30 mL EtOAc. The organic layers were washed with 30 mL brine, dried over MgSO₄, filtered and concentrated under vacuum. The compound was purified by silica gel chromatography on a 20 g column using a MPLC system (CombiFlash Companion, Isco Inc.) eluting with a gradient of n-heptane:EtOAc (100:0 to 70:30). Light brown liquid (156 mg, 56%) MS (ESI): m/z=137.071 [M+H]⁺.

Example 58

2-[3-(3-Cyclopropyl-[1,2,4]oxadiazol-5-yl)-4,4,6,6-tetramethyl-4,6-dihydro-thieno[2,3-c]furan-2-ylcarbamoyl]-cyclopent-1-enecarboxylic acid

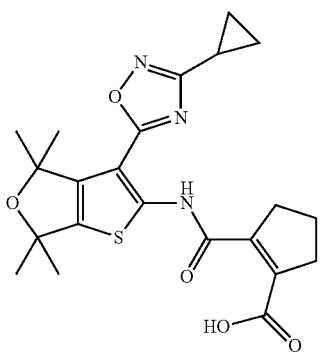 [SMILES: CC1(C)OC(C)(C)c2c1sc(NC(=O)C1=C(C(=O)O)CCC1)c2-c1nc(C2CC2)no1]

To a solution of 2-[3-(3-cyclopropyl-[1,2,4]oxadiazol-5-yl)-4,4,6,6-tetramethyl-4,6-dihydro-thieno[2,3-c]furan-2-yl]-5,6-dihydro-4H-cyclopenta[c]pyrrole-1,3-dione (0.06 g, 141 µmol) in THF (1 mL) was added 1M aqueous sodium hydroxide solution (423 µl, 423 µmol) and the yellow mixture was stirred at RT for 1.75 h. To the reaction mixture were added TBME (10 mL) and H₂O (3 mL) and 1M hydrochloric acid (423 µl, 423 µmol) was added dropwise. The layers were separated and the aqueous layer was extracted twice with TBME (10 mL). The organic layers were washed with brine (5 mL), dried over MgSO₄, filtered and evaporated. The residue was taken up in TBME and the resulting suspension was filtered to give the desired compound as a yellow solid (0.04 g; 64%). MS (ESI): m/z=444.16 [M+H]⁺.

Intermediates a) 2-[3-(3-Cyclopropyl-[1,2,4]oxadiazol-5-yl)-4,4,6,6-tetramethyl-4,6-dihydro-thieno[2,3-c]furan-2-yl1-5,6-dihydro-4H-cyclopenta[c]pyrrole-1,3-dione

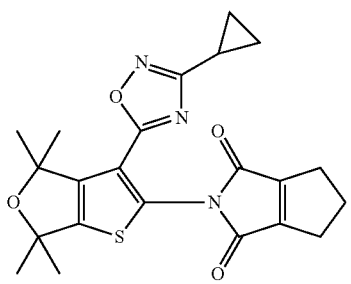 [SMILES: CC1(C)OC(C)(C)c2c1sc(N1C(=O)C3=C(CCC3)C1=O)c2-c1nc(C2CC2)no1]

To a solution of 3-(3-cyclopropyl-1,2,4-oxadiazol-5-yl)-4,4,6,6-tetramethyl-4,6-dihydrothieno[3,2-c]furan-2-amine (0.08 g, 262 µmol) in Et₂O (6 mL) were added 1-cyclopentene-1,2-dicarboxylic anhydride (39.8 mg, 288 µmol) and DMAP (1.6 mg, 13.1 µmol) and the reaction mixture was stirred at RT for 51 h, followed by heating at reflux for 2.5 h. To the reaction mixture were added Et₂O (4 mL), 1-cyclopentene-1,2-dicarboxylic anhydride (43.4 mg, 314 µmol) and DMAP (16.0 mg, 131 µmol) and the reaction mixture was stirred at reflux overnight. The reaction mixture was evaporated, the residue was taken up in CH₃CN (6.00 mL), treated with DBU (79.8 mg, 79.0 µL, 524 µmol) and 1-cyclopentene-1,2-dicarboxylic anhydride (39.8 mg, 288 µmol) and stirred at 65° C. for 1.25 h. The reaction mixture was poured on 1M aqueous HCl solution and EtOAc and the layers were separated. The aqueous layer was extracted twice with EtOAc. The organic layers were washed with brine, dried over MgSO₄, filtered, treated with silica gel and evaporated. The compound was purified by silica gel chromatography on a 20 g column using an MPLC system eluting with a gradient of CH₂Cl₂:MeOH (100:0 to 75:25). The product-containing fractions were pooled, evaporated and the residue purified by preparative HPLC (Gemini NX column) using a gradient of MeOH:H₂O (containing 0.1% formic acid) (20:80 to 98:2). Light yellow foam (0.068 g; 61%). MS (ESI): m/z=426.15 [M+H]⁺.

b) 3-(3-Cyclopropyl-1,2,4-oxadiazol-5-yl)-4,4,6,6-tetramethyl-4,6-dihydrothieno[3,2-c]furan-2-amine

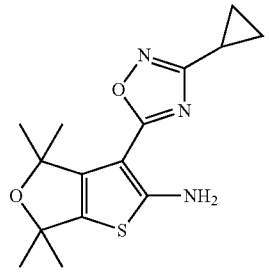 [SMILES: CC1(C)OC(C)(C)c2c1sc(N)c2-c1nc(C2CC2)no1]

To a suspension of N-[3-(3-cyclopropyl-[1,2,4]oxadiazol-5-yl)-4,4,6,6-tetramethyl-4,6-dihydro-thieno[2,3-c]furan-2-yl]-acetamide (0.122 g, 351 µmol) in MeOH (3 mL) was added sodium methoxide (5.4 M solution in MeOH, 81.3 µL, 439 µmol). The resulting light yellow solution was stirred at RT for 7 h and then poured on saturated aqueous NaHCO₃ solution and EtOAc and the layers were separated. The aqueous layer was extracted twice with EtOAc and the organic layers washed with brine, dried over MgSO₄, filtered, treated with silica gel and evaporated. The compound was purified by silica gel chromatography on a 20 g column using an MPLC system eluting with a gradient of n-heptane:EtOAc (100:0 to 65:35). Colorless solid (0.083 g; 77%). MS (ESI): m/z=306.4 [M+H]⁺.

c) N-[3-(3-Cyclopropyl-[1,2,4]oxadiazol-5-yl)-4,4,6,6-tetramethyl-4,6-dihydro-thieno[2,3-c]furan-2-yl]-acetamide

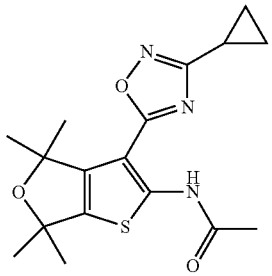 [SMILES: CC(=O)Nc1sc2c(c1-c1nc(C3CC3)no1)C(C)(C)OC2(C)C]

To a solution of (Z)—N-(3-((amino(cyclopropyl)methyleneaminooxy)carbonyl)-4,4,6,6-tetramethyl-4,6-dihydrothieno[3,2-c]furan-2-yl)acetamide (0.197 g, 539 µmol) in THF (4 mL) was added TBAF (1M solution in THF, 4.31 mL, 4.31 mmol) and the light brown solution was stirred at reflux for 2.75 h. The reaction mixture was poured on saturated aqueous NaHCO$_3$ solution and EtOAc and the layers were separated. The aqueous layer was extracted twice with EtOAc. The organic layers were washed once with brine, dried over MgSO$_4$, filtered, treated with silica gel and evaporated. The compound was purified by silica gel chromatography on a 20 g column using an MPLC system eluting with a gradient of n-heptane:EtOAc (100:0 to 50:50). Colorless solid (0.126 g; 67%). MS (ESI): m/z=348.14 [M+H]$^+$.

d) (Z)—N-(3-((amino(cyclopropyl)methyleneaminooxy)carbonyl)-4,4,6,6-tetramethyl-4,6-dihydrothieno[3,2-c]furan-2-yl)acetamide

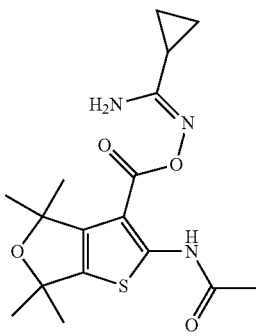 [SMILES: CC(=O)Nc1sc2c(c1C(=O)O/N=C(\N)C1CC1)C(C)(C)OC2(C)C]

To a solution of 2-acetylamino-4,4,6,6-tetramethyl-4,6-dihydro-thieno[2,3-c]furan-3-carboxylic acid (0.193 g, 681 µmol) in DMF (3.00 mL) were added HATU (259 mg, 681 µmol) and DIPEA (88.0 mg, 119 µL, 681 µmol) followed by addition of (Z)—N'-hydroxycyclopropanecarboximidamide (68.2 mg, 681 µmol, CAS RN 51285-13-3) and the yellow solution was stirred at RT for 16.75 h. The reaction mixture was poured on saturated aqueous NH$_4$Cl solution and EtOAc and the layers were separated. The aqueous layer was extracted twice with EtOAc. The organic layers were washed twice with H$_2$O and once with brine, dried over MgSO$_4$, filtered, treated with silica gel and evaporated. The compound was purified by silica gel chromatography on a 10 g column using a MPLC system eluting with a gradient of n-heptane:EtOAc (100:0 to 50:50). Light brown solid (0.2 g; 82%). MS (ESI): m/z=366.15 [M+H]$^+$.

e) 2-Acetylamino-4,4,6,6-tetramethyl-4,6-dihydro-thieno[2,3-c]furan-3-carboxylic acid

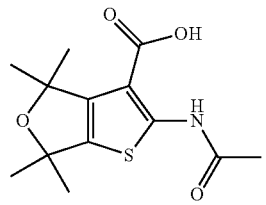 [SMILES: CC(=O)Nc1sc2c(c1C(=O)O)C(C)(C)OC2(C)C]

To a solution of 2-acetylamino-4,4,6,6-tetramethyl-4,6-dihydro-thieno[2,3-c]furan-3-carboxylic acid ethyl ester (0.52 g, 1.67 mmol) in dioxane (3 mL) was added H$_2$O (3 mL). The resulting light yellow suspension was treated with LiOH mono hydrate (105 mg, 2.5 mmol) and stirred at RT for 45 min. Heating was installed and stirring was continued at 60° C. for 2 h. The organic solvent was evaporated, the remaining aqueous suspension was diluted with EtOAc and H$_2$O and the layers were separated. The aqueous layers were washed twice with EtOAc and combined, then the pH was adjusted to approximately 2 using 1M aqueous HCl and extracted three times with EtOAc. The organic layers were dried over MgSO$_4$, filtered and evaporated to give the desired compound as a light brown solid (0.197 g; 41%). MS (ESI): m/z=282.01 [M−H]$^-$.

f) 2-Acetylamino-4,4,6,6-tetramethyl-4,6-dihydro-thieno[2,3-c]furan-3-carboxylic acid ethyl ester

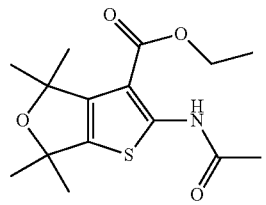 [SMILES: CCOC(=O)c1c(NC(C)=O)sc2c1C(C)(C)OC2(C)C]

To a solution of 2-amino-4,4,6,6-tetramethyl-4,6-dihydro-thieno[2,3-c]furan-3-carboxylic acid ethyl ester (0.61 g, 2.26 mmol) in CH$_3$CN (10 mL) was added DMAP (415 mg, 3.4 mmol). To the light red solution was added dropwise AcCl (213 mg, 193 µL, 2.72 mmol) over 10 minutes and stirring was continued at RT for 2.5 h. The light brown suspension was poured on saturated aqueous NH$_4$Cl solution and EtOAc and the layers were separated. The aqueous layer was extracted twice with EtOAc. The organic layers were dried over MgSO$_4$, filtered, treated with silica gel and evaporated. The compound was purified by silica gel chromatography on a 20 g column using an MPLC (ISCO) system eluting with a gradient of n-heptane:TBME (100:0 to 65:35). Light brown solid (0.444 g; 63%). MS (ESI): m/z=312.2 [M+H]$^+$.

g) 2-Amino-4,4,6,6-tetramethyl-4,6-dihydro-thieno[2,3-c]furan-3-carboxylic acid ethyl ester

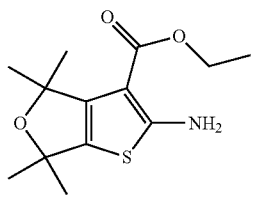 [SMILES: CCOC(=O)c1c(N)sc2c1C(C)(C)OC2(C)C]

The title compound was prepared in analogy to example 56, intermediate a, from cyano-[2,2,5,5-tetramethyl-dihydro-furan-(3Z)-ylidene]-acetic acid ethyl ester and using a gradient of n-heptane:EtOAc (100:0 to 65:35) for the chromatographic purification. Light brown solid (24%). MS (ESI): m/z=270.116 [M+H]$^+$.

h) Cyano-[2,2,5,5-tetramethyl-dihydro-furan-(3Z)-ylidene]-acetic acid ethyl ester

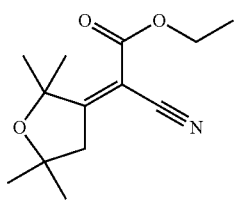 [SMILES: CCOC(=O)/C(C#N)=C1/CC(C)(C)OC1(C)C]

The title compound was prepared in analogy to example 56, intermediate b, from 2,2,5,5-tetramethyl-dihydro-furan-3-one (CAS RN 5455-94-7) and cyano-acetic acid ethyl ester and using a gradient of n-heptane:EtOAc (100:0 to 50:50) for the chromatographic purification. Colorless oil (29%). MS (ESI): m/z=236.13 [M+H]$^+$.

Example 59

2-[3-(4-Methyl-thiazol-2-yl)-4,7-dihydro-5H-thieno[2,3-c]pyran-2-ylcarbamoyl]-cyclopent-1-enecarboxylic acid

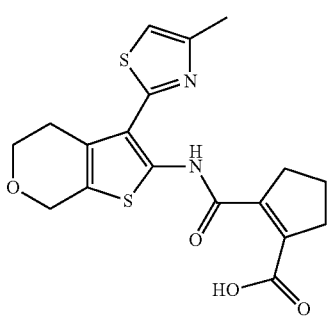

The compound was prepared in analogy to example 56, from 3-(4-methyl-thiazol-2-yl)-4,7-dihydro-5H-thieno[2,3-c]pyran-2-ylamine (example 56, intermediate a) and 1-cyclopentene-1,2-dicarboxylic anhydride. Brown solid (56%). MS (ESI): m/z=391.08 [M+H]$^+$.

Example 60

2-[(2-Carboxy-cyclopent-1-enecarbonyl)-amino]-3-(4-methyl-thiazol-2-yl)-4,7-dihydro-5H-thieno[2,3-c]pyridine-6-carboxylic acid tert-butyl ester

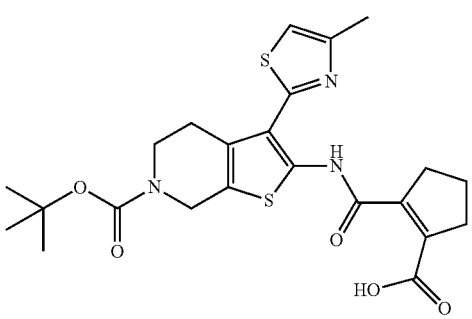 [SMILES: Cc1csc(-c2c(NC(=O)C3=C(C(=O)O)CCC3)sc3c2CCN(C(=O)OC(C)(C)C)C3)n1]

The compound was prepared in analogy to example 55, from 2-amino-3-(4-methyl-thiazol-2-yl)-4,7-dihydro-5H-thieno[2,3-c]pyridine-6-carboxylic acid tert-butyl ester and 1-cyclopentene-1,2-dicarboxylic anhydride for 18 h at 65° C. Light brown solid (6%). MS (ESI): m/z=490.146 [M+H]$^+$.

Intermediates a) 2-Amino-3-(4-methyl-thiazol-2-yl)-4,7-dihydro-5H-thieno[2,3-c]pyridine-6-carboxylic acid tert-butyl ester

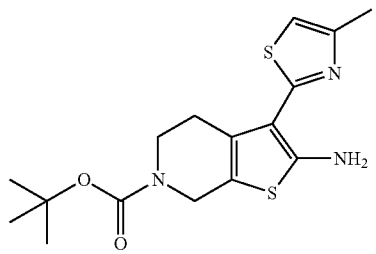 [SMILES: Cc1csc(-c2c(N)sc3c2CCN(C(=O)OC(C)(C)C)C3)n1]

The compound was prepared in analogy to example 56, intermediate a, from 4-[cyano-(4-methyl-thiazol-2-yl)-methylene]-piperidine-1-carboxylic acid tert-butyl ester. Yellow foam (75%). MS (ESI): m/z=352.115 [M+H]$^+$.

b) 4-[Cyano-(4-methyl-thiazol-2-yl)-methylene]-piperidine-1-carboxylic acid tert-butyl ester

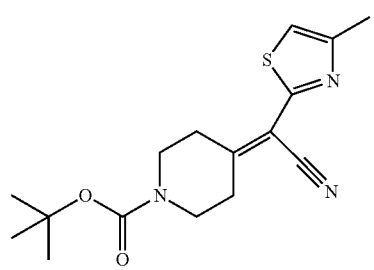 [SMILES: Cc1csc(C(C#N)=C2CCN(C(=O)OC(C)(C)C)CC2)n1]

The compound was prepared in analogy to example 56, intermediate b, from tert-butyl 4-oxopiperidine-1-carboxylate and 2-(4-methylthiazol-2-yl)acetonitrile. Yellow oil (71%). MS (ESI): m/z=320.143 [M+H]⁺.

Example 61

2-[3-(3-Trifluoromethyl-[1,2,4]oxadiazol-5-yl)-4,5,6,7-tetrahydro-benzo[b]thiophen-2-ylcarbamoyl]-cyclopent-1-enecarboxylic acid

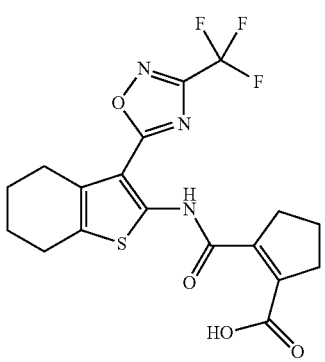

The compound was prepared in analogy to example 55, from 3-(3-trifluoromethyl-[1,2,4]oxadiazol-5-yl)-4,5,6,7-tetrahydro-benzo[b]thiophen-2-ylamine and 1-cyclopentene-1,2-dicarboxylic anhydride and purified by silica gel chromatography using a MPLC system eluting with a gradient of CH$_2$Cl$_2$:MeOH (100:0 to 95:5). Yellow solid (70%). MS (ESI): m/z=428.09 [M+H]⁺.

Intermediates a) 3-(3-Trifluoromethyl-[1,2,4]oxadiazol-5-yl)-4,5,6,7-tetrahydro-benzo[b]thiophen-2-ylamine

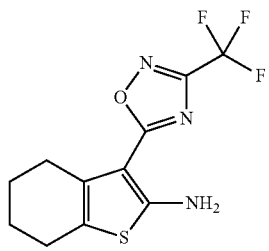 [SMILES: Nc1sc2c(c1-c1nc(C(F)(F)F)no1)CCCC2]

The compound was prepared in analogy to example 56, intermediate a, from cyclohexylidene-(3-trifluoromethyl-[1,2,4]oxadiazol-5-yl)-acetonitrile using a gradient of n-heptane:EtOAc (100:0 to 85:15) for the chromatographic purification. Light yellow solid (73%). MS (EI): m/z=289 [M].

b) Cyclohexylidene-(3-trifluoromethyl-[1,2,4]oxadiazol-5-yl)-acetonitrile

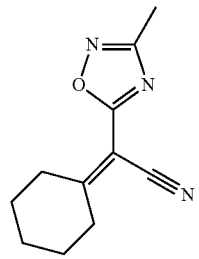

The compound was prepared in analogy to example 56, intermediate b, from cyclohexanone and 2-(3-(trifluoromethyl)-1,2,4-oxadiazol-5-yl)acetonitrile (CAS RN 1308384-47-5). Yellow oil (61%). MS (EI): m/z=257 [M].

Example 62

3-[3-(3-Trifluoromethyl-[1,2,4]oxadiazol-5-yl)-4,5,6,7-tetrahydro-benzo[b]thiophen-2-ylcarbamoyl]-bicyclo[2.2.2]oct-2-ene-2-carboxylic acid

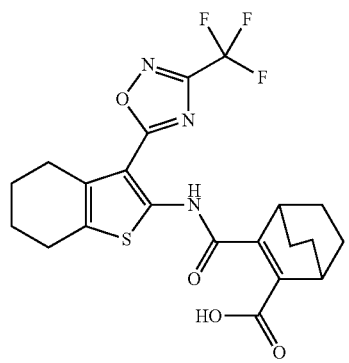 [SMILES: O=C(O)C1=C(C(=O)Nc2sc3c(c2-c2nc(C(F)(F)F)no2)CCCC3)C2CCC1CC2]

The title compound was prepared in analogy to example 55, from 3-(3-(trifluoromethyl)-1,2,4-oxadiazol-5-yl)-4,5,6,7-tetrahydrobenzo[b]thiophen-2-amine (example 61, intermediate a) and bicyclo[2.2.2]oct-2-ene-2,3-dicarboxylic anhydride after a reaction time of 4 h at 65° C. The compound was purified by silica gel chromatography on a 20 g column using an MPLC (ISCO) system eluting with a gradient of n-heptane:EtOAc (100:0 to 40:60). Yellow solid (77%). MS (ESI): m/z=468.12 [M+H]⁺.

Example 63

{2-[3-(4-Methyl-thiazol-2-yl)-4,5,6,7-tetrahydrobenzo[b]thiophen-2-ylcarbamoyl]-pyrrolidin-1-yl}-acetic acid

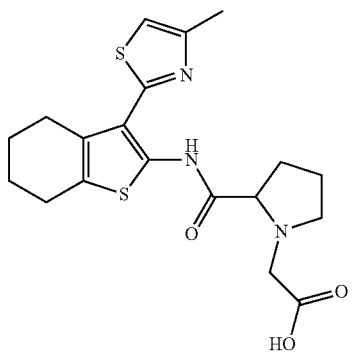 [SMILES: Cc1csc(-c2c(NC(=O)C3CCCN3CC(=O)O)sc3c2CCCC3)n1]

To a solution of tert-butyl 2-(2-(3-(4-methylthiazol-2-yl)-4,5,6,7-tetrahydrobenzo[b]thiophen-2-ylcarbamoyl)pyrrolidin-1-yl)acetate (0.022 g, 47.7 µmol) in CH$_2$Cl$_2$ (1 mL) were added TFA (109 mg, 73.4 µL, 953 µmol) and anisole (5.67 mg, 5.73 µL, 52.4 µmol) and the brown solution was stirred at RT for 2.75 h before another batch of TFA (109 mg, 73.4 µL, 953 µmol) was added. After total stirring for 7 h the reaction mixture was treated with toluene (1 mL) and evaporated. The product was purified by preparative HPLC (Gemini NX column) using a gradient of MeOH:H$_2$O (containing 0.1% formic acid) (20:80 to 98:2). Light brown solid (0.014 g; 72%). MS (ESI): m/z=406.13 [M+H]$^+$.

Intermediates a) tert-Butyl 2-(2-(3-(4-methylthiazol-2-yl)-4,5,6,7-tetrahydrobenzo[b]thiophen-2-ylcarbamoyl)pyrrolidin-1-yl)acetate

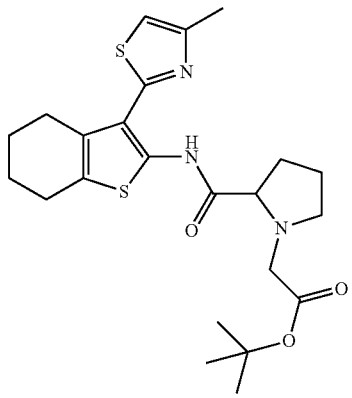 [SMILES: Cc1csc(-c2c(NC(=O)C3CCCN3CC(=O)OC(C)(C)C)sc3c2CCCC3)n1]

To a solution of 3-(4-methylthiazol-2-yl)-4,5,6,7-tetrahydrobenzo[b]thiophen-2-amine (0.1 g, 399 µmol) in CH$_2$Cl$_2$ (4 mL) were added lithium 1-(2-tert-butoxy-2-oxoethyl)pyrrolidine-2-carboxylate (104 mg, 399 µmol), 2-bromo-1-ethylpyridinium tetrafluoroborate (120 mg, 439 µmol) and DIPEA (103 mg, 140 µL, 799 µmol) and the brown solution was stirred at RT for 19 h. The reaction mixture was poured on saturated aqueous NH$_4$Cl solution and CH$_2$Cl$_2$ and the layers were separated. The aqueous layer was extracted three times with CH$_2$Cl$_2$. The organic layers were dried over MgSO$_4$, filtered, treated with silica gel and evaporated. The compound was purified by silica gel chromatography on a 20 g column using an MPLC system eluting with a gradient of n-heptane:EtOAc (100:0 to 60:40). Light brown solid (0.024 g; 13%). MS (ESI): m/z=462.19 [M+H]$^+$.

b) 3-(4-Methylthiazol-2-yl)-4,5,6,7-tetrahydrobenzo[b]thiophen-2-amine

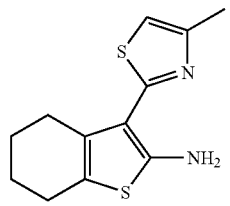 [SMILES: Cc1csc(-c2c(N)sc3c2CCCC3)n1]

The title compound was prepared in analogy to example 56, intermediate a, from cyclohexylidene-(4-methyl-thiazol-2-yl)-acetonitrile after a reaction time of 2 h at 65° C. The compound was purified by silica gel chromatography on a 50 g column using an MPLC (Flashmaster) system eluting with a gradient of n-heptane:EtOAc (100:0 to 70:30). Light brown oil (68%). MS (ESI): m/z=251.067 [M+H]$^+$.

c) Cyclohexylidene-(4-methyl-thiazol-2-yl)-acetonitrile

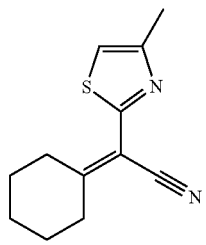

The title compound was prepared in analogy to example 56, intermediate b, from cyclohexanone and 2-(4-methyl-thiazol-2-yl)acetonitrile after a reaction time of 18 h at 100° C. The compound was purified by silica gel chromatography on a 50 g column using an MPLC (Flashmaster) system eluting with a gradient of n-heptane:EtOAc (100:0 to 75:35). Yellow solid (67%). MS (ESI): m/z=219.095 [M+H]$^+$.

d) Lithium 1-(2-tert-butoxy-2-oxoethyl)pyrrolidine-2-carboxylate

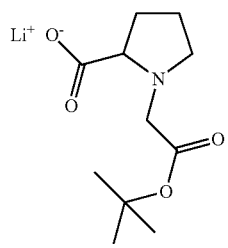 [SMILES: [Li+] ; CC(C)(C)OC(=O)CN1CCCC1C(=O)[O-]]

A turbid solution of methyl 1-(2-tert-butoxy-2-oxoethyl)pyrrolidine-2-carboxylate (0.15 g, 617 μmol) in dioxane (1.5 mL) and H₂O (1.5 mL) was treated with lithium hydroxide mono hydrate (25.9 mg, 617 μmol) and stirred at RT for 2.75 h. The reaction mixture was evaporated and dried at high vacuum at RT. Colorless solid (0.131 g, 90%) which was used in the next step without further purification.

e) Methyl 1-(2-tert-butoxy-2-oxoethyl)pyrrolidine-2-carboxylate

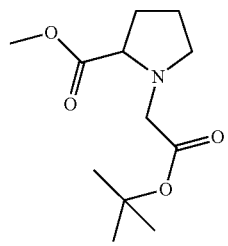 [SMILES: COC(=O)C1CCCN1CC(=O)OC(C)(C)C]

To an ice-cold suspension of methyl pyrrolidine-2-carboxylate hydrochloride (0.5 g, 3.02 mmol) in DMF (3 mL) was added NaH (290 mg, 6.64 mmol). The colorless suspension was stirred at RT for 30 min. before tert-butyl 2-bromoacetate (648 mg, 491 μL, 3.32 mmol) was added. The reaction mixture was stirred at RT for 4 h. The reaction mixture was poured on saturated aqueous NH₄Cl solution and EtOAc and the layers were separated. The aqueous layer was extracted twice with EtOAc. The organic layers were washed twice with H₂O and once with brine, dried over MgSO₄, filtered, treated with silica gel and evaporated. The compound was purified by silica gel chromatography on a 20 g column using an MPLC system eluting with a gradient of n-heptane:EtOAc (100:0 to 65:35). Colorless oil (0.561 g; 76%). MS (ESI): m/z=244.15 [M+H]⁺.

Example 64

3-[3-(3-Cyclopropyl-[1,2,4]oxadiazol-5-yl)-4,7-dihydro-5H-thieno[2,3-c]pyran-2-ylcarbamoyl]-bicyclo[2.2.2]oct-2-ene-2-carboxylic acid

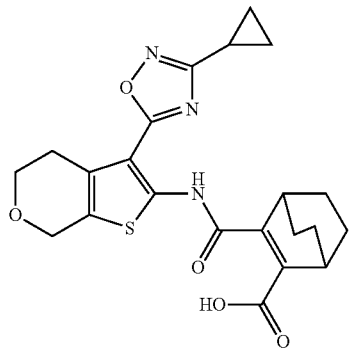 [SMILES: O=C(O)C1=C(C(=O)Nc2sc3c(c2-c2nc(C4CC4)no2)CCOC3)C2CCC1CC2]

The title compound was prepared in analogy to example 55, from 3-(3-cyclopropyl-1,2,4-oxadiazol-5-yl)-5,7-dihydro-4H-thieno[2,3-c]pyran-2-amine (example 55, intermediate) and bicyclo[2.2.2]oct-2-ene-2,3-dicarboxylic anhydride after a reaction time of 2.75 h at 65° C. The compound was purified by silica gel chromatography on a 10 g column using an MPLC system eluting with a gradient of n-heptane:TBME (100:0 to 0:100). Yellow solid (82%). MS (ESI): m/z=442.14 [M+H]⁺.

Example 65

2-[3-(4-Methyl-thiazol-2-yl)-6,6-dioxo-4,5,6,7-tetrahydro-6λ6-thieno[2,3-c]thiopyran-2-ylcarbamoyl]-cyclopent-1-enecarboxylic acid

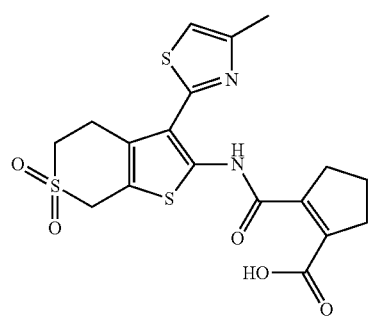 [SMILES: Cc1csc(-c2c(NC(=O)C3=C(C(=O)O)CCC3)sc3c2CCS(=O)(=O)C3)n1]

The title compound was prepared in analogy to example 57, from 3-(4-methyl-thiazol-2-yl)-6,6-dioxo-4,5,6,7-tetrahydro-6λ6-thieno[2,3-c]thiopyran-2-ylamine and 1-cyclopentene-1,2-dicarboxylic anhydride after a reaction time of 64 h at RT. The compound was purified by silica gel chromatography on a 10 g column using an MPLC (Flashmaster) system eluting with a gradient of CH₂Cl₂:MeOH (100:0 to 90:10). Brown solid (21%). MS (ESI): m/z=439.09 [M+H]⁺.

Intermediates a) 3-(4-Methyl-thiazol-2-yl)-6,6-dioxo-4,5,6,7-tetrahydro-6λ6-thieno[2,3-c]thiopyran-2-ylamine

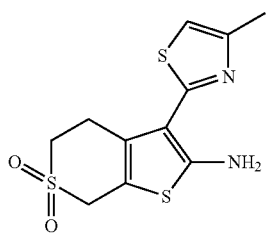 [SMILES: Cc1csc(-c2c(N)sc3c2CCS(=O)(=O)C3)n1]

The title compound was prepared in analogy to example 55, from (1,1-dioxo-tetrahydro-1λ6-thiopyran-4-ylidene)-(4-methyl-thiazol-2-yl)-acetonitrile after a reaction time of 2 h at 65° C. The compound was purified by silica gel chromatography on a 50 g column using an MPLC (Flashmaster) system eluting with a gradient of n-heptane:EtOAc (100:0 to 60:40). Red solid (27%). MS (ESI): m/z=301.014 [M+H]⁺.

b) (1,1-Dioxo-tetrahydro-1λ6-thiopyran-4-ylidene)-(4-methyl-thiazol-2-yl)-acetonitrile

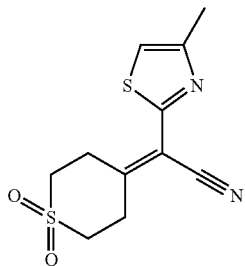 [SMILES: Cc1csc(C(C#N)=C2CCS(=O)(=O)CC2)n1]

The title compound was prepared in analogy to example 56, intermediate b, from 1,1-dioxo-tetrahydro-thiopyran-4-one and 2-(4-methylthiazol-2-yl)acetonitrile after a reaction time of 25 h at 100° C. The compound was purified by silica gel chromatography on a 50 g column using an MPLC system (CombiFlash Companion, Isco Inc.) eluting with a gradient of n-heptane:EtOAc (100:0 to 50:50). Brown solid (19%). MS (ESI): m/z=269.041 [M+H]$^+$.

Example 66

2-[3-(4-Methyl-thiazol-2-yl)-4,7-dihydro-5H-thieno[2,3-c]pyran-2-ylcarbamoyl]-cyclohex-1-enecarboxylic acid

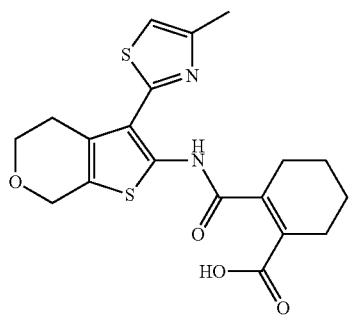 [SMILES: Cc1csc(-c2c(NC(=O)C3=C(C(=O)O)CCCC3)sc3c2CCOC3)n1]

The title compound was prepared in analogy to example 56, from 3-(4-methylthiazol-2-yl)-5,7-dihydro-4H-thieno[2,3-c]pyran-2-amine (example 56, intermediate a) and 1-cyclohexene-1,2-dicarboxylic anhydride (CAS RN 2426-02-0) after a reaction time of 22 h at RT. The yellow suspension was filtered and washed with Et$_2$O. Light yellow solid (28%). MS (ESI): m/z=405.09 [M+H]$^+$.

Example 67

2-[3-(3-Isopropyl-[1,2,4]oxadiazol-5-yl)-4,5,6,7-tetrahydro-benzo[b]thiophen-2-ylcarbamoyl]-cyclopent-1-enecarboxylic acid

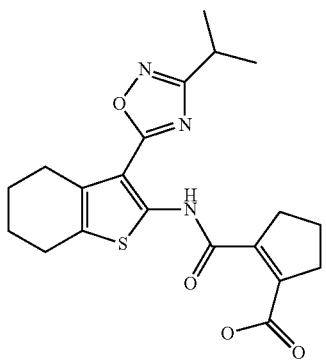 [SMILES: CC(C)c1noc(-c2c(NC(=O)C3=C(C(=O)O)CCC3)sc3c2CCCC3)n1]

The title compound was prepared in analogy to example 56, from 3-(3-isopropyl-1,2,4-oxadiazol-5-yl)-4,5,6,7-tetrahydrobenzo[b]thiophen-2-amine and 1-cyclopentene-1,2-dicarboxylic anhydride after a reaction time of 20 h at RT. The yellow suspension was filtered and washed with a small amount of Et$_2$O. Yellow solid (3%). MS (ESI): m/z=402.15 [M+H]$^+$. The mother liquor was purified by preparative HPLC (Gemini NX column) using a gradient of MeOH:H$_2$O (containing 0.1% formic acid) (20:80 to 98:2) to give a second batch of the title compound. Yellow solid (80%). MS (ESI): m/z=402.15 [M+H]$^+$.

Intermediates a) 3-(3-Isopropyl-1,2,4-oxadiazol-5-yl)-4,5,6,7-tetrahydrobenzo[b]thiophen-2-amine

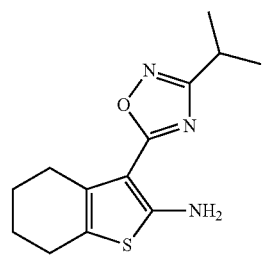 [SMILES: CC(C)c1noc(-c2c(N)sc3c2CCCC3)n1]

The title compound was prepared in analogy to example 55, intermediate, from 2-(3-isopropyl-1,2,4-oxadiazol-5-yl)acetonitrile and cyclohexanone after a reaction time of 2.5 h at 50° C. The compound was purified by silica gel chromatography on a 10 g column using an MPLC (ISCO) system eluting with a gradient of n-heptane:EtOAc (100:0 to 65:35). Off-white solid (57%). MS (ESI): m/z=264.12 [M+H]$^+$.

Example 68

3-[3-(3-Isopropyl-[1,2,4]oxadiazol-5-yl)-4,5,6,7-tetrahydro-benzo[b]thiophen-2-ylcarbamoyl]-bicyclo[2.2.2]oct-2-ene-2-carboxylic acid

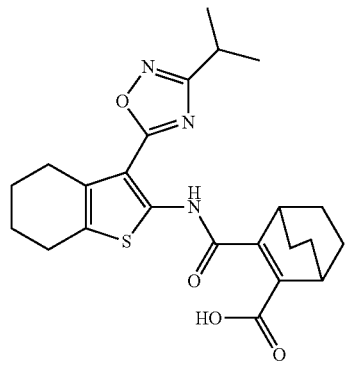 [SMILES: CC(C)c1noc(-c2c(NC(=O)C3=C(C(=O)O)C4CCC3CC4)sc3c2CCCC3)n1]

The title compound was prepared in analogy to example 56, from 3-(3-isopropyl-1,2,4-oxadiazol-5-yl)-4,5,6,7-tetrahydrobenzo[b]thiophen-2-amine (example 67, intermediate a) and bicyclo[2.2.2]oct-2-ene-2,3-dicarboxylic anhydride after a reaction time of 20 h at RT. The light yellow suspension was filtered and washed with a small amount of Et₂O. The mother liquor was purified by preparative HPLC (Gemini NX column) using a gradient of MeOH:H₂O (containing 0.1% formic acid) (20:80 to 98:2). Yellow gum (50%). MS (ESI): m/z=442.18 [M+H]⁺.

Example 69

2-[3-(3-Isopropyl-[1,2,4]oxadiazol-5-yl)-4,7-dihydro-5H-thieno[2,3-c]pyran-2-ylcarbamoyl]-cyclopent-1-enecarboxylic acid

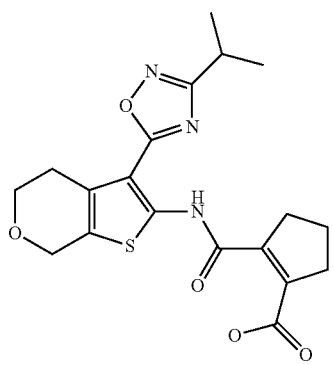 [SMILES: CC(C)c1noc(-c2c(NC(=O)C3=C(C(=O)O)CCC3)sc3c2CCOC3)n1]

The title compound was prepared in analogy to example 56, from 3-(3-isopropyl-1,2,4-oxadiazol-5-yl)-5,7-dihydro-4H-thieno[2,3-c]pyran-2-amine and 1-cyclopentene-1,2-dicarboxylic anhydride after a reaction time of 22.5 h at RT. The product was purified by preparative HPLC (Gemini NX column) using a gradient of MeOH:H₂O (containing 0.1% formic acid) (20:80 to 98:2). Yellow solid (76%). MS (ESI): m/z=404.13 [M+H]⁺.

Intermediate 3-(3-Isopropyl-1,2,4-oxadiazol-5-yl)-5,7-dihydro-4H-thieno[2,3-c]pyran-2-amine

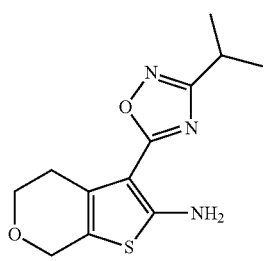 [SMILES: CC(C)c1noc(-c2c(N)sc3c2CCOC3)n1]

The title compound was prepared in analogy to example 55, intermediate, from 2-(3-isopropyl-1,2,4-oxadiazol-5-yl)acetonitrile and dihydro-2H-pyran-4(3H)-one after a reaction time of 3 h at 50° C. The compound was purified by silica gel chromatography on a 20 g column using an MPLC (ISCO) system eluting with a gradient of n-heptane:EtOAc (100:0 to 65:35). Off-white solid (63%). MS (ESI): m/z=266.10 [M+H]⁺.

Example 70

3-[3-(3-Isopropyl-[1,2,4]oxadiazol-5-yl)-4,7-dihydro-5H-thieno[2,3-c]pyran-2-ylcarbamoyl]-bicyclo[2.2.2]oct-2-ene-2-carboxylic acid

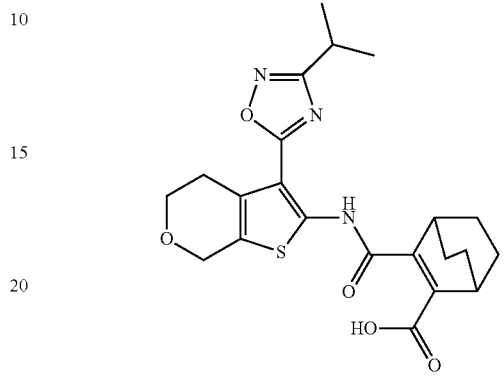

The title compound was prepared in analogy to example 56, from 3-(3-isopropyl-1,2,4-oxadiazol-5-yl)-5,7-dihydro-4H-thieno[2,3-c]pyran-2-amine (example 69, intermediate a) and bicyclo[2.2.2]oct-2-ene-2,3-dicarboxylic anhydride after a reaction time of 22.5 h at RT. The compound was purified by preparative HPLC (Gemini NX column) using a gradient of MeOH:H₂O (containing 0.1% formic acid) (20:80 to 98:2). Yellow solid (8%). MS (ESI): m/z=444.16 [M+H]⁺.

Example 71

2-[3-(3-Trifluoromethyl-[1,2,4]oxadiazol-5-yl)-4,7-dihydro-5H-thieno[2,3-c]pyran-2-ylcarbamoyl]-cyclopent-1-enecarboxylic acid

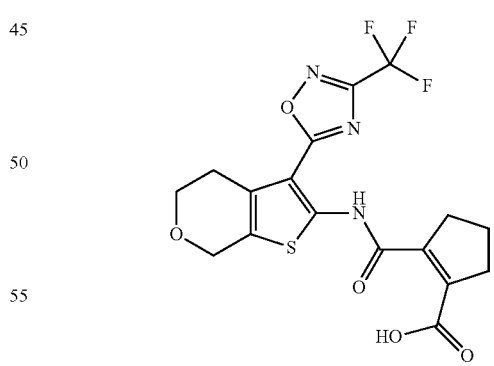

The title compound was prepared in analogy to example 56, from 3-(3-(trifluoromethyl)-1,2,4-oxadiazol-5-yl)-5,7-dihydro-4H-thieno[2,3-c]pyran-2-amine and 1-cyclopentene-1,2-dicarboxylic anhydride after a reaction time of 69 h at RT. The compound was purified by preparative HPLC (Gemini NX column) using a gradient of MeOH:H₂O (containing 0.1% formic acid) (20:80 to 98:2). Light brown solid (2%). MS (ESI): m/z=428.05 [M−H]⁻.

Intermediates a) 3-(3-(Trifluoromethyl)-1,2,4-oxadiazol-5-yl)-5,7-dihydro-4H-thieno[2,3-c]pyran-2-amine

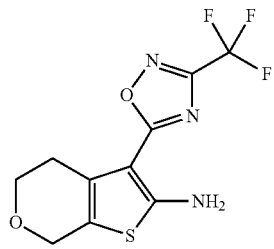 [SMILES: Nc1sc2c(c1-c1nc(C(F)(F)F)no1)CCOC2]

The title compound was prepared in analogy to example 56, intermediate a, from 2-(2H-pyran-4(3H,5H,6H)-ylidene)-2-(3-(trifluoromethyl)-1,2,4-oxadiazol-5-yl)acetonitrile after a reaction time of 2 h at 65° C. The compound was purified by silica gel chromatography on a 50 g column using an MPLC system (Flashmaster) eluting with a gradient of n-heptane:TBME (100:0 to 60:40). Orange solid (22%) MS (ESI): 290.02 [M−H]−.

b) 2-(2H-Pyran-4(3H,5H,6H)-ylidene)-2-(3-(trifluoromethyl)-1,2,4-oxadiazol-5-yl)acetonitrile

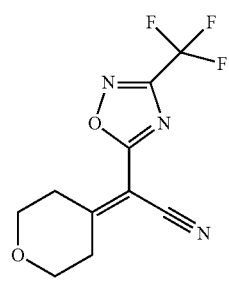 [SMILES: N#CC(=C1CCOCC1)c1nc(C(F)(F)F)no1]

The title compound was prepared in analogy to example 56, intermediate b, from dihydro-2H-pyran-4(3H)-one and 2-(3-(trifluoromethyl)-1,2,4-oxadiazol-5-yl)acetonitrile after a reaction time of 17 h at 100° C. The compound was purified by silica gel chromatography on a 50 g column using an MPLC system (Flashmaster) eluting with a gradient of n-heptane:EtOAc (100:0 to 50:50). Brown oil (62%) MS (EI): m/z=259 [M].

Example 72

2-(3-(3-Methyl-1,2,4-oxadiazol-5-yl)-5,7-dihydro-4H-spiro[benzo[b]thiophene-6,3'-oxetane]-2-ylcarbamoyl)cyclopent-1-enecarboxylic acid

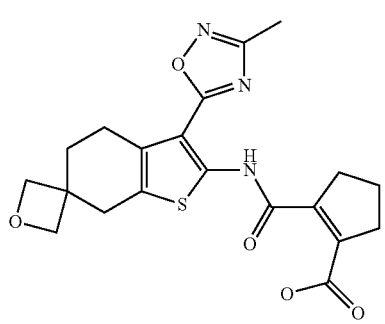 [SMILES: Cc1noc(-c2c(NC(=O)C3=C(C(=O)O)CCC3)sc3c2CCC2(COC2)C3)n1]

The title compound was prepared in analogy to example 57, from 3-(3-methyl-1,2,4-oxadiazol-5-yl)-5,7-dihydro-4H-spiro[benzo[b]thiophene-6,3'-oxetan]-2-amine and 1-cyclopentene-1,2-dicarboxylic anhydride after a reaction time of 28 h at RT. The product was purified by preparative HPLC (Gemini NX column) using a gradient of MeOH:H₂O (containing 0.1% formic acid) (20:80 to 98:2). Yellow solid (26%). MS (ESI): m/z=416.13 [M+H]+.

Intermediates a) 3-(3-Methyl-1,2,4-oxadiazol-5-yl)-5,7-dihydro-4H-spiro[benzo[b]thiophene-6,3'-oxetan]-2-amine

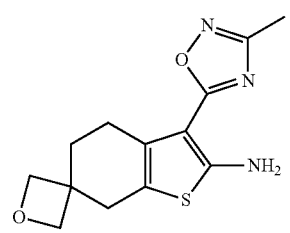 [SMILES: Cc1noc(-c2c(N)sc3c2CCC2(COC2)C3)n1]

The title compound was prepared in analogy to example 55, intermediate, from 2-oxaspiro[3.5]nonan-7-one and 2-(3-methyl-1,2,4-oxadiazol-5-yl)acetonitrile (CAS RN 1239771-67-5) after a reaction time of 2.5 h at 50° C. The compound was purified by silica gel chromatography on a 10 g column using an MPLC (ISCO) system eluting with a gradient of n-heptane:EtOAc (100:0 to 50:50). Light brown solid (75%). MS (ESI): m/z=278.10 [M+H]+.

b) 2-Oxaspiro[3.5]nonan-7-one

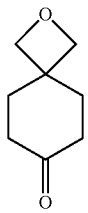

A solution of 2,8,11-trioxa-dispiro[3.2.4.2]tridecane (0.5 g, 2.71 mmol) in acetic acid 80% (10 mL) was heated to 65° C. for 6 h. The compound was purified by silica gel chromatography on a 10 g column using an MPLC (ISCO) system eluting with a gradient of n-heptane:EtOAc (100:0 to 0:100). Colorless solid (0.36 g; 94%). MS (EI): m/z=140 [M].

c) 2,8,11-Trioxa-dispiro[3.2.4.2]tridecane

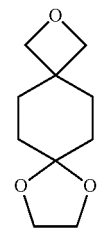

To a suspension of 1,4-dioxaspiro[4.5]decane-8,8-diyldimethanol (2.2 g, 10.9 mmol) in THF (50 mL), cooled down to −75° C. was added dropwise n-butyllithium (6.8 mL, 10.9 mmol, 1.6M solution in hexanes) over 8 min. while the temperature was maintained below −70° C. The reaction mixture was stirred at −75° C. for 30 min. before a solution of 2-methylbenzene-1-sulfonyl chloride (2.07 g, 10.9 mmol, 77%) in THF (10 mL) was added dropwise over 15 minutes. The reaction mixture was allowed to warm to RT overnight. The clear, pale yellow solution was cooled down to −75° C. and n-butyllithium (6.8 mL, 10.9 mmol, 1.6M solution in hexanes) was added dropwise over approx. 10 min. Stirring was continued at RT for 6 h. Then the reaction mixture was poured on saturated aqueous NH$_4$Cl solution and EtOAc and the layers were separated. The aqueous layer was extracted twice with EtOAc. The organic layers were dried over MgSO$_4$, filtered, treated with silica gel and evaporated. The compound was purified by silica gel chromatography on a 50 g column using a MPLC system eluting with a gradient of n-heptane:EtOAc (100:0 to 0:100). Colorless solid (0.52 g; 25%). MS (ESI): m/z=185.12 [M+H]$^+$.

d) 1,4-Dioxaspiro[4.5]decane-8,8-diyldimethanol

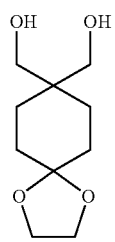

To an ice-cold solution of diethyl 1,4-dioxaspiro[4.5]decane-8,8-dicarboxylate (5.29 g, 18.5 mmol) in THF (60 mL) was added dropwise lithium aluminum hydride (24.6 mL, 24.6 mmol, 1M solution in THF). The reaction mixture was stirred at 0° C. for approx. 1 h, then at RT for 20 h. To the grey suspension was added continuously H$_2$O (1 mL) and 1M aqueous sodium hydroxide solution (1 mL) at 0° C. The suspension was stirred for approx. 1 h, then filtered over dicalite and washed with THF (approx. 50 mL). To the filtrate was added EtOAc (100 mL) and the solvent was evaporated until a suspension formed, which was filtered. The solid was washed with EtOAc and dried under high vacuum. Colorless solid (1.89 g; 50%). MS (EI): m/z=202 [M].

e) 1,4-Dioxaspiro[4.5]decane-8,8-dicarboxylate

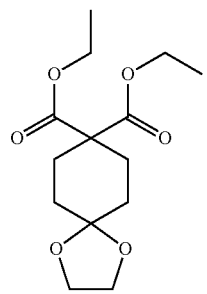 [SMILES: CCOC(=O)C1(C(=O)OCC)CCC2(CC1)OCCO2]

To a solution of diisopropylamine (2.83 g, 3.99 mL, 28.0 mmol) in THF (80 mL) was added n-butyllithium in hexanes (11.2 mL, 28.0 mmol, 1.6M solution in hexanes) below −70° C. The reaction mixture was stirred at −75° C. for 30 min., before a solution of ethyl 1,4-dioxaspiro[4.5]decane-8-carboxylate (5 g, 23.3 mmol; prepared in analogy to M. Malacria et al., *Synthesis* 1998, 4, 436-443) in THF (5 mL) was added below −70° C. over 5 min. The reaction mixture was stirred at −75° C. for 1 h. Ethyl chloroformate (2.53 g, 2.24 mL, 23.3 mmol) was added over 10 min. below −68° C. After stirring at −75° C. the reaction mixture was allowed to warm up to RT and then poured on saturated aqueous NH$_4$Cl solution (200 mL) and EtOAc (200 mL) and the layers were separated. The aqueous layer was extracted twice with EtOAc (50 mL). The organic layers were dried over MgSO$_4$, filtered, treated with silica gel and evaporated. The compound was purified by silica gel chromatography on a 50 g column using an MPLC system eluting with a gradient of n-heptane:EtOAc (100:0 to 65:35). Colorless oil (5.29 g; 79%).

Example 73

3-(3-(3-Methyl-1,2,4-oxadiazol-5-yl)-5,7-dihydro-4H-spiro[benzo[b]thiophene-6,3'-oxetane]-2-ylcarbamoyl)bicyclo[2.2.2]oct-2-ene-2-carboxylic acid

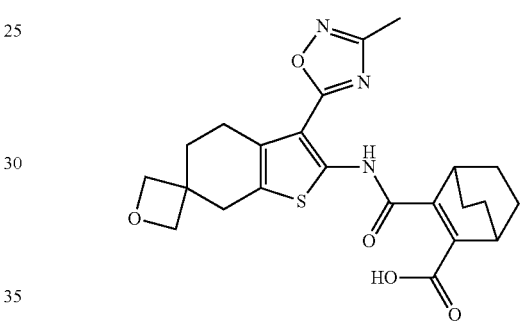

The title compound was prepared in analogy to example 57, from 3-(3-methyl-1,2,4-oxadiazol-5-yl)-5,7-dihydro-4H-spiro[benzo[b]thiophene-6,3'-oxetan]-2-amine (example 72, intermediate a) and bicyclo[2.2.2]oct-2-ene-2,3-dicarboxylic anhydride after a reaction time of 28 h at RT. The compound was purified by preparative HPLC (Gemini NX column) using a gradient of MeOH:H$_2$O (containing 0.1% formic acid) (20:80 to 98:2). Light brown solid (2%). MS (ESI): m/z=454.12 [M+H]$^+$.

Example 74

2-(3-(4-Methylthiazol-2-yl)-5,7-dihydro-4H-spiro[benzo[b]thiophene-6,3'-oxetane]-2-ylcarbamoyl)cyclopent-1-enecarboxylic acid

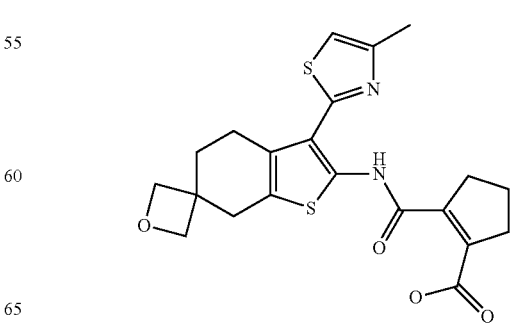

The title compound was prepared in analogy to example 56, from 3-(4-methylthiazol-2-yl)-5,7-dihydro-4H-spiro[benzo[b]thiophene-6,3'-oxetan]-2-amine and 1-cyclopentene-1,2-dicarboxylic anhydride after a reaction time of 5 h at RT. The turbid yellow solution was evaporated and the residue dissolved in DMSO (5 mL). A small part of this solution (approx. 10%) was purified by preparative HPLC (Gemini NX column) using a gradient of MeOH:H$_2$O (containing 0.1% formic acid) (20:80 to 98:2) to give a first batch of compound (yellow solid (2 mg). The suspension formed upon standing from the DMSO solution was filtered, washed with DMSO (approx. 2 mL) and H$_2$O (10 mL) and dried to give a second batch of compound. Yellow solid (0.062 g; 60%). MS (ESI): m/z=431.11 [M+H]$^+$.

Intermediates a) 3-(4-Methylthiazol-2-yl)-5,7-dihydro-4H-spiro[benzo[b]thiophene-6,3'-oxetan]-2-amine

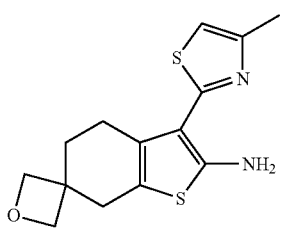 [SMILES: Cc1csc(-c2c(N)sc3c2CCC2(COC2)C3)n1]

The title compound was prepared in analogy to example 56, intermediate a, from 2-(4-methylthiazol-2-yl)-2-(2-oxaspiro[3.5]nonan-7-ylidene) after a reaction time of 2.33 h at 65° C. The compound was purified by silica gel chromatography on a 10 g column using an MPLC system eluting with a gradient of n-heptane:EtOAc (100:0 to 50:50). Light yellow solid (71%). MS (ESI): m/z=293.08 [M+H]$^+$.

b) 2-(4-Methylthiazol-2-yl)-2-(2-oxaspiro[3.5]nonan-7-ylidene)

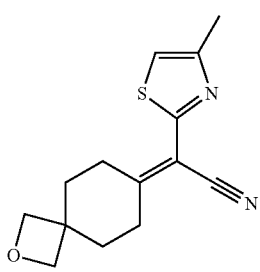 [SMILES: Cc1csc(C(C#N)=C2CCC3(CC2)COC3)n1]

The title compound was prepared in analogy to example 56, intermediate b, from 2-oxaspiro[3.5]nonan-7-one and 2-(4-methylthiazol-2-yl)acetonitrile (CAS RN 19785-39-8) after a reaction time of 4 h at 100° C. The compound was purified by silica gel chromatography on a 10 g column using an MPLC system eluting with a gradient of n-heptane:EtOAc (100:0 to 50:50). Orange solid (71%). MS (ESI): m/z=261.11 [M+H]$^+$.

Example 75

(1SR,2SR)-2-[3-(3-Isopropyl-[1,2,4]oxadiazol-5-yl)-4,7-dihydro-5H-thieno[2,3-c]pyran-2-ylcarbamoyl]-cyclohexanecarboxylic acid

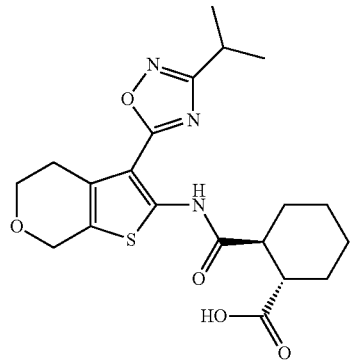 [SMILES: CC(C)c1noc(-c2c(NC(=O)[C@H]3CCCC[C@@H]3C(=O)O)sc3c2CCOC3)n1]

The title compound was prepared in analogy to example 56, from 3-(3-isopropyl-1,2,4-oxadiazol-5-yl)-5,7-dihydro-4H-thieno[2,3-c]pyran-2-amine (example 69, intermediate a) and trans-1,2-cyclohexanedicarboxylic anhydride after a reaction time of 68 h at RT. The compound was purified by preparative HPLC (Gemini NX column) using a gradient of MeOH:H$_2$O (containing 0.1% formic acid) (20:80 to 98:2). Colorless solid (33%). MS (ESI): m/z=420.16 [M+H]$^+$.

Example 76

(1RS,2SR)-2-[3-(3-Isopropyl-[1,2,4]oxadiazol-5-yl)-4,7-dihydro-5H-thieno[2,3-c]pyran-2-ylcarbamoyl]-cyclohexanecarboxylic acid

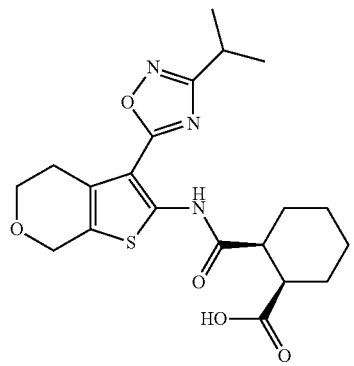 [SMILES: CC(C)c1noc(-c2c(NC(=O)[C@H]3CCCC[C@H]3C(=O)O)sc3c2CCOC3)n1]

The title compound was prepared in analogy to example 56, from 3-(3-isopropyl-1,2,4-oxadiazol-5-yl)-5,7-dihydro-4H-thieno[2,3-c]pyran-2-amine (example 69, intermediate a) and cis-1,2-cyclohexanedicarboxylic anhydride after a reaction time of 92 h at RT. The compound was purified by preparative HPLC (Gemini NX column) using a gradient of MeOH:H$_2$O (containing 0.1% formic acid) (20:80 to 98:2). The compound was purified a second time by silica gel chromatography on a 10 g column using an MPLC (Flashmaster) system eluting with a gradient of CH$_2$Cl$_2$:MeOH (100:0 to 90:10) to give the desired compound as a colorless foam (63%). MS (ESI): m/z=420.16 [M+H]$^+$.

Example 77

2-[4,4-Dimethyl-3-(3-methyl-[1,2,4]oxadiazol-5-yl)-5,6-dihydro-4H-cyclopenta[b]thiophen-2-ylcarbamoyl]-cyclopent-1-enecarboxylic acid

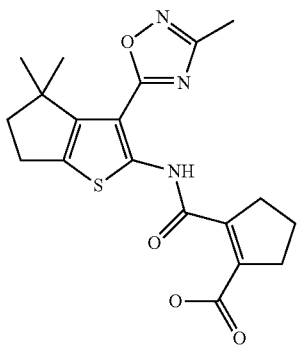 [SMILES: Cc1noc(-c2c(NC(=O)C3=C(C(=O)O)CCC3)sc3c2C(C)(C)CC3)n1]

The title compound was prepared in analogy to example 55, from 4,4-dimethyl-3-(3-methyl-[1,2,4]oxadiazol-5-yl)-5,6-dihydro-4H-cyclopenta[b]thiophen-2-ylamine and 1-cyclopentene-1,2-dicarboxylic anhydride after a reaction time of 5 h at 65° C. Yellow solid (54%) MS (ESI): m/z=388.13 [M+H]⁺.

Intermediates a) 4,4-Dimethyl-3-(3-methyl-[1,2,4]oxadiazol-5-yl)-5,6-dihydro-4H-cyclopenta[b]thiophen-2-ylamine

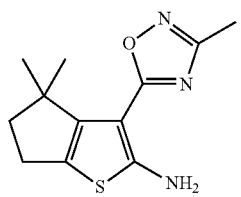 [SMILES: Cc1noc(-c2c(N)sc3c2C(C)(C)CC3)n1]

The title compound was prepared in analogy to example 56, intermediate a, from 2-(2,2-dimethylcyclopentylidene)-2-(3-methyl-1,2,4-oxadiazol-5-yl)acetonitrile. The compound was purified by silica gel chromatography on a 20 g column using a MPLC system eluting with a gradient of n-heptane:EtOAc (100:0 to 0:100). Orange powder (91%). MS (ESI): m/z=250 [M+H]⁺.

b) 2-(2,2-Dimethylcyclopentylidene)-2-(3-methyl-1,2,4-oxadiazol-5-yl)acetonitrile

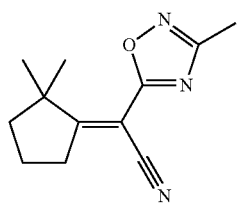 [SMILES: Cc1noc(/C(C#N)=C2/CCCC2(C)C)n1]

The title compound was prepared in analogy to example 56, intermediate b, from 2,2-dimethylcyclopentanone (CAS RN: 4541-32-6) and 2-(3-methyl-1,2,4-oxadiazol-5-yl)acetonitrile (Princeton BioMolecular Research, Inc.). The compound was purified by silica gel chromatography on a 50g column using a MPLC system eluting with a gradient of n-heptane:TBME (100:0 to 40:60). Light yellow solid (22%) MS (EI): m/z=217 [M]⁺.

Example 78

2-[3-(4-Methyl-oxazol-2-yl)-4,7-dihydro-5H-thieno[2,3-c]pyran-2-ylcarbamoyl]-cyclopent-1-enecarboxylic acid

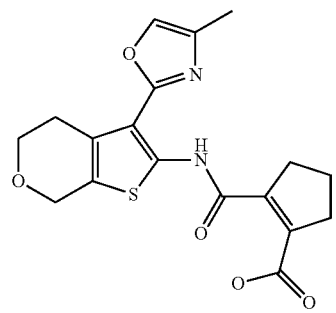 [SMILES: Cc1coc(-c2c(NC(=O)C3=C(C(=O)O)CCC3)sc3c2CCOC3)n1]

The title compound was prepared in analogy to example 57, from 3-(4-methyl-oxazol-2-yl)-4,7-dihydro-5H-thieno[2,3-c]pyran-2-ylamine and 1-cyclopentene-1,2-dicarboxylic anhydride. Yellow solid (38%). MS (ESI): m/z=373.087 [M−H]⁻.

Intermediates a) 3-(4-Methyl-oxazol-2-yl)-4,7-dihydro-5H-thieno[2,3-c]pyran-2-ylamine

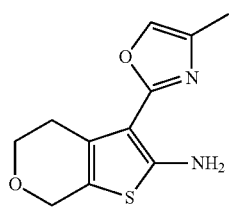 [SMILES: Cc1coc(-c2c(N)sc3c2CCOC3)n1]

The title compound was prepared in analogy to example 56, intermediate a, from (4-methyl-oxazol-2-yl)-(tetrahydro-pyran-4-ylidene)-acetonitrile. Light yellow solid (84%). MS (ESI): m/z=237.070 [M+H]⁺.

b) (4-Methyl-oxazol-2-yl)-(tetrahydro-pyran-4-ylidene)-acetonitrile

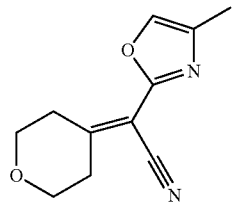

The title compound was prepared in analogy to example 56, intermediate b, from tetrahydro-pyran-4-one and (4-methyl-oxazol-2-yl)-acetonitrile. Light yellow solid (59%). MS (ESI): m/z=205.097 [M+H]$^+$.

c) (4-Methyl-oxazol-2-yl)-acetonitrile

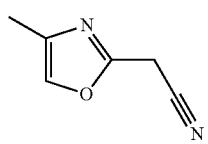

The title compound was prepared in analogy to example 56, intermediate c, from 2-(chloromethyl)-4-methyloxazole (CAS RN: 1196157-12-6). Light brown liquid (35%). MS (ESI): m/z=123.055 [M+H]$^+$.

Example 79

3-[3-(4-Methyl-oxazol-2-yl)-4,7-dihydro-5H-thieno[2,3-c]pyran-2-ylcarbamoyl]-bicyclo[2.2.2]oct-2-ene-2-carboxylic acid

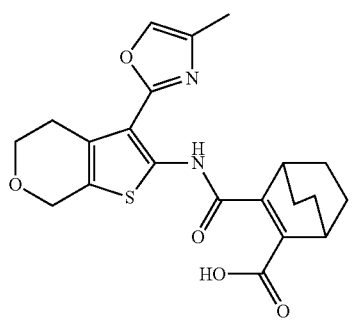 [SMILES: Cc1coc(-c2c(NC(=O)C3=C(C(=O)O)C4CCC3CC4)sc3c2CCOC3)n1]

The title compound was prepared in analogy to example 57, from 3-(4-methyl-oxazol-2-yl)-4,7-dihydro-5H-thieno[2,3-c]pyran-2-ylamine (example 78, intermediate a) and bicyclo[2.2.2]oct-2-ene-2,3-dicarboxylic anhydride. MS (ESI): m/z=415.133 [M+H]$^+$.

Example 80

3-[3-(3-Cyclopropyl-[1,2,4]oxadiazol-5-yl)-benzo[b]thiophen-2-ylcarbamoyl]-bicyclo[2.2.2]oct-2-ene-2-carboxylic acid

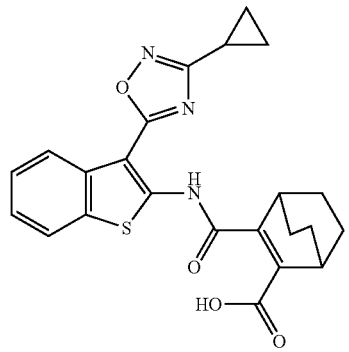 [SMILES: O=C(O)C1=C(C(=O)Nc2sc3ccccc3c2-c2nc(C3CC3)no2)C2CCC1CC2]

The title compound was prepared in analogy to example 55, from 3-(3-cyclopropyl-[1,2,4]oxadiazol-5-yl)-benzo[b]thiophen-2-ylamine and bicyclo[2.2.2]oct-2-ene-2,3-dicarboxylic anhydride. Yellow solid (82%). MS (ESI): m/z=436.13 [M+H]$^+$.

Intermediates a) 3-(3-Cyclopropyl-[1,2,4]oxadiazol-5-yl)-benzo[b]thiophen-2-ylamine

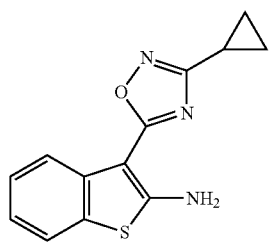 [SMILES: Nc1sc2ccccc2c1-c1nc(C2CC2)no1]

To an ice-cold solution of [3-(3-cyclopropyl-[1,2,4]oxadiazol-5-yl)-benzo[b]thiophen-2-yl]-carbamic acid tert-butyl ester (0.929 g, 2.6 mmol) in CH$_2$Cl$_2$ (6 mL) was added TFA (5.93 g, 4.00 mL, 52.0 mmol) and the solution was stirred at RT for 2.75 h. The reaction mixture was evaporated. The residue was poured on saturated aqueous NaHCO$_3$ solution and CH$_2$Cl$_2$ and the layers were separated. The aqueous layer was extracted three times with CH$_2$Cl$_2$. The organic layers were dried over MgSO$_4$, filtered, treated with silica gel and evaporated. The compound was purified twice by silica gel chromatography on a 20 g column using a MPLC system eluting with a gradient of n-heptane:EtOAc (100:0 to 65:35). Colorless solid (0.324 g; 48%). MS (ESI): m/z=258.07 [M+H]$^+$.

b) [3-(3-Cyclopropyl-[1,2,4]oxadiazol-5-yl)-benzo[b]thiophen-2-yl]-carbamic acid tert-butyl ester

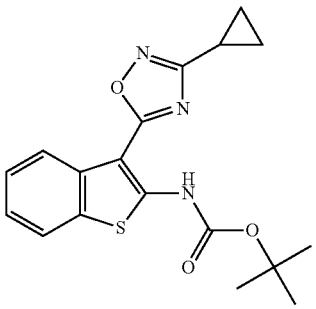 [SMILES: CC(C)(C)OC(=O)Nc1sc2ccccc2c1-c1nc(C2CC2)no1]

The title compound was prepared in analogy to example 58, intermediate c, from (Z)-tert-butyl 3-((amino(cyclopropyl)methyleneaminooxy)carbonyl)benzo[b]thiophen-2-yl-carbamate for 23 h at reflux. Colorless solid (70%). MS (ESI): m/z=358.3 [M+H]$^+$.

c) (Z)-tert-butyl 3-((amino(cyclopropyl)methyleneaminooxy)carbonyl)benzo[b]thiophen-2-ylcarbamate

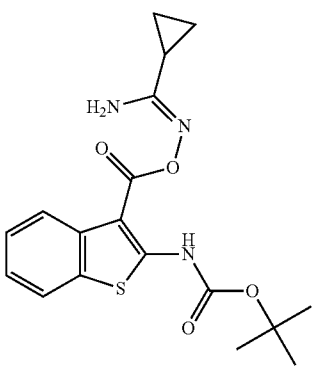 [SMILES: CC(C)(C)OC(=O)Nc1sc2ccccc2c1C(=O)O/N=C(\N)C1CC1]

The title compound was prepared in analogy to example 58, intermediate d, from 2-tert-butoxycarbonylamino-benzo[b]thiophene-3-carboxylic acid and N-hydroxy-cyclopropanecarboxamidine. The compound was purified by silica gel chromatography on a MPLC system eluting with a gradient of n-heptane:EtOAc (100:0 to 0:100). Colorless solid (73%). MS (ESI): m/z=376.4 [M+H]$^+$.

d) 2-tert-Butoxycarbonylamino-benzo[b]thiophene-3-carboxylic acid

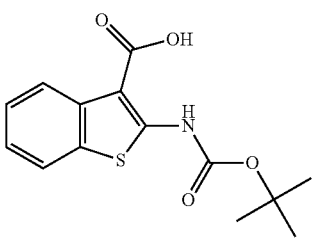 [SMILES: CC(C)(C)OC(=O)Nc1sc2ccccc2c1C(=O)O]

The title compound was prepared in analogy to example 58, intermediate e, from 2-tert-butoxycarbonylamino-benzo[b]thiophene-3-carboxylic acid ethyl ester. The compound was purified by silica gel chromatography on a 20 g column using an MPLC system (CombiFlash Companion, Isco Inc.) eluting with a gradient of n-heptane:EtOAc (100:0 to 0:100). Off-white solid (46%). MS (ESI): m/z=292.066 [M+H]$^+$.

e) 2-tert-Butoxycarbonylamino-benzo[b]thiophene-3-carboxylic acid ethyl ester

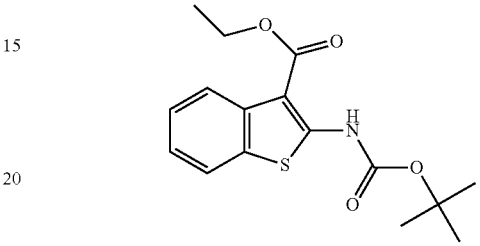

To a solution of ethyl 2-aminobenzo[b]thiophene-3-carboxylate (2.0 g, 9.04 mmol, CAS RN 7311-95-7) in THF (36 mL) was added DMAP (101 mg, 904 µmol). Then, di-tert-butyl dicarbonate (2.37 g, 10.8 mmol) in THF (8 mL) was added dropwise. The reaction mixture was stirred for 3 h at RT. The reaction mixture was poured on saturated aqueous NH$_4$Cl solution and EtOAc and the layers were separated. The aqueous layer was extracted a second time with EtOAc. The organic layers were washed with brine, dried over MgSO$_4$, filtered and concentrated under vacuum. The compound was purified by silica gel chromatography on a 50 g column using an MPLC system (CombiFlash Companion, Isco Inc.) eluting with a gradient of n-heptane:EtOAc (100:0 to 50:50). Colorless solid (2.4 g, 83%). MS (EI): m/z=321 [M]$^+$.

Example 81

2-[6,6-Dioxo-3-(3-trifluoromethyl-[1,2,4]oxadiazol-5-yl)-4,5,6,7-tetrahydro-6l6-thieno[2,3-c]thiopyran-2-ylcarbamoyl]-cyclopent-1-enecarboxylic acid

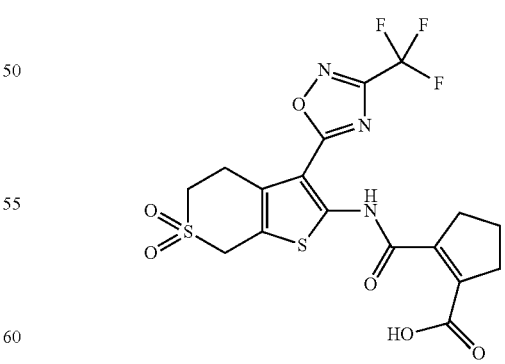

The title compound was prepared in analogy to example 55, from 6,6-dioxo-3-(3-trifluoromethyl-[1,2,4]oxadiazol-5-yl)-4,5,6,7-tetrahydro-6-thieno[2,3-c]thiopyran-2-ylamine and 1-cyclopentene-1,2-dicarboxylic anhydride. Yellow solid (20%). MS (ESI): m/z=476.02 [M−H]$^-$.

123

Intermediate 6,6-Dioxo-3-(3-trifluoromethyl-[1,2,4]oxadiazol-5-yl)-4,5,6,7-tetrahydro-6-thieno[2,3-c]thiopyran-2-ylamine

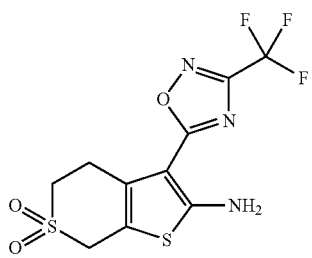 [SMILES: Nc1sc2c(c1-c1nc(C(F)(F)F)no1)CCS(=O)(=O)C2]

The title compound was prepared in analogy to example 55, intermediate, from 2-(3-(trifluoromethyl)-1,2,4-oxadiazol-5-yl)acetonitrile (CAS RN 1308384-47-5) and 1,1-dioxo-tetrahydro-1λ6-thiopyran-4-one (CAS RN 17396-35-9). The compound was purified twice by silica gel chromatography on a 50 g column using an MPLC (ISCO) system eluting with a gradient of n-heptane:EtOAc (100:0 to 0:100). The product was purified by preparative HPLC (Gemini NX column) using a gradient of MeOH:H$_2$O (containing 0.1% formic acid) (20:80 to 98:2). Light brown solid (6%). MS (ESI): m/z=337.989 [M−H]$^-$.

Example 82

2,2-Dimethyl-N-[3-(3-methyl-[1,2,4]oxadiazol-5-yl)-4,5,6,7-tetrahydro-benzo[b]thiophen-2-yl]-succinamic acid

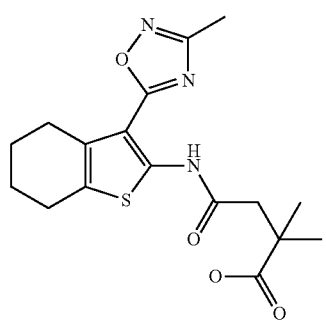 [SMILES: Cc1noc(-c2c(NC(=O)CC(C)(C)C(=O)O)sc3c2CCCC3)n1]

The title compound was prepared in analogy to example 56, from 3-(3-methyl-[1,2,4]oxadiazol-5-yl)-4,5,6,7-tetrahydro-benzo[b]thiophen-2-ylamine and 3,3-dimethyl-dihydro-furan-2,5-dione (CAS RN 17347-61-4) after a reaction time of 115 h at RT. The reaction was evaporated and the residue purified by preparative HPLC (Gemini NX column) using a gradient of MeOH:H$_2$O (containing 0.1% formic acid) (20:80 to 98:2). Colorless solid (35%). MS (ESI): m/z=364.13 [M+H]$^+$.

124

Intermediate 3-(3-Methyl-[1,2,4]oxadiazol-5-yl)-4,5,6,7-tetrahydro-benzo[b]thiophen-2-ylamine

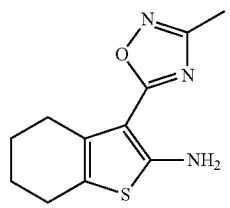 [SMILES: Cc1noc(-c2c(N)sc3c2CCCC3)n1]

The title compound was prepared in analogy to example 55, intermediate, from 2-(3-methyl-1,2,4-oxadiazol-5-yl)acetonitrile (Princeton BioMolecular Research, Inc.) and cyclohexanone. The compound was purified by silica gel chromatography on a 50g column using a MPLC system eluting with a gradient of n-heptane:EtOAc (100:0 to 50:50). Light yellow powder (93%) MS (ESI): m/z=236.2 [M+H]$^+$.

Example 83

2-[3-(3-Cyclopropyl-[1,2,4]oxadiazol-5-yl)-5,5-dimethyl-4,7-dihydro-5H-thieno[2,3-c]pyran-2-ylcarbamoyl]-cyclopent-1-enecarboxylic acid

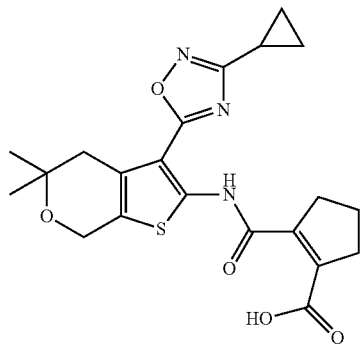 [SMILES: CC1(C)Cc2c(sc(NC(=O)C3=C(C(=O)O)CCC3)c2-c2nc(C3CC3)no2)CO1]

The title compound was prepared in analogy to example 57, from 3-(3-cyclopropyl-[1,2,4]oxadiazol-5-yl)-5,5-dimethyl-4,7-dihydro-5H-thieno[2,3-c]pyran-2-ylamine and 1-cyclopentene-1,2-dicarboxylic anhydride. Yellow solid (64%). MS (ESI): m/z=430.142 [M+H]$^+$.

Intermediates a) 3-(3-Cyclopropyl-[1,2,4]oxadiazol-5-yl)-5,5-dimethyl-4,7-dihydro-5H-thieno[2,3-c]pyran-2-ylamine

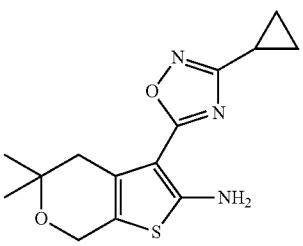 [SMILES: CC1(C)Cc2c(sc(N)c2-c2nc(C3CC3)no2)CO1]

The title compound was prepared in analogy to example 56, intermediate a, from (3-cyclopropyl-[1,2,4]oxadiazol-5-yl)-[2,2-dimethyl-tetrahydro-pyranylidene]-acetonitrile. Yellow solid (76%). MS (ESI): m/z=292.115 [M+H]$^+$.

b) (3-Cyclopropyl-[1,2,4]oxadiazol-5-yl)-[2,2-dimethyl-tetrahydro-pyranylidene]-acetonitrile

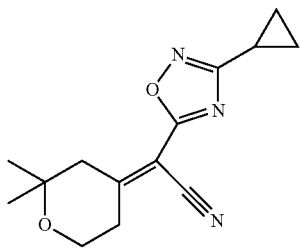 [SMILES: CC1(C)C/C(=C(/C#N)c2nc(C3CC3)no2)CCO1]

The title compound was prepared in analogy to example 56, intermediate b, from 2,2-dimethyl-tetrahydro-pyran-4-one (CAS RN 1194-16-7) and (3-cyclopropyl-[1,2,4]oxadiazol-5-yl)-acetonitrile (Princeton BioMolecular Research, Inc.) after a reaction time of 5 h at 100° C. Light yellow oil (86%). MS (EI): m/z=259 [M]$^+$.

Example 84

2-[3-(3-Cyclopropyl-[1,2,4]oxadiazol-5-yl)-5,5-dimethyl-4,7-dihydro-5H-thieno[2,3-c]pyran-2-ylcarbamoyl]-cyclohex-1-enecarboxylic acid

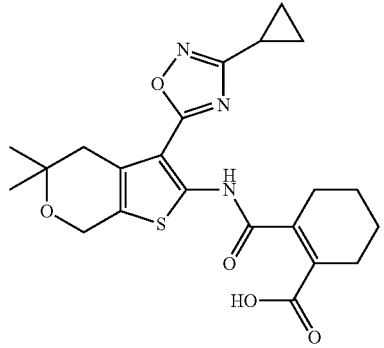 [SMILES: CC1(C)Cc2c(sc(NC(=O)C3=C(C(=O)O)CCCC3)c2-c2nc(C3CC3)no2)CO1]

The title compound was prepared in analogy to example 57, from 3-(3-cyclopropyl-[1,2,4]oxadiazol-5-yl)-5,5-dimethyl-4,7-dihydro-5H-thieno[2,3-c]pyran-2-ylamine (example 83, intermediate a) and 1-cyclohexene-1,2-dicarboxylic anhydride (CAS RN 2426-02-0). Light yellow solid (18%). MS (ESI): m/z=444.157 [M+H]$^+$.

Example 85

2-[3-(4-Trifluoromethyl-thiazol-2-yl)-4,5,6,7-tetrahydro-benzo[b]thiophen-2-ylcarbamoyl]-cyclopent-1-enecarboxylic acid

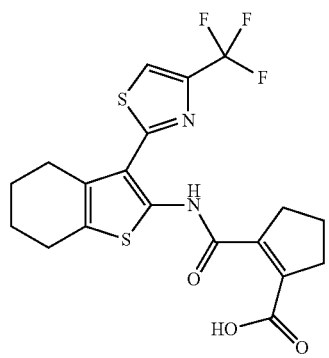 [SMILES: O=C(O)C1=C(C(=O)Nc2sc3c(c2-c2nc(C(F)(F)F)cs2)CCCC3)CCC1]

The title compound was prepared in analogy to example 57, from 3-(4-trifluoromethyl-thiazol-2-yl)-4,5,6,7-tetrahydro-benzo[b]thiophen-2-ylamine and 1-cyclopentene-1,2-dicarboxylic anhydride after a reaction time of 48 h at RT. Yellow solid (12%). MS (ESI): m/z=443.07 [M+H]$^+$.

Intermediates a) 3-(4-Trifluoromethyl-thiazol-2-yl)-4,5,6,7-tetrahydro-benzo[b]thiophen-2-ylamine

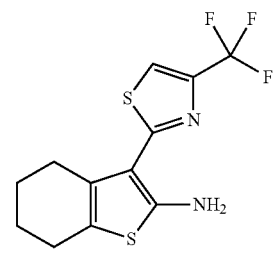 [SMILES: Nc1sc2c(c1-c1nc(C(F)(F)F)cs1)CCCC2]

The title compound was prepared in analogy to example 56, intermediate a, from cyclohexylidene-(4-trifluoromethyl-thiazol-2-yl)-acetonitrile. Light brown solid (71%). MS (ESI): m/z=305.04 [M+H]$^+$.

b) Cyclohexylidene-(4-trifluoromethyl-thiazol-2-yl)-acetonitrile

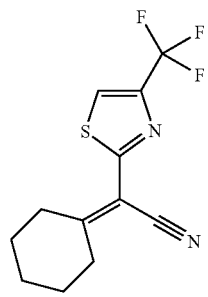 [SMILES: N#CC(=C1CCCCC1)c1nc(C(F)(F)F)cs1]

The title compound was prepared in analogy to example 56, intermediate b, from (4-trifluoromethyl-thiazol-2-yl)-acetonitrile (UkrOrgSynthesis Ltd.) and cyclohexanone after a reaction time of 1.75 h at 100° C. The compound was purified by silica gel chromatography on a 10 g column using a MPLC system eluting with n-heptane. Light brown oil (77%). MS (ESI): m/z=271.05 [M+H]$^+$.

Example 86

2-[3-(4-Trifluoromethyl-thiazol-2-yl)-4,5,6,7-tetrahydro-benzo[b]thiophen-2-ylcarbamoyl]-cyclohex-1-enecarboxylic acid

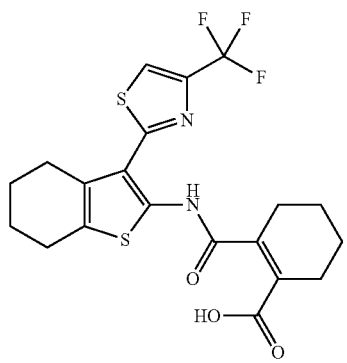 [SMILES: O=C(O)C1=C(C(=O)Nc2sc3c(c2-c2nc(C(F)(F)F)cs2)CCCC3)CCCC1]

The title compound was prepared in analogy to example 57, from 3-(4-trifluoromethyl-thiazol-2-yl)-4,5,6,7-tetrahydro-benzo[b]thiophen-2-ylamine (example 85, intermediate a) and 1-cyclohexene-1,2-dicarboxylic anhydride (CAS RN 2426-02-0) after a reaction time of 48 h at RT. Light brown solid (62%). MS (ESI): m/z=457.09 [M+H]$^+$.

Example 87

3-[3-(4-Trifluoromethyl-thiazol-2-yl)-4,5,6,7-tetrahydro-benzo[b]thiophen-2-ylcarbamoyl]-bicyclo[2.2.2]oct-2-ene-2-carboxylic acid

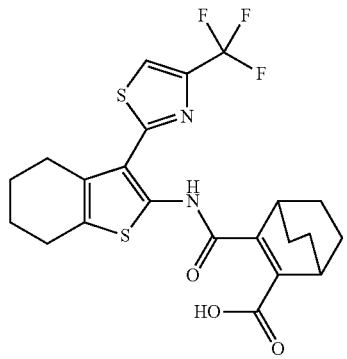

The title compound was prepared in analogy to example 57, from 3-(4-trifluoromethyl-thiazol-2-yl)-4,5,6,7-tetrahydro-benzo[b]thiophen-2-ylamine (example 85, intermediate a) and bicyclo[2.2.2]oct-2-ene-2,3-dicarboxylic anhydride after a reaction time of 48 h at RT. Yellow solid (67%). MS (ESI): m/z=483.10 [M+H]$^+$.

Example 88

2-[3-(3-Cyclopropyl-[1,2,4]oxadiazol-5-yl)-6-methyl-4,5,6,7-tetrahydro-benzo[b]thiophen-2-ylcarbamoyl]-cyclopent-1-enecarboxylic acid

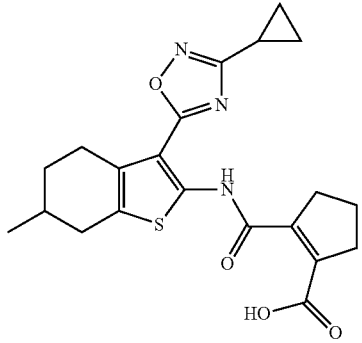 [SMILES: CC1CCc2c(sc(NC(=O)C3=C(C(=O)O)CCC3)c2-c2nc(C3CC3)no2)C1]

The title compound was prepared in analogy to example 57, from 3-(3-cyclopropyl-[1,2,4]oxadiazol-5-yl)-6-methyl-4,5,6,7-tetrahydro-benzo[b]thiophen-2-ylamine and 1-cyclopentene-1,2-dicarboxylic anhydride after a reaction time of 42 h at RT. Yellow solid (65%). MS (ESI): m/z=414.15 [M+H]$^+$.

Intermediate 3-(3-cyclopropyl-[1,2,4]oxadiazol-5-yl)-6-methyl-4,5,6,7-tetrahydro-benzo[b]thiophen-2-ylamine

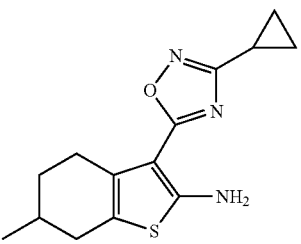 [SMILES: CC1CCc2c(sc(N)c2-c2nc(C3CC3)no2)C1]

The title compound was prepared in analogy to example 55, intermediate, from 4-methyl-cyclohexanone (CAS RN 589-92-4) and (3-cyclopropyl-[1,2,4]oxadiazol-5-yl)-acetonitrile (Princeton BioMolecular Research, Inc.). Light brown solid (86%). MS (ESI): m/z=276.2 [M+H]$^+$.

Example 89

2-[3-(4-Trifluoromethyl-thiazol-2-yl)-4,7-dihydro-5H-thieno[2,3-c]pyran-2-ylcarbamoyl]-cyclopent-1-enecarboxylic acid

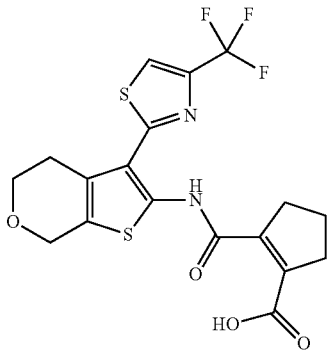

The title compound was prepared in analogy to example 57, from 3-(4-trifluoromethyl-thiazol-2-yl)-4,7-dihydro-5H-thieno[2,3-c]pyran-2-ylamine and 1-cyclopentene-1,2-dicarboxylic anhydride after a reaction time of 42 h at RT. The compound was precipitated from DMSO. Yellow solid (28%). MS (ESI): m/z=445.05 [M+H]$^+$.

Intermediates a) 3-(4-Trifluoromethyl-thiazol-2-yl)-4,7-dihydro-5H-thieno[2,3-c]pyran-2-ylamine

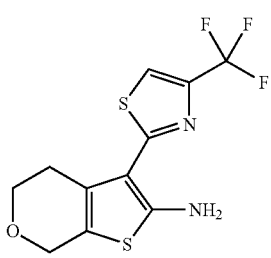 [SMILES: Nc1sc2c(c1-c1nc(C(F)(F)F)cs1)CCOC2]

The title compound was prepared in analogy to example 56, intermediate a, from (tetrahydro-pyran-4-ylidene)-(4-trifluoromethyl-thiazol-2-yl)-acetonitrile. The compound was purified by silica gel chromatography on a 20 g column using a MPLC system eluting with a gradient of n-heptane:TBME (100:0 to 65:35). Light brown solid (66%). MS (ESI): m/z=307.02 [M+H]$^+$.

b) (Tetrahydro-pyran-4-ylidene)-(4-trifluoromethyl-thiazol-2-yl)-acetonitrile

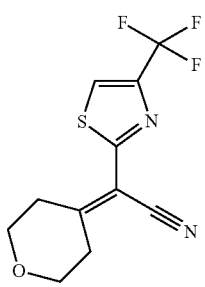 [SMILES: N#CC(=C1CCOCC1)c1nc(C(F)(F)F)cs1]

The title compound was prepared in analogy to example 56, intermediate b, from (4-trifluoromethyl-thiazol-2-yl)-acetonitrile (UkrOrgSynthesis Ltd.) and tetrahydro-pyran-4-one after a reaction time of 2 h at 100° C. Light brown solid (68%). MS (ESI): m/z=273.03 [M−H]$^-$.

Example 90

2-[3-(4-Trifluoromethyl-thiazol-2-yl)-4,7-dihydro-5H-thieno[2,3-c]pyran-2-ylcarbamoyl]-cyclohex-1-enecarboxylic acid

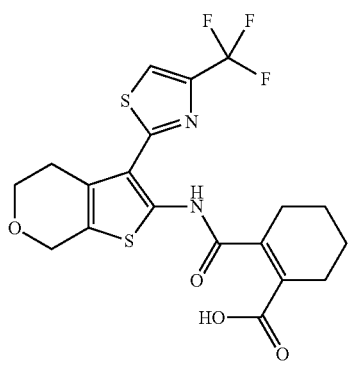 [SMILES: O=C(O)C1=C(C(=O)Nc2sc3c(c2-c2nc(C(F)(F)F)cs2)CCOC3)CCCC1]

The title compound was prepared in analogy to example 57, from 3-(4-trifluoromethyl-thiazol-2-yl)-4,7-dihydro-5H-thieno[2,3-c]pyran-2-ylamine (example 89, intermediate a) and 1-cyclohexene-1,2-dicarboxylic anhydride (CAS RN 2426-02-0) after a reaction time of 42 h at RT. Light yellow solid (75%). MS (ESI): m/z=459.07 [M+H]$^+$.

Example 91

3-[3-(4-Trifluoromethyl-thiazol-2-yl)-4,7-dihydro-5H-thieno[2,3-c]pyran-2-ylcarbamoyl]-bicyclo[2.2.2]oct-2-ene-2-carboxylic acid

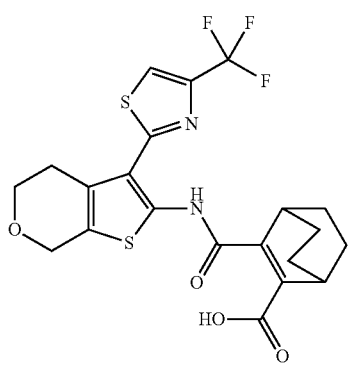 [SMILES: O=C(O)C1=C(C(=O)Nc2sc3c(c2-c2nc(C(F)(F)F)cs2)CCOC3)C2CCC1CC2]

The title compound was prepared in analogy to example 57, from 3-(4-trifluoromethyl-thiazol-2-yl)-4,7-dihydro-5H-thieno[2,3-c]pyran-2-ylamine (example 89, intermediate a) and bicyclo[2.2.2]oct-2-ene-2,3-dicarboxylic anhydride after a reaction time of 42 h at RT. Yellow solid (70%). MS (ESI): m/z=485.08 [M+H]$^+$.

Example 92

2-[3-(3-Cyclopropyl-[1,2,4]oxadiazol-5-yl)-6-methyl-4,5,6,7-tetrahydro-benzo[b]thiophen-2-ylcarbamoyl]-cyclohex-1-enecarboxylic acid

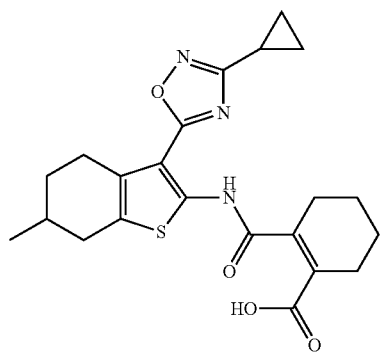 [SMILES: CC1CCc2c(sc(NC(=O)C3=C(C(=O)O)CCCC3)c2-c2nc(C3CC3)no2)C1]

The title compound was prepared in analogy to example 57, from 3-(3-cyclopropyl-[1,2,4]oxadiazol-5-yl)-6-methyl-4,5,6,7-tetrahydro-benzo[b]thiophen-2-ylamine (example 88, intermediate) and 1-cyclohexene-1,2-dicarboxylic anhydride (CAS RN 2426-02-0) after a reaction time of 42 h at RT. Light yellow solid (82%). MS (ESI): m/z=428.16 [M+H]$^+$.

Example 93

3-[3-(3-Cyclopropyl-[1,2,4]oxadiazol-5-yl)-6-methyl-4,5,6,7-tetrahydro-benzo[b]thiophen-2-ylcarbamoyl]-bicyclo[2.2.2]oct-2-ene-2-carboxylic acid

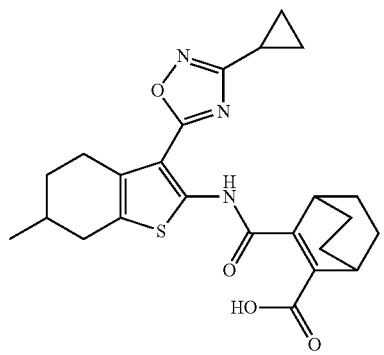 [SMILES: CC1CCc2c(sc(NC(=O)C3=C(C(=O)O)C4CCC3CC4)c2-c2nc(C3CC3)no2)C1]

The title compound was prepared in analogy to example 57, from 3-(3-cyclopropyl-[1,2,4]oxadiazol-5-yl)-6-methyl-4,5,6,7-tetrahydro-benzo[b]thiophen-2-ylamine (example 88, intermediate) and bicyclo[2.2.2]oct-2-ene-2,3-dicarboxylic anhydride after a reaction time of 42 h at RT. Yellow solid (71%). MS (ESI): m/z=454.18 [M+H]$^+$.

Example 94

2-[4,4-Dimethyl-3-(3-methyl-[1,2,4]oxadiazol-5-yl)-5,6-dihydro-4H-cyclopenta[b]thiophen-2-ylcarbamoyl]-cyclohex-1-enecarboxylic acid

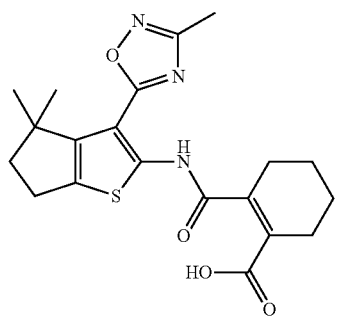 [SMILES: Cc1noc(-c2c(NC(=O)C3=C(C(=O)O)CCCC3)sc3c2C(C)(C)CC3)n1]

The title compound was prepared in analogy to example 55, from 4,4-dimethyl-3-(3-methyl-[1,2,4]oxadiazol-5-yl)-5,6-dihydro-4H-cyclopenta[b]thiophen-2-ylamine (example 77, intermediate a) and 1-cyclohexene-1,2-dicarboxylic anhydride (CAS RN 2426-02-0) after a reaction time of 5.5 h at 65° C. Light brown solid (50%). MS (ESI): m/z=402.15 [M+H]$^+$.

Example 95

3-[4,4-Dimethyl-3-(3-methyl-[1,2,4]oxadiazol-5-yl)-5,6-dihydro-4H-cyclopenta[b]thiophen-2-ylcarbamoyl]-bicyclo[2.2.2]oct-2-ene-2-carboxylic acid

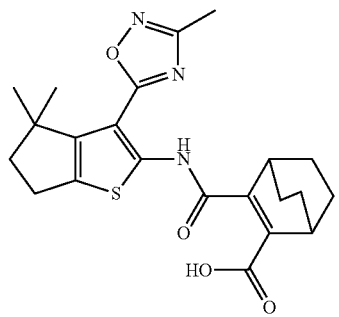 [SMILES: Cc1noc(-c2c(NC(=O)C3=C(C(=O)O)C4CCC3CC4)sc3c2C(C)(C)CC3)n1]

The title compound was prepared in analogy to example 55, from 4,4-dimethyl-3-(3-methyl-[1,2,4]oxadiazol-5-yl)-5,6-dihydro-4H-cyclopenta[b]thiophen-2-ylamine (example 77, intermediate a) and bicyclo[2.2.2]oct-2-ene-2,3-dicarboxylic anhydride after a reaction time of 5.5 h at 65° C. Light brown solid (64%). MS (ESI): m/z=428.16 [M+H]$^+$.

Example 96

2-[3-(4-Cyclopropyl-thiazol-2-yl)-4,7-dihydro-5H-thieno[2,3-c]pyran-2-ylcarbamoyl]-cyclopent-1-enecarboxylic acid

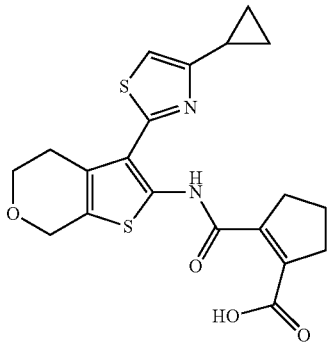 [SMILES: O=C(O)C1=C(C(=O)Nc2sc3c(c2-c2nc(C4CC4)cs2)CCOC3)CCC1]

The title compound was prepared in analogy to example 57, from 3-(4-cyclopropyl-thiazol-2-yl)-4,7-dihydro-5H-thieno[2,3-c]pyran-2-ylamine and 1-cyclopentene-1,2-dicarboxylic anhydride. Yellow solid (51%). MS (ESI): m/z=417.093 [M+H]$^+$.

Intermediates a) 3-(4-Cyclopropyl-thiazol-2-yl)-4,7-dihydro-5H-thieno[2,3-c]pyran-2-ylamine

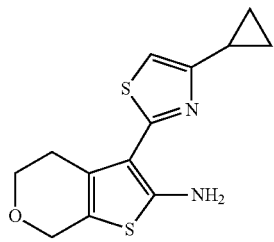 [SMILES: Nc1sc2c(c1-c1nc(C3CC3)cs1)CCOC2]

The title compound was prepared in analogy to example 56, intermediate a, from (4-cyclopropyl-thiazol-2-yl)-(tetrahydro-pyran-4-ylidene)-acetonitrile after a reaction time of 5 h at 65° C. Light brown solid (63%). MS (ESI): m/z=279.062 [M+H]$^+$.

b) (4-Cyclopropyl-thiazol-2-yl)-(tetrahydro-pyran-4-ylidene)-acetonitrile

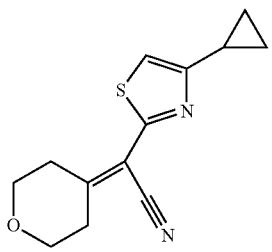 [SMILES: N#CC(=C1CCOCC1)c1nc(C2CC2)cs1]

The title compound was prepared in analogy to example 56, intermediate b, from tetrahydro-pyran-4-one and (4-cyclopropyl-thiazol-2-yl)-acetonitrile (prepared in analogy to S. M. Hussain et al., *Tetrahedron* 1988, 44(1) 241-246) after a reaction time of 6 h. Light yellow oil (68%). MS (ESI): m/z=247.090 [M+H]$^+$.

Example 97

3-[3-(4-Cyclopropyl-thiazol-2-yl)-4,7-dihydro-5H-thieno[2,3-c]pyran-2-ylcarbamoyl]-bicyclo[2.2.2]oct-2-ene-2-carboxylic acid

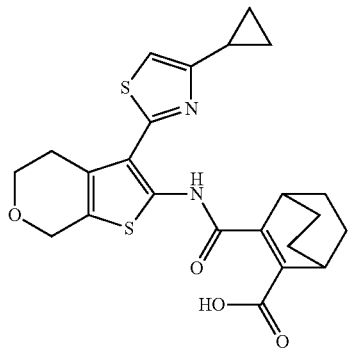 [SMILES: O=C(O)C1=C(C(=O)Nc2sc3c(c2-c2nc(C4CC4)cs2)CCOC3)C2CCC1CC2]

The title compound was prepared in analogy to example 57, from 3-(4-cyclopropyl-thiazol-2-yl)-4,7-dihydro-5H-thieno[2,3-c]pyran-2-ylamine (example 96, intermediate a) and bicyclo[2.2.2]oct-2-ene-2,3-dicarboxylic anhydride. Yellow solid (73%). MS (ESI): m/z=457.125 [M+H]$^+$.

Example 98

3-[3-(3-Cyclopropyl-[1,2,4]oxadiazol-5-yl)-5,5-dimethyl-4,7-dihydro-5H-thieno[2,3-c]pyran-2-ylcarbamoyl]-bicyclo[2.2.2]oct-2-ene-2-carboxylic acid

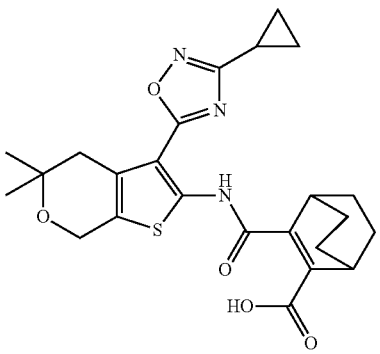 [SMILES: CC1(C)Cc2c(sc(NC(=O)C3=C(C(=O)O)C4CCC3CC4)c2-c2nc(C3CC3)no2)CO1]

The title compound was prepared in analogy to example 57, from 3-(3-cyclopropyl-[1,2,4]oxadiazol-5-yl)-5,5-dimethyl-4,7-dihydro-5H-thieno[2,3-c]pyran-2-ylamine (example 83, intermediate a) and 1-cyclopentene-1,2-dicarboxylic anhydride. Yellow solid (73%). MS (ESI): m/z=470.175 [M+H]$^+$.

Example 99

3,3-Dimethyl-4-[3-(3-methyl-[1,2,4]oxadiazol-5-yl)-4,5,6,7-tetrahydro-benzo[b]thiophen-2-ylcarbamoyl]-butyric acid

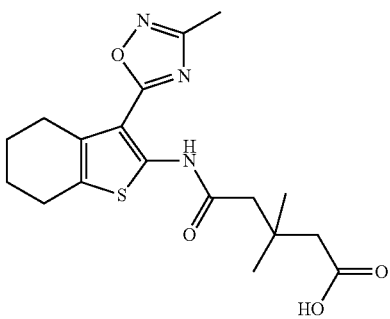 [SMILES: Cc1noc(-c2c(NC(=O)CC(C)(C)CC(=O)O)sc3c2CCCC3)n1]

To a solution of 3-(3-methyl-[1,2,4]oxadiazol-5-yl)-4,5,6,7-tetrahydro-benzo[b]thiophen-2-ylamine (example 82, intermediate) (100 mg, 425 µmol) in TBME (6.0 mL) were added 4,4-dimethyl-dihydro-pyran-2,6-dione (66.5 mg, 467 µmol, CAS RN 4160-82-1) and DMAP (2.6 mg, 21.2 µmol) and the solution was stirred at reflux for 68 h. The product was purified by preparative HPLC (Gemini NX column) using a gradient of MeOH:H$_2$O (containing 0.1% formic acid) (20:80 to 98:2). Colorless solid (0.024 g; 15%). MS (ESI): m/z=378.15 [M+H]$^+$.

Example 100

2-[3-(3-Methyl-[1,2,4]oxadiazol-5-yl)-4,7-dihydro-5H-thieno[2,3-c]pyran-2-ylcarbamoyl]-cyclohex-1-enecarboxylic acid

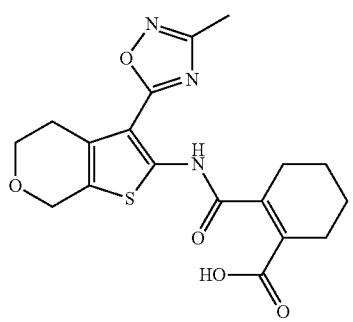 [SMILES: Cc1noc(-c2c(NC(=O)C3=C(C(=O)O)CCCC3)sc3c2CCOC3)n1]

The title compound was prepared in analogy to example 57, from 3-(3-methyl-[1,2,4]oxadiazol-5-yl)-4,7-dihydro-5H-thieno[2,3-c]pyran-2-ylamine and 1-cyclohexene-1,2-dicarboxylic anhydride (CAS RN 2426-02-0) in a mixture from Et$_2$O:CH$_2$Cl$_2$ (3:1v/v). Off-white solid (32%). MS (ESI): m/z=390.11 [M+H]$^+$.

Intermediate 3-(3-Methyl-[1,2,4]oxadiazol-5-yl)-4,7-dihydro-5H-thieno[2,3-c]pyran-2-ylamine

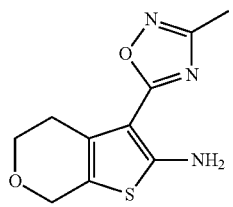 [SMILES: Cc1noc(-c2c(N)sc3c2CCOC3)n1]

The title compound was prepared in analogy to example 55, intermediate, from tetrahydro-pyran-4-one and (3-methyl-[1,2,4]oxadiazol-5-yl)-acetonitrile (Princeton BioMolecular Research, Inc.). Light brown solid (78%). MS (ESI): m/z=238.06 [M+H]$^+$.

Example 101

2-[3-(4,5-Dimethyl-thiazol-2-yl)-4,7-dihydro-5H-thieno[2,3-c]pyran-2-ylcarbamoyl]-cyclopent-1-enecarboxylic acid

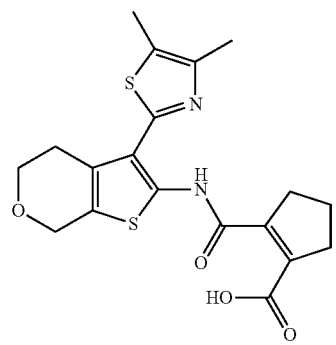 [SMILES: Cc1nc(-c2c(NC(=O)C3=C(C(=O)O)CCC3)sc3c2CCOC3)sc1C]

The title compound was prepared in analogy to example 57, from 3-(4,5-dimethyl-thiazol-2-yl)-4,7-dihydro-5H-thieno[2,3-c]pyran-2-ylamine and 1-cyclopentene-1,2-dicarboxylic anhydride. The compound was precipitated from DMSO. Yellow solid (69%). MS (ESI): m/z=405.095 [M+H]$^+$.

Intermediates a) 3-(4,5-Dimethyl-thiazol-2-yl)-4,7-dihydro-5H-thieno[2,3-c]pyran-2-ylamine

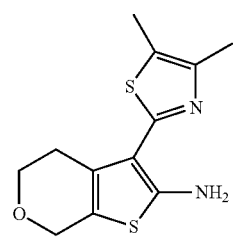

The title compound was prepared in analogy to example 56, intermediate a, from (4,5-dimethyl-thiazol-2-yl)-(tetrahydro-pyran-4-ylidene)-acetonitrile after a reaction time of 5 h at 65° C. Yellow solid (51%). MS (ESI): m/z=267.063 [M+H]⁺.

b) (4,5-Dimethyl-thiazol-2-yl)-(tetrahydro-pyran-4-ylidene)-acetonitrile

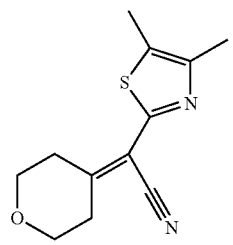

The title compound was prepared in analogy to example 56, intermediate b, from tetrahydro-pyran-4-one and (4,5-dimethyl-thiazol-2-yl)-acetonitrile (prepared in analogy to S. M. Hussain et al., *Tetrahedron* 1988, 44(1) 241-246) after a reaction time of 6 h at 110° C. Light yellow solid (70%). MS (ESI): m/z=235.091 [M+H]⁺.

Example 102

2-[3-(3-Cyclopropyl-[1,2,4]oxadiazol-5-yl)-4,4-dimethyl-4,5,6,7-tetrahydro-benzo[b]thiophen-2-ylcarbamoyl]-cyclopent-1-enecarboxylic acid

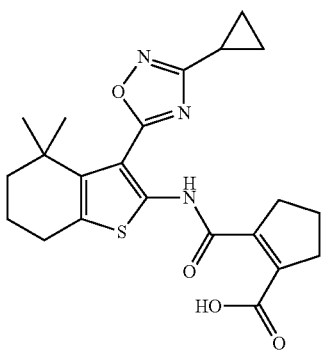 [SMILES: CC1(C)CCCc2sc(NC(=O)C3=C(C(=O)O)CCC3)c(-c3nc(C4CC4)no3)c21]

The title compound was prepared in analogy to example 55, from 3-(3-cyclopropyl-[1,2,4]oxadiazol-5-yl)-4,4-dimethyl-4,5,6,7-tetrahydro-benzo[b]thiophen-2-ylamine and 1-cyclopentene-1,2-dicarboxylic anhydride after a reaction time of 6 h at 65° C. Yellow solid (40%). MS (ESI): m/z=428.165 [M+H]⁺.

Intermediates a) 3-(3-Cyclopropyl-[1,2,4]oxadiazol-5-yl)-4,4-dimethyl-4,5,6,7-tetrahydro-benzo[b]thiophen-2-ylamine

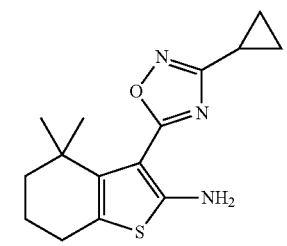 [SMILES: CC1(C)CCCc2sc(N)c(-c3nc(C4CC4)no3)c21]

The title compound was prepared in analogy to example 56, intermediate a, from (3-cyclopropyl-[1,2,4]oxadiazol-5-yl)-[2,2-dimethyl-cyclohexylidene]-acetonitrile after a reaction time of 5 h at 65° C. Light yellow solid (69%). MS (ESI): m/z=290.132 [M+H]⁺.

b) (3-Cyclopropyl-[1,2,4]oxadiazol-5-yl)-[2,2-dimethyl-cyclohexylidene]-acetonitrile

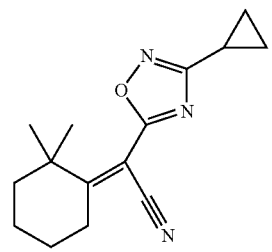 [SMILES: CC1(C)CCCC/C1=C(\C#N)c1nc(C2CC2)no1]

The title compound was prepared in analogy to example 56, intermediate b, from 2,2-dimethyl-cyclohexanone and (3-cyclopropyl-[1,2,4]oxadiazol-5-yl)-acetonitrile (Princeton BioMolecular Research, Inc.) after a reaction time of 6 h at 110° C. Light yellow oil (21%). MS (EI): m/z=257 [M]⁺.

Example 103

3-[3-(3-Cyclopropyl-[1,2,4]oxadiazol-5-yl)-4,4-dimethyl-4,5,6,7-tetrahydro-benzo[b]thiophen-2-ylcarbamoyl]-bicyclo[2.2.2]oct-2-ene-2-carboxylic acid

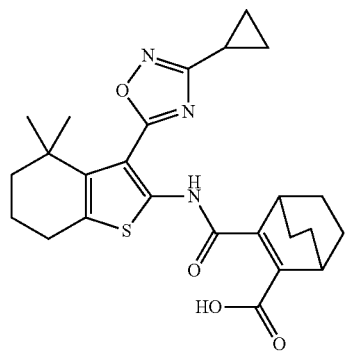 [SMILES: CC1(C)CCCc2sc(NC(=O)C3=C(C(=O)O)C4CCC3CC4)c(-c3nc(C4CC4)no3)c21]

The title compound was prepared in analogy to example 55, from 3-(3-cyclopropyl-[1,2,4]oxadiazol-5-yl)-4,4-dimethyl-4,5,6,7-tetrahydro-benzo[b]thiophen-2-ylamine (example 103, intermediate a) and bicyclo[2.2.2]oct-2-ene-2,3-dicarboxylic anhydride after a reaction time of 6 h at 65° C. Yellow solid (39%). MS (ESI): m/z=468.195 [M+H]$^+$.

Example 104

3-[3-(3-Methyl-[1,2,4]oxadiazol-5-yl)-4,7-dihydro-5H-thieno[2,3-c]pyran-2-ylcarbamoyl]-bicyclo[2.2.2]oct-2-ene-2-carboxylic acid

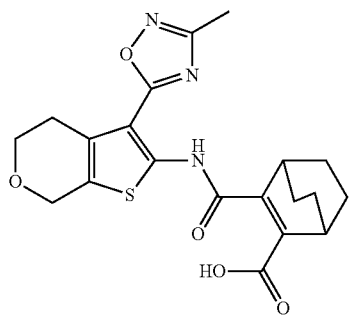 [SMILES: Cc1noc(-c2c(NC(=O)C3=C(C(=O)O)C4CCC3CC4)sc3c2CCOC3)n1]

The title compound was prepared in analogy to example 57, from 3-(3-methyl-[1,2,4]oxadiazol-5-yl)-4,7-dihydro-5H-thieno[2,3-c]pyran-2-ylamine (example 100, intermediate) and bicyclo[2.2.2]oct-2-ene-2,3-dicarboxylic anhydride in a mixture from Et$_2$O:CH$_2$Cl$_2$ 3:1. Yellow solid (27%). MS (ESI): m/z=416.13 [M+H]$^+$.

Example 105

2-[3-(3-Methyl-[1,2,4]oxadiazol-5-yl)-4,7-dihydro-5H-thieno[2,3-c]pyran-2-ylcarbamoyl]-cyclopent-1-enecarboxylic acid

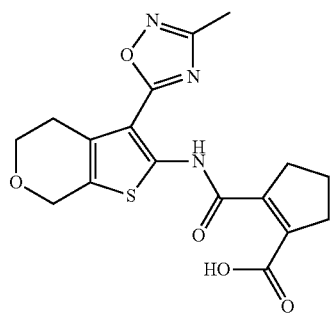 [SMILES: Cc1noc(-c2c(NC(=O)C3=C(C(=O)O)CCC3)sc3c2CCOC3)n1]

The title compound was prepared in analogy to example 55, from 3-(3-methyl-[1,2,4]oxadiazol-5-yl)-4,7-dihydro-5H-thieno[2,3-c]pyran-2-ylamine (example 100, intermediate) and 1-cyclopentene-1,2-dicarboxylic anhydride. Light yellow solid (60%). MS (ESI): m/z=376.10 [M+H]$^+$.

Example 106

(1RS,2SR)-2-[3-(3-Trifluoromethyl-[1,2,4]oxadiazol-5-yl)-4,7-dihydro-5H-thieno[2,3-c]pyran-2-ylcarbamoyl]-cyclohexanecarboxylic acid

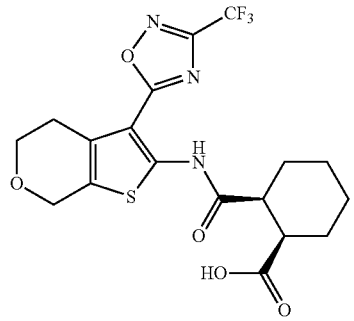 [SMILES: O=C(Nc1sc2c(c1-c1nc(C(F)(F)F)no1)CCOC2)[C@H]1CCCC[C@H]1C(=O)O]

The title compound was prepared in analogy to example 56, from 3-(3-trifluoromethyl-[1,2,4]oxadiazol-5-yl)-4,7-dihydro-5H-thieno[2,3-c]pyran-2-ylamine (example 71, intermediate a) and cis-1,2-cyclohexanedicarboxylic anhydride (CAS RN 13149-00-3) in TBME for a reaction time of 21 h at reflux. The reaction was evaporated. The product was purified by preparative HPLC (Gemini NX column) using a gradient of MeOH:H$_2$O (containing 0.1% formic acid) (20:80 to 98:2). Colorless solid (58%). MS (ESI): m/z=446.10 [M+H]$^+$.

Example 107

2-[3-(4-Cyclopropyl-thiazol-2-yl)-4,7-dihydro-5H-thieno[2,3-c]pyran-2-ylcarbamoyl]-cyclohex-1-enecarboxylic acid

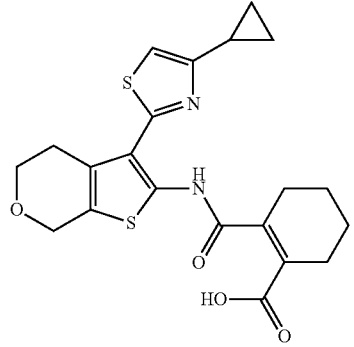 [SMILES: O=C(O)C1=C(C(=O)Nc2sc3c(c2-c2nc(C4CC4)cs2)CCOC3)CCCC1]

The title compound was prepared in analogy to example 57, from 3-(4-cyclopropyl-thiazol-2-yl)-4,7-dihydro-5H-thieno[2,3-c]pyran-2-ylamine and 1-cyclohexene-1,2-dicarboxylic anhydride. The product was purified a second time by silica gel chromatography on 10 g column using an MPLC (Flashmaster) system eluting with a gradient of CH$_2$Cl$_2$:CH$_3$OH (100:0 to 80:20). Light yellow solid (15%). MS (ESI): m/z=431.109 [M+H]$^+$.

Examples 108 and 109

(+)-2-[3-(3-Cyclopropyl-[1,2,4]oxadiazol-5-yl)-6-methyl-4,5,6,7-tetrahydro-benzo[b]thiophen-2-ylcarbamoyl]-cyclohex-1-enecarboxylic acid and (−)-2-[3-(3-Cyclopropyl-[1,2,4]oxadiazol-5-yl)-6-methyl-4,5,6,7-tetrahydro-benzo[b]thiophen-2-ylcarbamoyl]-cyclohex-1-enecarboxylic acid

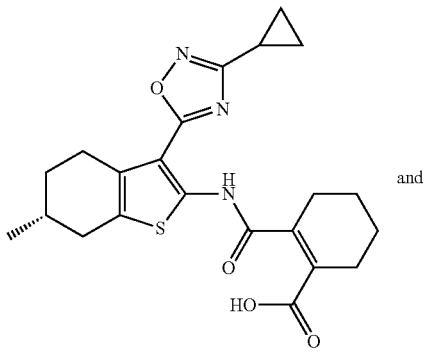

and

The title compounds were obtained by chiral separation of 2-[3-(3-cyclopropyl-[1,2,4]oxadiazol-5-yl)-6-methyl-4,5,6,7-tetrahydro-benzo[b]thiophen-2-ylcarbamoyl]-cyclohex-1-enecarboxylic acid (0.11 g, example 92) using a Chiralpak-AD-H column and an isocratic mixture of n-heptane:EtOH (+0.5% HCOOH) 60:40 as eluent, with the (+)-enantiomer eluting first. The products were further purified by preparative HPLC (Gemini NX column) using a gradient of MeOH:H$_2$O (containing 0.1% formic acid) (20:80 to 98:2).

(+)-2-[3-(3-Cyclopropyl-[1,2,4]oxadiazol-5-yl)-6-methyl-4,5,6,7-tetrahydro-benzo[b]thiophen-2-ylcarbamoyl]-cyclohex-1-enecarboxylic acid: Light brown solid (0.038 g; 34%). MS (ESI): m/z=428.16 [M+H]$^+$.

(−)-2-[3-(3-Cyclopropyl-[1,2,4]oxadiazol-5-yl)-6-methyl-4,5,6,7-tetrahydro-benzo[b]thiophen-2-ylcarbamoyl]-cyclohex-1-enecarboxylic acid: Light brown solid (0.035 g; 31%). MS (ESI): m/z=428.16 [M+H]$^+$.

Example 110

2-{3-[3-(2-Methoxy-ethyl)-[1,2,4]oxadiazol-5-yl]-4,7-dihydro-5H-thieno[2,3-c]pyran-2-ylcarbamoyl}-cyclohex-1-enecarboxylic acid

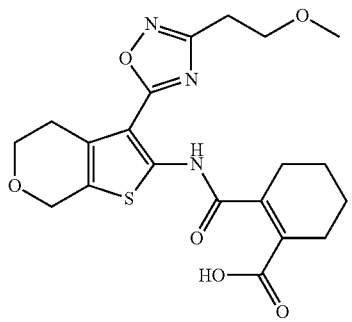 [SMILES: COCCc1noc(-c2c(NC(=O)C3=C(C(=O)O)CCCC3)sc3c2CCOC3)n1]

The title compound was prepared in analogy to example 57, from 3-[3-(2-methoxy-ethyl)-[1,2,4]oxadiazol-5-yl]-4,7-dihydro-5H-thieno[2,3-c]pyran-2-ylamine and 1-cyclohexene-1,2-dicarboxylic anhydride (CAS RN 2426-02-0) in a mixture from Et$_2$O:CH$_2$Cl$_2$ 1:1 after a reaction time of 168 h. Colorless solid (14%). MS (ESI): m/z=434.14 [M+H]$^+$.

Intermediate

3-[3-(2-Methoxy-ethyl)-[1,2,4]oxadiazol-5-yl]-4,7-dihydro-5H-thieno[2,3-c]pyran-2-ylamine

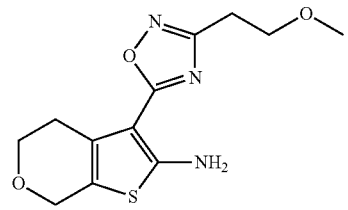 [SMILES: COCCc1noc(-c2c(N)sc3c2CCOC3)n1]

The title compound was prepared in analogy to example 55, intermediate, from tetrahydro-pyran-4-one and [3-(2-methoxy-ethyl)-[1,2,4]oxadiazol-5-yl]-acetonitrile (Princeton BioMolecular Research, Inc.). Light brown solid (79%). MS (ESI): m/z=282.09 [M+H]$^+$.

Example 111

3-{3-[3-(2-Methoxy-ethyl)-[1,2,4]oxadiazol-5-yl]-4,7-dihydro-5H-thieno[2,3-c]pyran-2-ylcarbamoyl}-bicyclo[2.2.2]oct-2-ene-2-carboxylic acid

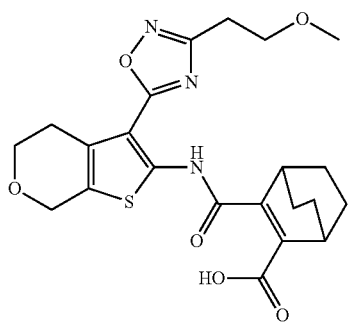 [SMILES: COCCc1noc(-c2c(NC(=O)C3=C(C(=O)O)C4CCC3CC4)sc3c2CCOC3)n1]

The title compound was prepared in analogy to example 57, from 3-[3-(2-methoxy-ethyl)-[1,2,4]oxadiazol-5-yl]-4,7-dihydro-5H-thieno[2,3-c]pyran-2-ylamine (example 110, intermediate) and bicyclo[2.2.2]oct-2-ene-2,3-dicarboxylic anhydride in a mixture of Et₂O:CH₂Cl₂ (1:1 v/v) after a reaction time of 168 h. Light brown solid (14%). MS (ESI): m/z=460.16 [M+H]⁺.

Example 112

(1RS,5SR)-5-[3-(3-Methyl-[1,2,4]oxadiazol-5-yl)-4,5,6,7-tetrahydro-benzo[b]thiophen-2-ylcarbamoyl]-bicyclo[3.1.0]hexane-1-carboxylic acid methyl ester

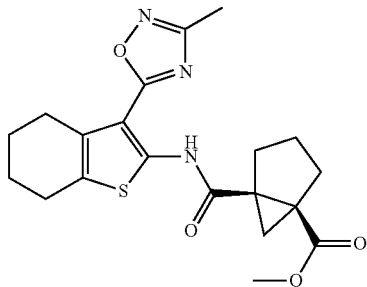 [SMILES: COC(=O)[C@]12CCC[C@@]1(C(=O)Nc1sc3c(c1-c1nc(C)no1)CCCC3)C2]

To bicyclo[3.1.0]hexane-1,5-dicarboxylic acid monomethyl ester (78.3 mg, 425 µmol, prepared in analogy to R. R. Reitz et al., *J. Org. Chem.* 1970, 35(8), 2666-2669) was added DMF (3.11 mg, 3.3 µL, 42.5 µmol) and thionylchloride (1.01 g, 620 µL, 8.5 mmol) and the solution was heated to reflux for 30 min. The reaction mixture was concentrated under vacuum and the residue was diluted three times with toluene followed by evaporation to completely remove thionylchloride. The residue was dissolved in CH₂Cl₂ (2 mL). This solution was added to a solution of 3-(3-methyl-[1,2,4]oxadiazol-5-yl)-4,5,6,7-tetrahydro-benzo[b]thiophen-2-ylamine (100 mg, 425 µmol, example 82, intermediate) and N-ethyldiisopropylamine (110 mg, 148 µL, 850 µmol) in CH₂Cl₂ (3 mL) and the light brown solution was stirred at RT for 18 h. The reaction mixture was poured on 30 mL 10% aqueous NaHCO₃ solution and 30 mL EtOAc and the layers were separated. The aqueous layer was extracted a second time with 30 mL EtOAc. The organic layers were washed with 30 mL brine, dried over MgSO₄, filtered and evaporated. The compound was purified by silica gel chromatography on a 20 g column using an MPLC (Flashmaster) system eluting with a gradient of n-heptane:EtOAc (100:0 to 75:25). Colorless foam (114 mg, 67%). MS (ESI): m/z=402.148 [M+H]⁺.

Example 113

(1RS,5SR)-5-[3-(3-Methyl-[1,2,4]oxadiazol-5-yl)-4,5,6,7-tetrahydro-benzo[b]thiophen-2-ylcarbamoyl]-bicyclo[3.1.0]hexane-1-carboxylic acid

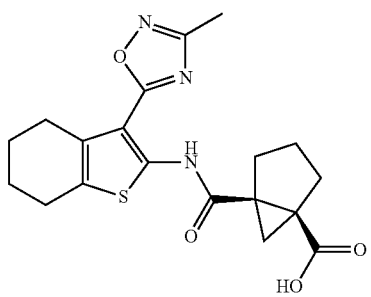 [SMILES: Cc1noc(-c2c(NC(=O)[C@@]34CCC[C@]3(C(=O)O)C4)sc3c2CCCC3)n1]

To a solution of (1RS,5SR)-5-[3-(3-methyl-[1,2,4]oxadiazol-5-yl)-4,5,6,7-tetrahydro-benzo[b]thiophen-2-ylcarbamoyl]-bicyclo[3.1.0]hexane-1-carboxylic acid methyl ester (105 mg, 262 µmol, example 112) in dioxane (3 mL) was added H₂O (3 mL) and LiOH monohydrate (13.7 mg, 327 µmol) and the resulting clear solution was stirred at room temperature for 8 h. The reaction mixture was poured on 30 mL 1M aqueous HCl and 30 mL EtOAc and the layers were separated. The aqueous layer was extracted a second time with 30 mL EtOAc. The organic layers were washed with 30 mL brine, dried over MgSO₄, filtered and concentrated under vacuum. The compound was purified by silica gel chromatography on a 20 g column using an MPLC (Flashmaster) system eluting with a gradient of CH₂Cl₂:MeOH (100:0 to 85:15). Colorless solid (83 mg, 82%). MS (ESI): m/z=388.132 [M+H]⁺.

Examples 114 and 115

(1R,2R)- and (1S,2S)-2-[3-(4-Trifluoromethyl-thiazol-2-yl)-4,7-dihydro-5H-thieno[2,3-c]pyran-2-ylcarbamoyl]-cyclohexanecarboxylic acid

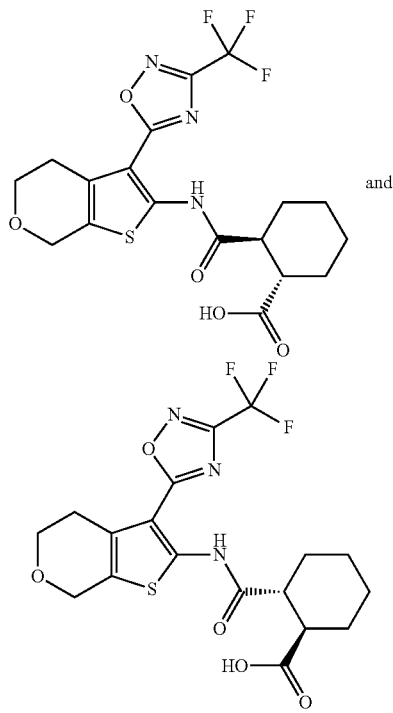

The title compounds were prepared in analogy to example 55, from 3-(4-trifluoromethyl-thiazol-2-yl)-4,7-dihydro-5H-thieno[2,3-c]pyran-2-ylamine (example 71, intermediate a) and 1,2-cyclohexanedicarboxylic anhydride (CAS RN 14166-21-3) and subsequent chiral separation of the racemic mixture on a Chiralpak-AD column using an isocratic mixture of n-heptane:EtOH (+0.5% HCOOH) (60:40).

First eluting enantiomer: Colorless solid (10%). MS (ESI): m/z=444.09 [M−H]⁻.

Second eluting enantiomer: Colorless solid (13%). MS (ESI): m/z=444.09 [M−H]⁻.

Examples 116 and 117

(1R,2S)- and (1S,2R)-2-[3-(4-Trifluoromethyl-thiazol-2-yl)-4,7-dihydro-5H-thieno[2,3-c]pyran-2-ylcarbamoyl]-cyclohexanecarboxylic acid

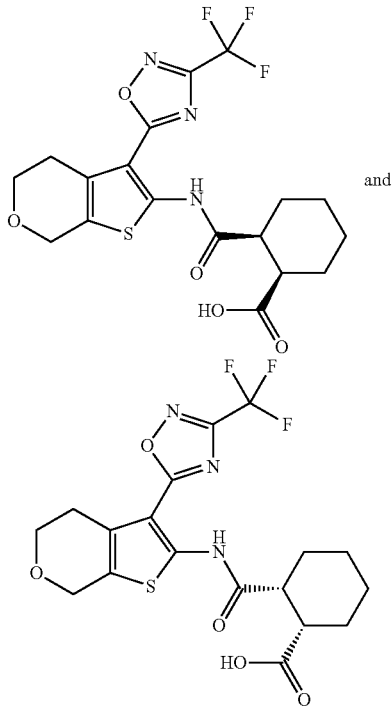

The title compounds were prepared in analogy to example 55, from 3-(4-trifluoromethyl-thiazol-2-yl)-4,7-dihydro-5H-thieno[2,3-c]pyran-2-ylamine (example 71, intermediate a) and 1,2-cyclohexanedicarboxylic anhydride (CAS RN 14166-21-3) and subsequent chiral separation of the racemic mixture on a Chiralpak-AD column using an isocratic mixture of n-heptane: EtOH (+0.5% HCOOH) (60:40).

Third eluting enantiomer: Colorless solid (2.7%). MS (ESI): m/z=444.09 [M–H]⁻.

Fourth eluting enantiomer: Colorless solid (3.8%). MS (ESI): m/z=444.09 [M–H]⁻.

Example 118

2-[5-(3-Cyclopropyl-[1,2,4]oxadiazol-5-yl)-3-thia-tricyclo[5.2.1.0*2,6*]deca-2(6),4-dien-4-ylcarbamoyl]-cyclopent-1-enecarboxylic acid

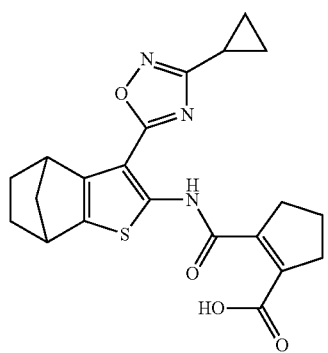 [SMILES: O=C(O)C1=C(C(=O)Nc2sc3c(c2-c2nc(C4CC4)no2)C2CCC3C2)CCC1]

The title compound was prepared in analogy to example 55, from 5-(3-cyclopropyl-[1,2,4]oxadiazol-5-yl)-3-thia-tricyclo[5.2.1.0*2,6*]deca-2(6),4-dien-4-ylamine and 1-cyclopentene-1,2-dicarboxylic anhydride. Yellow solid (33%). MS (ESI): m/z=412.13 [M+H]⁺.

Intermediate 5-(3-Cyclopropyl-[1,2,4]oxadiazol-5-yl)-3-thia-tricyclo[5.2.1.0*2,6*]deca-2(6),4-dien-4-ylamine

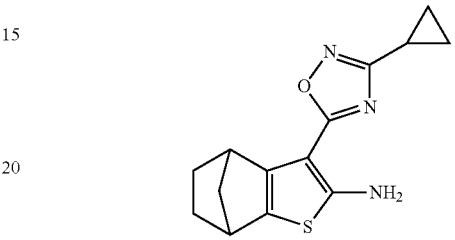

To a solution of (3-cyclopropyl-[1,2,4]oxadiazol-5-yl)-acetonitrile (0.4 g, 2.68 mmol, Princeton BioMolecular Research, Inc.) in EtOH (10 mL) were added bicyclo[2.2.1]heptan-2-one (295 mg, 2.68 mmol, CAS RN 497-38-1) and sulfur (86.0 mg, 2.68 mmol) and the light yellow suspension was stirred at 50° C. for 20 min. To this mixture was added dropwise morpholine (9.35 g, 9.35 mL, 107 mmol) over 5 min. to give a brown solution which was stirred at 50° C. for 2.5 h. The reaction mixture was poured on H₂O (100 mL) and EtOAc (100 mL) and the layers were separated. The aqueous layer was extracted twice with EtOAc. The organic layers were washed once with brine, dried over MgSO₄, filtered, treated with silica gel and evaporated. The compound was purified by silica gel chromatography on a 50 g column using an MPLC system eluting with a gradient of n-heptane:TBME (100:0 to 65:35). The crude intermediate 2-(bicyclo[2.2.1]heptan-2-ylidene)-2-(3-cyclopropyl-1,2,4-oxadiazol-5-yl)acetonitrile was dissolved in EtOH (5 mL) sulfur (45.2 mg, 1.41 mmol) and DBU (536 mg, 531 µL, 3.52 mmol) was added and the dark brown solution was stirred at 65° C. for 2 h followed by stirring at RT overnight. The reaction mixture was poured on H₂O and EtOAc and the layers were separated. The aqueous layer was extracted twice with EtOAc. The organic layers were washed once with brine, dried over MgSO₄, filtered, treated with silica gel and evaporated. The compound was purified by silica gel chromatography on a 20 g column using an MPLC system eluting with a gradient of n-heptane:TBME (100:0 to 35:65). The crude product was purified by silica gel chromatography on a 10 g column using an MPLC (ISCO) system eluting with a gradient of n-heptane:EtOAc (100:0 to 50:50). Light brown gum (0.03 g; 7.7%). MS (EI): m/z=273 [M].

Example 119

2-{3-[3-(2-Methoxy-ethyl)-[1,2,4]oxadiazol-5-yl]-4,7-dihydro-5H-thieno[2,3-c]pyran-2-ylcarbamoyl}-cyclopent-1-enecarboxylic acid

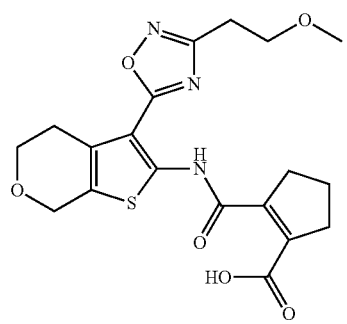 [SMILES: COCCc1noc(-c2c(NC(=O)C3=C(C(=O)O)CCC3)sc3c2CCOC3)n1]

The title compound was prepared in analogy to example 55, from 3-[3-(2-methoxy-ethyl)-[1,2,4]oxadiazol-5-yl]-4,7-dihydro-5H-thieno[2,3-c]pyran-2-ylamine (example 110, intermediate). Yellow solid (59%). MS (ESI): m/z=420.12 [M+H]$^+$.

Example 120

2-[3-(3-Methyl-[1,2,4]oxadiazol-5-yl)-5,6,7,8-tetrahydro-4H-cyclohepta[b]thiophen-2-ylcarbamoyl]-cyclopent-1-enecarboxylic acid

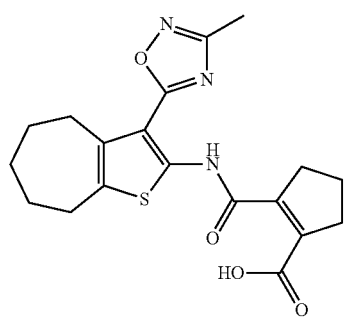 [SMILES: Cc1noc(-c2c(NC(=O)C3=C(C(=O)O)CCC3)sc3c2CCCCC3)n1]

To a solution of 3-(3-methyl-[1,2,4]oxadiazol-5-yl)-5,6,7,8-tetrahydro-4H-cyclohepta[b]thiophen-2-ylamine (150 mg, 0.602 mmol) in 10 mL CH$_3$CN were added DMAP (146 mg, 1.20 mmol, CAS RN 1122-58-3) and 1-cyclopentene-1,2-dicarboxylic anhydride (139 mg, 0.782 mmol, CAS RN 3205-94-5) and the reaction mixture was stirred at 60° C. for 12 h. The product was purified by preparative HPLC (NH$_4$OAc/CH$_3$CN). Yellow solid (18 mg, 8%). MS (ESI): m/z=388.3 [M+H]$^+$.

Intermediate 3-(3-Methyl-[1,2,4]oxadiazol-5-yl)-5,6,7,8-tetrahydro-4H-cyclohepta[b]thiophen-2-ylamine

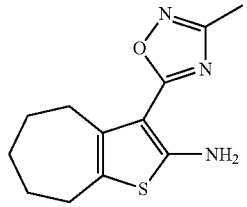 [SMILES: Cc1noc(-c2c(N)sc3c2CCCCC3)n1]

To a solution of (3-methyl-[1,2,4]oxadiazol-5-yl)-acetonitrile (560 mg, 4.54 mmol, (Princeton BioMolecular Research, Inc.). in 5 mL EtOH was added cycloheptanone (0.388 mL, 4.54 mmol, CAS RN 502-42-1) and sulfur (145 mg, 4.54 mmol, CAS RN 7704-34-9) and the reaction mixture was heated to 50° C. for 30 minutes. Then 6 mL morpholine was added dropwise to the reaction mixture and stirring was continued for another 3 h at 50° C. The product was purified by column chromatography eluting with a gradient of n-hexane:EtOAc (80:20). Light yellow solid (1 g, 88%) MS (ESI): m/z=250.2 [M+H]$^+$.

Example 121

2-[3-(3-Methyl-[1,2,4]oxadiazol-5-yl)-5,6,7,8-tetrahydro-4H-cyclohepta[b]thiophen-2-ylcarbamoyl]-cyclohex-1-enecarboxylic acid

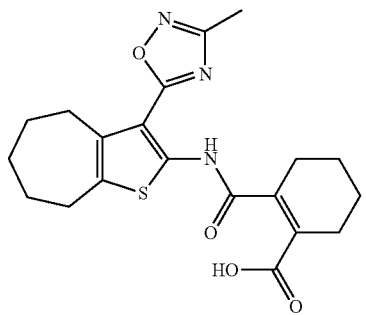 [SMILES: Cc1noc(-c2c(NC(=O)C3=C(C(=O)O)CCCC3)sc3c2CCCCC3)n1]

To a solution of 3-(3-methyl-[1,2,4]oxadiazol-5-yl)-5,6,7,8-tetrahydro-4H-cyclohepta[b]-thiophen-2-yl-amine (100 mg, 0.401 mmol, example 120, intermediate) in 4 mL dry THF was added 1-cyclohexene-1,2-dicarboxylic anhydride (CAS RN 2426-02-0) (79 mg, 0.521 mmol, CAS RN 2426-02-0) and the reaction mixture was stirred at 25° C. for 16 h. The product was purified by column chromatography eluting with a gradient of n-hexane:EtOAc (75:35 to 70:30. Brown solid (40 mg, 25%) MS (ESI): m/z=402.0 [M+H]$^+$.

Example 122

3-[3-(3-Methyl-[1,2,4]oxadiazol-5-yl)-5,6,7,8-tetrahydro-4H-cyclohepta[b]thiophen-2-ylcarbamoyl]-bicyclo[2.2.2]oct-2-ene-2-carboxylic acid

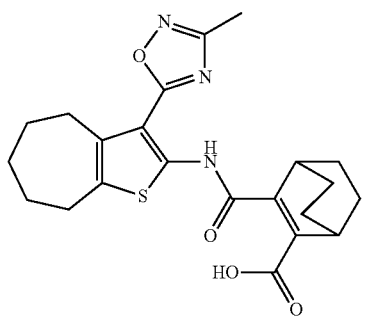 [SMILES: Cc1noc(-c2c(NC(=O)C3=C(C(=O)O)C4CCC3CC4)sc3c2CCCCC3)n1]

The title compound was prepared in analogy to example 121, from 3-(3-methyl-[1,2,4]oxadiazol-5-yl)-5,6,7,8-tetrahydro-4H-cyclohepta[b]thiophen-2-ylamine (example 120, intermediate) and bicyclo[2.2.2]oct-2-ene-2,3-dicarboxylic anhydride (CAS RN 151813-29-5) and using a gradient of n-hexane:EtOAc (50:50 to 30:70) for the chromatographic purification. Yellow solid (23%). MS (ESI): m/z=428.4 [M+H]$^+$.

Example 123

2-[3-(3-Cyclopropyl-[1,2,4]oxadiazol-5-yl)-5,6,7,8-tetrahydro-4H-cyclohepta[b]thiophen-2-ylcarbamoyl]-cyclopent-1-enecarboxylic acid

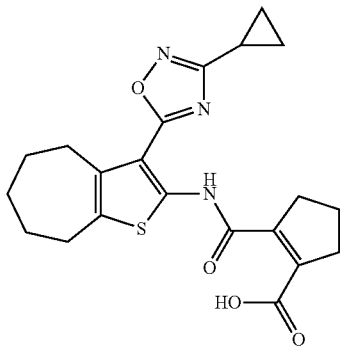 [SMILES: O=C(O)C1=C(C(=O)Nc2sc3c(c2-c2nc(C4CC4)no2)CCCCC3)CCC1]

The title compound was prepared in analogy to example 121, from 3-(3-cyclopropyl-[1,2,4]oxadiazol-5-yl)-5,6,7,8-tetrahydro-4H-cyclohepta[b]thiophen-2-ylamine and 1-cyclopentene-1,2-dicarboxylic anhydride (CAS RN 3205-94-5) and using a gradient of n-hexane:EtOAc (80:20 to 70:40) for the chromatographic purification. Yellow solid (50%). MS (ESI): m/z=414.0 [M+H]$^+$.

Intermediate 3-(3-Cyclopropyl-[1,2,4]oxadiazol-5-yl)-5,6,7,8-tetrahydro-4H-cyclohepta[b]-thiophen-2-ylamine

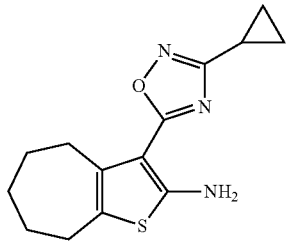 [SMILES: Nc1sc2c(c1-c1nc(C3CC3)no1)CCCCC2]

The title compound was prepared in analogy to example 120, intermediate, from (3-cyclopropyl-[1,2,4]oxadiazol-5-yl)-acetonitrile (Princeton BioMolecular Research, Inc.), cycloheptanone (CAS RN 502-41-1) and sulfur. Yellow solid (94%). MS (ESI): m/z=276.2 [M+H]$^+$.

Example 124

2-[3-(3-Cyclopropyl-[1,2,4]oxadiazol-5-yl)-5,6,7,8-tetrahydro-4H-cyclohepta[b]-thiophen-2-ylcarbamoyl]-cyclohex-1-enecarboxylic acid

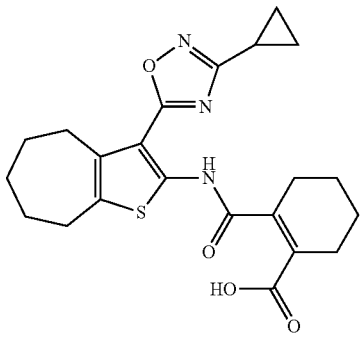 [SMILES: O=C(O)C1=C(C(=O)Nc2sc3c(c2-c2nc(C4CC4)no2)CCCCC3)CCCC1]

The title compound was prepared in analogy to example 121, from 3-(3-cyclopropyl-[1,2,4]oxadiazol-5-yl)-5,6,7,8-tetrahydro-4H-cyclohepta[b]thiophen-2-ylamine (example 123, intermediate) and 1-cyclohexene-1,2-dicarboxylic anhydride (CAS RN 2426-02-0) (CAS RN 2426-02-0). Brown solid (45%). MS (ESI): m/z=428.0 [M+H]$^+$.

Example 125

3-[3-(3-Cyclopropyl-[1,2,4]oxadiazol-5-yl)-5,6,7,8-tetrahydro-4H-cyclohepta[b]-thiophen-2-ylcarbamoyl]-bicyclo[2.2.2]oct-2-ene-2-carboxylic acid

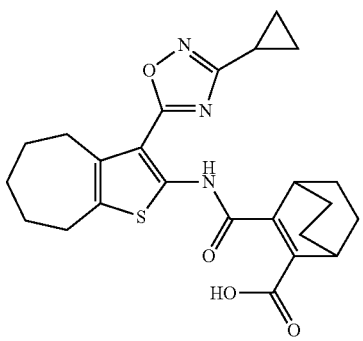 [SMILES: O=C(O)C1=C(C(=O)Nc2sc3c(c2-c2nc(C4CC4)no2)CCCCC3)C2CCC1CC2]

The title compound was prepared was prepared in analogy to example 121, from 3-(3-cyclopropyl-[1,2,4]oxadiazol-5-yl)-5,6,7,8-tetrahydro-4H-cyclohepta[b]thiophen-2-ylamine (example 123, intermediate) and bicyclo[2.2.2]oct-2-ene-2,3-dicarboxylic anhydride (CAS RN 151813-29-5). Yellow solid (44%). MS (ESI): m/z=454.0 [M+H]$^+$.

Example 126

2-[3-(3-Trifluoromethyl-[1,2,4]oxadiazol-5-yl)-5,6,7,8-tetrahydro-4H-cyclohepta[b]-thiophen-2-ylcarbamoyl]-cyclopent-1-enecarboxylic acid

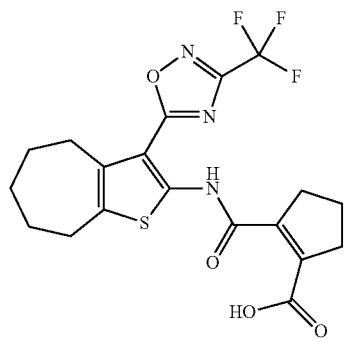 [SMILES: O=C(O)C1=C(C(=O)Nc2sc3c(c2-c2nc(C(F)(F)F)no2)CCCCC3)CCC1]

The title compound was prepared in analogy to example 121, from 3-(3-trifluoromethyl-[1,2,4]oxadiazol-5-yl)-5,6,7,8-tetrahydro-4H-cyclohepta[b]thiophen-2-ylamine and 1-cyclopentene-1,2-dicarboxylic anhydride (CAS RN 3205-94-5). Yellow solid (34%). MS (ESI): m/z=442.0 [M+H]$^+$.

Intermediate 3-(3-Trifluoromethyl-[1,2,4]oxadiazol-5-yl)-5,6,7,8-tetrahydro-4H-cyclohepta[b]-thiophen-2-ylamine

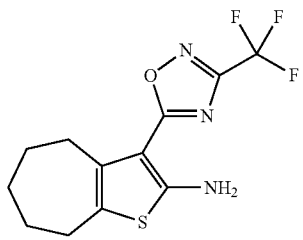 [SMILES: Nc1sc2c(c1-c1nc(C(F)(F)F)no1)CCCCC2]

The title compound was prepared in analogy to example 120, intermediate, from (3-trifluoromethyl-[1,2,4]oxadiazol-5-yl)-acetonitrile (CAS RN 1308384-47-5), cycloheptanone (CAS RN 502-42-1) and sulfur (CAS RN 7704-34-9). Light yellow solid (88%). MS (ESI): m/z=304.0 [M+H]$^+$.

Example 127

2-[3-(3-Trifluoromethyl-[1,2,4]oxadiazol-5-yl)-5,6,7,8-tetrahydro-4H-cyclohepta[b]-thiophen-2-ylcarbamoyl]-cyclohex-1-enecarboxylic acid

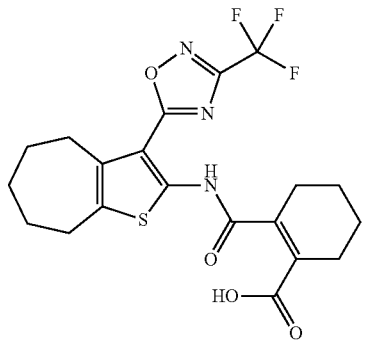 [SMILES: O=C(O)C1=C(C(=O)Nc2sc3c(c2-c2nc(C(F)(F)F)no2)CCCCC3)CCCC1]

To a solution of 3-(3-trifluoromethyl-[1,2,4]oxadiazol-5-yl)-5,6,7,8-tetrahydro-4H-cyclo-hepta[b]thiophen-2-ylamine (60 mg, 0.198 mmol, example 126, intermediate) in 10 mL THF was added lithium bis(trimethylsilyl)amide (0.39 mL, 0.39 mmol, 1M solution in THF; CAS RN 4039-32-1) at −78° C. and the resulting mixture was stirred at −78° C. for 30 min. Then 1-cyclohexene-1,2-dicarboxylic anhydride (CAS RN 2426-02-0, 39 mg, 0.257 mmol) in 1 mL THF was added to the reaction mixture at −78° C. and the reaction mixture was stirred at 25° C. for 12 h. The reaction mixture was quenched with 5 mL saturated NH$_4$Cl solution and extracted with 2×15 mL EtOAc. The combined organic layers were dried over Na$_2$SO$_4$ and evaporated. The residue was purified by column chromatography eluting with a gradient of CH$_2$Cl$_2$:MeOH (100:0 to 95:5). Yellow solid (25 mg, 28%). MS (ESI): m/z=454.2 [M−H]$^-$.

Example 128

3-[3-(3-Trifluoromethyl-[1,2,4]oxadiazol-5-yl)-5,6,7,8-tetrahydro-4H-cyclohepta[b]-thiophen-2-ylcarbamoyl]-bicyclo[2.2.2]oct-2-ene-2-carboxylic acid

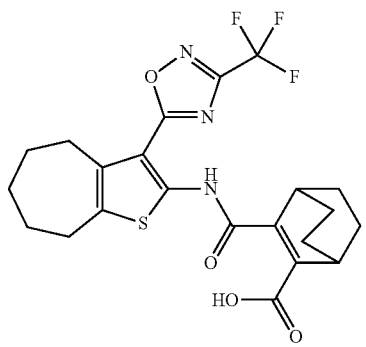 [SMILES: O=C(O)C1=C(C(=O)Nc2sc3c(c2-c2nc(C(F)(F)F)no2)CCCCC3)C2CCC1CC2]

The title compound was prepared in analogy to example 127, from 3-(3-trifluoromethyl-[1,2,4]oxadiazol-5-yl)-5,6,7,8-tetrahydro-4H-cyclohepta[b]thiophen-2-ylamine (example 126, intermediate) and bicyclo[2.2.2]oct-2-ene-2,3- dicarboxylic anhydride (CAS RN 151813-29-5). Yellow solid (44%). MS (ESI): m/z=482.0 [M+H]⁺.

Example 129

2-[3-(3-Methyl-[1,2,4]oxadiazol-5-yl)-5,6-dihydro-4H-cyclopenta[b]thiophen-2-yl-carbamoyl]-cyclopent-1-enecarboxylic acid

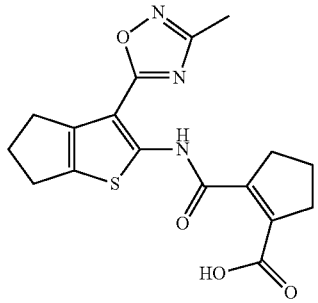 [SMILES: Cc1noc(-c2c(NC(=O)C3=C(C(=O)O)CCC3)sc3c2CCC3)n1]

The title compound was prepared in analogy to example 121, from 3-(3-methyl-[1,2,4]oxadiazol-5-yl)-5,6-dihydro-4H-cyclopenta[b]thiophen-2-yl-amine and 1-cyclopentene-1,2-dicarboxylic anhydride (CAS RN 3205-94-5). Yellow solid (11%). MS (ESI): m/z=360.0 [M+H]⁺.

Intermediate 3-(3-Methyl-[1,2,4]oxadiazol-5-yl)-5,6-dihydro-4H-cyclopenta[b]thiophen-2-ylamine

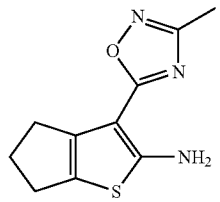

The title compound was prepared in analogy to example 120, intermediate, from (3-methyl-[1,2,4]oxadiazol-5-yl)-acetonitrile (Princeton BioMolecular Research, Inc.), cyclopentanone (CAS RN 120-92-3) and sulfur (CAS RN 7704-34-9). Light yellow solid (78%). MS (ESI): m/z=222.0 [M+H]⁺.

Example 130

2-[3-(3-Methyl-[1,2,4]oxadiazol-5-yl)-5,6-dihydro-4H-cyclopenta[b]thiophen-2-yl-carbamoyl]-cyclohex-1-enecarboxylic acid

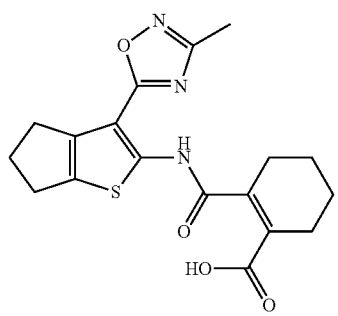 [SMILES: Cc1noc(-c2c(NC(=O)C3=C(C(=O)O)CCCC3)sc3c2CCC3)n1]

The title compound was prepared was prepared in analogy to example 121, from 3-(3-methyl-[1,2,4]oxadiazol-5-yl)-5,6-dihydro-4H-cyclopenta[b]thiophen-2-yl-amine (example 129, intermediate) and 1-cyclohexene-1,2-dicarboxylic anhydride (CAS RN 2426-02-0) and using a gradient of n-hexane:EtOAc (50:50 to 30:70) for the chromatographic purification. Yellow solid (12%). MS (ESI): m/z=374.2 [M+H]⁺.

Example 131

3-[3-(3-Methyl-[1,2,4]oxadiazol-5-yl)-5,6-dihydro-4H-cyclopenta[b]thiophen-2-yl-carbamoyl]-bicyclo[2.2.2]oct-2-ene-2-carboxylic acid

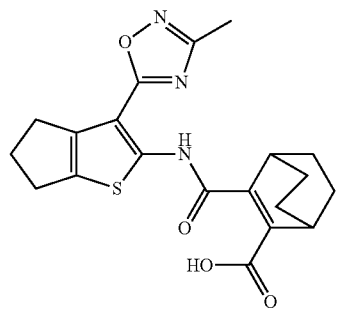 [SMILES: Cc1noc(-c2c(NC(=O)C3=C(C(=O)O)C4CCC3CC4)sc3c2CCC3)n1]

The title compound was prepared in analogy to example 121, from 3-(3-methyl-[1,2,4]oxadiazol-5-yl)-5,6-dihydro-4H-cyclopenta[b]thiophen-2-yl-amine (example 129, intermediate) and bicyclo[2.2.2]oct-2-ene-2,3-dicarboxylic anhydride (CAS RN 151813-29-5, 105 mg, 0.587 mmol) and using a gradient of n-hexane:EtOAc (50:50 to 30:70) for the chromatographic purification. Yellow solid (23%). MS (ESI): m/z=400.2 [M+H]⁺.

Example 132

2-[3-(3-Cyclopropyl-[1,2,4]oxadiazol-5-yl)-5,6-dihydro-4H-cyclopenta[b]thiophen-2-yl-carbamoyl]-cyclopent-1-enecarboxylic acid

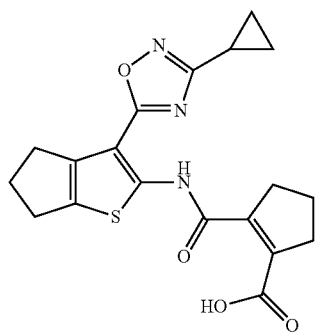 [SMILES: O=C(O)C1=C(C(=O)Nc2sc3c(c2-c2nc(C4CC4)no2)CCC3)CCC1]

The title compound was prepared in analogy to example 121, from 3-(3-cyclopropyl-[1,2,4]oxadiazol-5-yl)-5,6-dihydro-4H-cyclopenta[b]thiophen-2-ylamine and 1-cyclopentene-1,2-dicarboxylic anhydride (CAS RN 3205-94-5, 78 mg, 0.566 mmol) and using a gradient of n-hexane:

Intermediate 3-(3-Cyclopropyl-[1,2,4]oxadiazol-5-yl)-5,6-di-hydro-4H-cyclopenta[b]thiophen-2-yl-amine

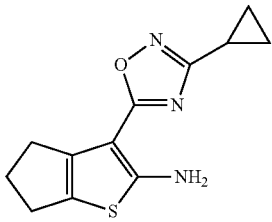 [SMILES: Nc1sc2c(c1-c1nc(C3CC3)no1)CCC2]

The title compound was prepared in analogy to example 120, intermediate, from (3-cyclopropyl-[1,2,4]oxadiazol-5-yl)-acetonitrile (Princeton BioMolecular Research, Inc.), cyclopentanone (CAS RN 120-92-3) and sulfur (CAS RN 7704-34-9). Yellow solid (48%). MS (ESI): m/z=248.2 [M+H]$^+$.

EtOAc (80:20 to 50:50) for the chromatographic purification. Yellow solid (65 mg, 42%). MS (ESI): m/z=384.2 [M–H]$^-$.

Example 133

2-[3-(3-Cyclopropyl-[1,2,4]oxadiazol-5-yl)-5,6-di-hydro-4H-cyclopenta[b]thiophen-2-yl-carbamoyl]-cyclohex-1-enecarboxylic acid

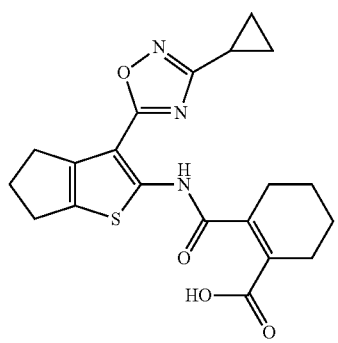 [SMILES: O=C(O)C1=C(C(=O)Nc2sc3c(c2-c2nc(C4CC4)no2)CCC3)CCCC1]

The title compound was prepared in analogy to example 121, from 3-(3-cyclopropyl-[1,2,4]oxadiazol-5-yl)-5,6-di-hydro-4H-cyclopenta[b]thiophen-2-yl-amine (example 132, intermediate) and 1-cyclohexene-1,2-dicarboxylic anhydride (CAS RN 2426-02-0) and using a gradient of n-hexane:EtOAc (70:30 to 40:60) for the chromatographic purification. Brown solid (15%). MS (ESI): m/z=400.0 [M+H]$^+$.

Example 134

3-[3-(3-Cyclopropyl-[1,2,4]oxadiazol-5-yl)-5,6-di-hydro-4H-cyclopenta[b]thiophen-2-ylcarbamoyl]-bicyclo[2.2.2]oct-2-ene-2-carboxylic acid

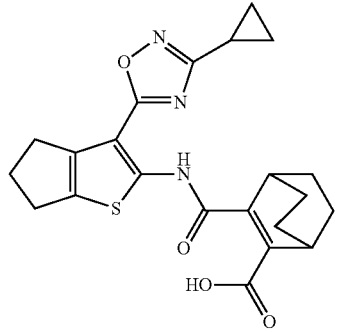 [SMILES: O=C(O)C1=C(C(=O)Nc2sc3c(c2-c2nc(C4CC4)no2)CCC3)C2CCC1CC2]

The title compound was prepared in analogy to example 121, from 3-(3-cyclopropyl-[1,2,4]oxadiazol-5-yl)-5,6-di-hydro-4H-cyclopenta[b]thiophen-2-ylamine (example 132, intermediate) and bicyclo[2.2.2]oct-2-ene-2,3-dicarboxylic anhydride (CAS RN 151813-29-5) and using a gradient of n-hexane:EtOAc (75:25 to 25:75) for the chromatographic purification. Yellow solid (16%). MS (ESI): m/z=424.4 [M–H]$^-$.

Example 135

2-[3-(3-Trifluoromethyl-[1,2,4]oxadiazol-5-yl)-5,6-dihydro-4H-cyclopenta[b]thiophen-2-ylcarbamoyl]-cyclopent-1-enecarboxylic acid

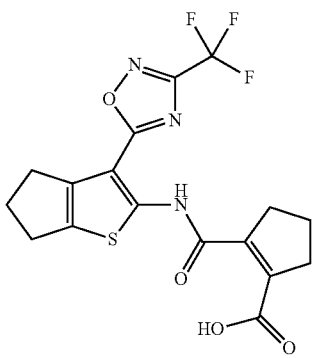 [SMILES: O=C(O)C1=C(C(=O)Nc2sc3c(c2-c2nc(C(F)(F)F)no2)CCC3)CCC1]

The title compound was prepared in analogy to example 127, from 3-(3-trifluoromethyl-[1,2,4]oxadiazol-5-yl)-5,6-dihydro-4H-cyclopenta[b]thiophen-2-ylamine and 1-cyclopentene-1,2-dicarboxylic anhydride (CAS RN 3205-94-5). Brown solid (58%). MS (ESI): m/z=414.0 [M+H]$^+$.

157

Intermediate 3-(3-Trifluoromethyl-[1,2,4]oxadiazol-5-yl)-5,6-dihydro-4H-cyclopenta[b]thiophen-2-ylamine

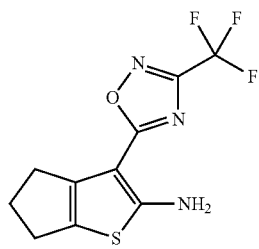 [SMILES: Nc1sc2c(c1-c1nc(C(F)(F)F)no1)CCC2]

The title compound was prepared in analogy to example 120, intermediate, from (3-trifluoromethyl-[1,2,4]oxadiazol-5-yl)-acetonitrile (CAS RN 1308384-47-5), cyclopentanone (CAS RN 120-92-3) and sulfur (CAS RN 7704-34-9). Yellow solid (90%). MS (ESI): m/z=274 [M−H]⁻.

Example 136

2-[3-(3-Trifluoromethyl-[1,2,4]oxadiazol-5-yl)-5,6-dihydro-4H-cyclopenta[b]thiophen-2-ylcarbamoyl]-cyclohex-1-enecarboxylic acid

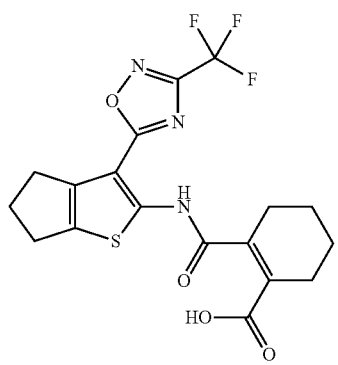 [SMILES: O=C(O)C1=C(C(=O)Nc2sc3c(c2-c2nc(C(F)(F)F)no2)CCC3)CCCC1]

The title compound was prepared in analogy to example 120, from 3-(3-trifluoromethyl-[1,2,4]oxadiazol-5-yl)-5,6-dihydro-4H-cyclopenta[b]-thiophen-2-ylamine (example 135, intermediate) in anhydrous Et₂O with 1-cyclohexene-1,2-dicarboxylic anhydride (CAS RN 2426-02-0) and DMAP (CAS RN 1122-58-3) at 25° C. for 40 h. The reaction mixture was evaporated and the resulting crude product was purified by column chromatography eluting with a gradient of CH₂Cl₂:MeOH (100:0 to 95:5). Yellow solid (18%). MS (ESI): m/z=428.2 [M+H]⁺.

158

Example 137

3-[3-(3-Trifluoromethyl-[1,2,4]oxadiazol-5-yl)-5,6-dihydro-4H-cyclopenta[b]thiophen-2-ylcarbamoyl]-bicyclo[2.2.2]oct-2-ene-2-carboxylic acid

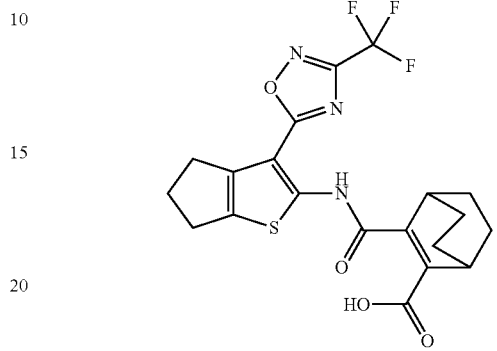

The title compound was prepared in analogy to example 127, from 3-(3-trifluoromethyl-[1,2,4]oxadiazol-5-yl)-5,6-dihydro-4H-cyclopenta[b]thiophen-2-ylamine (example 135, intermediate) and bicyclo[2.2.2]oct-2-ene-2,3-dicarboxylic anhydride (CAS RN 151813-29-5). Brown solid (30%). MS (ESI): m/z=454.0 [M+H]⁺.

Example 138

2-[3-(4-Methyl-thiazol-2-yl)-5,6-dihydro-4H-cyclopenta[b]thiophen-2-ylcarbamoyl]-cyclopent-1-enecarboxylic acid

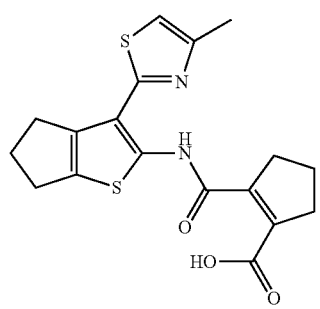 [SMILES: Cc1csc(-c2c(NC(=O)C3=C(C(=O)O)CCC3)sc3c2CCC3)n1]

The title compound was prepared in analogy to example 120, from 3-(4-methyl-thiazol-2-yl)-5,6-dihydro-4H-cyclopenta[b]thiophen-2-yl-amine, 1-cyclopentene-1,2-dicarboxylic anhydride (CAS RN 3205-94-5) and DMAP (CAS RN 1122-58-3) in anhydrous Et₂O at 25° C. for 40 h. The reaction mixture was evaporated off and the resulting crude product was purified by column chromatography eluting with a gradient of CH₂Cl₂:MeOH (100:0 to 95:5) followed by recrystallization from CH₂Cl₂/n-hexane. Yellow solid (11%). MS (ESI): m/z=375.0 [M+H]⁺.

Intermediates a) 3-(4-Methyl-thiazol-2-yl)-5,6-dihydro-4H-cyclopenta[b]thiophen-2-ylamine

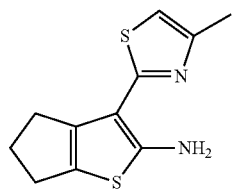

To a solution of cyclopentylidene-(4-methyl-thiazol-2-yl)-acetonitrile (630 mg, 3.084 mmol) in 50 mL EtOH were added 1,8-diazabicyclo[5.4.0]undec-7-ene (CAS RN 6674-22-2, 1.15 mL, 7.71 mmol) and sulfur (CAS RN 7704-34-9, 99 mg, 3.084 mmol) and the reaction mixture was stirred for 2 h at 65° C. The dark solution was poured on 50 mL 10% aqueous NaHCO$_3$ solution and 50 mL EtOAc and the layers were separated. The aqueous layer was extracted a second time with 30 mL EtOAc. The combined organic layer was washed with 40 mL brine, dried over anhydrous Na$_2$SO$_4$, filtered and concentrated under vacuum. The resulting crude product was purified by column chromatography using a gradient of n-hexane:EtOAc (90:10 to 80:20). Brown solid (370 mg, 51%). MS (ESI): m/z=237.0 [M+H]$^+$.

b) Cyclopentylidene-(4-methyl-thiazol-2-yl)-acetonitrile

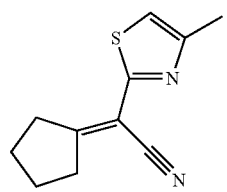

To a solution of (4-methyl-thiazol-2-yl)-acetonitrile (500 mg, 3.618 mmol, CAS RN 19785-39-8) in 5 mL toluene were added cyclopentanone (0.32 mL, 3.62 mmol, CAS RN 120-92-3) and NH$_4$OAc (558 mg, 7.24 mmol, CAS RN 631-61-8). The reaction mixture was stirred at 100° C. for 18 h and then poured on a mixture of 50 mL 10% aqueous NaHCO$_3$ solution and 50 mL EtOAc and the layers were separated. The aqueous layer was extracted with 25 mL EtOAc. The organic layers were washed with 40 mL brine, dried over anhydrous Na$_2$SO$_4$, filtered and concentrated under vacuum to get the crude product which was purified by column chromatography using a gradient of n-hexane:EtOAc (90:10 to 80:20). Brown solid (635 mg, 86%). MS (ESI): m/z=205.0 [M+H]$^+$.

Example 139

2-[3-(4-Methyl-thiazol-2-yl)-5,6-dihydro-4H-cyclopenta[b]thiophen-2-ylcarbamoyl]-cyclohex-1-enecarboxylic acid

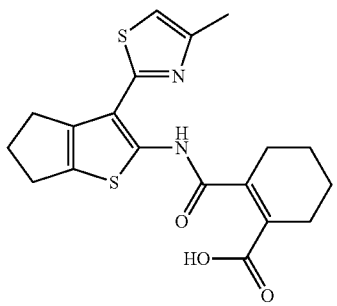 [SMILES: Cc1csc(-c2c(NC(=O)C3=C(C(=O)O)CCCC3)sc3c2CCC3)n1]

The title compound was prepared in analogy to example 120, from 3-(4-methyl-thiazol-2-yl)-5,6-dihydro-4H-cyclopenta[b]thiophen-2-yl-amine (example 138, intermediate a), 1-cyclohexene-1,2-dicarboxylic anhydride (CAS RN 2426-02-0) and DMAP (CAS RN 1122-58-3) in anhydrous Et$_2$O at 25° C. for 40 h. The reaction mixture was evaporated off and the resulting crude product was purified by column chromatography eluting with a gradient of CH$_2$Cl$_2$:MeOH (100:0 to 95:5) followed by recrystallization from CH$_2$Cl$_2$/n-hexane. Yellow solid (11%). MS (ESI): m/z=389.2 [M+H]$^+$.

Example 140

3-[3-(4-Methyl-thiazol-2-yl)-5,6-dihydro-4H-cyclopenta[b]thiophen-2-ylcarbamoyl]-bicyclo[2.2.2]oct-2-ene-2-carboxylic acid

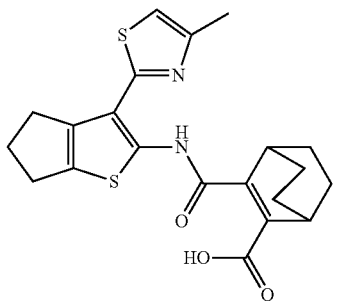 [SMILES: Cc1csc(-c2c(NC(=O)C3=C(C(=O)O)C4CCC3CC4)sc3c2CCC3)n1]

The title compound was prepared in analogy to example 127, from 3-(4-methyl-thiazol-2-yl)-5,6-dihydro-4H-cyclopenta[b]thiophen-2-ylamine (example 138, intermediate a) and bicyclo[2.2.2]oct-2-ene-2,3-dicarboxylic anhydride (CAS RN 151813-29-5). Brown solid (26%). MS (ESI): m/z=413.2 [M−H]$^-$.

Example 141

2-[6,6-Difluoro-3-(3-methyl-[1,2,4]oxadiazol-5-yl)-4,5,6,7-tetrahydro-benzo[b]thiophen-2-ylcarbamoyl]-cyclopent-1-enecarboxylic acid

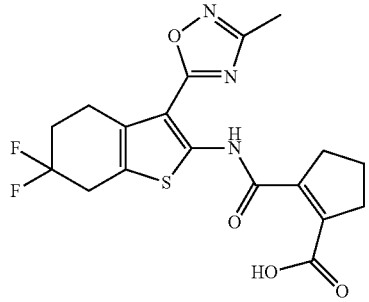 [SMILES: Cc1noc(-c2c(NC(=O)C3=C(C(=O)O)CCC3)sc3c2CCC(F)(F)C3)n1]

The title compound was prepared in analogy to example 127, from 6,6-difluoro-3-(3-methyl-[1,2,4]oxadiazol-5-yl)-4,5,6,7-tetrahydro-benzo[b]-thiophen-2-ylamine and 1-cyclopentene-1,2-dicarboxylic anhydride (CAS RN 3205-94-5). Yellow solid (37%). MS (ESI): m/z=410.2 [M+H]+.

Intermediate 6,6-Difluoro-3-(3-methyl-[1,2,4]oxadiazol-5-yl)-4,5,6,7-tetrahydro-benzo[b]thiophen-2-ylamine

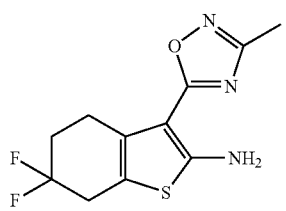 [SMILES: Cc1noc(-c2c(N)sc3c2CCC(F)(F)C3)n1]

The title compound was prepared in analogy to example 120, intermediate, from (3-methyl-[1,2,4]oxadiazol-5-yl)-acetonitrile (Princeton BioMolecular Research, Inc.), 4,4-difluoro-cyclohexanone (CAS RN 22515-18-0) and sulfur (CAS RN 7704-34-9). Light yellow solid (86%). MS (ESI): m/z=272.0 [M+H]+.

Example 142

2-[6,6-Difluoro-3-(3-methyl-[1,2,4]oxadiazol-5-yl)-4,5,6,7-tetrahydro-benzo[b]thiophen-2-ylcarbamoyl]-cyclohex-1-enecarboxylic acid

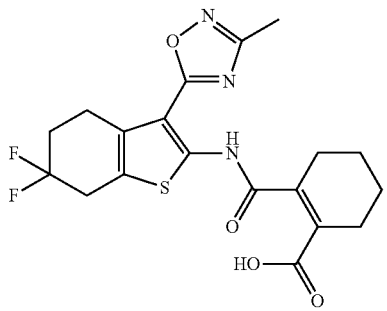 [SMILES: Cc1noc(-c2c(NC(=O)C3=C(C(=O)O)CCCC3)sc3c2CCC(F)(F)C3)n1]

The title compound was prepared in analogy to example 127, from 6,6-difluoro-3-(3-methyl-[1,2,4]oxadiazol-5-yl)-4,5,6,7-tetrahydro-benzo[b]thiophen-2-ylamine (example 141, intermediate) and 1-cyclohexene-1,2-dicarboxylic anhydride (CAS RN 2426-02-0). Light yellow solid (15%). MS (ESI): m/z=424.2 [M+H]+.

Example 143

3-[6,6-Difluoro-3-(3-methyl-[1,2,4]oxadiazol-5-yl)-4,5,6,7-tetrahydro-benzo[b]thiophen-2-ylcarbamoyl]-bicyclo[2.2.2]oct-2-ene-2-carboxylic acid

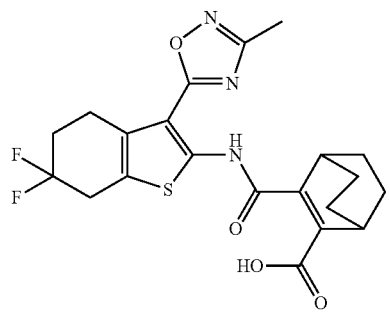 [SMILES: Cc1noc(-c2c(NC(=O)C3=C(C(=O)O)C4CCC3CC4)sc3c2CCC(F)(F)C3)n1]

The title compound was prepared in analogy to example 127, from 6,6-difluoro-3-(3-methyl-[1,2,4]oxadiazol-5-yl)-4,5,6,7-tetrahydro-benzo[b]thiophen-2-ylamine (example 141, intermediate) and bicyclo[2.2.2]oct-2-ene-2,3-dicarboxylic anhydride (85 mg, CAS RN 151813-29-5). Yellow solid (42%). MS (ESI): m/z=448.2 [M−H]−.

Example 144

2-[3-(3-Cyclopropyl-[1,2,4]oxadiazol-5-yl)-6,6-difluoro-4,5,6,7-tetrahydro-benzo[b]-thiophen-2-ylcarbamoyl]-cyclopent-1-enecarboxylic acid

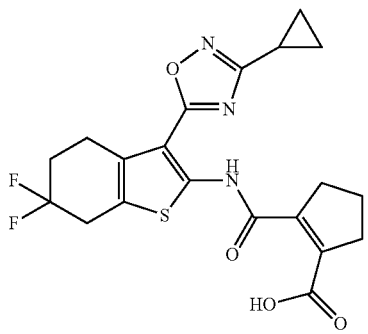 [SMILES: O=C(O)C1=C(C(=O)Nc2sc3c(c2-c2nc(C4CC4)no2)CCC(F)(F)C3)CCC1]

The title compound was prepared in analogy to example 127, from 3-(3-cyclopropyl-[1,2,4]oxadiazol-5-yl)-6,6-difluoro-4,5,6,7-tetrahydro-benzo[b]-thiophen-2-ylamine and 1-cyclopentene-1,2-dicarboxylic anhydride (CAS RN 3205-94-5). The product was additionally purified by recrystallization from CH2Cl2/n-hexane. Yellow solid (20%). MS (ESI): m/z=436.0 [M+H]+.

Intermediate 3-(3-Cyclopropyl-[1,2,4]oxadiazol-5-yl)-6,6-difluoro-4,5,6,7-tetrahydro-benzo[b]-thiophen-2-ylamine

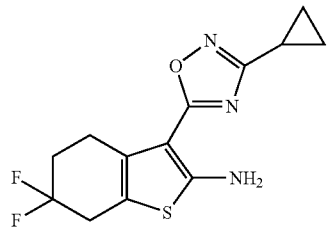 [SMILES: Nc1sc2c(c1-c1nc(C3CC3)no1)CCC(F)(F)C2]

The title compound was prepared in analogy to example 120, intermediate, from (3-cyclopropyl-[1,2,4]oxadiazol-5-yl)-acetonitrile (Princeton BioMolecular Research, Inc.), 4,4-difluorocyclohexanone (CAS RN 22515-18-0) and sulfur (CAS RN 7704-34-9). Yellow solid (92%). MS (ESI): m/z=298.4 [M+H]$^+$.

Example 145

2-[3-(3-Cyclopropyl-[1,2,4]oxadiazol-5-yl)-6,6-difluoro-4,5,6,7-tetrahydro-benzo[b]-thiophen-2-ylcarbamoyl]-cyclohex-1-enecarboxylic acid

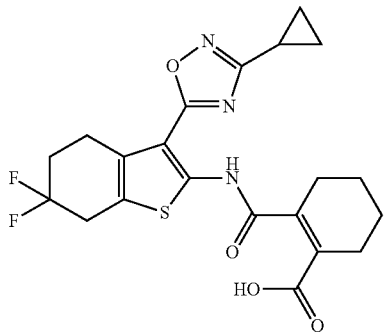 [SMILES: O=C(O)C1=C(C(=O)Nc2sc3c(c2-c2nc(C4CC4)no2)CCC(F)(F)C3)CCCC1]

The title compound was prepared in analogy to example 127, from 3-(3-cyclopropyl-[1,2,4]oxadiazol-5-yl)-6,6-difluoro-4,5,6,7-tetrahydro-benzo[b]-thiophen-2-ylamine (example 144, intermediate) and 1-cyclohexene-1,2-dicarboxylic anhydride (CAS RN 2426-02-0. Brown solid (18%). MS (ESI): m/z=450.2 [M+H]$^+$.

Example 146

3-[3-(3-Cyclopropyl-[1,2,4]oxadiazol-5-yl)-6,6-difluoro-4,5,6,7-tetrahydro-benzo[b]-thiophen-2-ylcarbamoyl]-bicyclo[2.2.2]oct-2-ene-2-carboxylic acid

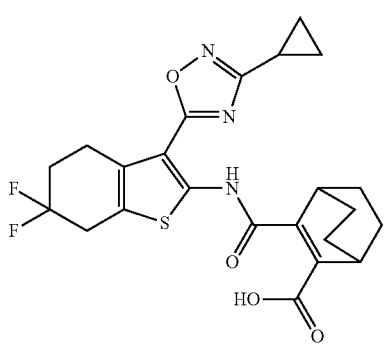 [SMILES: O=C(O)C1=C(C(=O)Nc2sc3c(c2-c2nc(C4CC4)no2)CCC(F)(F)C3)C2CCC1CC2]

The title compound was prepared in analogy to example 127, from 3-(3-cyclopropyl-[1,2,4]oxadiazol-5-yl)-6,6-difluoro-4,5,6,7-tetrahydro-benzo[b]-thiophen-2-ylamine (example 144, intermediate) and bicyclo[2.2.2]oct-2-ene-2,3-dicarboxylic anhydride (CAS RN 151813-29-5). Yellow solid (75%). MS (ESI): m/z=474.0 [M−H]$^−$.

Example 147

2-[6,6-Difluoro-3-(3-trifluoromethyl-[1,2,4]oxadiazol-5-yl)-4,5,6,7-tetrahydro-benzo[b]-thiophen-2-ylcarbamoyl]-cyclopent-1-enecarboxylic acid

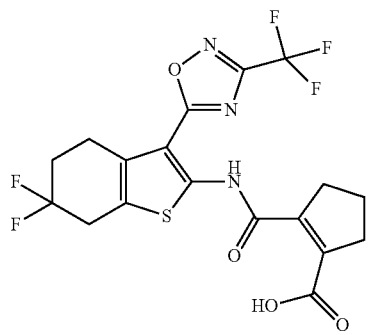 [SMILES: O=C(O)C1=C(C(=O)Nc2sc3c(c2-c2nc(C(F)(F)F)no2)CCC(F)(F)C3)CCC1]

The title compound was prepared in analogy to example 127, from 6,6-difluoro-3-(3-trifluoromethyl-[1,2,4]oxadiazol-5-yl)-4,5,6,7-tetrahydro-benzo[b]thiophen-2-ylamine and 1-cyclopentene-1,2-dicarboxylic anhydride (CAS RN 3205-94-5) using preparative HPLC (NH$_4$OAc/CH$_3$CN) for purification. Yellow solid (32%). MS (ESI): m/z=462.0 [M−H]$^−$.

Intermediate 6,6-Difluoro-3-(3-trifluoromethyl-[1,2,4]oxadiazol-5-yl)-4,5,6,7-tetrahydro-benzo[b]thiophen-2-ylamine

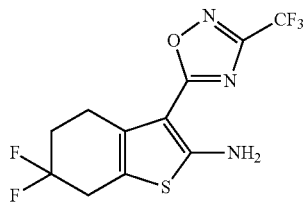 [SMILES: Nc1sc2c(c1-c1nc(C(F)(F)F)no1)CCC(F)(F)C2]

The title compound was prepared in analogy to example 120, intermediate, from (3-trifluoromethyl-[1,2,4]oxadiazol-5-yl)-acetonitrile (CAS RN 1308384-47-5), 4,4-difluoro-cyclohexanone (CAS RN 22515-18-0) and sulfur (CAS RN 7704-34-9). Yellow solid (87%). MS (ESI): m/z=324.2 [M−H]$^−$.

Example 148

2-[6,6-Difluoro-3-(3-trifluoromethyl-[1,2,4]oxadiazol-5-yl)-4,5,6,7-tetrahydro-benzo[b]-thiophen-2-ylcarbamoyl]-cyclohex-1-enecarboxylic acid

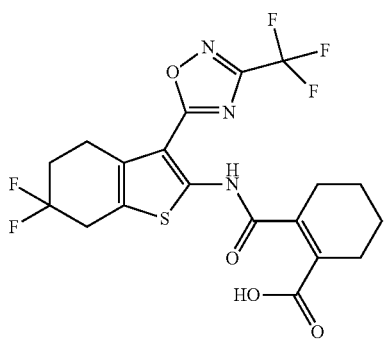 [SMILES: O=C(O)C1=C(C(=O)Nc2sc3c(c2-c2nc(C(F)(F)F)no2)CCC(F)(F)C3)CCCC1]

The title compound was prepared in analogy to example 127, from 6,6-difluoro-3-(3-trifluoromethyl-[1,2,4]oxadiazol-5-yl)-4,5,6,7-tetrahydro-benzo-[b]thiophen-2-ylamine (example 147, intermediate) and 1-cyclohexene-1,2-dicarboxylic anhydride (CAS RN 2426-02-0). Brown solid (62%). MS (ESI): m/z=478.0 [M+H]$^+$.

Example 149

3-[6,6-Difluoro-3-(3-trifluoromethyl-[1,2,4]oxadiazol-5-yl)-4,5,6,7-tetrahydro-benzo[b]-thiophen-2-ylcarbamoyl]-bicyclo[2.2.2]oct-2-ene-2-carboxylic acid

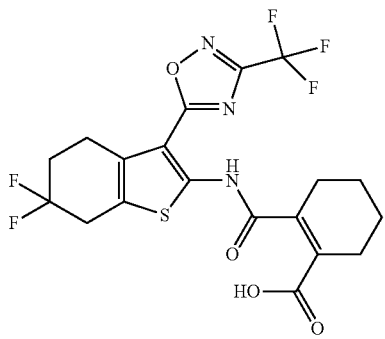 [SMILES: O=C(O)C1=C(C(=O)Nc2sc3c(c2-c2nc(C(F)(F)F)no2)CCC(F)(F)C3)CCCC1]

The title compound was prepared in analogy to example 127, from 6,6-difluoro-3-(3-trifluoromethyl-[1,2,4]oxadiazol-5-yl)-4,5,6,7-tetrahydro-benzo-[b]thiophen-2-ylamine (example 147, intermediate) and bicyclo[2.2.2]oct-2-ene-2,3-dicarboxylic anhydride (CAS RN 151813-29-5). Yellow solid (19%). MS (ESI): m/z=504.2 [M+H]$^+$.

Example 150

2-[6,6-Difluoro-3-(4-methyl-thiazol-2-yl)-4,5,6,7-tetrahydro-benzo[b]thiophen-2-yl-carbamoyl]-cyclopent-1-enecarboxylic acid

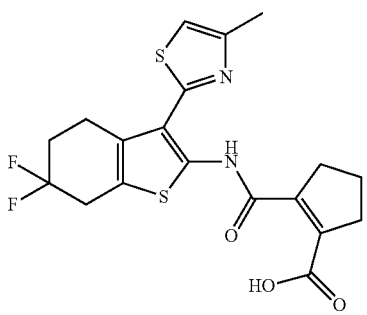 [SMILES: Cc1csc(-c2c(NC(=O)C3=C(C(=O)O)CCC3)sc3c2CCC(F)(F)C3)n1]

The title compound was prepared in analogy to example 120, from 6,6-difluoro-3-(4-methyl-thiazol-2-yl)-4,5,6,7-tetrahydro-benzo[b]thiophen-2-ylamine, DMAP (CAS RN 1122-58-3) and 1-cyclopentene-1,2-dicarboxylic anhydride (CAS RN 3205-94-5, 80 mg, 0.576 mmol) in CH$_3$CN. The product was purified by column chromatography using a gradient of CH$_2$Cl$_2$:MeOH (100:0 to 95:5). Yellow solid (40%). MS (ESI): m/z=423.4 [M−H]$^-$.

Intermediates a) 6,6-Difluoro-3-(4-methyl-thiazol-2-yl)-4,5,6,7-tetrahydro-benzo[b]thiophen-2-ylamine

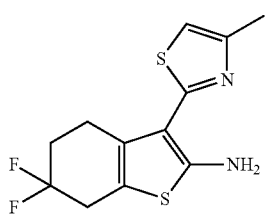 [SMILES: Cc1csc(-c2c(N)sc3c2CCC(F)(F)C3)n1]

The title compound was prepared in analogy to example 138, intermediate a, from (4,4-difluoro-cyclohexylidene)-(4-methyl-thiazol-2-yl)-acetonitrile, 1,8-diaza-bicyclo[5.4.0]undec-7-ene (CAS RN 6674-22-2) and sulfur (CAS RN 7704-34-9). Brown solid (82%). MS (ESI): m/z=287.2 [M+H]$^+$.

b) (4,4-Difluoro-cyclohexylidene)-(4-methyl-thiazol-2-yl)-acetonitrile

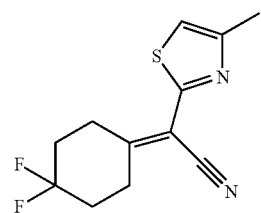 [SMILES: Cc1csc(C(C#N)=C2CCC(F)(F)CC2)n1]

The title compound was prepared in analogy to example 138, intermediate b, from 4,4-difluoro-cyclohexanone (CAS RN 22515-18-0) and (4-methyl-thiazol-2-yl)-acetonitrile (CAS RN 19785-39-8). Light yellow solid (69%). MS (ESI): m/z=255.2 [M+H]+.

Example 151

2-[6,6-Difluoro-3-(4-methyl-thiazol-2-yl)-4,5,6,7-tetrahydro-benzo[b]thiophen-2-ylcarbamoyl]-cyclohex-1-enecarboxylic acid

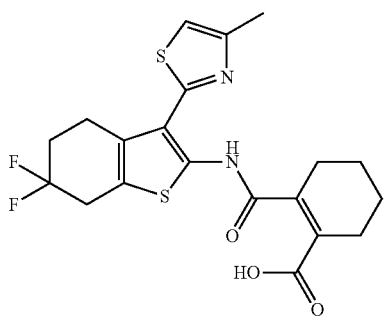 [SMILES: Cc1csc(-c2c(NC(=O)C3=C(C(=O)O)CCCC3)sc3c2CCC(F)(F)C3)n1]

The title compound was prepared in analogy to example 120, from 6,6-difluoro-3-(4-methyl-thiazol-2-yl)-4,5,6,7-tetrahydro-benzo[b]thiophen-2-ylamine (example 150, intermediate), 1-cyclohexene-1,2-dicarboxylic anhydride (CAS RN 2426-02-0) and DMAP (6 mg, 0.052 mmol, CAS RN 1122-58-3) in Et₂O at 25° C. for 40 h. The product was purified by column chromatography using a gradient of CH₂Cl₂:MeOH (100:0 to 95:5) and additionally using recrystallization from CH₂Cl₂/n-hexane. Yellow solid (14%). MS (ESI): m/z=439.0 [M+H]+.

Example 152

3-[6,6-Difluoro-3-(4-methyl-thiazol-2-yl)-4,5,6,7-tetrahydro-benzo[b]thiophen-2-ylcarbamoyl]-bicyclo[2.2.2]oct-2-ene-2-carboxylic acid

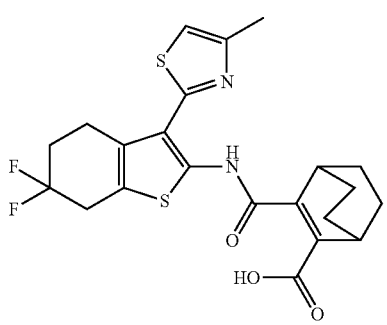 [SMILES: Cc1csc(-c2c(NC(=O)C3=C(C(=O)O)C4CCC3CC4)sc3c2CCC(F)(F)C3)n1]

To a solution of 6,6-difluoro-3-(4-methyl-thiazol-2-yl)-4,5,6,7-tetrahydro-benzo[b]thiophen-2-ylamine (50 mg, 0.175 mmol, example 150, intermediate) in 4 mL dry THF was added bicyclo[2.2.2]oct-2-ene-2,3-dicarboxylic anhydride (40 mg, 0.22 mmol, CAS RN 151813-29-5) and the reaction mixture was stirred at 25° C. for 16 h. The solvent was evaporated and the resulting crude was purified by column chromatography eluting with a gradient of n-hexane:EtOAc (75:35 to 70:30). Yellow solid (40%). MS (ESI): m/z=465.0 [M+H]+.

Example 153

(1RS,2SR)-2-[3-(3-Cyclopropyl-[1,2,4]oxadiazol-5-yl)-6,6-difluoro-4,5,6,7-tetrahydro-benzo[b]thiophen-2-ylcarbamoyl]-cyclohexanecarboxylic acid

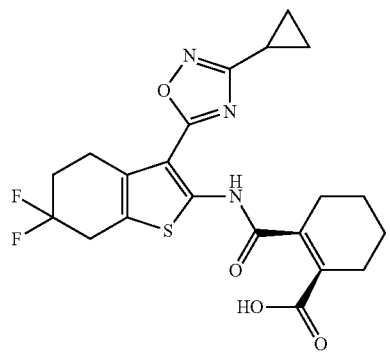

The title compound was prepared in analogy to example 152, from 3-(3-cyclopropyl-[1,2,4]oxadiazol-5-yl)-6,6-difluoro-4,5,6,7-tetrahydro-benzo[b]thiophen-2-ylamine (example 144, intermediate) and cis-1,2-cyclohexanedicarboxylic anhydride (CAS RN 13149-00-3). The product was purified by preparative HPLC (NH₄OAc/CH₃CN). Off-white solid (26%). MS (ESI): m/z=452.4 [M+H]+.

Example 154

(1SR,2SR)-2-[3-(3-Cyclopropyl-[1,2,4]oxadiazol-5-yl)-6,6-difluoro-4,5,6,7-tetrahydro-benzo[b]thiophen-2-ylcarbamoyl]-cyclohexanecarboxylic acid

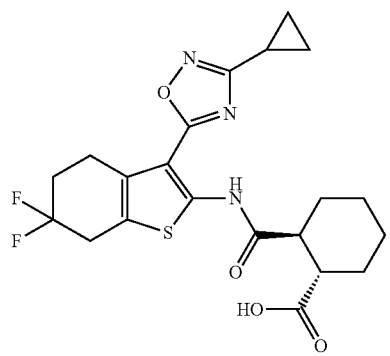 [SMILES: O=C(O)[C@H]1CCCC[C@@H]1C(=O)Nc1sc2c(c1-c1nc(C3CC3)no1)CCC(F)(F)C2]

The title compound was prepared in analogy to example 152, from 3-(3-cyclopropyl-[1,2,4]oxadiazol-5-yl)-6,6-difluoro-4,5,6,7-tetrahydro-benzo[b]-thiophen-2-ylamine (example 144, intermediate) and trans-1,2-cyclohexanedicarboxylic anhydride (CAS RN 14166-21-3). Off-white solid (15%). MS (ESI): m/z=453.0 [M+H]+.

Example 155

(1RS,2SR)-2-[6,6-Difluoro-3-(4-methyl-thiazol-2-yl)-4,5,6,7-tetrahydro-benzo[b]thiophen-2-ylcarbamoyl]-cyclohexanecarboxylic acid

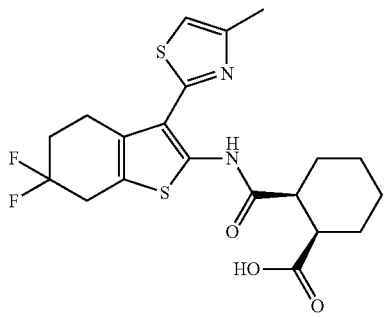 [SMILES: Cc1csc(-c2c(NC(=O)[C@H]3CCCC[C@H]3C(=O)O)sc3c2CCC(F)(F)C3)n1]

The title compound was prepared in analogy to example 152, from 6,6-difluoro-3-(4-methyl-thiazol-2-yl)-4,5,6,7-tetrahydro-benzo[b]thiophen-2-ylamine (example 150, intermediate) and cis-1,2-cyclohexanedicarboxylic anhydride (CAS RN 13149-00-3). Off-white solid (65%). MS (ESI): m/z=441.2 [M+H]+.

Example 156

(1SR,2SR)-2-[6,6-Difluoro-3-(4-methyl-thiazol-2-yl)-4,5,6,7-tetrahydro-benzo[b]thiophen-2-ylcarbamoyl]-cyclohexanecarboxylic acid

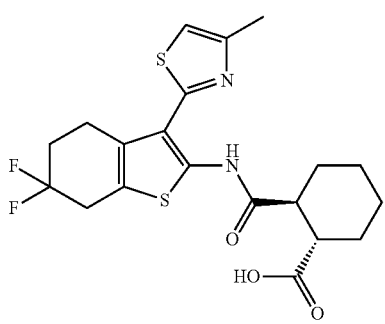 [SMILES: Cc1csc(-c2c(NC(=O)[C@H]3CCCC[C@@H]3C(=O)O)sc3c2CCC(F)(F)C3)n1]

The title compound was prepared was prepared in analogy to example 152, from 6,6-difluoro-3-(4-methyl-thiazol-2-yl)-4,5,6,7-tetrahydro-benzo[b]thiophen-2-ylamine (example 150, intermediate) and trans-1,2-cyclohexanedicarboxylic anhydride (CAS RN 14166-21-3). Off-white solid (46%). MS (ESI): m/z=441.0 [M+H]+.

Example 157

(1RS,2SR)-2-[3-(3-Cyclopropyl-[1,2,4]oxadiazol-5-yl)-5,6,7,8-tetrahydro-4H-cyclohepta[b]-thiophen-2-ylcarbamoyl]-cyclohexanecarboxylic acid

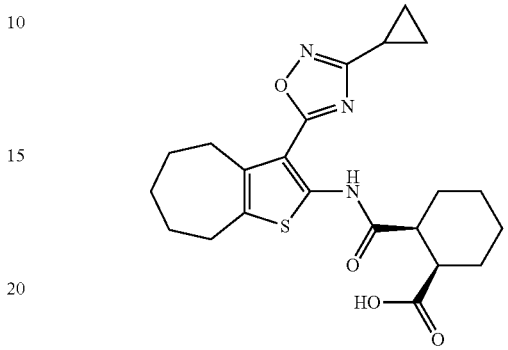

The title compound was prepared was prepared in analogy to example 152, from 3-(3-cyclopropyl-[1,2,4]oxadiazol-5-yl)-5,6,7,8-tetrahydro-4H-cyclohepta[b]-thiophen-2-ylamine (example 123, intermediate) and cis-1,2-cyclohexanedicarboxylic anhydride (CAS RN 13149-00-3). Off-white solid (47%). MS (ESI): m/z=430.2 [M+H]+.

Example 158

(1SR,2SR)-2-[3-(3-Cyclopropyl-[1,2,4]oxadiazol-5-yl)-5,6,7,8-tetrahydro-4H-cyclohepta[b]-thiophen-2-ylcarbamoyl]-cyclohexanecarboxylic acid

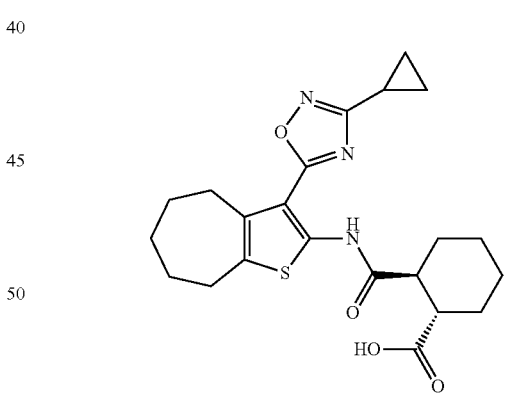

The title compound was prepared was prepared in analogy to example 152, from 3-(3-cyclopropyl-[1,2,4]oxadiazol-5-yl)-5,6,7,8-tetrahydro-4H-cyclohepta[b]-thiophen-2-ylamine (example 123, intermediate) trans-1,2-cyclohexanedicarboxylic anhydride (CAS RN 14166-21-3). The product was purified by prep HPLC (NH4OAc/CH3CN). Off-white solid (38%). MS (ESI): m/z=430.2 [M+H]+.

Example 159

(1RS,2SR)-2-[3-(4-Methyl-thiazol-2-yl)-5,6,7,8-tetrahydro-4H-cyclohepta[b]thiophen-2-ylcarbamoyl]-cyclohexanecarboxylic acid

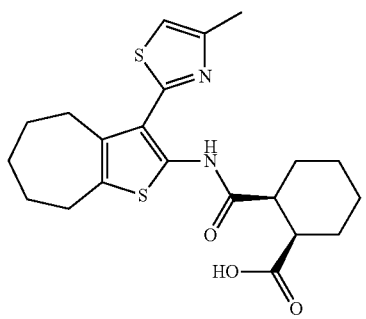 [SMILES: Cc1csc(-c2c(NC(=O)[C@H]3CCCC[C@H]3C(=O)O)sc3c2CCCCC3)n1]

The title compound was prepared was prepared in analogy to example 152, from 3-(4-methyl-thiazol-2-yl)-5,6,7,8-tetrahydro-4H-cyclohepta[b]thiophen-2-ylamine and cis-1,2-cyclohexanedicarboxylic anhydride (CAS RN 13149-00-3). The product was purified by preparative HPLC (NH$_4$OAc/CH$_3$CN). Off-white solid (13%). MS (ESI): m/z=418.8 [M+H]$^+$.

Intermediates a) 3-(4-Methyl-thiazol-2-yl)-5,6,7,8-tetrahydro-4H-cyclohepta[b]thiophen-2-ylamine

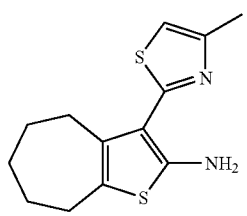 [SMILES: Cc1csc(-c2c(N)sc3c2CCCCC3)n1]

The title compound was prepared in analogy to example 138, intermediate a, from cycloheptylidene-(4-methyl-thiazol-2-yl)-acetonitrile and sulfur (CAS RN 7704-34-9). Yellow liquid (46%). MS (ESI): m/z=264.8 [M+H]$^+$.

b) Cycloheptylidene-(4-methyl-thiazol-2-yl)-acetonitrile

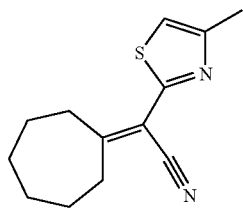 [SMILES: Cc1csc(C(C#N)=C2CCCCCC2)n1]

The title compound was prepared in analogy to example 138, intermediate b, from cycloheptanone (CAS RN 502-42-1) and (4-methyl-thiazol-2-yl)-acetonitrile (CAS RN 19785-39-8). Yellow liquid (96%). MS (ESI): m/z=233.2 [M+H]$^+$.

Example 160

(1SR,2SR)-2-[3-(4-Methyl-thiazol-2-yl)-5,6,7,8-tetrahydro-4H-cyclohepta[b]thiophen-2-ylcarbamoyl]-cyclohexanecarboxylic acid

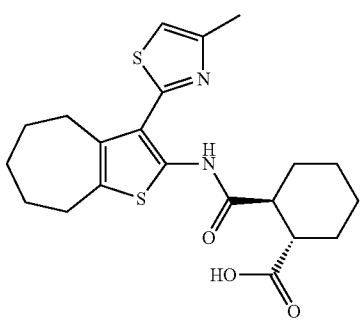 [SMILES: Cc1csc(-c2c(NC(=O)[C@H]3CCCC[C@@H]3C(=O)O)sc3c2CCCCC3)n1]

The title compound was prepared was prepared in analogy to example 152, from 3-(4-methyl-thiazol-2-yl)-5,6,7,8-tetrahydro-4H-cyclohepta[b]thiophen-2-ylamine (example 159, intermediate a) and trans-1,2-cyclohexanedicarboxylic anhydride (CAS RN 14166-21-3). Off-white solid (51%). MS (ESI): m/z=419.0 [M+H]$^+$.

Example 161

(1RS,2SR)-2-[3-(3-Cyclopropyl-[1,2,4]oxadiazol-5-yl)-5,6-dihydro-4H-cyclopenta[b]-thiophen-2-ylcarbamoyl]-cyclohexanecarboxylic acid

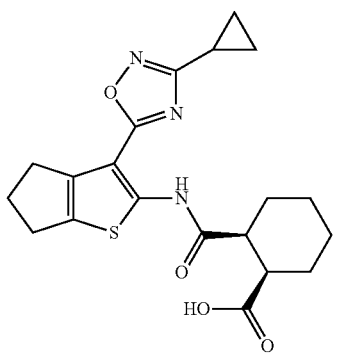 [SMILES: O=C(Nc1sc2c(c1-c1nc(C3CC3)no1)CCC2)[C@H]1CCCC[C@H]1C(=O)O]

The title compound was prepared was prepared in analogy to example 152, from 3-(3-cyclopropyl-[1,2,4]oxadiazol-5-yl)-4,5,6,6a-tetrahydro-3aH-cyclopenta[b]-thiophen-2-ylamine (example 132, intermediate) and cis-1,2-cyclohexanedicarboxylic anhydride (CAS RN 13149-00-3). The product was purified by prep HPLC (NH$_4$OAc/CH$_3$CN). Off-white solid (62%). MS (ESI): m/z=402.2 [M+H]$^+$.

Example 162

(1SR,2SR)-2-[3-(3-Cyclopropyl-[1,2,4]oxadiazol-5-yl)-5,6-dihydro-4H-cyclopenta[b]-thiophen-2-ylcarbamoyl]-cyclohexanecarboxylic acid

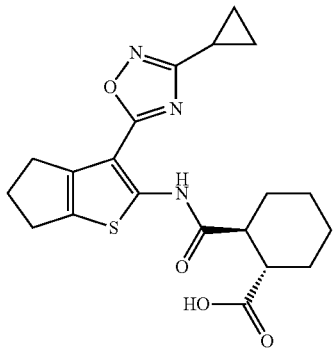 [SMILES: O=C(O)[C@H]1CCCC[C@@H]1C(=O)Nc1sc2c(c1-c1nc(C3CC3)no1)CCC2]

The title compound was prepared was prepared in analogy to example 152, from 3-(3-cyclopropyl-[1,2,4]oxadiazol-5-yl)-4,5,6,6a-tetrahydro-3aH-cyclopenta[b]-thiophen-2-ylamine (example 132, intermediate) and trans-1,2-cyclohexanedicarboxylic anhydride (CAS RN 14166-21-3). Off-white solid (62%). MS (ESI): m/z=402.2 [M+H]$^+$.

Example 163

(1RS,2SR)-2-[3-(4-Methyl-thiazol-2-yl)-5,6-dihydro-4H-cyclopenta[b]thiophen-2-yl-carbamoyl]-cyclohexanecarboxylic acid

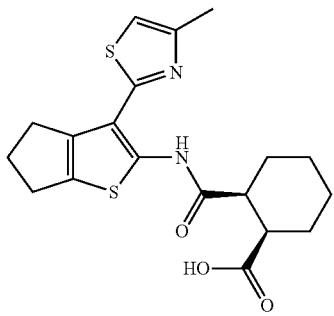 [SMILES: Cc1csc(-c2c(NC(=O)[C@H]3CCCC[C@H]3C(=O)O)sc3c2CCC3)n1]

The title compound was prepared in analogy to example 152, from 3-(4-methyl-thiazol-2-yl)-5,6-dihydro-4H-cyclopenta[b]thiophen-2-ylamine (example 138, intermediate a) and cis-1,2-cyclohexanedicarboxylic anhydride (CAS RN 13149-00-3). The product was purified by chromatographic purification using a gradient of CH$_2$Cl$_2$:MeOH (100:0 to 97:3). Yellow solid (35%). MS (ESI): m/z=391.2 [M+H]$^+$.

Example 164

(1SR,2SR)-2-[3-(4-Methyl-thiazol-2-yl)-5,6-dihydro-4H-cyclopenta[b]thiophen-2-yl-carbamoyl]-cyclohexanecarboxylic acid

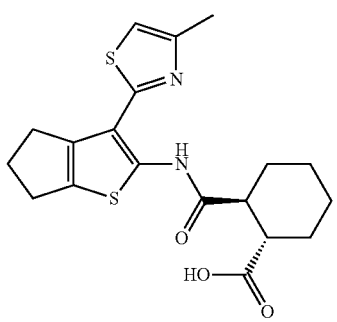 [SMILES: Cc1csc(-c2c(NC(=O)[C@H]3CCCC[C@@H]3C(=O)O)sc3c2CCC3)n1]

The title compound was prepared was prepared in analogy to example 152, from 3-(4-methyl-thiazol-2-yl)-5,6-dihydro-4H-cyclopenta[b]thiophen-2-ylamine (example 138, intermediate a) and trans-1,2-cyclohexanedicarboxylic anhydride (CAS RN 14166-21-3). Brown solid (39%). MS (ESI): m/z=389.2 [M−H]$^-$.

Example 165

(1RS,2SR)-2-[3-(3-Cyclopropyl-[1,2,4]oxadiazol-5-yl)-5,6,7,8-tetrahydro-4H-cyclohepta[b]thiophen-2-ylcarbamoyl]-cyclohexanecarboxylic acid

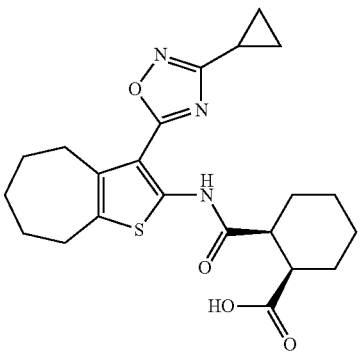 [SMILES: O=C(Nc1sc2c(c1-c1nc(C3CC3)no1)CCCCC2)[C@H]1CCCC[C@H]1C(=O)O]

The title compound was prepared in analogy to example 121, from 3-(3-cyclopropyl-[1,2,4]oxadiazol-5-yl)-5,6,7,8-tetrahydro-4H-cyclohepta[b]thiophen-2-ylamine (example 123, intermediate) and cis-1,2-cyclohexanedicarboxylic anhydride (CAS RN 13149-00-3) and using a gradient of n-hexane:EtOAc (90:10 to 30:70) for the chromatographic purification. Off-white solid (47%). MS (ESI): m/z=430.2 [M+H]$^+$.

Example 166

2-[3-(3-Cyclopropyl-[1,2,4]oxadiazol-5-yl)-6-ethyl-4,5,6,7-tetrahydro-benzo[b]thiophen-2-ylcarbamoyl]-cyclopent-1-enecarboxylic acid

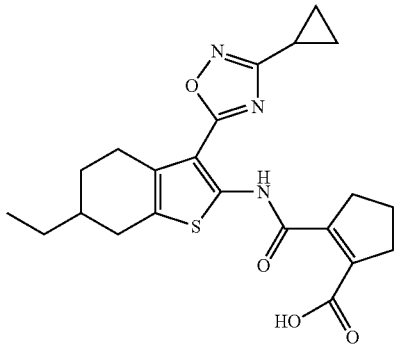 [SMILES: CCC1CCc2c(sc(NC(=O)C3=C(C(=O)O)CCC3)c2-c2nc(C3CC3)no2)C1]

The title compound was prepared in analogy to example 127, from 3-(3-cyclopropyl-[1,2,4]oxadiazol-5-yl)-6-ethyl-4,5,6,7-tetrahydro-benzo[b]thiophen-2-ylamine and cyclopentene-1,2-dicarboxylic anhydride (CAS RN 3205-94-5) and using a gradient of $CH_2Cl_2$:MeOH (99:1 to 98:2) for the chromatographic purification. Yellow solid (35%). MS (ESI): m/z=428.2 $[M+H]^+$.

Intermediate 3-(3-Cyclopropyl-[1,2,4]oxadiazol-5-yl)-6-ethyl-4,5,6,7-tetrahydro-benzo[b]thiophen-2-ylamine The title compound was synthesized in analogy to example 55, intermediate, from 4-ethylcyclohexanone, (3-cyclopropyl-[1,2,4]oxadiazol-5-yl)-acetonitrile (Princeton BioMolecular Research, Inc.) and sulfur powder and using a gradient of n-hexane:EtOAc (90:10 to 80:20) for the chromatographic purification. Yellow solid (97%). MS (ESI): m/z=290.2 $[M+H]^+$.

Examples 167 and 168

2-[(S)-3-(3-Cyclopropyl-[1,2,4]oxadiazol-5-yl)-6-ethyl-4,5,6,7-tetrahydro-benzo[b]thiophen-2-ylcarbamoyl]-cyclopent-1-enecarboxylic acid and 2-[(R)-3-(3-Cyclopropyl-[1,2,4]oxadiazol-5-yl)-6-ethyl-4,5,6,7-tetrahydro-benzo[b]thiophen-2-ylcarbamoyl]-cyclopent-1-enecarboxylic acid

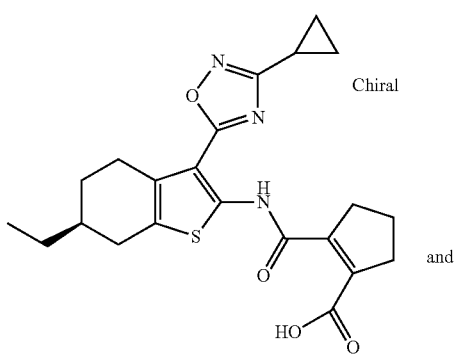

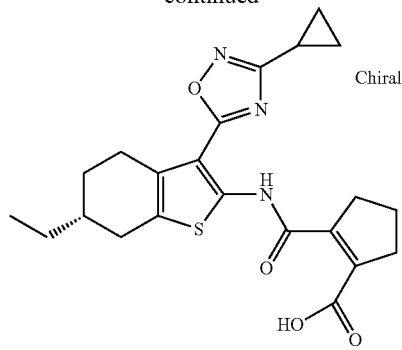

The title compounds were obtained by chiral separation of 2-[3-(3-cyclopropyl-[1,2,4]-oxadiazol-5-yl)-6-ethyl-4,5,6,7-tetrahydro-benzo[b]thiophen-2-ylcarbamoyl]-cyclopent-1-enecarboxylic acid (example 166) using a Chiral Pak IC (20×250 mm) column and EtOH (+0.5% TFA) as eluant.

First eluting enantiomer: Yellow solid. MS (ESI): m/z=428.2 $[M+H]^+$.

Second eluting enantiomer: Yellow solid. MS (ESI): m/z=428.2 $[M+H]^+$.

Example 169

3-[3-(3-Cyclopropyl-[1,2,4]oxadiazol-5-yl)-6-ethyl-4,5,6,7-tetrahydro-benzo[b]thiophen-2-ylcarbamoyl]-bicyclo[2.2.2]oct-2-ene-2-carboxylic acid

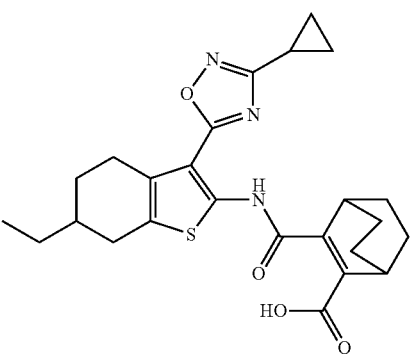 [SMILES: CCC1CCc2c(sc(NC(=O)C3=C(C(=O)O)C4CCC3CC4)c2-c2nc(C3CC3)no2)C1]

The title compound was prepared in analogy to example 127, from 3-(3-cyclopropyl-[1,2,4]oxadiazol-5-yl)-6-ethyl-4,5,6,7-tetrahydro-benzo[b]thiophen-2-ylamine (example 184, intermediate) and bicyclo[2.2.2]oct-2-ene-2,3-dicarboxylic anhydride (CAS RN 151813-29-5) and using a gradient of $CH_2Cl_2$:MeOH (99:1 to 98:2) for the chromatographic purification. Brown solid (29%). MS (ESI): m/z=468.2 $[M+H]^+$.

Examples 170 and 171

3-[(S)-3-(3-Cyclopropyl-[1,2,4]oxadiazol-5-yl)-6-ethyl-4,5,6,7-tetrahydro-benzo[b]thiophen-2-ylcarbamoyl]-bicyclo[2.2.2]oct-2-ene-2-carboxylic acid and 3-[(R)-3-(3-Cyclopropyl-[1,2,4]oxadiazol-5-yl)-6-ethyl-4,5,6,7-tetrahydro-benzo[b]thiophen-2-ylcarbamoyl]-bicyclo[2.2.2]oct-2-ene-2-carboxylic acid

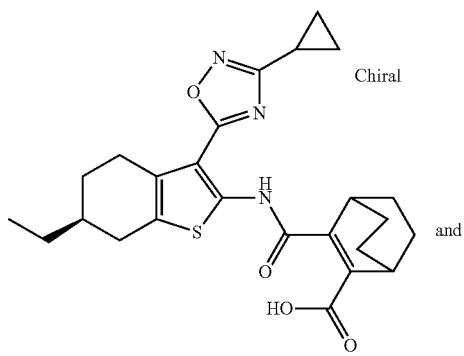

and

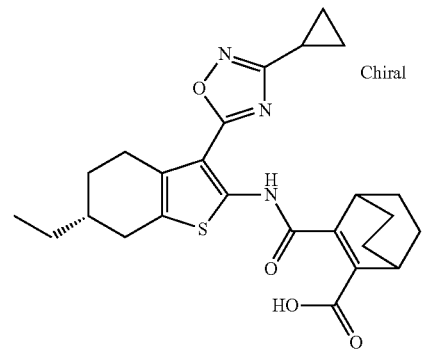

The title compounds were obtained by chiral separation of 3-[3-(3-cyclopropyl-[1,2,4]-oxadiazol-5-yl)-6-ethyl-4,5,6,7-tetrahydro-benzo[b]thiophen-2-ylcarbamoyl]-bicyclo[2.2.2]oct-2-ene-2-carboxylic acid (example 169) using a Chiral Pak IC (20×250 mm) column and EtOH (+0.5% TFA) as eluant.

First eluting enantiomer: Yellow solid. MS (ESI): m/z=468.0 [M+H]$^+$.

Second eluting enantiomer: Yellow solid. MS (ESI): m/z=468.0 [M+H]$^+$.

Example 172

2-[3-(3-Cyclopropyl-[1,2,4]oxadiazol-5-yl)-6-trifluoromethyl-4,5,6,7-tetrahydro-benzo[b]thiophen-2-ylcarbamoyl]-cyclopent-1-enecarboxylic acid

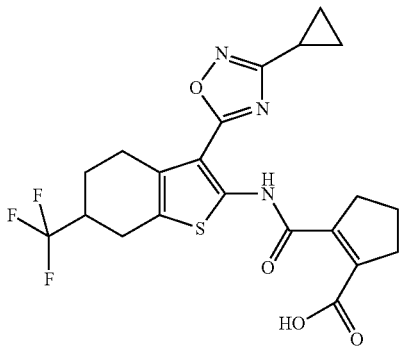 [SMILES: O=C(O)C1=C(C(=O)Nc2sc3c(c2-c2nc(C4CC4)no2)CCC(C(F)(F)F)C3)CCC1]

The title compound was prepared in analogy to example 127, from 3-(3-cyclopropyl-[1,2,4]oxadiazol-5-yl)-6-trifluoromethyl-4,5,6,7-tetrahydro-benzo[b]thiophen-2-ylamine and cyclopentene-1,2-dicarboxylic anhydride (CAS RN 3205-94-5) using a gradient of CH$_2$Cl$_2$:MeOH (99:1 to 98:2) for the chromatographic purification. Yellow solid (42%). MS (ESI): m/z=468.2 [M+H]$^+$.

Intermediate 3-(3-Cyclopropyl-[1,2,4]oxadiazol-5-yl)-6-trifluoromethyl-4,5,6,7-tetrahydro-benzo[b]-thiophen-2-ylamine The title compound was synthesized in analogy to example 55, from 4-(trifluoromethyl)cyclohex an-1-one (CAS RN 75091-99-5), (3-cyclopropyl-[1,2,4]oxadiazol-5-yl)-acetonitrile (Princeton BioMolecular Research, Inc.) and sulfur powder using a gradient of n-hexane:EtOAc (90:10 to 80:20) for the chromatographic purification. Colorless solid (82%). MS (ESI): m/z=330.2 [M+H]$^+$.

Examples 173 and 174

2-[(S)-3-(3-Cyclopropyl-[1,2,4]oxadiazol-5-yl)-6-trifluoromethyl-4,5,6,7-tetrahydro-benzo[b]thiophen-2-ylcarbamoyl]-cyclopent-1-enecarboxylic acid and 2-[(R)-3-(3-Cyclopropyl-[1,2,4]oxadiazol-5-yl)-6-trifluoromethyl-4,5,6,7-tetrahydro-benzo[b]thiophen-2-ylcarbamoyl]-cyclopent-1-enecarboxylic acid

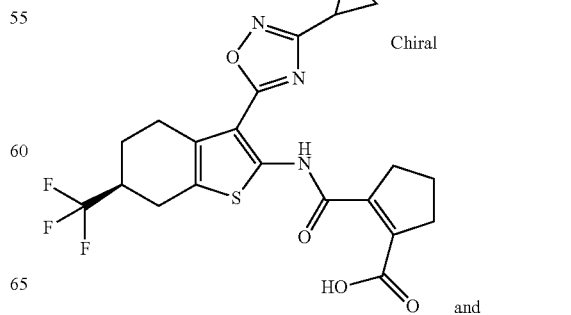

and

-continued

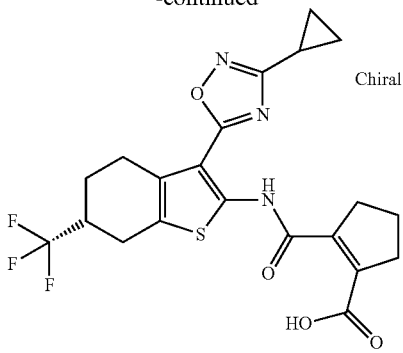

Chiral

The title compounds were obtained by chiral separation of 2-[3-(3-cyclopropyl-[1,2,4]-oxadiazol-5-yl)-6-trifluoromethyl-4,5,6,7-tetrahydro-benzo[b]thiophen-2-ylcarbamoyl]-cyclopent-1-enecarboxylic acid (example 172) using a Chiral Pak IC (20×250 mm) column and EtOH (+0.1% DEA) as eluant.

First eluting enantiomer: Yellow solid. MS (ESI): m/z=468.2 [M+H]⁺.

Second eluting enantiomer: Yellow solid. MS (ESI): m/z=468.2 [M+H]⁺.

Example 175

2-[3-(3-Cyclopropyl-[1,2,4]oxadiazol-5-yl)-6-trifluoromethyl-4,5,6,7-tetrahydro-benzo[b]thiophen-2-ylcarbamoyl]-cyclohex-1-enecarboxylic acid

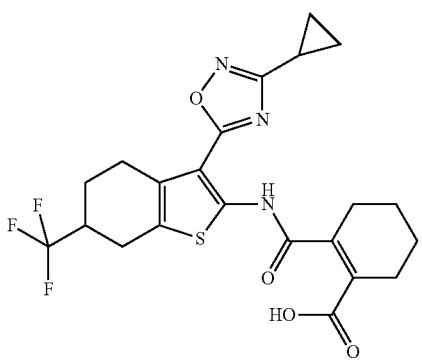 [SMILES: O=C(O)C1=C(C(=O)Nc2sc3c(c2-c2nc(C4CC4)no2)CCC(C(F)(F)F)C3)CCCC1]

The title compound was prepared in analogy to example 57, from 3-(3-cyclopropyl-[1,2,4]oxadiazol-5-yl)-6-trifluoromethyl-4,5,6,7-tetrahydro-benzo[b]thiophen-2-ylamine (example 172, intermediate) and 1-cyclohexene-1,2-dicarboxylic anhydride (CAS RN 2426-02-0) using a gradient of CH₂Cl₂:MeOH (99:1 to 98:2) for the chromatographic purification followed by crystallization from CH₂Cl₂/n-hexane. Off-white solid (34%). MS (ESI): m/z=482.4 [M+H]⁺.

Example 176

3-[3-(3-Cyclopropyl-[1,2,4]oxadiazol-5-yl)-6-trifluoromethyl-4,5,6,7-tetrahydro-benzo[b]thiophen-2-ylcarbamoyl]-bicyclo[2.2.2]oct-2-ene-2-carboxylic acid

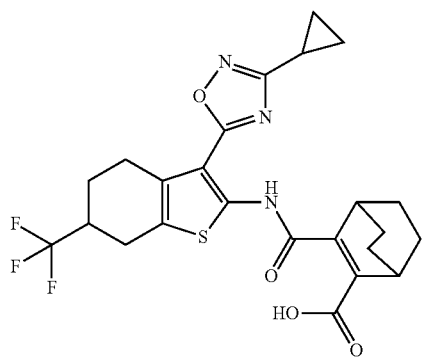 [SMILES: O=C(O)C1=C(C(=O)Nc2sc3c(c2-c2nc(C4CC4)no2)CCC(C(F)(F)F)C3)C2CCC1CC2]

The title compound was prepared in analogy to example 127, from 3-(3-cyclopropyl-[1,2,4]oxadiazol-5-yl)-6-trifluoromethyl-4,5,6,7-tetrahydro-benzo[b]thiophen-2-ylamine (example 172, intermediate) and bicyclo[2.2.2]oct-2-ene-2,3-dicarboxylic anhydride (CAS RN 151813-29-5) and using a gradient of CH₂Cl₂ (99:1 to 98:2) for the chromatographic purification. Yellow solid (35%). MS (ESI): m/z=508.4 [M+H]⁺.

Examples 177 and 178

3-[(S)-3-(3-Cyclopropyl-[1,2,4]oxadiazol-5-yl)-6-trifluoromethyl-4,5,6,7-tetrahydro-benzo[b]thiophen-2-ylcarbamoyl]-bicyclo[2.2.2]oct-2-ene-2-carboxylic acid and 3-[(R)-3-(3-Cyclopropyl-[1,2,4]oxadiazol-5-yl)-6-trifluoromethyl-4,5,6,7-tetrahydro-benzo[b]thiophen-2-ylcarbamoyl]-bicyclo[2.2.2]oct-2-ene-2-carboxylic acid

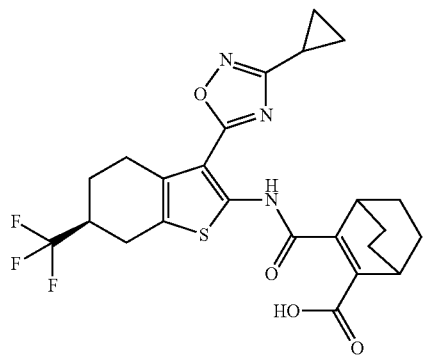

and

-continued

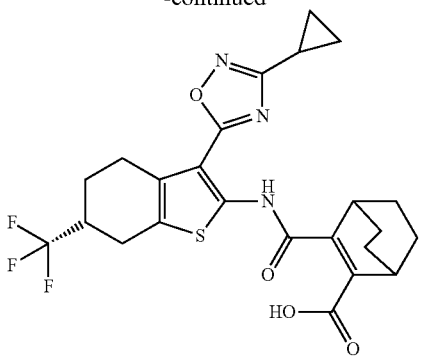

The title compounds were obtained by chiral separation of 3-[3-(3-cyclopropyl-[1,2,4]oxadiazol-5-yl)-6-trifluoromethyl-4,5,6,7-tetrahydro-benzo[b]thiophen-2-ylcarbamoyl]-bicyclo[2.2.2]oct-2-ene-2-carboxylic acid (example 176), using a Chiral Pak IC (20×250 mm) column and EtOH (+0.5% TFA) as eluant.

First eluting enantiomer: Yellow solid. MS (ESI): m/z=508.2 [M+H]$^+$.

Second eluting enantiomer: Yellow solid. MS (ESI): m/z=508.2 [M+H]$^+$.

Example 179

3-[6-Ethyl-3-(4-methyl-thiazol-2-yl)-4,5,6,7-tetrahydro-benzo[b]thiophen-2-ylcarbamoyl]-bicyclo[2.2.2]oct-2-ene-2-carboxylic acid

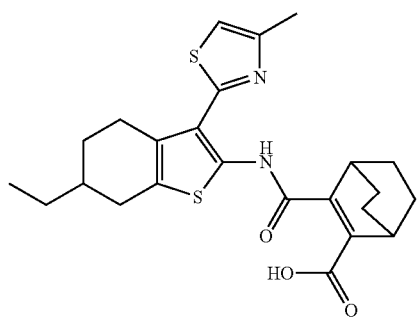 [SMILES: CCC1CCc2c(sc(NC(=O)C3=C(C(=O)O)C4CCC3CC4)c2-c2nc(C)cs2)C1]

The title compound was prepared in analogy to example 57, from 6-ethyl-3-(4-methylthiazol-2-yl)-4,5,6,7-tetrahydro-benzo[b]thiophen-2-ylamine and bicyclo[2.2.2]oct-2-ene-2,3-dicarboxylic anhydride (CAS RN 151813-29-5) using a gradient of CH$_2$Cl$_2$:MeOH (99:1 to 98:2) for the chromatographic purification, followed by crystallization from CH$_2$Cl$_2$/n-hexane. Off-white solid (13%). MS (ESI): m/z=457.0 [M+H]$^+$.

Intermediates a) 6-Ethyl-3-(4-methylthiazol-2-yl)-4,5,6,7-tetrahydrobenzo[b]thiophen-2-ylamine The title compound was synthesized in analogy to example 56, intermediate a, from 2-(4-ethylcyclohexylidene)-2-(4-methylthiazol-2-yl)acetonitrile and elemental sulphur and using a gradient of n-hexane:EtOAc (90:10 to 80:20). Yellow liquid (62%). MS (ESI): m/z=278.8 [M+H]$^+$.

b) 2-(4-Ethylcyclohexylidene)-2-(4-methylthiazol-2-yl)acetonitrile

The title compound was synthesized in analogy to example 56, intermediate b, from 4-ethyl-cyclohexanone and (4-methyl-thiazol-2-yl)-acetonitrile (CAS RN 19785-39-8) and using a gradient of n-hexane:EtOAc (90:10 to 80:20) for the chromatographic purification. Brown liquid (56%). MS (ESI): m/z=247.2 [M+H]$^+$.

Examples 180 and 181

3-[(S)-6-Ethyl-3-(4-methyl-thiazol-2-yl)-4,5,6,7-tetrahydro-benzo[b]thiophen-2-ylcarbamoyl]-bicyclo[2.2.2]oct-2-ene-2-carboxylic acid and 3-[(R)-6-Ethyl-3-(4-methyl-thiazol-2-yl)-4,5,6,7-tetrahydro-benzo[b]thiophen-2-ylcarbamoyl]-bicyclo[2.2.2]oct-2-ene-2-carboxylic acid

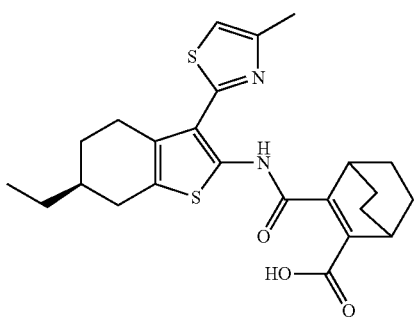

and

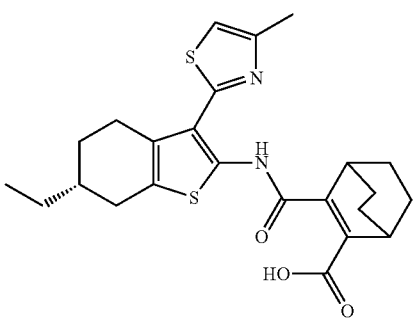

The title compounds were obtained by chiral separation of 3-[6-ethyl-3-(4-methyl-thiazol-2-yl)-4,5,6,7-tetrahydro-benzo[b]thiophen-2-ylcarbamoyl]-bicyclo[2.2.2]oct-2-ene-2-carboxylic acid (example 179) using a Chiral Pak IC (20×250 mm) column and EtOH (+0.5% TFA) as eluant.

First eluting enantiomer: Yellow solid. MS (ESI): m/z=457.0 [M+H]$^+$.

Second eluting enantiomer: Yellow solid. MS (ESI): m/z=457.6 [M+H]$^+$.

Example 182

2-[6-Ethyl-3-(4-methyl-thiazol-2-yl)-4,5,6,7-tetra-hydro-benzo[b]thiophen-2-ylcarbamoyl]-cyclopent-1-enecarboxylic acid

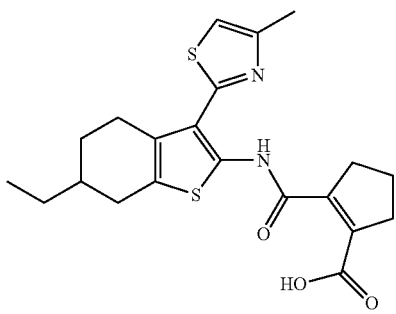 [SMILES: CCC1CCc2c(sc(NC(=O)C3=C(C(=O)O)CCC3)c2-c2nc(C)cs2)C1]

The title compound was prepared in analogy to example 57, from 6-ethyl-3-(4-methyl-thiazol-2-yl)-4,5,6,7-tetrahydro-benzo[b]thiophen-2-ylamine (example 179, intermediate a) and cyclopentene-1,2-dicarboxylic anhydride (CAS RN 3205-94-5) using a gradient of $CH_2Cl_2$:MeOH (99:1 to 98:2) for the chromatographic purification, followed by crystallization from $CH_2Cl_2$/n-hexane. Yellow solid (57%). MS (ESI): m/z=417.0 $[M+H]^+$.

Examples 183 and 184

2-[(S)-6-Ethyl-3-(4-methyl-thiazol-2-yl)-4,5,6,7-tetrahydro-benzo[b]thiophen-2-ylcarbamoyl]-cyclopent-1-enecarboxylic acid and 2-[(R)-6-Ethyl-3-(4-methyl-thiazol-2-yl)-4,5,6,7-tetrahydro-benzo[b]thiophen-2-ylcarbamoyl]-cyclopent-1-enecarboxylic acid

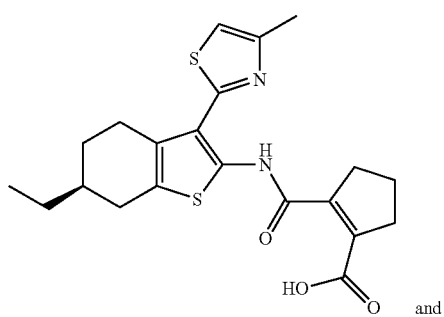

and

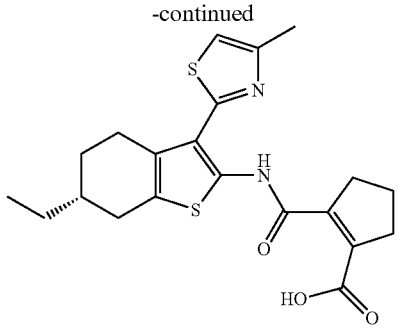

The title compounds were obtained by chiral separation of 2-[6-ethyl-3-(4-methyl-thiazol-2-yl)-4,5,6,7-tetrahydro-benzo[b]thiophen-2-ylcarbamoyl]-cyclopent-1-enecarboxylic acid (example 182) using a Chiral Pak IC (20×250 mm) column and EtOH (+0.5% TFA) as eluant.

First eluting enantiomer: Yellow solid. MS (ESI): m/z=417.0 $[M+H]^+$.

Second eluting enantiomer: Yellow solid. MS (ESI): m/z=417.6 $[M+H]^+$.

Example 185

3-[3-(4-Methyl-thiazol-2-yl)-6-trifluoromethyl-4,5,6,7-tetrahydro-benzo[b]thiophen-2-ylcarbamoyl]-bicyclo[2.2.2]oct-2-ene-2-carboxylic acid

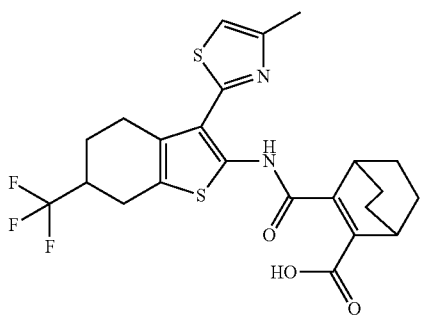

The title compound was prepared from 3-(4-methyl-thiazol-2-yl)-6-trifluoromethyl-4,5,6,7-tetrahydro-benzo[b]thiophen-2-ylamine and bicyclo[2.2.2]oct-2-ene-2,3-dicarboxylic anhydride (CAS RN 151813-29-5), using a gradient of $CH_2Cl_2$:MeOH (99:1 to 98:2) for the chromatographic purification followed by crystallization from $CH_2Cl_2$/n-hexane. Yellow solid (26%). MS (ESI): m/z=497.0 $[M+H]^+$.

Intermediates a) 3-(4-Methyl-thiazol-2-yl)-6-trifluoromethyl-4,5,6,7-tetrahydro-benzo[b]thiophen-2-ylamine The title compound was synthesized in analogy to example 56, intermediate a, from (4-methyl-thiazol-2-yl)-(4-trifluoromethyl-cyclohexylidene)-acetonitrile and elemental sulphur, using a gradient of n-hexane:EtOAc (90:10 to 80:20) for the chromatographic purification. Yellow solid (56%). MS (ESI): m/z=318.8 $[M+H]^+$.

b) (4-Methyl-thiazol-2-yl)-(4-trifluoromethyl-cyclohexylidene)-acetonitrile

The title compound was synthesized in analogy to example 56, intermediate b, from 4-trifluoromethyl-cyclohexanone (CAS RN 75091-99-5) and (4-methyl-thiazol-2-yl)-acetonitrile (CAS RN 19785-39-8), using a gradient of n-hexane:EtOAc (90:10 to 80:20) for the chromatographic purification. Brown Solid (77%). MS (ESI): m/z=287.0 [M+H]$^+$.

Examples 186 and 187

3-[(S)-3-(4-Methyl-thiazol-2-yl)-6-trifluoromethyl-4,5,6,7-tetrahydro-benzo[b]thiophen-2-ylcarbamoyl]-bicyclo[2.2.2]oct-2-ene-2-carboxylic acid and 3-[(R)-3-(4-Methyl-thiazol-2-yl)-6-trifluoromethyl-4,5,6,7-tetrahydro-benzo[b]thiophen-2-ylcarbamoyl]-bicyclo[2.2.2]oct-2-ene-2-carboxylic acid

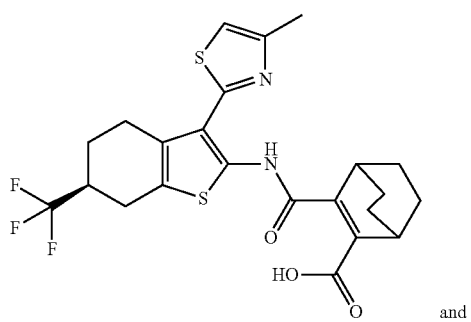
and
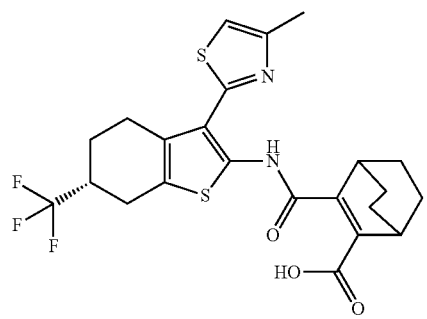 [SMILES: Cc1csc(-c2c(NC(=O)C3=C(C(=O)O)C4CCC3CC4)sc3c2CCC(C(F)(F)F)C3)n1]

The title compounds were obtained by chiral separation of 3-[3-(4-methyl-thiazol-2-yl)-6-trifluoromethyl-4,5,6,7-tetrahydro-benzo[b]thiophen-2-ylcarbamoyl]-bicyclo[2.2.2]oct-2-ene-2-carboxylic acid (example 185) using a Chiral Pak IC (20×250 mm) column and EtOH (+0.1% DEA) as eluant.

First eluting enantiomer: Yellow solid. MS (ESI): m/z=497.0 [M+H]$^+$.

Second eluting enantiomer: Yellow solid. MS (ESI): m/z=497.6 [M+H]$^+$.

Example 188

2-[3-(4-Methyl-thiazol-2-yl)-6-trifluoromethyl-4,5,6,7-tetrahydro-benzo[b]thiophen-2-ylcarbamoyl]-cyclopent-1-enecarboxylic acid

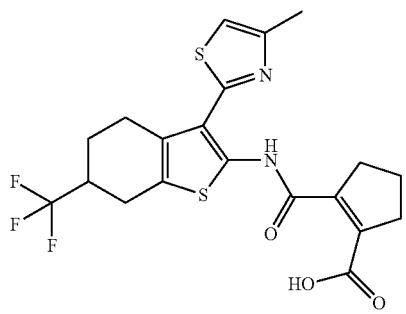 [SMILES: Cc1csc(-c2c(NC(=O)C3=C(C(=O)O)CCC3)sc3c2CCC(C(F)(F)F)C3)n1]

The title compound was prepared in analogy to example 57, from 3-(4-methyl-thiazol-2-yl)-6-trifluoromethyl-4,5,6,7-tetrahydro-benzo[b]thiophen-2-ylamine (example 185, intermediate a) and cyclopentene-1,2-dicarboxylic anhydride (CAS RN 3205-94-5), using a gradient of CH$_2$Cl$_2$:MeOH (99:1 to 98:2) for the chromatographic purification followed by crystallization from CH$_2$Cl$_2$/n-hexane. Yellow solid (42%). MS (ESI): m/z=457.0 [M+H]$^+$.

Examples 189 and 190

2-[(S)-3-(4-Methyl-thiazol-2-yl)-6-trifluoromethyl-4,5,6,7-tetrahydro-benzo[b]thiophen-2-ylcarbamoyl]-cyclopent-1-enecarboxylic acid and 2-[(R)-3-(4-Methyl-thiazol-2-yl)-6-trifluoromethyl-4,5,6,7-tetrahydro-benzo[b]thiophen-2-ylcarbamoyl]-cyclopent-1-enecarboxylic acid

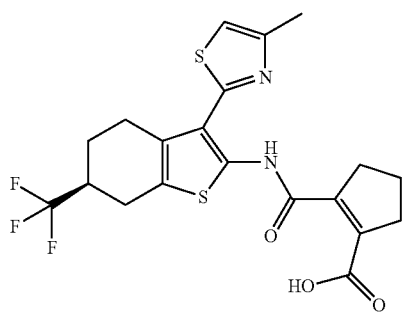
and

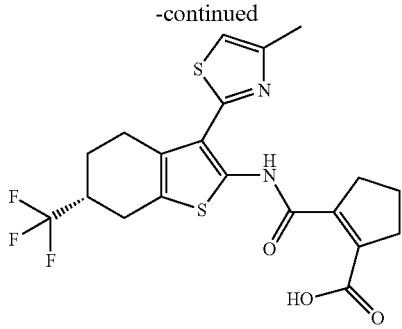

The title compounds were obtained by chiral separation of 2-[3-(4-methyl-thiazol-2-yl)-6-trifluoromethyl-4,5,6,7-tetrahydro-benzo[b]thiophen-2-ylcarbamoyl]-cyclopent-1-enecarboxylic acid (example 188) using a Chiral Pak IC (20×250 mm) column and EtOH (+0.1% DEA) as eluant.

First eluting enantiomer: Yellow solid. MS (ESI): m/z=457.0 [M+H]$^+$.

Second eluting enantiomer: Yellow solid. MS (ESI): m/z=457.6 [M+H]$^+$.

Example 191

2-[3-(4-Methyl-thiazol-2-yl)-6-trifluoromethyl-4,5,6,7-tetrahydro-benzo[b]thiophen-2-ylcarbamoyl]-cyclohex-1-enecarboxylic acid

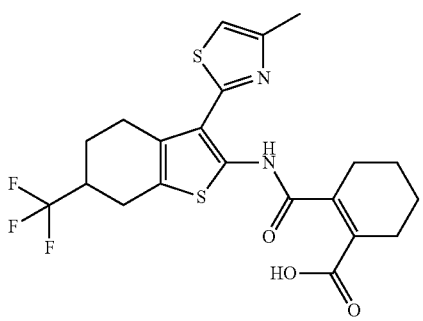 [SMILES: Cc1csc(-c2c(NC(=O)C3=C(C(=O)O)CCCC3)sc3c2CCC(C(F)(F)F)C3)n1]

The title compound was prepared in analogy to example 57, from 3-(4-methyl-thiazol-2-yl)-6-trifluoromethyl-4,5,6,7-tetrahydro-benzo[b]thiophen-2-ylamine (example 185, intermediate a) and 1-cyclohexene-1,2-dicarboxylic anhydride (CAS RN 2426-02-0) and using a gradient of CH$_2$Cl$_2$:MeOH (99:1 to 98:2) for the chromatographic purification, followed by crystallization from CH$_2$Cl$_2$/n-hexane. Yellow solid (32%). MS (ESI): m/z=471.0 [M+H]$^+$.

Example 192

2-[3-(3-Cyclopropyl-[1,2,4]oxadiazol-5-yl)-6-ethyl-4,5,6,7-tetrahydro-benzo[b]thiophen-2-ylcarbamoyl]-cyclohex-1-enecarboxylic acid

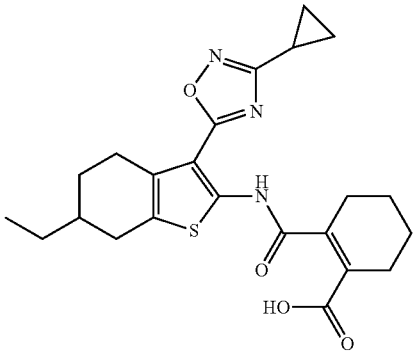 [SMILES: CCC1CCc2c(sc(NC(=O)C3=C(C(=O)O)CCCC3)c2-c2nc(C3CC3)no2)C1]

The title compound was prepared in analogy to example 57, from 3-(3-cyclopropyl-[1,2,4]oxadiazol-5-yl)-6-ethyl-4,5,6,7-tetrahydro-benzo[b]thiophen-2-ylamine (example 166, intermediate) and 1-cyclohexene-1,2-dicarboxylic anhydride (CAS RN 2426-02-0) and using a gradient of CH$_2$Cl$_2$:MeOH (99:1 to 98:2) for the chromatographic purification, followed by crystallization from CH$_2$Cl$_2$/n-hexane. Brown solid (38%). MS (ESI): m/z=442.2 [M+H]$^+$.

Example 193

2-[6-Ethyl-3-(4-methyl-thiazol-2-yl)-4,5,6,7-tetrahydro-benzo[b]thiophen-2-ylcarbamoyl]-cyclohex-1-enecarboxylic acid

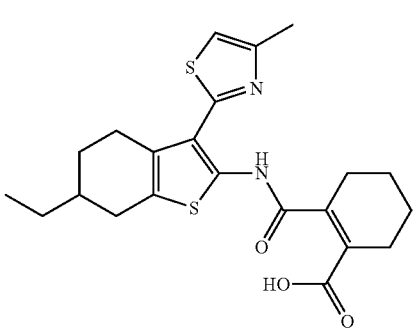 [SMILES: CCC1CCc2c(sc(NC(=O)C3=C(C(=O)O)CCCC3)c2-c2nc(C)cs2)C1]

The title compound was prepared in analogy to example 57, from 6-ethyl-3-(4-methyl-thiazol-2-yl)-4,5,6,7-tetrahydro-benzo[b]thiophen-2-ylamine (example 179, intermediate a) 1-cyclohexene-1,2-dicarboxylic anhydride (CAS RN 2426-02-0) and using a gradient of CH$_2$Cl$_2$:MeOH (99:1 to 98:2) for the chromatographic purification, followed by crystallization from CH$_2$Cl$_2$/n-hexane. Light green solid (26%). MS (ESI): m/z=431.0 [M+H]$^+$.

Example 194

3-[3-(3-Cyclopropyl-[1,2,4]oxadiazol-5-yl)-4,7-di-hydro-5H-thieno[2,3-c]pyran-2-ylcarbamoyl]-isonicotinic acid

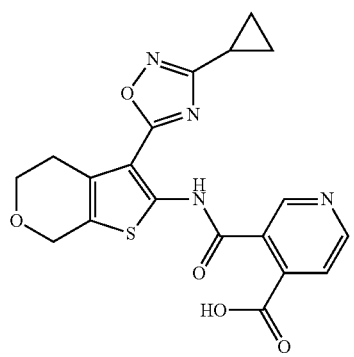 [SMILES: O=C(O)c1ccncc1C(=O)Nc1sc2c(c1-c1nc(C3CC3)no1)CCOC2]

To a solution of 3-[3-(3-cyclopropyl-[1,2,4]oxadiazol-5-yl)-4,7-dihydro-5H-thieno[2,3-c]pyran-2-ylcarbamoyl]-isonicotinic acid methyl ester (50 mg, 0.117 mmol) in THF (2 mL) were added H$_2$O (2 mL) and LiOH (6 mg, 0.234 mmol) at 25° C. and the reaction mixture was stirred at 25° C. for 30 min. The solvent was evaporated and the residue was dissolved in 5 mL H$_2$O and washed with 15 mL EtOAc. The aqueous layer was then acidified with 2M aqueous HCl solution and extracted three times with 20 mL EtOAc. The combined organic layers were washed with 10 mL brine, dried over Na$_2$SO$_4$ and evaporated under reduced pressure. The resulting crude product was purified by preparative HPLC (NH$_4$OAc/CH$_3$CN). Off-white solid (30 mg, 62%). MS (ESI): m/z=413.2 [M+H]$^+$.

Intermediate

3-[3-(3-Cyclopropyl-[1,2,4]oxadiazol-5-yl)-4,7-di-hydro-5H-thieno[2,3-c]pyran-2-ylcarbamoyl]-isonicotinic acid methyl ester To a solution of 3-(3-cyclopropyl-1,2,4-oxadiazol-5-yl)-5,7-dihydro-4H-thieno[2,3-c]pyran-2-amine (example 55, intermediate) (150 mg, 0.57 mmol) in THF (8 mL) were added pyridine-3,4-dicarboxylic acid 4-methyl ester (CAS RN 24202-74-2) (155 mg, 0.854 mmol), DIPEA (0.471 mL, 2.848 mmol) and propylphosphonic anhydride (50% w/v solution in EtOAc) (1.8 mL, 2.85 mmol). The reaction mixture was heated at 150° C. in a sealed tube for 8 hours. The reaction mixture was cooled, diluted with 30 mL EtOAc and washed with 20 mL H$_2$O and 30 mL brine. The organic layer was dried over Na$_2$SO$_4$ and concentrated under reduced pressure. The resulting crude was purified by preparative HPLC (CH$_3$CN/formic acid). Light green solid (53 mg, 22%). MS (ESI): m/z=427.4 (M+H)'.

Example 195

3-[3-(3-Cyclopropyl-[1,2,4]oxadiazol-5-yl)-4,5,6,7-tetrahydro-benzo[b]thiophen-2-ylcarbamoyl]-isonicotinic acid

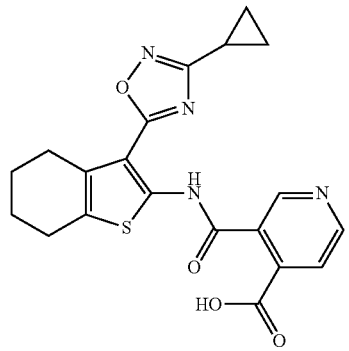 [SMILES: O=C(O)c1ccncc1C(=O)Nc1sc2c(c1-c1nc(C3CC3)no1)CCCC2]

The title compound was prepared in analogy to example 194, from 3-[3-(3-cyclopropyl-[1,2,4]oxadiazol-5-yl)-4,5,6,7-tetrahydro-benzo[b]thiophen-2-ylcarbamoyl]-isonicotinic acid methyl ester and using preparative HPLC (NH$_4$OAc/CH$_3$CN) for the chromatographic purification. Yellow solid (19%). MS (ESI): m/z=411.0 [M+H]$^+$.

Intermediate

3-[3-(3-Cyclopropyl-[1,2,4]oxadiazol-5-yl)-4,5,6,7-tetrahydro-benzo[b]thiophen-2-ylcarbamoyl]-isonicotinic acid methyl ester The title compound was prepared in analogy to example 194, intermediate, from 3-(3-cyclopropyl-1,2,4-oxadiazol-5-yl)-4,5,6,7-tetrahydrobenzo[b]thiophen-2-amine (example 27, intermediate b) and pyridine-3,4-dicarboxylic acid 4-methyl ester (CAS 24202-74-2), using a gradient of n-hexane:EtOAc (90:10 to 80:20) for the chromatographic purification. Light green solid (45%). MS (ESI): m/z=425.4 [M+H]$^+$.

Example 196

2-[6,6-Difluoro-3-(3-methyl-[1,2,4]thiadiazol-5-yl)-4,5,6,7-tetrahydro-benzo[b]thiophen-2-ylcarbamoyl]-cyclopent-1-enecarboxylic acid

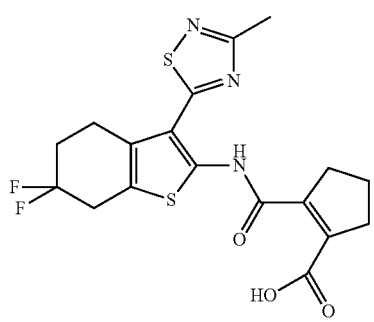 [SMILES: Cc1nsc(-c2c(NC(=O)C3=C(C(=O)O)CCC3)sc3c2CCC(F)(F)C3)n1]

The title compound was prepared in analogy to example 57, from 6,6-difluoro-3-(3-methyl-[1,2,4]thiadiazol-5-yl)-4,5,6,7-tetrahydro-benzo[b]thiophen-2-ylamine and cyclopentene-1,2-dicarboxylic anhydride (CAS RN 3205-94-5) and using a gradient of $CH_2Cl_2$:MeOH (99:1 to 98:2) for the chromatographic purification, followed by crystallization from $CH_2Cl_2$/n-hexane. Yellow solid (22%). MS (ESI): m/z=424.2 [M–H]$^-$.

Intermediate a) 6,6-Difluoro-3-(3-methyl-[1,2,4]thiadiazol-5-yl)-4,5,6,7-tetrahydro-benzo[b]thiophen-2-ylamine The title compound was synthesized in analogy to example 55, intermediate, from 4,4-difluoro-cyclohexanone (CAS RN 22515-18-0), (3-methyl-[1,2,4]thiadiazol-5-yl)-acetonitrile and elemental sulfur, using a gradient of n-hexane:EtOAc (90:10 to 80:20) for the chromatographic purification. Yellow solid (68%). MS (ESI): m/z=286.2 [M–H]$^-$.

b) (3-Methyl-[1,2,4]thiadiazol-5-yl)-acetonitrile

To a solution of 5-chloro-3-methyl-[1,2,4]thiadiazole (800 mg, 5.94 mmol; CAS RN 21734-85-0) in dry THF (15 mL) was added dry $CH_3CN$ (0.625 mL, 11.89 mmol). The reaction mixture was cooled to 0° C. and lithium bis(trimethylsilyl)amide (1M solution in THF) (11.89 mL, 11.89 mmol) was added dropwise at the same temperature. The reaction mixture was stirred at 25° C. for 5 hours. The reaction mixture was quenched with 5 mL saturated $NH_4Cl$ solution at 0° C. and extracted with EtOAc (3×30 mL). The combined organic layers were washed with 60 mL brine, dried over anhydrous $Na_2SO_4$, filtered and concentrated under vacuum. The crude product was purified by silica gel column chromatography eluting with a gradient of n-hexane:EtOAc (90:10 to 80:20 (740 mg, 89%).

Example 197

2-[6,6-Difluoro-3-(3-methyl-[1,2,4]thiadiazol-5-yl)-4,5,6,7-tetrahydro-benzo[b]thiophen-2-ylcarbamoyl]-cyclohex-1-enecarboxylic acid

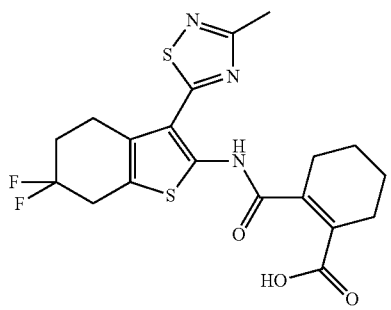 [SMILES: Cc1nsc(-c2c(NC(=O)C3=C(C(=O)O)CCCC3)sc3c2CCC(F)(F)C3)n1]

The title compound was prepared in analogy to example 57, from 6,6-difluoro-3-(3-methyl-[1,2,4]thiadiazol-5-yl)-4,5,6,7-tetrahydro-benzo[b]thiophen-2-ylamine (example 196, intermediate a) and 1-cyclohexene-1,2-dicarboxylic anhydride (CAS RN 2426-02-0), using a gradient of $CH_2Cl_2$:MeOH (99:1 to 98:2) for the chromatographic purification, followed by crystallization from $CH_2Cl_2$/n-hexane. Off-white solid (15%). MS (ESI): m/z=438.4 [M–H]$^-$.

Example 198

2-[3-(3-Cyclopropyl-[1,2,4]thiadiazol-5-yl)-6,6-difluoro-4,5,6,7-tetrahydro-benzo[b]thiophen-2-ylcarbamoyl]-cyclopent-1-enecarboxylic acid

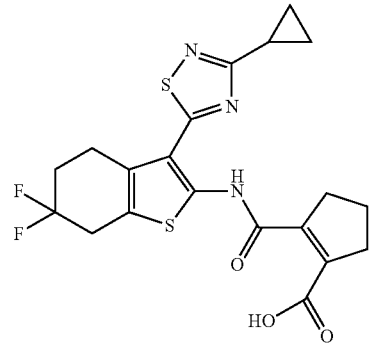 [SMILES: O=C(O)C1=C(C(=O)Nc2sc3c(c2-c2nc(C4CC4)ns2)CCC(F)(F)C3)CCC1]

The title compound was prepared in analogy to example 57, from 3-(3-cyclopropyl-[1,2,4]thiadiazol-5-yl)-6,6-difluoro-4,5,6,7-tetrahydro-benzo[b]thiophen-2-ylamine and 1-cyclopentene-1,2-dicarboxylic anhydride (CAS RN 3205-94-5), using a gradient of $CH_2Cl_2$:MeOH (99:1 to 98:2) for the chromatographic purification, followed by crystallization from $CH_2Cl_2$/n-hexane. Yellow solid (38%). MS (ESI): m/z=452.2 [M+H]$^+$.

Intermediates a) 6,6-Difluoro-3-(3-methyl-[1,2,4]thiadiazol-5-yl)-4,5,6,7-tetrahydro-benzo[b]thiophen-2-ylamine The title compound was synthesized in analogy to example 55, intermediate, from 4,4-difluoro-cyclohexanone (CAS RN 22515-18-0), (3-cyclopropyl-[1,2,4]thiadiazol-5-yl)-acetonitrile and elemental sulfur, using a gradient of n-hexane:EtOAc (90:10 to 80:20) for the chromatographic purification. Yellow solid (64%). MS (ESI): m/z=314.2 [M+H]$^+$.

b) (3-Cyclopropyl-[1,2,4]thiadiazol-5-yl)-acetonitrile

The title compound was synthesized in analogy to example 196, intermediate b, from 5-chloro-3-cyclopropyl-[1,2,4]thiadiazole (EvoBlocks, Ltd.) and acetonitrile and using a gradient of n-hexane:EtOAc (90:10 to 80:20) for the chromatographic purification. Brown solid (75%).

Example 199

2-[3-(3-Cyclopropyl-[1,2,4]thiadiazol-5-yl)-6,6-difluoro-4,5,6,7-tetrahydro-benzo[b]thiophen-2-ylcarbamoyl]-cyclohex-1-enecarboxylic acid

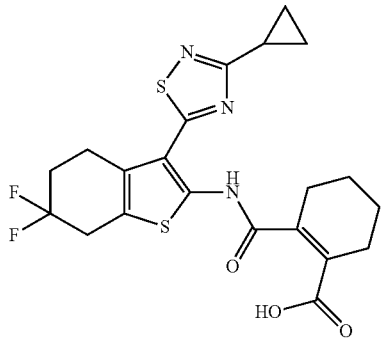 [SMILES: O=C(O)C1=C(C(=O)Nc2sc3c(c2-c2nc(C4CC4)ns2)CCC(F)(F)C3)CCCC1]

The title compound was prepared in analogy to example 57, from 3-(3-cyclopropyl-[1,2,4]thiadiazol-5-yl)-6,6-difluoro-4,5,6,7-tetrahydro-benzo[b]thiophen-2-ylamine (example 198, intermediate a) and 1-cyclohexene-1,2-dicarboxylic anhydride (CAS RN 2426-02-0) and using a gradient of $CH_2Cl_2$:MeOH (99:1 to 98:2) for the chromatographic purification, followed by crystallization from $CH_2Cl_2$/n-hexane. Yellow solid (19%). MS (ESI): m/z=466.2 [M+H]$^+$.

Example 200

2-[3-(3-Cyclopropyl-[1,2,4]oxadiazol-5-yl)-6-fluoro-4,5,6,7-tetrahydro-benzo[b]thiophen-2-ylcarbamoyl]-cyclopent-1-enecarboxylic acid

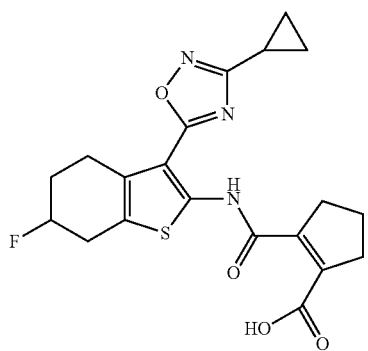 [SMILES: O=C(O)C1=C(C(=O)Nc2sc3c(c2-c2nc(C4CC4)no2)CCC(F)C3)CCC1]

The title compound was prepared in analogy to example 57, from 3-(3-cyclopropyl-[1,2,4]oxadiazol-5-yl)-6-fluoro-4,5,6,7-tetrahydro-benzo[b]thiophen-2-ylamine and 1-cyclopentene-1,2-dicarboxylic anhydride (CAS RN 3205-94-5) and using a gradient of $CH_2Cl_2$:MeOH (99:1 to 98:2) for the chromatographic purification, followed by crystallization from $CH_2Cl_2$/n-hexane. Yellow solid (21%). MS (ESI): m/z=418.4 [M+H]$^+$.

Intermediates a) 3-(3-Cyclopropyl-[1,2,4]oxadiazol-5-yl)-6-fluoro-4,5,6,7-tetrahydro-benzo[b]thiophen-2-ylamine The title compound was synthesized in analogy to example 55, intermediate, from 4-fluoro-cyclohexanone (102), (3-cyclopropyl-[1,2,4]oxadiazol-5-yl)-acetonitrile and elemental sulfur, using a gradient of n-hexane:EtOAc (90:10 to 80:20). Yellow solid (36%). MS (ESI): m/z=280.0 [M+H]$^+$.

b) 4-Fluoro-cyclohexanone

To a solution of 4-fluoro-cyclohexanol (140 mg, 1.18 mmol) in $CH_2Cl_2$ (10 mL) were added pyridinium chlorochromate (PCC; 411 mg, 1.90 mmol) and $MgSO_4$ (1 g) and the reaction mixture was stirred at 25° C. for 2 h. The reaction mixture was filtered through a silica gel pad and the filtrate was concentrated under reduced pressure. Light yellow sticky solid (44%).

c) 4-Fluoro-cyclohexanol

To a solution of (4-fluoro-cyclohexyloxymethyl)-benzene (1.2 g, 5.39 mmol) in a mixture of THF/MeOH (20 mL, 1:1 v/v) was added $LiOH.H_2O$ (8 mL, 1.2 M in $H_2O$) and the reaction mixture was stirred for 5 h at 25° C. The reaction mixture was diluted with $H_2O$ and extracted 5 times with 20 mL MeOH:$CH_2Cl_2$ (10:90). The combined organic layers were dried over $Na_2SO_4$ and concentrated. Yellow oil (78%). MS (ESI): m/z=118.0 [M]$^+$.

d) (4-Fluoro-cyclohexyloxymethyl)-benzene

To a solution of 4-benzyloxy-cyclohexanol (13.5 g, 61.29 mmol) in $CH_2Cl_2$ (50 mL) was added diethylaminosulfur trifluoride (DAST; 8.03 mL, 61.29 mmol) at −78° C. and the reaction mixture was stirred at this temperature for 10 min, then at 0° C. for 1 h and at 25° C. for 2 h. The reaction mixture was diluted with 20 mL $CH_2Cl_2$, washed with 20 mL brine, dried over $Na_2SO_4$ and evaporated. The crude product was purified by silica gel column chromatography eluting with a gradient of n-hexane:EtOAc (95:5 to 90:10). Colorless liquid (9%).

e) 4-Benzyloxy-cyclohexanol

To a solution of cyclohexane-1,4-diol (10 g, 86.08 mmol) in $CHCl_3$ (100 mL) were added slowly pyridine (10.53 mL, 129.13 mmol) and benzoyl chloride (13.11 mL, 111.91 mmol) at 25° C. under argon atmosphere. The reaction mixture was stirred at 25° C. for 12 hours. The reaction mixture was diluted with 80 mL $CH_2Cl_2$ and washed with 200 mL $H_2O$. The organic layer was dried over $Na_2SO_4$ and evaporated. The crude product was purified by silica gel column chromatography eluting with a gradient of n-hexane: EtOAc (80:20 to 70:30). Colorless liquid (58%).

Example 201

2-[3-(3-Methyl-[1,2,4]thiadiazol-5-yl)-4,5,6,7-tetrahydro-benzo[b]thiophen-2-ylcarbamoyl]-cyclopent-1-enecarboxylic acid

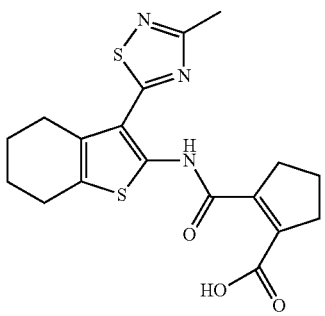 [SMILES: Cc1nsc(-c2c(NC(=O)C3=C(C(=O)O)CCC3)sc3c2CCCC3)n1]

The title compound was prepared in analogy to example 57, from 3-(3-methyl-[1,2,4]thiadiazol-5-yl)-4,5,6,7-tetrahydro-benzo[b]thiophen-2-ylamine and 1-cyclopentene-1,2-dicarboxylic anhydride (CAS RN 3205-94-5), using a gradient of CH$_2$Cl$_2$:MeOH (99:1 to 98:2) for the chromatographic purification, followed by crystallization from CH$_2$Cl$_2$/n-hexane. Yellow solid (32%). MS (ESI): m/z=390.2 [M+H]$^+$.

Intermediate 3-(3-Methyl-[1,2,4]thiadiazol-5-yl)-4,5,6,7-tetrahydro-benzo[b]thiophen-2-ylamine The title compound was synthesized in analogy to example 55, intermediate, from cyclohexanone, (3-methyl-[1,2,4]thiadiazol-5-yl)-acetonitrile (example 196, intermediate b) and elemental sulfur, using a gradient of n-hexane:EtOAc (90:10 to 80:20) for the chromatographic purification. Yellow solid (70%). MS (ESI): m/z=252.0 [M+H]$^+$.

Example 202

2-[3-(3-Methyl-[1,2,4]thiadiazol-5-yl)-4,5,6,7-tetrahydro-benzo[b]thiophen-2-ylcarbamoyl]-cyclohex-1-enecarboxylic acid

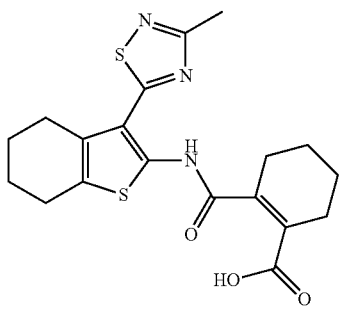 [SMILES: Cc1nsc(-c2c(NC(=O)C3=C(C(=O)O)CCCC3)sc3c2CCCC3)n1]

The title compound was prepared in analogy to example 57, from 3-(3-methyl-[1,2,4]thiadiazol-5-yl)-4,5,6,7-tetrahydro-benzo[b]thiophen-2-ylamine (example 201, intermediate) and 1-cyclohexene-1,2-dicarboxylic anhydride (CAS RN 2426-02-0), using a gradient of CH$_2$Cl$_2$:MeOH (99:1 to 98:2) for the chromatographic purification, followed by crystallization from CH$_2$Cl$_2$/n-hexane. Yellow solid (25%). MS (ESI): m/z=404.4 [M+H]$^+$.

Example 203

2-[3-(3-Cyclopropyl-[1,2,4]oxadiazol-5-yl)-6-fluoro-4,5,6,7-tetrahydro-benzo[b]thiophen-2-ylcarbamoyl]-cyclohex-1-enecarboxylic acid

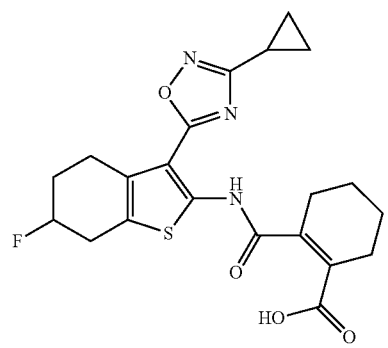 [SMILES: O=C(O)C1=C(C(=O)Nc2sc3c(c2-c2nc(C4CC4)no2)CCC(F)C3)CCCC1]

The title compound was prepared in analogy to example 57, from 3-(3-cyclopropyl-[1,2,4]oxadiazol-5-yl)-6-fluoro-4,5,6,7-tetrahydro-benzo[b]thiophen-2-ylamine (example 200, intermediate a) and 1-cyclohexene-1,2-dicarboxylic anhydride (CAS RN 2426-02-0), using a gradient of CH$_2$Cl$_2$:MeOH (99:1 to 98:2) for the chromatographic purification, followed by crystallization from CH$_2$Cl$_2$/n-hexane. Off-white solid (18%). MS (ESI): m/z=432.4 [M+H]$^+$.

Example 204

3-[3-(3-Methyl-[1,2,4]thiadiazol-5-yl)-4,5,6,7-tetrahydro-benzo[b]thiophen-2-ylcarbamoyl]-bicyclo[2.2.2]oct-2-ene-2-carboxylic acid

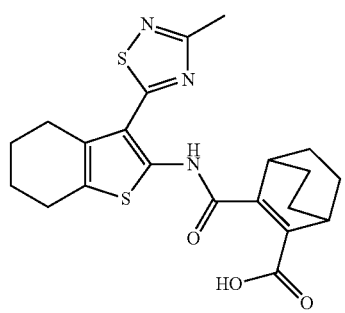 [SMILES: Cc1nsc(-c2c(NC(=O)C3=C(C(=O)O)C4CCC3CC4)sc3c2CCCC3)n1]

The title compound was prepared in analogy to example 57, from 3-(3-methyl-[1,2,4]thiadiazol-5-yl)-4,5,6,7-tetrahydro-benzo[b]thiophen-2-ylamine (example 201, intermediate) and bicyclo[2.2.2]oct-2-ene-2,3-dicarboxylic anhydride (CAS RN 151813-29-5), using a gradient of CH$_2$Cl$_2$:MeOH (99:1 to 98:2) followed by crystallization from CH$_2$Cl$_2$/n-hexane. Yellow solid (36%). MS (ESI): m/z=428.2 [M−H]$^-$.

Example 205

3-[6,6-Difluoro-3-(3-methyl-[1,2,4]thiadiazol-5-yl)-4,5,6,7-tetrahydro-benzo[b]thiophen-2-ylcarbamoyl]-bicyclo[2.2.2]oct-2-ene-2-carboxylic acid

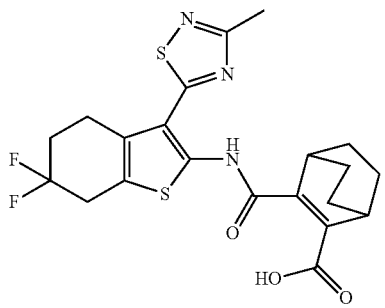 [SMILES: Cc1nsc(-c2c(NC(=O)C3=C(C(=O)O)C4CCC3CC4)sc3c2CCC(F)(F)C3)n1]

The title compound was prepared in analogy to example 57, from 6,6-difluoro-3-(3-methyl-[1,2,4]thiadiazol-5-yl)-4,5,6,7-tetrahydro-benzo[b]thiophen-2-ylamine (example 196, intermediate a) and bicyclo[2.2.2]oct-2-ene-2,3-dicarboxylic anhydride (CAS RN 151813-29-5), using a gradient of $CH_2Cl_2$:MeOH (99:1 to 98:2) for the chromatographic purification followed by crystallization from $CH_2Cl_2$/n-hexane. Off-white solid (17%). MS (ESI): m/z=466.0 $[M+H]^+$.

Example 206

2-[3-(3-Cyclopropyl-[1,2,4]thiadiazol-5-yl)-4,5,6,7-tetrahydro-benzo[b]thiophen-2-ylcarbamoyl]-cyclopent-1-enecarboxylic acid

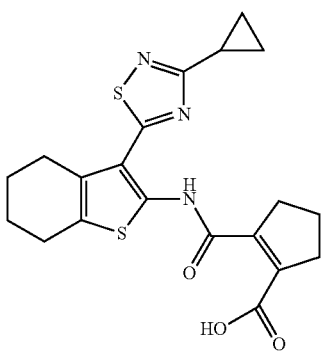 [SMILES: O=C(O)C1=C(C(=O)Nc2sc3c(c2-c2nc(C4CC4)ns2)CCCC3)CCC1]

The title compound was prepared in analogy to example 57, from 3-(3-cyclopropyl-[1,2,4]thiadiazol-5-yl)-4,5,6,7-tetrahydro-benzo[b]thiophen-2-ylamine and 1-cyclopentene-1,2-dicarboxylic anhydride (CAS RN 3205-94-5) and using a gradient of $CH_2Cl_2$:MeOH (99:1 to 98:2) for the chromatographic purification, followed by crystallization from $CH_2Cl_2$/n-hexane. Yellow solid (39%). MS (ESI): m/z=416.0 $[M+H]^+$.

Intermediate 3-(3-Cyclopropyl-[1,2,4]thiadiazol-5-yl)-4,5,6,7-tetrahydro-benzo[b]thiophen-2-ylamine The title compound was synthesized in analogy to example 55, intermediate, from cyclohexanone, (3-cyclopropyl-[1,2,4]thiadiazol-5-yl)-acetonitrile (example 198, intermediate b) and elemental sulfur, using a gradient of n-hexane:EtOAc (90:10 to 80:20) for the chromatographic purification. Yellow solid (84%). MS (ESI): m/z=278.2 $[M+H]^+$.

Example 207

2-[3-(3-Cyclopropyl-[1,2,4]thiadiazol-5-yl)-4,5,6,7-tetrahydro-benzo[b]thiophen-2-ylcarbamoyl]-cyclohex-1-enecarboxylic acid

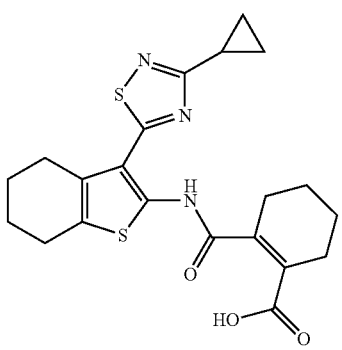 [SMILES: O=C(O)C1=C(C(=O)Nc2sc3c(c2-c2nc(C4CC4)ns2)CCCC3)CCCC1]

The title compound was prepared in analogy to example 57, from 3-(3-cyclopropyl-[1,2,4]thiadiazol-5-yl)-4,5,6,7-tetrahydro-benzo[b]thiophen-2-ylamine (example 206, intermediate) and 1-cyclohexene-1,2-dicarboxylic anhydride (CAS RN 2426-02-0), using a gradient of $CH_2Cl_2$:MeOH (99:1 to 98:2) for the chromatographic purification, followed by crystallization from $CH_2Cl_2$/n-hexane. Off-white solid (15%). MS (ESI): m/z=430.0 $[M+H]^+$.

Example 208

(R)-1-[3-(3-Cyclopropyl-[1,2,4]oxadiazol-5-yl)-6,6-difluoro-4,5,6,7-tetrahydro-benzo[b]thiophen-2-ylcarbamoyl]-pyrrolidine-2-carboxylic acid

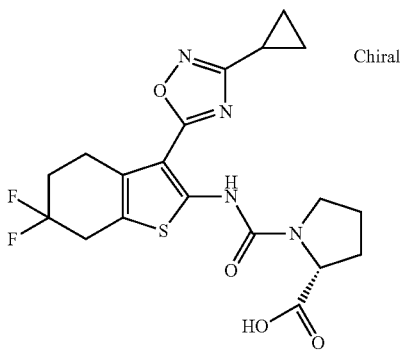 [SMILES: O=C(O)[C@H]1CCCN1C(=O)Nc1sc2c(c1-c1nc(C3CC3)no1)CCC(F)(F)C2]

The title compound was prepared in analogy to example 27, from 3-cyclopropyl-5-(6,6-difluoro-2-isocyanato-4,5,6,7-tetrahydro-benzo[b]thiophen-3-yl)-[1,2,4]oxadiazole and D-proline. The product was purified by silica gel column chromatography eluting with a gradient of MeOH:$CH_2Cl_2$ (2:98 to 5:95). Off-white solid (44%). MS (ESI): m/z=439.2 (M+H)'.

Intermediate

3-Cyclopropyl-5-(6,6-difluoro-2-isocyanato-4,5,6,7-tetrahydro-benzo[b]thiophen-3-yl)-[1,2,4]oxadiazole The title compound was prepared in analogy to example 27, intermediate a, from 3-(3-cyclopropyl-[1,2,4]oxadiazol-5-yl)-6,6-difluoro-4,5,6,7-tetrahydro-benzo[b]thiophen-2-ylamine (example 144, intermediate) after a reaction time of 2 h at 25° C. Colorless solid (98%) which was used in next step without purification.

Example 209

(R)-1-[3-(3-Cyclopropyl-[1,2,4]oxadiazol-5-yl)-5,6-dihydro-4H-cyclopenta[b]thiophen-2-ylcarbamoyl]-pyrrolidine-2-carboxylic acid

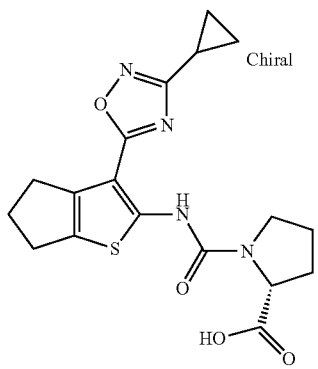 [SMILES: O=C(O)[C@H]1CCCN1C(=O)Nc1sc2c(c1-c1nc(C3CC3)no1)CCC2]

The title compound was prepared in analogy to example 27, from 3-cyclopropyl-5-(2-isocyanato-5,6-dihydro-4H-cyclopenta[b]thiophen-3-yl)-[1,2,4]oxadiazole and D-proline and using a gradient of $CH_2Cl_2$:MeOH (98:2 to 95:5) for the chromatographic purification, followed by crystallization from $CH_2Cl_2$/n-hexane. White solid (6%). MS (ESI): m/z=389.2 [M+H]$^+$.

Intermediate

3-Cyclopropyl-5-(2-isocyanato-5,6-dihydro-4H-cyclopenta[b]thiophen-3-yl)-[1,2,4]oxadiazole The title compound was prepared in analogy to example 27, intermediate a, from 3-(3-cyclopropyl-[1,2,4]oxadiazol-5-yl)-5,6-dihydro-4H-cyclopenta[b]thiophen-2-ylamine (example 132, intermediate). Colorless solid (98%) which was used in next step without further purification.

Example 210

2-[4-(3-Cyclopropyl-[1,2,4]oxadiazol-5-yl)-2-thiabicyclo[3.2.0]hepta-1(5),3-dien-3-ylcarbamoyl]-cyclopent-1-enecarboxylic acid

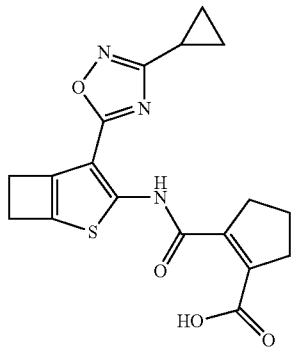 [SMILES: O=C(O)C1=C(C(=O)Nc2sc3c(c2-c2nc(C4CC4)no2)CC3)CCC1]

The title compound was prepared in analogy to example 127, from 4-(3-cyclopropyl-[1,2,4]oxadiazol-5-yl)-2-thiabicyclo[3.2.0]hepta-1(5),3-dien-3-ylamine and 1-cyclopentene-1,2-dicarboxylic anhydride (CAS RN 3205-94-5) and using preparative HPLC ($NH_4OAc/CH_3CN$) for the chromatographic purification. Yellow solid (4%). MS (ESI): m/z=372.0 [M+H]$^+$.

Intermediate 2-(3-Cyclopropyl-1,2,4-oxadiazol-5-yl)-4-thiabicyclo[3.2.0]hepta-1(5),2-dien-3-amine The title compound was synthesized in analogy to example 55, intermediate, from cyclobutanone, (3-cyclopropyl-[1,2,4]oxadiazol-5-yl)-acetonitrile (Princeton BioMolecular Research, Inc.) and elemental sulfur, using preparative HPLC ($NH_4OAc/CH_3CN$) for the chromatographic purification. Brown solid (6%). MS (ESI): m/z=234.4 [M+H]$^+$.

Example 211

3-[3-(3-Cyclopropyl-[1,2,4]thiadiazol-5-yl)-4,5,6,7-tetrahydro-benzo[b]thiophen-2-ylcarbamoyl]-bicyclo[2.2.2]oct-2-ene-2-carboxylic acid

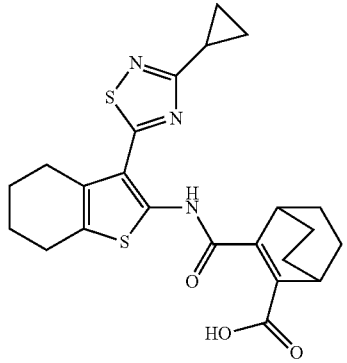 [SMILES: O=C(O)C1=C(C(=O)Nc2sc3c(c2-c2nc(C4CC4)ns2)CCCC3)C2CCC1CC2]

The title compound was prepared in analogy to example 57, from 3-(3-cyclopropyl-[1,2,4]thiadiazol-5-yl)-4,5,6,7-tetrahydro-benzo[b]thiophen-2-ylamine (example 206, intermediate) and bicyclo[2.2.2]oct-2-ene-2,3-dicarboxylic anhydride (CAS RN 151813-29-5), using a gradient of CH$_2$Cl$_2$:MeOH (99:1 to 98:2) for the chromatographic purification, followed by crystallization from CH$_2$Cl$_2$/n-hexane. Yellow solid (22%). MS (ESI): m/z=456.0 [M+H]$^+$.

Example 212

3-[3-(3-Cyclopropyl-[1,2,4]thiadiazol-5-yl)-6,6-difluoro-4,5,6,7-tetrahydro-benzo[b]thiophen-2-ylcarbamoyl]-bicyclo[2.2.2]oct-2-ene-2-carboxylic acid

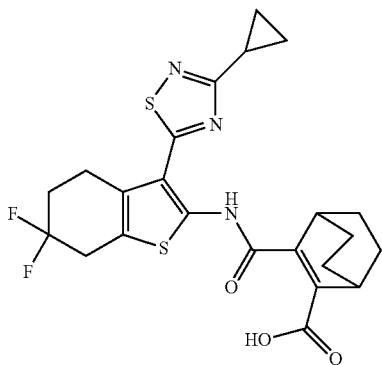 [SMILES: O=C(O)C1=C(C(=O)Nc2sc3c(c2-c2nc(C4CC4)ns2)CCC(F)(F)C3)C2CCC1CC2]

The title compound was prepared in analogy to example 57, from 3-(3-cyclopropyl-[1,2,4]thiadiazol-5-yl)-6,6-difluoro-4,5,6,7-tetrahydro-benzo[b]thiophen-2-ylamine (example 198, intermediate a) and bicyclo[2.2.2]oct-2-ene-2,3-dicarboxylic anhydride (CAS RN 151813-29-5), using a gradient of CH$_2$Cl$_2$:MeOH (99:1 to 98:2) for the chromatographic purification, followed by crystallization from CH$_2$Cl$_2$/n-hexane. Light yellow solid (17%). MS (ESI): m/z=492.2 [M+H]$^+$.

Example 213

(R)-1-[3-(3-Cyclopropyl-[1,2,4]oxadiazol-5-yl)-5,6,7,8-tetrahydro-4H-cyclohepta[b]thiophen-2-ylcarbamoyl]-pyrrolidine-2-carboxylic acid

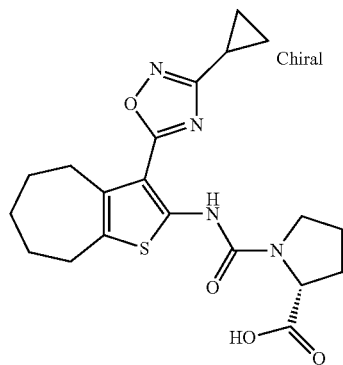 [SMILES: O=C(O)[C@H]1CCCN1C(=O)Nc1sc2c(c1-c1nc(C3CC3)no1)CCCCC2]

The title compound was prepared in analogy to example 57, from 3-cyclopropyl-5-(2-isocyanato-5,6,7,8-tetrahydro-4H-cyclohepta[b]thiophen-3-yl)-[1,2,4]oxadiazole and D-proline and using a gradient of CH$_2$Cl$_2$:MeOH (98:2 to 95:5) for the chromatographic purification, followed by crystallization from CH$_2$Cl$_2$/n-hexane. Off-white solid (29%). MS (ESI): m/z=417.0 [M+H]$^+$.

Intermediate

3-Cyclopropyl-5-(2-isocyanato-5,6,7,8-tetrahydro-4H-cyclohepta[b]thiophen-3-yl)-[1,2,4]oxadiazole The title compound was synthesized in analogy to example 27, intermediate a, from 3-(3-cyclopropyl-[1,2,4]oxadiazol-5-yl)-5,6,7,8-tetrahydro-4H-cyclohepta[b]thiophen-2-ylamine (example 123, intermediate). The solvent was evaporated and the resulting compound was used the next step with out further purification. Colorless solid (97%).

Example 214

(2R,4S)-1-[3-(3-Cyclopropyl-[1,2,4]oxadiazol-5-yl)-4,5,6,7-tetrahydro-benzo[b]thiophen-2-ylcarbamoyl]-4-hydroxy-pyrrolidine-2-carboxylic acid

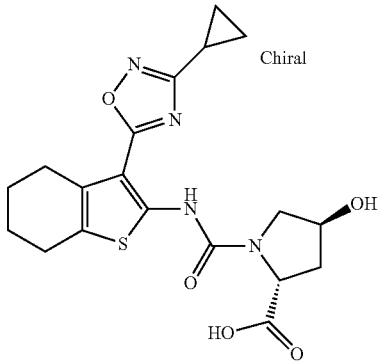 [SMILES: O=C(O)[C@H]1C[C@H](O)CN1C(=O)Nc1sc2c(c1-c1nc(C3CC3)no1)CCCC2]

The title compound was prepared in analogy to example 27, from 3-cyclopropyl-5-(2-isocyanato-4,5,6,7-tetrahydrobenzo[b]thiophen-3-yl)-1,2,4-oxadiazole (example 27, intermediate a) and (2R,4S)-4-hydroxy-pyrrolidine-2-carboxylic acid (CAS RN 3398-22-9) and using a gradient of CH$_2$Cl$_2$:MeOH (98:2 to 95:5) for the chromatographic purification, followed by crystallization from CH$_2$Cl$_2$/n-hexane. Off-white solid (12%). MS (ESI): m/z=419.4 [M+H]$^+$.

Example 215

(2R,4R)-1-[3-(3-Cyclopropyl-[1,2,4]oxadiazol-5-yl)-4,5,6,7-tetrahydro-benzo[b]thiophen-2-ylcarbamoyl]-4-hydroxy-pyrrolidine-2-carboxylic acid

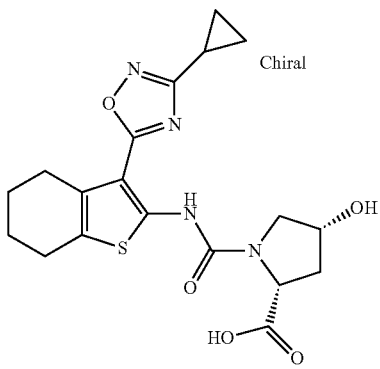 [SMILES: O=C(O)[C@H]1C[C@@H](O)CN1C(=O)Nc1sc2c(c1-c1nc(C3CC3)no1)CCCC2]

The title compound was prepared in analogy to example 27, from 3-cyclopropyl-5-(2-isocyanato-4,5,6,7-tetrahydrobenzo[b]thiophen-3-yl)-1,2,4-oxadiazole (example 27, intermediate a) and (2R,4R)-4-hydroxy-pyrrolidine-2-carboxylic acid (CAS RN 2584-71-6) and using a gradient of $CH_2Cl_2$:MeOH (98:2 to 95:5) for the chromatographic purification, followed by crystallization from $CH_2Cl_2$/n-hexane. Yellow solid (8%). MS (ESI): m/z=417.4 [M–H]$^-$.

Example 216

2-[5-(3-Cyclopropyl-[1,2,4]oxadiazol-5-yl)-3,4-dihydro-2H-thieno[2,3-b]pyran-6-ylcarbamoyl]-cyclohex-1-enecarboxylic acid

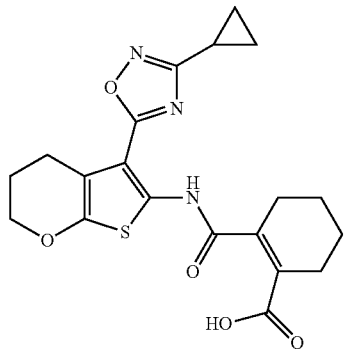 [SMILES: O=C(O)C1=C(C(=O)Nc2sc3c(c2-c2nc(C4CC4)no2)CCCO3)CCCC1]

The title compound was prepared in analogy to example 57, from 5-(3-cyclopropyl-[1,2,4]oxadiazol-5-yl)-3,4-dihydro-2H-thieno[2,3-b]pyran-6-ylamine and 1-cyclohexene-1,2-dicarboxylic anhydride (CAS RN 2426-02-0), using a gradient of $CH_2Cl_2$:MeOH (99:1 to 98:2) for the chromatographic purification, followed by crystallization from $CH_2Cl_2$/n-hexane. Yellow solid (12%). MS (ESI): m/z=416.2 [M+H]$^+$.

Intermediate 5-(3-Cyclopropyl-[1,2,4]oxadiazol-5-yl)-3,4-dihydro-2H-thieno[2,3-b]pyran-6-ylamine The title compound was synthesized in analogy to example 55, intermediate, from dihydro-pyran-3-one (CAS RN 23462-75-1), (3-cyclopropyl-[1,2,4]oxadiazol-5-yl)-acetonitrile (Princeton BioMolecular Research, Inc.) and elemental sulfur, using a gradient of n-hexane:EtOAc (90:10 to 80:20) for the chromatographic purification. Light yellow solid (45%). MS (ESI): m/z=264.2 [M+H]$^+$.

Example 217

2-[5-(3-Cyclopropyl-[1,2,4]oxadiazol-5-yl)-3,4-dihydro-2H-thieno[2,3-b]pyran-6-ylcarbamoyl]-cyclopent-1-enecarboxylic acid

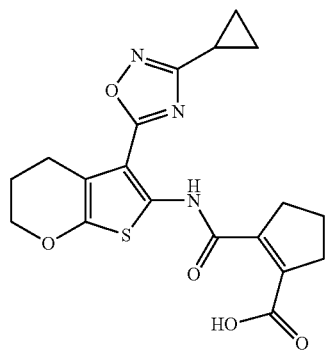 [SMILES: O=C(O)C1=C(C(=O)Nc2sc3c(c2-c2nc(C4CC4)no2)CCCO3)CCC1]

The title compound was prepared in analogy to example 57, from 5-(3-cyclopropyl-[1,2,4]oxadiazol-5-yl)-3,4-dihydro-2H-thieno[2,3-b]pyran-6-ylamine (example 234, intermediate) and 1-cyclopentene-1,2-dicarboxylic anhydride (CAS RN 3205-94-5), using a gradient of $CH_2Cl_2$:MeOH (99:1 to 98:2) for the chromatographic purification, followed by crystallization from $CH_2Cl_2$/n-hexane. Yellow solid (24%). MS (ESI): m/z=400.2 [M–H]$^-$.

Example 218

2-[3-(3-Cyclopropyl-[1,2,4]oxadiazol-5-yl)-4,5,6,7-tetrahydro-benzo[b]thiophen-2-ylcarbamoyl]-4,4-dimethyl-cyclopent-1-enecarboxylic acid

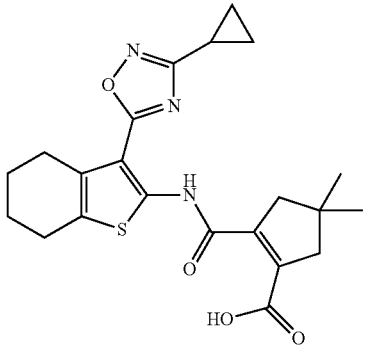 [SMILES: CC1(C)CC(C(=O)O)=C(C(=O)Nc2sc3c(c2-c2nc(C4CC4)no2)CCCC3)C1]

The title compound was prepared in analogy to example 113, from 2-[3-(3-cyclopropyl-[1,2,4]oxadiazol-5-yl)-4,5,6,7-tetrahydro-benzo[b]thiophen-2-ylcarbamoyl]-4,4-dimethyl-cyclopent-1-enecarboxylic acid methyl ester and using a gradient of CH$_2$Cl$_2$:MeOH (99:1 to 98:2) followed by crystallization from CH$_2$Cl$_2$/n-hexane. Yellow solid (70%). MS (ESI): m/z=428.4 [M+H]$^+$.

Intermediates a) 2-[3-(3-Cyclopropyl-[1,2,4]oxadiazol-5-yl)-4,5,6,7-tetrahydro-benzo[b]thiophen-2-ylcarbamoyl]-4,4-dimethyl-cyclopent-1-enecarboxylic acid methyl ester To a solution of 4,4-dimethyl-cyclopent-1-ene-1,2-dicarboxylic acid monomethyl ester (152 mg, 0.765 mmol) in thionyl chloride (5 mL) was added DMF (0.1 mL) and the reaction mixture was heated to reflux for 2 h. The reaction mixture was concentrated under reduced pressure and the residue was diluted with 10 mL toluene and evaporated to remove excess thionyl chloride. The crude acid chloride was dissolved in CH$_2$Cl$_2$ (5 mL) and was added dropwise to a solution of 3-(3-cyclopropyl-[1,2,4]oxadiazol-5-yl)-4,5,6,7-tetrahydro-benzo[b]-thiophen-2-ylamine (200 mg, 0.765 mmol) and DIPEA (0.253 mL, 1.531 mmol) in CH$_2$Cl$_2$ (5 mL) at 25° C. The reaction mixture stirred at 25° C. for 12 h, diluted with 20 mL CH$_2$Cl$_2$ and washed with 20 mL H$_2$O. The organic layer was dried over anhydrous Na$_2$SO$_4$, filtered and evaporated. The crude product was purified by silica gel column chromatography eluting with a gradient of n-hexane:EtOAc (90:10 to 80:20). Brown solid (175 mg, 52%). MS (ESI): m/z=442.2 (M+H)'.

b) 4,4-Dimethyl-cyclopent-1-ene-1,2-dicarboxylic acid monomethyl ester

A mixture of acetic anhydride (0.435 mL, 4.632 mmol), DIPEA (0.765 mL, 4.632 mmol) and sodium formate (472 mg, 6.947 mmol) was stirred at 25° C. for 1 h. To the colorless solution were added 4,4-dimethyl-2-trifluoromethanesulfonyloxy-cyclopent-1-enecarboxylic acid methyl ester (700 mg, 2.316 mmol) dissolved in DMF (10 mL), followed by Pd(OAc)$_2$ (26 mg, 0.116 mmol) and LiCl (295 mg, 6.947 mmol). The resulting dark brown reaction mixture was stirred at 25° C. for 12 h. The reaction mixture was poured into 20 mL 2M HCl solution and extracted two times with 20 mL EtOAc. The combined organic part was washed with 50 mL H$_2$O and 20 mL brine, dried over anhydrous Na$_2$SO$_4$, filtered and concentrated under reduced pressure. The residue was purified by silica gel column chromatography eluting with a gradient of CH$_2$Cl$_2$:MeOH (99:1 to 98:2). Brown liquid (402 mg, 88%).

c) 4,4-Dimethyl-2-trifluoromethanesulfonyloxy-cyclopent-1-enecarboxylic acid methyl ester To a solution of 4,4-dimethyl-2-oxo-cyclopentanecarboxylic acid methyl ester (500 mg, 2.93 mmol; CAS RN 60585-44-6) in CH$_2$Cl$_2$ (10 mL) was added DIPEA (2.379 mL, 14.39 mmol) at −78° C. After stirring for 10 min. at −78° C., trifluoromethanesulfonic anhydride (0.585 mL, 3.525 mmol) was added dropwise at −78° C. and the reaction mixture stirred at −78° C. for 12 h. The reaction mixture was allowed to warm to 25° C. and poured into 50 mL H$_2$O. The layers were separated and the organic phase was washed with 50 mL 10% aqueous citric acid solution, dried and evaporated. The resulting crude product was purified by silica gel column chromatography eluting with a gradient of n-hexane:EtOAc (98:2 to 95:5). Brown liquid (710 mg, 80%).

Example 219

2-[3-(3-Cyclopropyl-[1,2,4]oxadiazol-5-yl)-6,7-dihydro-4H-thieno[3,2-c]pyran-2-ylcarbamoyl]-cyclopent-1-enecarboxylic acid

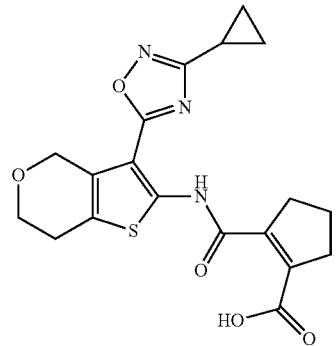 [SMILES: O=C(O)C1=C(C(=O)Nc2sc3c(c2-c2nc(C4CC4)no2)COCC3)CCC1]

The title compound was prepared in analogy to example 57, from 3-(3-cyclopropyl-[1,2,4]oxadiazol-5-yl)-6,7-dihydro-4H-thieno[3,2-c]pyran-2-ylamine and 1-cyclopentene-1,2-dicarboxylic anhydride (CAS RN 3205-94-5), using a gradient of CH$_2$Cl$_2$:MeOH (99:1 to 98:2) followed by crystallization from CH$_2$Cl$_2$/n-hexane. Yellow solid (24%). MS (ESI): m/z=400.2 [M−H]$^+$.

Intermediate 3-(3-Cyclopropyl-[1,2,4]oxadiazol-5-yl)-6,7-dihydro-4H-thieno[3,2-c]pyran-2-ylamine The title compound was synthesized in analogy to example 55, intermediate, from dihydro-pyran-3-one (CAS RN 23462-75-1), (3-cyclopropyl-[1,2,4]oxadiazol-5-yl)-acetonitrile (Princeton BioMolecular Research, Inc.) and sulfur powder, using a gradient of n-hexane: EtOAc (95:5 to 90:10) for the chromatographic purification. Light yellow solid (6%). MS (ESI): m/z=262.2 [M−H]$^+$.

Example 220

2-[3-(3-Cyclopropyl-[1,2,4]oxadiazol-5-yl)-6,7-dihydro-4H-thieno[3,2-c]pyran-2-ylcarbamoyl]-cyclohex-1-enecarboxylic acid

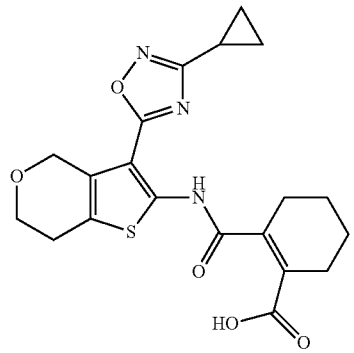 [SMILES: O=C(O)C1=C(C(=O)Nc2sc3c(c2-c2nc(C4CC4)no2)COCC3)CCCC1]

The title compound was prepared in analogy to example 57, from 3-(3-cyclopropyl-[1,2,4]oxadiazol-5-yl)-6,7-dihydro-4H-thieno[3,2-c]pyran-2-ylamine (example 219, intermediate) and 1-cyclohexene-1,2-dicarboxylic anhydride (CAS RN 2426-02-0), using a gradient of $CH_2Cl_2$:MeOH (99:1 to 98:2) for the chromatographic purification, followed by crystallization from $CH_2Cl_2$/n-hexane. Light yellow solid (71%). MS (ESI): m/z=416.2 [M+H]$^+$.

Example 221

3-[3-(3-Cyclopropyl-[1,2,4]oxadiazol-5-yl)-4,7-dihydro-5H-thieno[2,3-c]pyran-2-ylcarbamoyl]-5-methyl-1H-pyrazole-4-carboxylic acid

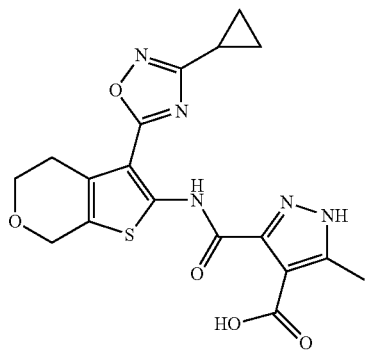 [SMILES: Cc1[nH]nc(C(=O)Nc2sc3c(c2-c2nc(C4CC4)no2)CCOC3)c1C(=O)O]

A suspension of tert-butyl 3-(3-(3-cyclopropyl-1,2,4-oxadiazol-5-yl)-5,7-dihydro-4H-thieno[2,3-c]pyran-2-ylcarbamoyl)-5-methyl-1H-pyrazole-4-carboxylate (0.02 g, 42.4 µmol) in formic acid (781 mg, 651 µl, 17.0 mmol) was stirred at RT for 3.5 h. The suspension was poured on 1M aqueous HCl solution and EtOAC and the layers were separated. The aqueous layer was extracted twice with EtOAC and the combined organic layers were washed with brine, dried over $MgSO_4$, filtered and evaporated. Light brown solid (0.017 g; 96%). MS (ESI): m/z=414.09 [M-H]$^-$.

Intermediates a) tert-Butyl 3-(3-(3-cyclopropyl-1,2,4-oxadiazol-5-yl)-5,7-dihydro-4H-thieno[2,3-c]pyran-2-ylcarbamoyl)-5-methyl-1H-pyrazole-4-carboxylate To a solution of 3-(3-cyclopropyl-1,2,4-oxadiazol-5-yl)-5,7-dihydro-4H-thieno[2,3-c]pyran-2-amine (0.084 g, 319 µmol; example 55, intermediate) and 4-(tert-butoxycarbonyl)-5-methyl-1H-pyrazole-3-carboxylic acid (72.2 mg, 319 µmol) in $CH_2Cl_2$ (4 mL) were added 2-bromo-1-ethylpyridinium tetrafluoroborate (105 mg, 383 µmol; CAS RN 878-23-9) and DIPEA (82.5 mg, 111 µL, 638 µmol) and the yellow solution was stirred at RT for 67 h. The reaction mixture was evaporated and the product was purified by preparative HPLC (Gemini NX column) using a gradient of MeOH:$H_2O$ (containing 0.1% formic acid) (20:80 to 98:2). Light brown solid (0.02 g; 13%). MS (ESI): m/z=472.16 [M+H]$^+$.

b) 4-(tert-Butoxycarbonyl)-5-methyl-1H-pyrazole-3-carboxylic acid

To a solution of 4-benzyl 1-tert-butyl 2-acetyl-3-aminomaleate (0.5 g, 1.57 mmol) in EtOH (10 mL) was added hydrazine hydrate (78.4 mg, 76.1 µL, 1.57 mmol) and the clear, colorless solution was heated to reflux for 1.5 h. The reaction mixture was treated with silica gel and evaporated. The compound was purified by silica gel chromatography on a 20 g column using a MPLC system eluting with a gradient of n-heptane:EtOAc (100:0 to 50:50). Colorless solid (0.085 g; 24%). MS (ESI): m/z=225.09 [M-H]$^-$.

c) 4-Benzyl 1-tert-butyl 2-acetyl-3-aminomaleate

To a solution of tert-butyl 3-oxobutanoate (3.3 g, 3.46 mL, 20.9 mmol, CAS RN 1694-31-1) and benzyl cyanoformate (3.36 g, 2.99 mL, 20.9 mmol, CAS RN 5532-86-5) in $CH_2Cl_2$ (10.0 mL) was added zinc(II) acetyl acetonate (275 mg, 1.04 mmol, CAS RN 108503-47-5) and the resulting light yellow reaction mixture was stirred at RT for 2 h. The reaction mixture was evaporated, the residue taken up in $Et_2O$ (60 mL), and the suspension was filtered over dicalite. The solid was washed with $Et_2O$ (40 mL) and the filtrate was evaporated. The compound was purified by silica gel chromatography on a 50 g column using an MPLC (ISCO) system eluting with a gradient of n-heptane:EtOAc (100:0 to 65:35). The product-containing fractions were combined and evaporated until a suspension formed. The suspension was filtered and the filter cake washed with n-heptane to give the desired compound as an E/Z mixture. Colorless solid (2.66 g, 40%). MS (ESI): m/z=318.14 [M-H]$^-$. The impure product-containing fractions were combined and evaporated until a suspension formed. The suspension was filtered and washed with n-heptane to give another batch of compound. Colorless solid (2.72 g; 40.8%). MS (ESI): m/z=[M+H]$^+$.

Example 222

2-[3-(3-Cyclopropyl-[1,2,4]oxadiazol-5-yl)-6-hydroxy-6-methyl-4,5,6,7-tetrahydro-benzo[b]thiophen-2-ylcarbamoyl]-cyclopent-1-enecarboxylic acid

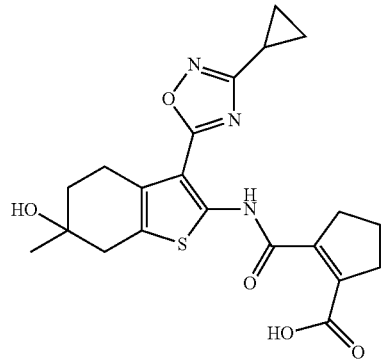 [SMILES: CC1(O)CCc2c(sc(NC(=O)C3=C(C(=O)O)CCC3)c2-c2nc(C3CC3)no2)C1]

The title compound was prepared in analogy to example 55, from 2-amino-3-(3-cyclopropyl-1,2,4-oxadiazol-5-yl)-6-methyl-5,7-dihydro-4H-benzothiophen-6-ol and 1-cyclopentene-1,2-dicarboxylic anhydride (CAS RN 3205-94-5) after a reaction time of 4 h, using preparative HPLC (Gemini NX) with a gradient of MeOH:$H_2O$ (with 0.05% formic acid) (80:20 to 98:2) for the chromatographic purification. Yellow solid (35%). MS (ESI): m/z=428.130 [M-H]$^-$.

Intermediates a) 2-Amino-3-(3-cyclopropyl-1,2,4-oxadiazol-5-yl)-6-methyl-5,7-dihydro-4H-benzothiophen-6-ol The title compound was prepared in analogy to example 56, intermediate a, from 2-(3-cyclopropyl-1,2,4-oxadiazol-5-yl)-2-(4-hydroxy-4-methyl-cyclohexylidene)acetonitrile after a reaction time of 3 h at 65° C. The desired compound was purified by silica gel chromatography using a MPLC system (CombiFlash Companion, Isco Inc.) eluting with a gradient of n-heptane:EtOAc (100:0 to 50:50). Light yellow solid (75%). MS (ESI): m/z=292.111 [M+H]$^+$.

b) 2-(3-Cyclopropyl-1,2,4-oxadiazol-5-yl)-2-(4-hydroxy-4-methyl-cyclohexylidene)acetonitrile The title compound was prepared in analogy to example 56, intermediate b, from 4-hydroxy-4-methylcyclohexanone (300 mg, 2.34 mmol, CAS RN 17429-02-6) and 2-(3-cyclopropyl-1,2,4-oxadiazol-5-yl)acetonitrile (Princeton BioMolecular Research, Inc.) after a reaction time of 3 h at 110° C. The product was purified by silica gel chromatography on a 20 g column using a MPLC system (CombiFlash Companion, Isco Inc.) eluting with a gradient of n-heptane: EtOAc (100:0 to 50:50). Red oil (69%). MS (ESI): m/z=260.139 [M+H]$^+$.

Example 223

3-[3-(3-Cyclopropyl-[1,2,4]oxadiazol-5-yl)-6-hydroxy-6-methyl-4,5,6,7-tetrahydro-benzo[b]thiophen-2-ylcarbamoyl]-bicyclo[2.2.2]oct-2-ene-2-carboxylic acid

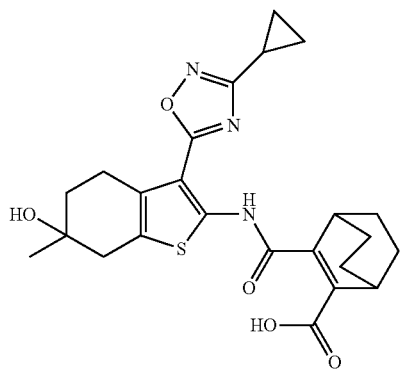 [SMILES: CC1(O)CCc2c(sc(NC(=O)C3=C(C(=O)O)C4CCC3CC4)c2-c2nc(C3CC3)no2)C1]

The title compound was prepared in analogy to example 55, from 2-amino-3-(3-cyclopropyl-1,2,4-oxadiazol-5-yl)-6-methyl-5,7-dihydro-4H-benzothiophen-6-ol (example 222, intermediate a) and bicyclo[2.2.2]oct-2-ene-2,3-dicarboxylic anhydride (CAS RN 151813-29-5) after a reaction time of 4 h at 65° C. The product was purified by preparative HPLC (Gemini NX) with a gradient of MeOH:H$_2$O (with 0.05% formic acid) (80:20 to 98:2). Yellow solid (84%). MS (ESI): m/z=468.161 [M−H]$^-$.

Example 224

2-[3-(3-Cyclopropyl-[1,2,4]oxadiazol-5-yl)-6-hydroxy-6-methyl-4,5,6,7-tetrahydro-benzo[b]thiophen-2-ylcarbamoyl]-cyclohex-1-enecarboxylic acid

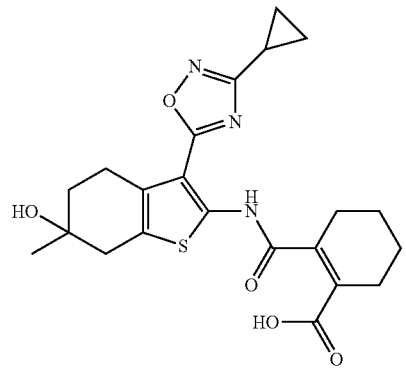 [SMILES: CC1(O)CCc2c(sc(NC(=O)C3=C(C(=O)O)CCCC3)c2-c2nc(C3CC3)no2)C1]

The title compound was prepared in analogy to example 55, from 2-amino-3-(3-cyclopropyl-1,2,4-oxadiazol-5-yl)-6-methyl-5,7-dihydro-4H-benzothiophen-6-ol (example 222, intermediate a) and 1-cyclohexene-1,2-dicarboxylic anhydride (CAS RN 2426-02-0). The residue was purified by preparative HPLC (Gemini NX) with a gradient of MeOH:H$_2$O (with 0.05% formic acid) (80:20 to 98:2). Light brown solid (68%). MS (ESI): m/z=442.145 [M−H]$^-$.

Examples 225 and 226

3-[3-(3-Cyclopropyl-[1,2,4]oxadiazol-5-yl)-4,7-dihydro-5H-thieno[2,3-c]pyran-2-ylcarbamoyl]-pyridine-2-carboxylic acid and 2-[3-(3-Cyclopropyl-[1,2,4]oxadiazol-5-yl)-4,7-dihydro-5H-thieno[2,3-c]pyran-2-ylcarbamoyl]-nicotinic acid

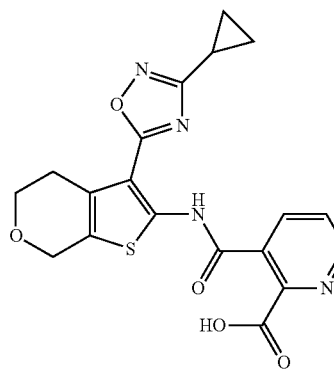

and

-continued

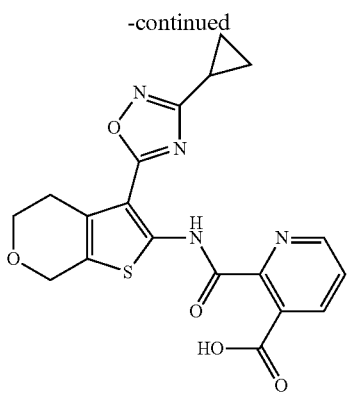

To a suspension of methyl 2-(3-(3-cyclopropyl-1,2,4-oxadiazol-5-yl)-5,7-dihydro-4H-thieno[2,3-c]pyran-2-ylcarbamoyl)nicotinate (0.048 g, 113 μmol) in dioxane (2 mL) and H₂O (2 mL) was added lithium hydroxide monohydrate (5.67 mg, 135 μmol). After 100 min. was added another batch of dioxane (4 mL). After 4.5 h another batch of lithium hydroxide monohydrate (2.83 mg, 67.5 μmol) was added and stirring was continued for 1.75 h. After stirring for 6.25 h at RT, the light brown solution was poured on 1M aqueous HCl solution (3 mL) and EtOAc and the layers were separated. The aqueous layer was extracted twice with EtOAc and the organic layers were washed with brine, dried over MgSO₄, filtered and evaporated. The products were purified and separated by preparative HPLC (Gemini NX column) using a gradient of MeOH:H₂O (containing 0.1% formic acid) (20:80 to 98:2).

3-[3-(3-Cyclopropyl-[1,2,4]oxadiazol-5-yl)-4,7-dihydro-5H-thieno[2,3-c]pyran-2-ylcarbamoyl]-pyridine-2-carboxylic acid: Light brown solid (0.021 g; 45%). MS (ESI): m/z=413.09 [M+H]⁺.

2-[3-(3-Cyclopropyl-[1,2,4]oxadiazol-5-yl)-4,7-dihydro-5H-thieno[2,3-c]pyran-2-ylcarbamoyl]-nicotinic acid: Light brown solid (0.009 g; 19%). MS (ESI): m/z=413.09 [M+H]⁺.

Intermediate

Methyl 2-(3-(3-cyclopropyl-1,2,4-oxadiazol-5-yl)-5,7-dihydro-4H-thieno[2,3-c]pyran-2-ylcarbamoyl)nicotinate To a solution of 3-(3-cyclopropyl-1,2,4-oxadiazol-5-yl)-5,7-dihydro-4H-thieno[2,3-c]pyran-2-amine (0.1 g, 380 μmol; example 55, intermediate) in CH₂Cl₂ (3 mL) were added 3-(methoxycarbonyl)picolinic acid (68.8 mg, 380 μmol, CAS RN 24195-02-6), 2-bromo-1-ethylpyridinium tetrafluoroborate (125 mg, 456 μmol, CAS RN 878-23-9) and DIPEA (98.2 mg, 133 μL, 760 μmol) and the light yellow solution was stirred at RT for 48 h. The reaction mixture was evaporated and the product was purified by preparative HPLC (Gemini NX column) using a gradient of MeOH:H₂O (containing 0.1% formic acid) (20:80 to 98:2). Light yellow solid (0.051 g; 31%). MS (ESI): m/z=427.11 [M+H]⁺.

Example 227

(1RS,5SR)-5-[3-(3-Cyclopropyl-[1,2,4]oxadiazol-5-yl)-4,7-dihydro-5H-thieno[2,3-c]pyran-2-ylcarbamoyl]-bicyclo[3.1.0]hexane-1-carboxylic acid

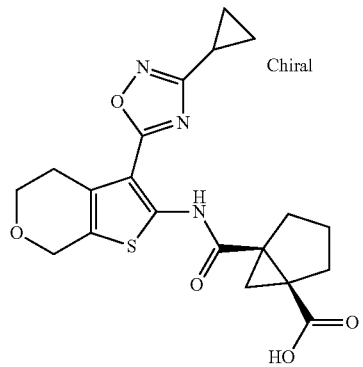 [SMILES: O=C(O)[C@]12CCC[C@@]1(C(=O)Nc1sc3c(c1-c1nc(C4CC4)no1)CCOC3)C2]

The title compound was prepared in analogy to example 113, from methyl (1RS,5SR)-1-[[3-(3-cyclopropyl-1,2,4-oxadiazol-5-yl)-5,7-dihydro-4H-thieno[2,3-c]pyran-2-yl]carbamoyl]bicyclo[3.1.0]hexane-5-carboxylate. During evaporation of the organic layer a suspension formed which was filtered and washed with EtOAc. The resulting colorless solid, containing some starting material, was homogenized in CH₂Cl₂ (5 mL) and filtered. The product and its mother liquor were purified by preparative HPLC (Gemini NX column) using a gradient of MeOH:H₂O (containing 0.1% formic acid) (20:80 to 98:2). Colorless solid (58%). MS (ESI): m/z=416.13 [M+H]⁺.

Intermediate

Methyl (1RS,5SR)-1-[[3-(3-cyclopropyl-1,2,4-oxadiazol-5-yl)-5,7-dihydro-4H-thieno[2,3-c]pyran-2-yl]carbamoyl]bicyclo[3.1.0]hexane-5-carboxylate The title compound was prepared in analogy to example 112, from 3-(3-cyclopropyl-1,2,4-oxadiazol-5-yl)-5,7-dihydro-4H-thieno[2,3-c]pyran-2-amine (example 55, intermediate) and bicyclo[3.1.0]hexane-1,5-dicarboxylic acid monomethyl ester (78.3 mg, 425 μmol, prepared in analogy to R. R. Reitz et al., *J. Org. Chem.* 1970, 35(8), 2666-2669). The compound was purified by silica gel chromatography on a 20 g column using a MPLC system eluting with a gradient of n-heptane:EtOAc (100:0 to 50:50). Colorless solid (52%). MS (ESI): m/z=430.13 [M+H]⁺.

Example 228

3-[3-(3-Cyclopropyl-[1,2,4]oxadiazol-5-yl)-4,7-di-hydro-5H-thieno[2,3-c]pyran-2-ylcarbamoyl]-1,5-dimethyl-1H-pyrazole-4-carboxylic acid

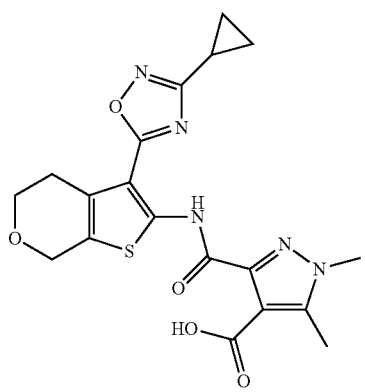 [SMILES: Cc1c(C(=O)O)c(C(=O)Nc2sc3c(c2-c2nc(C4CC4)no2)CCOC3)nn1C]

The title compound was prepared in analogy to example 221, from tert-butyl 3-(3-(3-cyclopropyl-1,2,4-oxadiazol-5-yl)-5,7-dihydro-4H-thieno[2,3-c]pyran-2-ylcarbamoyl)-1,5-dimethyl-1H-pyrazole-4-carboxylate. Colorless solid (80%). MS (ESI): m/z=430.12 [M+H]$^+$.

Intermediates a) tert-Butyl 3-(3-(3-cyclopropyl-1,2,4-oxadiazol-5-yl)-5,7-dihydro-4H-thieno[2,3-c]pyran-2-ylcarbamoyl)-1,5-dimethyl-1H-pyrazole-4-carboxylate The title compound was prepared in analogy to example 225, intermediate, from 3-(3-cyclopropyl-1,2,4-oxadiazol-5-yl)-5,7-dihydro-4H-thieno[2,3-c]pyran-2-amine (example 55, intermediate), 4-(tert-butoxycarbonyl)-1,5-dimethyl-1H-pyrazole-3-carboxylic acid and 2-bromo-1-ethylpyridinium tetrafluoroborate after a reaction time of 82 h. The product was purified by preparative HPLC (Gemini NX column) using a gradient of MeOH:H$_2$O (containing 0.1% formic acid) (20:80 to 98:2). Light brown solid (20%). MS (ESI): m/z=486.18 [M+H]$^+$.

b) 4-(tert-Butoxycarbonyl)-1,5-dimethyl-pyrazole-3-carboxylic acid

To a solution of O3-benzyl O4-tert-butyl 1,5-dimethyl-1H-pyrazole-3,4-dicarboxylate (0.161 g, 487 µmol) in EtOAc (3 mL) and MeOH (3 mL) was added palladium on carbon (10%; 5.19 mg, 48.7 µmol) and the reaction mixture was stirred under a hydrogen atmosphere of 1.5 bar at RT for 3.5 h. The reaction mixture was filtered over a micro-filter and the filtrate was evaporated. Colorless solid (0.106 g; 90%).

c) O3-benzyl O4-tert-butyl 1,5-dimethylpyrazole-3,4-dicarboxylate

To a solution of 3-benzyl 4-tert-butyl 5-methyl-1H-pyrazole-3,4-dicarboxylate (0.42 g, 1.33 mmol) in DMF (6 mL) was added NaH (55% dispersion in mineral oil; 57.9 mg, 1.33 mmol) and the reaction mixture was stirred at RT for 30 min. before MeI (283 mg, 125 µL, 1.99 mmol) was added. Stirring was continued at RT for 3.25 h, then the reaction mixture was poured on saturated aqueous NH$_4$Cl solution and EtOAc and the layers were separated. The aqueous layer was extracted twice with EtOAc. The organic layers were washed twice with H$_2$O and once with brine, dried over MgSO$_4$, filtered, treated with silica gel and evaporated. The compound was purified twice by silica gel chromatography on a 20 g column using a MPLC system eluting with a gradient of n-heptane:EtOAc (100:0 to 50:50). Colorless oil (0.212 g; 48%). MS (ESI): m/z=[M-C$_4$H$_8$]$^+$. Also obtained from this reaction was O3-benzyl O4-tert-butyl 2,5-dimethylpyrazole-3,4-dicarboxylate. Colorless oil (0.155 g; 35%). MS (ESI): m/z=331.5 [M+H]$^+$.

d) O3-benzyl O4-tert-butyl 5-methyl-1H-pyrazole-3,4-dicarboxylate

To a solution of 4-benzyl 1-tert-butyl 2-acetyl-3-aminomaleate (0.5 g, 1.57 mmol; example 221, intermediate c) in EtOH (10 mL) was added hydrazine hydrate (78.4 mg, 76.1 µL, 1.57 mmol) and the clear, colorless solution was heated to reflux for 1.5 h. The reaction mixture was treated with silica gel and evaporated and the compound was purified by silica gel chromatography on a 20 g column using a MPLC system eluting with a gradient of n-heptane: EtOAc (100:0 to 50:50). Colorless solid (0.131 g; 26%). MS (ESI): m/z=315.14 [M–H]$^-$.

Example 229

2-[3-(6-Chloro-pyridin-2-yl)-4,5,6,7-tetrahydrobenzo[b]thiophen-2-ylcarbamoyl]-cyclopent-1-enecarboxylic acid

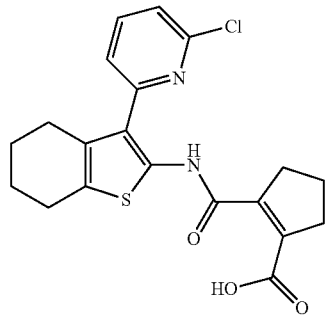 [SMILES: O=C(O)C1=C(C(=O)Nc2sc3c(c2-c2cccc(Cl)n2)CCCC3)CCC1]

The title compound was prepared in analogy to example 113, from methyl 2-[[3-(6-chloro-2-pyridyl)-4,5,6,7-tetrahydrobenzothiophen-2-yl]carbamoyl]cyclopentene-1-carboxylate. The compound was purified by silica gel chromatography using an MPLC (Flashmaster) system eluting with a gradient of CH$_2$Cl$_2$:MeOH (100:0 to 90:10), followed by preparative HPLC (Gemini NX column) with a gradient of MeOH:H$_2$O (containing 0.1% formic acid) (80:20 to 98:2). Yellow solid (7%). MS (ESI): m/z=403.088 [M+H]$^+$.

Intermediates a) Methyl 2-[[3-(6-chloro-2-pyridyl)-4,5,6,7-tetrahydrobenzothiophen-2-yl]carbamoyl]cyclopentene-1-carboxylate To a solution of methyl 2-[(3-iodo-4,5,6,7-tetrahydrobenzothiophen-2-yl)carbamoyl] cyclopentene-1-carboxylate (100 mg, 232 µmol) in DME (4 mL) was added 6-chloropyridine-2-boronic acid pinacol ester (55.5 mg, 232 µmol, CAS RN 652148-92-0) and 2M aqueous Na$_2$CO$_3$ solution (1 mL). The reaction mixture was stirred for 15 min. under argon atmosphere, then Pd(II)acetate (2.6 mg, 11.6 µmol) and PPh$_3$ (6.08 mg, 23.2 µmol) were added. The reaction mixture was stirred at 90° C. for 3 h. The reaction mixture was poured on 30 mL 10% aqueous NaHCO$_3$ solution and 30 mL EtOAc and the layers were separated. The aqueous layer was extracted a second time with 30 mL EtOAc. The organic layers were washed with 30 mL brine, dried over MgSO$_4$, filtered and concentrated under vacuum. The compound was purified by silica gel chromatography on a 20 g column using an MPLC (Flashmaster) system eluting with a gradient of n-heptane:EtOAc (100:0 to 40:60). Yellow foam (38 mg, 39.3%). MS (ESI): m/z=417.102 [M+H]$^+$.

b) Methyl 2-[(3-iodo-4,5,6,7-tetrahydrobenzothiophen-2-yl)carbamoyl]cyclopentene-1-carboxylate To a solution of methyl 2-(4,5,6,7-tetrahydrobenzothiophen-2-ylcarbamoyl)cyclopentene-1-carboxylate (546 mg, 1.79 mmol) in THF (8 mL) was added iodine (681 mg, 2.68 mmol) at 0° C. The reaction mixture was stirred at RT for 3 h. Another batch of iodine (340 mg, 1.34 mmol) was added and the reaction mixture was stirred at RT for 18 h. The reaction mixture was poured on 30 mL 10% aqueous NaHCO$_3$ solution and 30 mL EtOAc and the layers were separated. The aqueous layer was extracted a second time with 30 mL EtOAc. The organic layers were washed with 30 mL brine, dried over MgSO$_4$, filtered and concentrated under vacuum. The compound was purified by silica gel chromatography on a 20 g column using an MPLC (Flashmaster) system eluting with a gradient of n-heptane:EtOAc (100:0 to 75:25). Light yellow solid (384 mg, 49.8%). MS (ESI): m/z=432.013 [M+H]$^+$.

c) Methyl 2-(4,5,6,7-tetrahydrobenzothiophen-2-ylcarbamoyl)cyclopentene-1-carboxylate To a solution of 2-amino-4,5,6,7-tetrahydrobenzo[b]thiophene-3-carboxylic acid (1 g, 5.07 mmol, CAS RN 5936-58-3) in 2-propanol (10 mL) was added oxalic acid (502 mg, 5.58 mmol). The reaction mixture was stirred at 35° C. for 0.5 h. The reaction mixture was cooled down to 0° C., filtered and washed with 3 mL 2-propanol. The filtrate was concentrated under vacuum. The residue (4,5,6,7-tetrahydrobenzothiophen-2-amine) was dissolved in CH$_2$Cl$_2$ (18 mL) and DIPEA (1.97 g, 2.66 ml, 15.2 mmol) was added. Methyl 2-chlorocarbonylcyclopentene-1-carboxylate (preparation see below) was dissolved in 8 mL CH$_2$Cl$_2$ was added and the reaction mixture was stirred at RT for 22 h. The reaction mixture was poured on 30 mL 10% aqueous NaHCO$_3$ solution and 30 mL CH$_2$Cl$_2$ and the layers were separated. The aqueous layer was extracted a second time with 30 mL CH$_2$Cl$_2$. The organic layers were washed with 30 mL brine, dried over MgSO$_4$, filtered and concentrated under vacuum. The compound was purified by silica gel chromatography on a 50 g column using an MPLC system (CombiFlash Companion, Isco Inc.) eluting with a gradient of n-heptane:EtOAc (100:0 to 70:30). Yellow oil (538 mg, 34.7%). MS (ESI): m/z=306.117 [M+H]$^+$.

Preparation of the acid chloride: To a solution of 2-methoxycarbonylcyclopentene-1-carboxylic acid (863 mg, 5.07 mmol, prepared in analogy to Heterocycles, 2009, 77(1), 179) in thionyl chloride (9 ml, 5.07 mmol) was added three drops of DMF. The colorless solution was stirred at 90° C. for 1 h and then concentrated under vacuum. The residue was dissolved in 6 mL toluene and concentrated under vacuum. This was repeated three times to remove all volatiles.

Example 230

2-[3-(5-Chloro-pyridin-2-yl)-4,5,6,7-tetrahydrobenzo[b]thiophen-2-ylcarbamoyl]-cyclopent-1-enecarboxylic acid

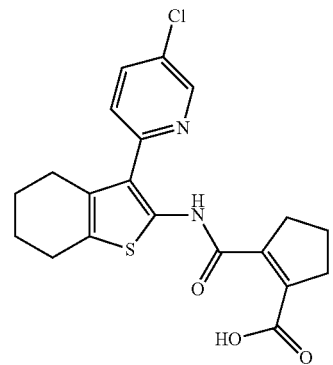 [SMILES: O=C(O)C1=C(C(=O)Nc2sc3c(c2-c2ccc(Cl)cn2)CCCC3)CCC1]

The title compound was prepared in analogy to example 113, from methyl 2-[[3-(5-chloro-2-pyridyl)-4,5,6,7-tetrahydrobenzothiophen-2-yl]carbamoyl]cyclopentene-1-carboxylate. The compound was purified by silica gel chromatography using an MPLC (Flashmaster) system eluting with a gradient of CH$_2$Cl$_2$:MeOH (100:0 to 90:10). The product-containing fractions were concentrated under vacuum and the residue was purified by silica gel chromatography on a 5 g column using an MPLC (Flashmaster) system eluting for 15 min. with EtOAc, 5 min. with CH$_2$Cl$_2$ and then with a gradient of CH$_2$Cl$_2$:MeOH (100:0 to 90:10). Yellow solid (30%). MS (ESI): m/z=403.086 [M+H]$^+$.

Intermediate a) Methyl 2-[[3-(5-chloro-2-pyridyl)-4,5,6,7-tetrahydrobenzothiophen-2-yl]carbamoyl]cyclopentene-1-carboxylate To a solution of 5-chloro-2-iodopyridine (44.4 mg, 185 µmol, CAS RN 244221-57-6) in THF (4 mL) was added isopropylmagnesiumchloride (2M solution in THF, 92.7 µL, 185 µmol) at −40° C. The reaction mixture was stirred for 20 min. at −40° C. Freshly prepared 1M ZnCl$_2$ solution in THF (742 µL, 742 µmol; preparation see below) was added at −40° C. The reaction mixture was stirred at RT for 90 min. A solution of methyl 2-[(3-iodo-4,5,6,7-tetrahydrobenzothiophen-2-yl)carbamoyl]cyclopentene-1-carboxylate (80 mg, 185 µmol, example 229, intermediate b) in THF (4 mL) and tetrakis(triphenylphosphine)palladium(0) (10.7 mg, 9.27 µmol) was added. The reaction mixture was stirred at reflux for 3 h. The reaction mixture was poured on 30 mL 10% aqueous NaHCO$_3$ solution and 30 mL EtOAc and the layers were separated. The aqueous layer was extracted a second time with 30 mL EtOAc. The organic layers were washed with 30 mL brine, dried over MgSO$_4$, filtered and concentrated under vacuum. The compound was purified by silica gel chromatography on a 20 g column using an MPLC (Flashmaster) system eluting with a gradient of n-heptane: EtOAc (100:0 to 70:30). Yellow solid (45 mg, 58.2%). MS (ESI): m/z=417.104 [M+H]+.

1M $ZnCl_2$ solution in THF was prepared by melting solid $ZnCl_2$ under high vacuum by heating with a heat gun. The flask was allowed to cool down and then ventilated with argon. The dry $ZnCl_2$ was then dissolved under argon with the required amount of THF.

Example 231

2-[6,6-Difluoro-3-(4-isopropyl-thiazol-2-yl)-4,5,6,7-tetrahydro-benzo[b]thiophen-2-ylcarbamoyl]-cyclopent-1-enecarboxylic acid

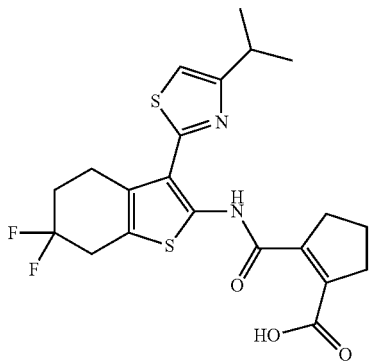 [SMILES: CC(C)c1csc(-c2c(NC(=O)C3=C(C(=O)O)CCC3)sc3c2CCC(F)(F)C3)n1]

The title compound was prepared in analogy to example 127, from 6,6-difluoro-3-(4-isopropylthiazol-2-yl)-5,7-dihydro-4H-benzothiophen-2-amine and 1-cyclopentene-1,2-dicarboxylic anhydride (CAS RN 3205-94-5). The product was purified by preparative HPLC (Gemini NX column) with a gradient of MeOH:$H_2O$ (containing 0.1% formic acid) (80:20 to 98:2). Yellow solid (76%). MS (ESI): m/z=453.111 [M+H]+.

Intermediate a) 6,6-Difluoro-3-(4-isopropylthiazol-2-yl)-5,7-dihydro-4H-benzothiophen-2-amine The title compound was prepared in analogy to example 56, intermediate a, from 2-(4,4-difluorocyclohexylidene)-2-(4-isopropylthiazol-2-yl)acetonitrile, using a gradient of n-heptane:EtOAc (100:0 to 70:30) for the chromatographic purification. Light yellow solid (73%). MS (ESI): m/z=315.080 [M+H]+.

b) 2-(4,4-Difluorocyclohexylidene)-2-(4-isopropylthiazol-2-yl)acetonitrile

The title compound was prepared in analogy to example 56, intermediate b, from difluorocyclohexanone (CAS RN 22515-18-0) and 2-(4-isopropylthiazol-2-yl)acetonitrile (Ukrorgsyntez Ltd). The compound was purified by silica gel chromatography using an MPLC system (CombiFlash Companion, Isco Inc.) eluting with a gradient of n-heptane: EtOAc (100:0 to 50:50). Light yellow solid (76%). MS (ESI): m/z=283.107 [M+H]+.

Example 232

3-[6,6-Difluoro-3-(4-isopropyl-thiazol-2-yl)-4,5,6,7-tetrahydro-benzo[b]thiophen-2-ylcarbamoyl]-bicyclo[2.2.2]oct-2-ene-2-carboxylic acid

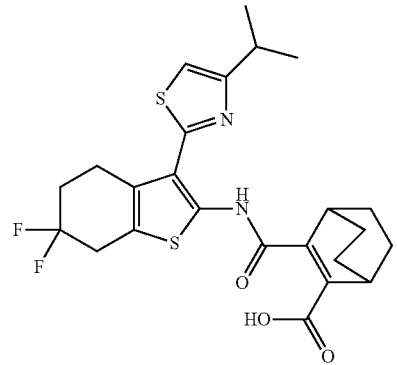 [SMILES: CC(C)c1csc(-c2c(NC(=O)C3=C(C(=O)O)C4CCC3CC4)sc3c2CCC(F)(F)C3)n1]

The title compound was prepared in analogy to example 127, from 6,6-difluoro-3-(4-isopropylthiazol-2-yl)-5,7-dihydro-4H-benzothiophen-2-amine (example 231, intermediate a) and bicyclo[2.2.2]oct-2-ene-2,3-dicarboxylic anhydride (CAS RN 151813-29-5). The product was purified by preparative HPLC (Gemini NX column) with a gradient of MeOH:$H_2O$ (containing 0.1% formic acid) (80:20 to 98:2). Yellow solid (70%). MS (ESI): m/z=493.143 [M+H]+.

Example 233

2-[6,6-Difluoro-3-(4-isopropyl-thiazol-2-yl)-4,5,6,7-tetrahydro-benzo[b]thiophen-2-ylcarbamoyl]-cyclohex-1-enecarboxylic acid

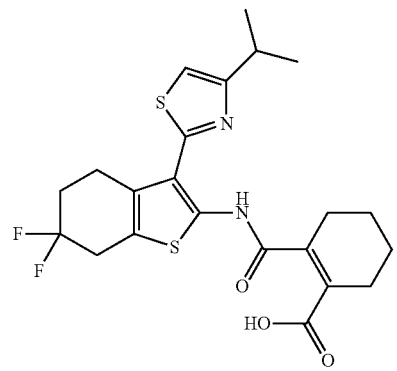 [SMILES: CC(C)c1csc(-c2c(NC(=O)C3=C(C(=O)O)CCCC3)sc3c2CCC(F)(F)C3)n1]

The title compound was prepared in analogy to example 127, from 6,6-difluoro-3-(4-isopropylthiazol-2-yl)-5,7-dihydro-4H-benzothiophen-2-amine (example 231, intermediate a) and 1-cyclohexene-1,2-dicarboxylic anhydride (CAS RN 2426-02-0). The product was purified by preparative HPLC (Gemini NX column) with a gradient of MeOH:$H_2O$ (containing 0.1% formic acid) (80:20 to 98:2). Light yellow solid (52%). MS (ESI): m/z=467.127 [M+H]+.

Example 234

2-[3-(4-Methyl-thiazol-2-yl)-4,5,6,7-tetrahydro-benzo[b]thiophen-2-ylcarbamoyl]-nicotinic acid

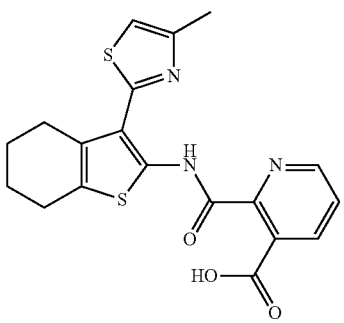 [SMILES: Cc1csc(-c2c(NC(=O)c3ncccc3C(=O)O)sc3c2CCCC3)n1]

The title compound was prepared in analogy to example 221, from tert-butyl 2-(3-(4-methylthiazol-2-yl)-4,5,6,7-tetrahydrobenzo[b]thiophen-2-ylcarbamoyl)nicotinate. During evaporation of the solvent precipitation occurred. The suspension was stored in the fridge for 60 h, filtered and the filter cake washed with EtOAc and dried in high vacuum. Light brown solid (65%). MS (ESI): m/z=400.08 [M+H]$^+$.

Intermediate tert-Butyl 2-(3-(4-methylthiazol-2-yl)-4,5,6,7-tetrahydrobenzo[b]thiophen-2-ylcarbamoyl)nicotinate The title compound was prepared in analogy to example 225, intermediate, from 3-(4-methylthiazol-2-yl)-4,5,6,7-tetrahydrobenzo[b]thiophen-2-amine (0.2 g, 799 μmol; example 63, intermediate b) in CH$_2$Cl$_2$ (3 mL) and 3-(tert-butoxycarbonyl)picolinic acid (178 mg, 799 μmol; prepared by reaction of furo[3,4-b]pyridine-5,7-dione (CAS RN 699-98) with potassium tert-butoxide in tert-butyl alcohol) after a reaction time of 19 h at RT. The compound was purified by silica gel chromatography on a 20 g column using an MPLC (ISCO) system eluting with a gradient of n-heptane:EtOAc (100:0 to 50:50). Light brown solid (57%). MS (ESI): m/z=456.14 [M+H]$^+$.

Example 235

2-[6,6-Difluoro-3-(4-methyl-thiazol-2-yl)-4,5,6,7-tetrahydro-benzo[b]thiophen-2-ylcarbamoyl]-nicotinic acid

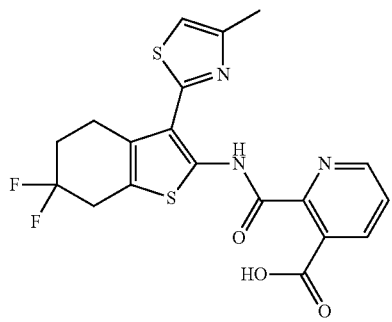 [SMILES: Cc1csc(-c2c(NC(=O)c3ncccc3C(=O)O)sc3c2CCC(F)(F)C3)n1]

The title compound was prepared in analogy to example 221, from tert-butyl 2-[[6,6-difluoro-3-(4-methylthiazol-2-yl)-5,7-dihydro-4H-benzothiophen-2-yl]carbamoyl]pyridine-3-carboxylate after a reaction time of 23 h at RT. The solution was poured on 1M aqueous HCl solution and EtOAc and the layers were separated. The aqueous layer was extracted twice with EtOAc. The organic layers were washed once with brine, dried over MgSO$_4$, filtered and evaporated until a precipitation started. The suspension was stored in the fridge for 60 h, filtered, and the filter cake washed with EtOAc. Light brown solid (58%). MS (ESI): m/z=426.06 [M+H]$^+$.

Intermediate tert-Butyl 2-[[6,6-difluoro-3-(4-methylthiazol-2-yl)-5,7-dihydro-4H-benzothiophen-2-yl]carbamoyl]pyridine-3-carboxylate The title compound was prepared in analogy to example 225, intermediate, from 6,6-difluoro-3-(4-methyl-thiazol-2-yl)-4,5,6,7-tetrahydro-benzo[b]thiophen-2-ylamine (example 150, intermediate a) and 3-(tert-butoxycarbonyl)picolinic acid (prepared by reaction of furo[3,4-b]pyridine-5,7-dione (CAS RN 699-98) with potassium tert-butoxide in tert-butyl alcohol). The compound was purified by silica gel chromatography on a 20 g column using an MPLC (ISCO) system eluting with a gradient of n-heptane:EtOAc (100:0 to 50:50). Light brown solid (57%). MS (ESI): m/z=456.14 [M+H]$^+$.

Example 236

2-[3-(3-Cyclopropyl-[1,2,4]oxadiazol-5-yl)-5,5-dimethyl-4,5,6,7-tetrahydro-benzo[b]thiophen-2-ylcarbamoyl]-cyclopent-1-enecarboxylic acid

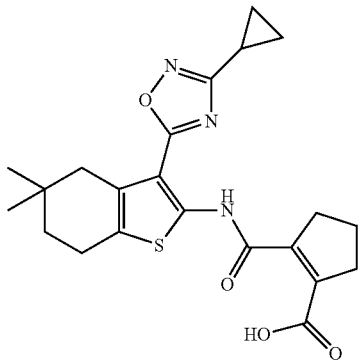 [SMILES: CC1(C)CCc2sc(NC(=O)C3=C(C(=O)O)CCC3)c(-c3nc(C4CC4)no3)c2C1]

The title compound was prepared in analogy to example 127, from 3-(3-cyclopropyl-1,2,4-oxadiazol-5-yl)-5,5-dimethyl-6,7-dihydro-4H-benzothiophen-2-amine and 1-cyclopentene-1,2-dicarboxylic anhydride (CAS RN 3205-94-5). The compound was purified by preparative HPLC (Phenomenex Gemini column) with a gradient of CH$_3$CN:H$_2$O (with 0.1% formic acid) (50:50 to 95:5). Yellow solid (79%). MS (ESI): m/z=428.164 [M+H]$^+$.

Intermediates a) 3-(3-Cyclopropyl-1,2,4-oxadiazol-5-yl)-5,5-dimethyl-6,7-dihydro-4H-benzothiophen-2-amine The title compound was prepared in analogy to example 127, from 2-(3-cyclopropyl-1,2,4-oxadiazol-5-yl)-2-(3,3-dimethylcyclohexylidene)acetonitrile after a reaction time of 5 h at 65° C. The compound was purified by preparative HPLC (Gemini NX) with a gradient of MeOH:H$_2$O (with 0.1% formic acid) (80:20 to 98:2). Off-white solid (41%). MS (ESI): m/z=290.133 [M+H]$^+$.

b) 2-(3-cyclopropyl-1,2,4-oxadiazol-5-yl)-2-(3,3-dimethylcyclohexylidene)acetonitrile The title compound was prepared in analogy to example 56, intermediate b, from 3,3-dimethylcyclohexanone (CAS RN 2979-19-3) and 2-(3-cyclopropyl-1,2,4-oxadiazol-5-yl)acetonitrile (Princeton BioMolecular Research, Inc.) after a reaction time of 3 h at 110° C. The compound was purified by silica gel chromatography on a 20 g column using an MPLC system (CombiFlash Companion, Isco Inc.) eluting with a gradient of n-heptane:EtOAc (100:0 to 20:80). Colorless liquid (90%). MS (ESI): m/z=256.146 [M−H]⁻.

Example 237

2-[3-(3-Cyclopropyl-[1,2,4]oxadiazol-5-yl)-5,5-dimethyl-4,5,6,7-tetrahydro-benzo[b]thiophen-2-ylcarbamoyl]-cyclohex-1-enecarboxylic acid

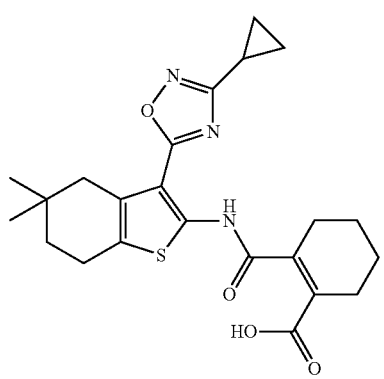 [SMILES: CC1(C)CCc2sc(NC(=O)C3=C(C(=O)O)CCCC3)c(-c3nc(C4CC4)no3)c2C1]

The title compound was prepared in analogy to example 127, from 3-(3-cyclopropyl-1,2,4-oxadiazol-5-yl)-5,5-dimethyl-6,7-dihydro-4H-benzothiophen-2-amine (example 236, intermediate a) and 1-cyclohexene-1,2-dicarboxylic anhydride (CAS RN 2426-02-0). The compound was purified by preparative HPLC (Phenomenex Gemini column) with a gradient of $CH_3CN:H_2O$ (with 0.1% formic acid) (50:50 to 95:5). Off-white solid (70%). MS (ESI): m/z=442.179 [M+H]⁺.

Example 238

3-[3-(3-Cyclopropyl-[1,2,4]oxadiazol-5-yl)-5,5-dimethyl-4,5,6,7-tetrahydro-benzo[b]thiophen-2-ylcarbamoyl]-bicyclo[2.2.2]oct-2-ene-2-carboxylic acid

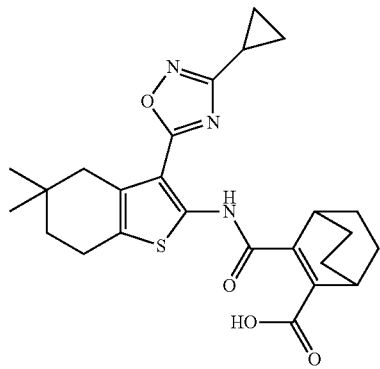 [SMILES: CC1(C)CCc2sc(NC(=O)C3=C(C(=O)O)C4CCC3CC4)c(-c3nc(C4CC4)no3)c2C1]

The title compound was prepared in analogy to example 127, from 3-(3-cyclopropyl-1,2,4-oxadiazol-5-yl)-5,5-dimethyl-6,7-dihydro-4H-benzothiophen-2-amine (example 236, intermediate a) and bicyclo[2.2.2]oct-2-ene-2,3-dicarboxylic anhydride (CAS RN 151813-29-5). The compound was purified by preparative HPLC (Phenomenex Gemini column) with a gradient of $CH_3CN:H_2O$ (with 0.1% formic acid) (50:50 to 95:5). Yellow solid (81%). MS (ESI): m/z=468.195 [M+H]⁺.

Example 239

2-[3-(3-Cyclopropyl-[1,2,4]oxadiazol-5-yl)-4,5,6,7-tetrahydro-benzo[b]thiophen-2-ylcarbamoyl]-cyclohex-1-enecarboxylic acid

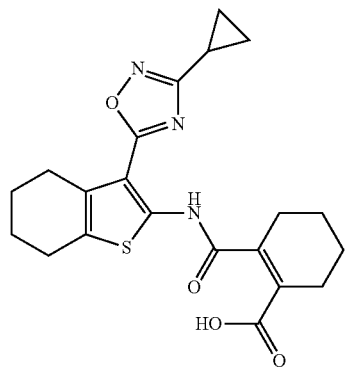 [SMILES: O=C(O)C1=C(C(=O)Nc2sc3c(c2-c2nc(C4CC4)no2)CCCC3)CCCC1]

The title compound was prepared in analogy to example 127, from 3-(3-cyclopropyl-1,2,4-oxadiazol-5-yl)-4,5,6,7-tetrahydrobenzo[b]thiophen-2-amine (example 27, intermediate b) and 1-cyclohexene-1,2-dicarboxylic anhydride (CAS RN 2426-02-0). During evaporation a suspension formed which was filtered. The filter cake was washed with EtOAc and dried under high vacuum. Light brown solid (74%). MS (ESI): m/z=414.15 [M+H]⁺.

Example 240

2-[3-(3-Cyclopropyl-[1,2,4]oxadiazol-5-yl)-6-methoxy-6-methyl-4,5,6,7-tetrahydro-benzo[b]thiophen-2-ylcarbamoyl]-cyclopent-1-enecarboxylic acid

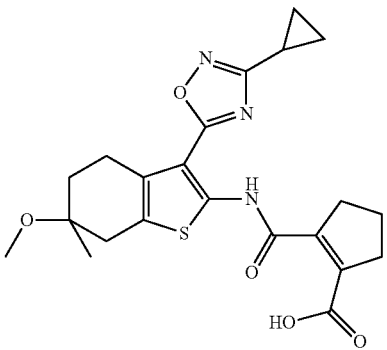 [SMILES: COC1(C)CCc2c(sc(NC(=O)C3=C(C(=O)O)CCC3)c2-c2nc(C3CC3)no2)C1]

The title compound was prepared in analogy to example 127, from 3-(3-cyclopropyl-1,2,4-oxadiazol-5-yl)-6-methoxy-6-methyl-4,5,6,7-tetrahydrobenzo[b]thiophen-2-amine and 1-cyclopentene-1,2-dicarboxylic anhydride (CAS RN 3205-94-5). During evaporation a suspension formed which was filtered. The filter cake was washed with EtOAc and dried under high vacuum. Yellow solid (58%). MS (ESI): m/z=444.16 [M+H]$^+$.

Intermediates 3-(3-Cyclopropyl-1,2,4-oxadiazol-5-yl)-6-methoxy-6-methyl-4,5,6,7-tetrahydrobenzo[b]thiophen-2-amine The title compound was prepared in analogy to example 55, intermediate, from 4-methoxy-4-methylcyclohexanone (CAS RN 23438-15-5) and 2-(3-cyclopropyl-1,2,4-oxadiazol-5-yl)acetonitrile (Princeton BioMolecular Research, Inc.) and elemental sulfur. The compound was purified by silica gel chromatography on a 20 g column using an MPLC system (CombiFlash Companion, Isco Inc.) eluting with a gradient of n-heptane:EtOAc (100:0 to 75:25). Light yellow solid (73%). MS (ESI): m/z=306.127 [M+H]$^+$.

Example 241

2-[6,6-Difluoro-3-(3-trifluoromethyl-[1,2,4]oxadiazol-5-yl)-4,5,6,7-tetrahydro-benzo[b]thiophen-2-ylcarbamoyl]-nicotinic acid

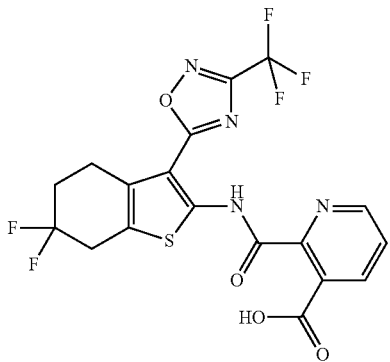 [SMILES: O=C(O)c1cccnc1C(=O)Nc1sc2c(c1-c1nc(C(F)(F)F)no1)CCC(F)(F)C2]

To a solution of benzyl 2-(6,6-difluoro-3-(3-(trifluoromethyl)-1,2,4-oxadiazol-5-yl)-4,5,6,7-tetrahydrobenzo[b]thiophen-2-ylcarbamoyl)nicotinate (0.022 g, 39.0 µmol) in EtOAc (1 mL) and MeOH (1 mL) was treated with palladium on carbon (10%, 2.07 mg, 19.5 µmol) and the suspension was hydrogenated at RT at a pressure of 1.5 bar for 18 h. The suspension was filtered over a microfilter and evaporated. The residue was dissolved in EtOAc (0.5 mL) and MeOH (0.5 mL) and palladium on carbon (10%, 2.07 mg, 19.5 µmol) was added. The reaction mixture was hydrogenated at RT at a pressure of 1.5 bar for 6 h. The suspension was filtered over a microfilter and evaporated. The product was purified on a preparative HPLC (Gemini NX column) using a gradient of MeOH:H$_2$O (containing 0.1% formic acid) (20:80 to 98:2). Light brown solid (8 mg; 43.3%). MS (ESI): m/z=473.03 [M−H]$^-$.

Intermediate

Benzyl 2-(3-(3-(trifluoromethyl)-1,2,4-oxadiazol-5-yl)-4,5,6,7-tetrahydrobenzo[b]thiophen-2-ylcarbamoyl)nicotinate The title compound was prepared in analogy to example 112, from benzyl 2-chlorocarbonylpyridine-3-carboxylate (prepared from 3-(benzyloxycarbonyl)picolinic acid which in turn was obtained from reaction of furo[3,4-b]pyridine-5,7-dione (CAS RN 699-98) with sodium benzyloxide (CAS RN 20194-18-7)) and 3-(3-(trifluoromethyl)-1,2,4-oxadiazol-5-yl)-4,5,6,7-tetrahydrobenzo[b]thiophen-2-amine (example 147, intermediate) after stirring for 144 h at RT. The compound was purified by silica gel chromatography on a 20 g column using an MPLC system eluting with a gradient of n-heptane:EtOAc (100:0 to 70:30). Light yellow solid (15%). MS (ESI): m/z=529.11 [M+H]$^+$.

Example 242

2-[3-(3-Trifluoromethyl-[1,2,4]oxadiazol-5-yl)-4,5,6,7-tetrahydro-benzo[b]thiophen-2-ylcarbamoyl]-nicotinic acid

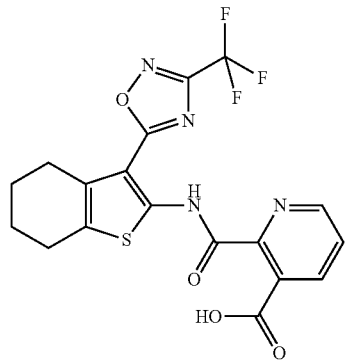 [SMILES: O=C(O)c1cccnc1C(=O)Nc1sc2c(c1-c1nc(C(F)(F)F)no1)CCCC2]

The title compound was prepared in analogy to example 241, from benzyl 2-(3-(3-(trifluoromethyl)-1,2,4-oxadiazol-5-yl)-4,5,6,7-tetrahydrobenzo[b]thiophen-2-ylcarbamoyl)nicotinate. The product was purified on a preparative HPLC (Gemini NX column) using a gradient of MeOH:H$_2$O (containing 0.1% formic acid) (20:80 to 98:2). Yellow solid (45%). MS (ESI): m/z=437.05 [M−H]$^-$.

Intermediate

Benzyl 2-(3-(3-(trifluoromethyl)-1,2,4-oxadiazol-5-yl)-4,5,6,7-tetrahydrobenzo[b]thiophen-2-ylcarbamoyl)nicotinate The title compound was prepared in analogy to example 112, from benzyl 2-chlorocarbonylpyridine-3-carboxylate (prepared from 3-(benzyloxycarbonyl)picolinic acid which in turn was obtained from reaction of furo[3,4-b]pyridine-5,7-dione (CAS RN 699-98) with sodium benzyloxide (CAS RN 20194-18-7)) and 3-(3-(trifluoromethyl)-1,2,4-oxadiazol-5-yl)-4,5,6,7-tetrahydrobenzo[b]thiophen-2-amine (example 61, intermediate a). The compound was purified by silica gel chromatography on a 20 g column using an MPLC system eluting with a gradient of n-heptane:EtOAc (100:0 to 70:30). Light yellow solid (15%). MS (ESI): m/z=529.11 [M+H]+.

Examples 243 and 244

(−)-2-[3-(3-Cyclopropyl-[1,2,4]oxadiazol-5-yl)-6-methoxy-6-methyl-4,5,6,7-tetrahydro-benzo[b]thiophen-2-ylcarbamoyl]-cyclopent-1-enecarboxylic acid and (+)-2-[3-(3-Cyclopropyl-[1,2,4]oxadiazol-5-yl)-6-methoxy-6-methyl-4,5,6,7-tetrahydro-benzo[b]thiophen-2-ylcarbamoyl]-cyclopent-1-enecarboxylic acid

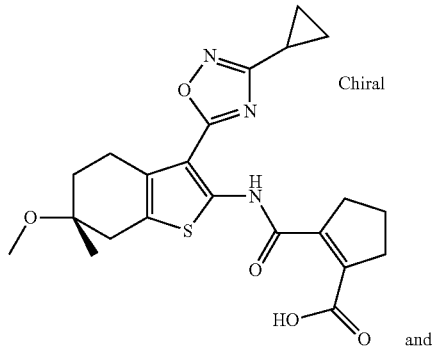

and

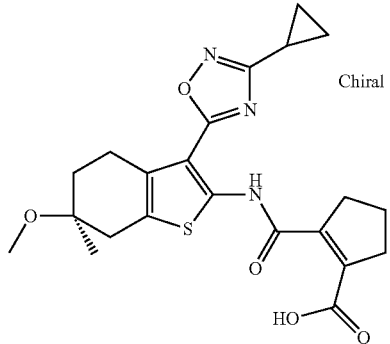

The title compounds were prepared by chiral separation of 2-(3-(3-cyclopropyl-1,2,4-oxadiazol-5-yl)-6-methoxy-6-methyl-4,5,6,7-tetrahydrobenzo[b]thiophen-2-ylcarbamoyl) cyclopent-1-enecarboxylic acid (example 240) using a Reprosil Chiral NRR column with (EtOH+0.5% HCOOH): n-heptane (40:60) as a eluant.

(−)-2-[3-(3-Cyclopropyl-[1,2,4]oxadiazol-5-yl)-6-methoxy-6-methyl-4,5,6,7-tetrahydro-benzo[b]thiophen-2-ylcarbamoyl]-cyclopent-1-enecarboxylic acid: Yellow solid (37%). MS (ESI): m/z=444.16 [M+H]+.

(+)-2-[3-(3-Cyclopropyl-[1,2,4]oxadiazol-5-yl)-6-methoxy-6-methyl-4,5,6,7-tetrahydro-benzo[b]thiophen-2-ylcarbamoyl]-cyclopent-1-enecarboxylic acid: Yellow solid (40%). MS (ESI): m/z=444.16 [M+H]+.

Examples 245 and 246

5-[3-(3-Cyclopropyl-[1,2,4]oxadiazol-5-yl)-4,5,6,7-tetrahydro-benzo[b]thiophen-2-ylcarbamoyl]-3,6-dihydro-2H-pyran-4-carboxylic acid and 4-[3-(3-Cyclopropyl-[1,2,4]oxadiazol-5-yl)-4,5,6,7-tetrahydro-benzo[b]thiophen-2-ylcarbamoyl]-5,6-dihydro-2H-pyran-3-carboxylic acid

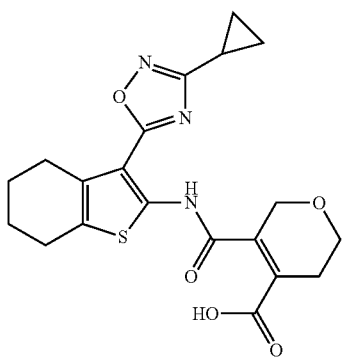

and

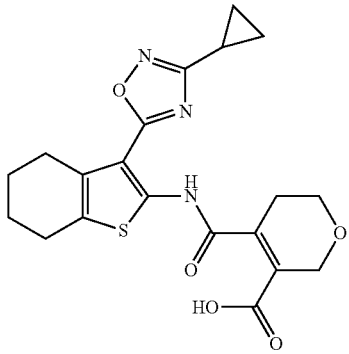

The title compounds were prepared in analogy to example 113, from ethyl 5-[[3-(3-cyclopropyl-1,2,4-oxadiazol-5-yl)-4,5,6,7-tetrahydrobenzothiophen-2-yl]carbamoyl]-3,6-dihydro-2H-pyran-4-carboxylate and subsequent separation of the position isomers by preparative HPLC (Chiralpak-AD column) using an isocratic mixture of EtOH (+0.5% formic acid):n-heptane (3:7). The structures of the position isomers were determined by crystallography.

First eluting isomer: 5-[3-(3-Cyclopropyl-[1,2,4]oxadiazol-5-yl)-4,5,6,7-tetrahydro-benzo[b]thiophen-2-ylcarbamoyl]-3,6-dihydro-2H-pyran-4-carboxylic acid. Colorless solid (49%). MS (ESI): m/z=416.13 [M+H]+.

Second eluting isomer: 4-[3-(3-Cyclopropyl-[1,2,4]oxadiazol-5-yl)-4,5,6,7-tetrahydro-benzo[b]thiophen-2-ylcarbamoyl]-5,6-dihydro-2H-pyran-3-carboxylic acid. Colorless solid (34%). MS (ESI): m/z=416.13 [M+H]+.

Intermediates a) Ethyl 5-[[3-(3-cyclopropyl-1,2,4-oxadiazol-5-yl)-4,5,6,7-tetrahydrobenzothiophen-2-yl]carbamoyl]-3,6-dihydro-2-1-1-pyran-4-carboxylate The title compound was prepared in analogy to example 112, from ethyl 5-chlorocarbonyl-3,6-dihydro-2H-pyran-4- carboxylate (prepared from 4-(ethoxycarbonyl)-5,6-dihydro-2H-pyran-3-carboxylic acid in analogy to example 112) and 3-(3-cyclopropyl-1,2,4-oxadiazol-5-yl)-4,5,6,7-tetrahydrobenzo[b]thiophen-2-amine (example 27, intermediate b). The compound was purified three times by silica gel chromatography, twice on a 50 g column and once on a 120 g column using an MPLC system eluting with a gradient of n-heptane:EtOAc (100:0 to 60:40). The product-containing fractions were evaporated until a suspension formed. The suspension was filtered, the filter cake washed with n-heptane and dried in high vacuum. Light yellow solid (1.169 g; 34.4%). MS (ESI): m/z=444.6 [M+H]+.

b) 4-(Ethoxycarbonyl)-5,6-dihydro-2H-pyran-3-carboxylic acid

A mixture of acetic anhydride (5.19 g, 4.8 mL, 50.9 mmol), DIPEA (6.58 g, 8.89 mL, 50.9 mmol) and sodium formate (5.19 g, 76.3 mmol) was stirred at RT for 1 h. A solution of ethyl 5-(trifluoromethylsulfonyloxy)-3,6-dihydro-2H-pyran-4-carboxylate (8.6 g, 25.4 mmol; prepared according to WO2010038167) in DMF (50 mL) was added dropwise, followed by the addition of palladium (II) acetate (286 mg, 1.27 mmol) and LiCl (3.24 g, 76.3 mmol). After stirring at RT for 1.5 h the black suspension was poured on 2M aqueous HCl solution (100 mL) and EtOAc (100 mL) and the layers were separated. The aqueous layer was extracted twice with EtOAc (100 mL). The organic layers were washed twice with H2O and once with brine, dried over MgSO4, filtered, treated with silica gel and evaporated. The compound was purified by silica gel chromatography on a 120 g column using an MPLC system eluting with a gradient of CH2Cl2:MeOH (100:0 to 80:20). Light brown oil (4.14 g; 81.3%). MS (ESI): m/z=199.06 [M−H]−.

Example 247

2-[3-(3-Cyclopropyl-[1,2,4]oxadiazol-5-yl)-6,6-dioxo-4,5,6,7-tetrahydro-6λ6-thieno[2,3-c]thiopyran-2-ylcarbamoyl]-cyclopent-1-enecarboxylic acid

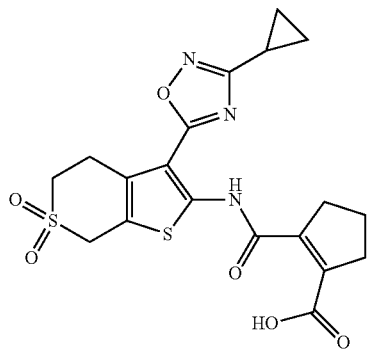 [SMILES: O=C(O)C1=C(C(=O)Nc2sc3c(c2-c2nc(C4CC4)no2)CCS(=O)(=O)C3)CCC1]

The title compound was prepared in analogy to example 127, from 3-(3-cyclopropyl-1,2,4-oxadiazol-5-yl)-6,6-dioxo-5,7-dihydro-4H-thieno[2,3-c]thiopyran-2-amine and 1-cyclopentene-1,2-dicarboxylic anhydride (CAS RN 3205-94-5). The compound was purified by preparative HPLC (Phenomenex Gemini column) with a gradient of CH3CN:H2O (with 0.1% formic acid) (50:50 to 95:5). Brown solid (6%). MS (ESI): m/z=450.077 [M+H]+.

Intermediate 3-(3-Cyclopropyl-1,2,4-oxadiazol-5-yl)-6,6-dioxo-5,7-dihydro-4H-thieno[2,3-c]thiopyran-2-amine The title compound was prepared in analogy to example 55, intermediate, from 1,1-dioxothian-4-one (CAS RN 17396-35-9), 2-(3-cyclopropyl-1,2,4-oxadiazol-5-yl)acetonitrile (Princeton BioMolecular Research, Inc.) and elemental sulfur. The compound was purified by silica gel chromatography on a 20 g column using an MPLC system (CombiFlash Companion, Isco Inc.) eluting with a gradient of n-heptane:EtOAc (100:0 to 60:40). Off-white solid (68%). MS (ESI): m/z=310.031 [M−H]−.

Example 248

2-{2-[(2-Carboxy-cyclopent-1-enecarbonyl)-amino]-6,6-difluoro-4,5,6,7-tetrahydro-benzo[b]thiophen-3-yl}-thiazole-4-carboxylic acid ethyl ester

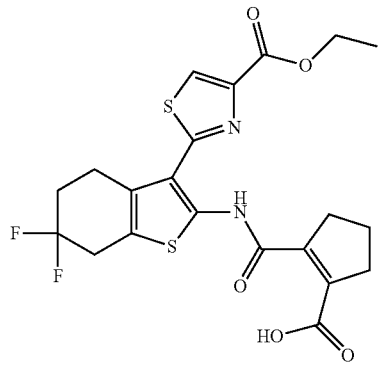 [SMILES: CCOC(=O)c1csc(-c2c(NC(=O)C3=C(C(=O)O)CCC3)sc3c2CCC(F)(F)C3)n1]

The title compound was prepared in analogy to example 127, from ethyl 2-(2-amino-6,6-difluoro-5,7-dihydro-4H-benzothiophen-3-yl)thiazole-4-carboxylate and 1-cyclopentene-1,2-dicarboxylic anhydride (CAS RN 3205-94-5). The compound was purified by preparative HPLC (Phenomenex Gemini column) with a gradient of CH3CN:H2O (with 0.1% formic acid) (50:50 to 95:5). Light brown solid (18.1 mg, 18.5%). MS (ESI): m/z=483.086 [M+H]+.

Intermediates a) Ethyl 2-(2-amino-6,6-difluoro-5,7-dihydro-4H-benzothiophen-3-yl)thiazole-4-carboxylate The title compound was prepared in analogy to example 56, intermediate a, from ethyl 2-[cyano-(4,4-difluorocyclohexylidene)methyl]thiazole-4-carboxylate. The compound was purified by silica gel chromatography using an MPLC system (CombiFlash Companion, Isco Inc.) eluting with a gradient of n-heptane:EtOAc (100:0 to 50:50). Light yellow solid (21%). MS (ESI): m/z=345.054 [M+H]+.

b) Ethyl 2-[cyano-(4,4-difluorocyclohexylidene)methyl]thiazole-4-carboxylate

The title compound was prepared in analogy to example 56, intermediate b, from 4,4-difluorocyclohexanone (CAS RN 22515-18-0) and ethyl 2-(cyanomethyl)thiazole-4-carboxylate (Enamine Ltd.). The compound was purified by silica gel chromatography on a 20 g column using an MPLC system (CombiFlash Companion, Isco Inc.) eluting with a gradient of n-heptane: EtOAc (100:0 to 80:20). Off-white solid (86%). MS (ESI): m/z=313.082 [M+H]+.

Examples 249 and 250

2-[(S)-3-(3-Cyclopropyl-[1,2,4]oxadiazol-5-yl)-6-fluoro-4,5,6,7-tetrahydro-benzo[b]thiophen-2-ylcarbamoyl]-cyclohex-1-enecarboxylic acid and 2-[(R)-3-(3-Cyclopropyl-[1,2,4]oxadiazol-5-yl)-6-fluoro-4,5,6,7-tetrahydro-benzo[b]thiophen-2-ylcarbamoyl]-cyclohex-1-enecarboxylic acid

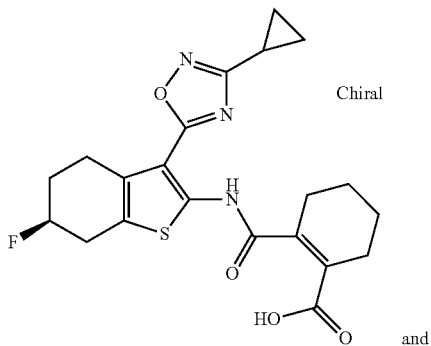

and

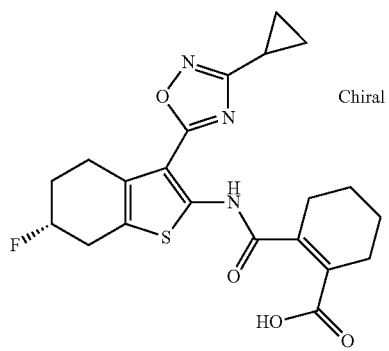

The title compounds were obtained by chiral separation of 2-[3-(3-cyclopropyl-[1,2,4]oxadiazol-5-yl)-6-fluoro-4,5,6,7-tetrahydro-benzo[b]thiophen-2-ylcarbamoyl]-cyclohex-1-enecarboxylic acid (example 203) using a Chiralpak AD-H column using an isocratic mixture of EtOH (+0.5% HCOOH):n-heptane (40:60).

First eluting enantiomer: Light brown solid (32%). MS (ESI): m/z=430.12 [M−H]−.

Second eluting enantiomer: Light brown solid (0.011 g; 27%). MS (ESI): m/z=430.12 [M−H]−.

Example 251 and 252

5-[3-(3-Cyclopropyl-[1,2,4]oxadiazol-5-yl)-6,6-difluoro-4,5,6,7-tetrahydro-benzo[b]thiophen-2-ylcarbamoyl]-3,6-dihydro-2H-pyran-4-carboxylic acid and 4-[3-(3-Cyclopropyl-[1,2,4]oxadiazol-5-yl)-6,6-difluoro-4,5,6,7-tetrahydro-benzo[b]thiophen-2-ylcarbamoyl]-5,6-dihydro-2H-pyran-3-carboxylic acid

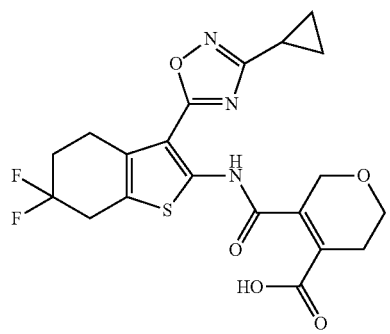

and

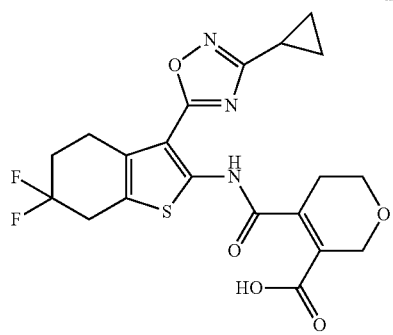

The title compounds were prepared in analogy to example 113, from ethyl 5-[[3-(3-cyclopropyl-1,2,4-oxadiazol-5-yl)-6,6-difluoro-5,7-dihydro-4H-benzothiophen-2-yl]carbamoyl]-3,6-dihydro-2H-pyran-4-carboxylate and subsequent separation of the position isomers by preparative HPLC (Chiralpak-AD column) using a isocratic mixture of EtOH (+0.5% formic acid):n-heptane (40:60). The structures of the position isomers were determined by crystallography.

5-[3-(3-Cyclopropyl-[1,2,4]oxadiazol-5-yl)-6,6-difluoro-4,5,6,7-tetrahydro-benzo[b]thiophen-2-ylcarbamoyl]-3,6-dihydro-2H-pyran-4-carboxylic acid: Light yellow solid (39%) MS (ESI): m/z=452.1084 [M+H]+.

4-[3-(3-Cyclopropyl-[1,2,4]oxadiazol-5-yl)-6,6-difluoro-4,5,6,7-tetrahydro-benzo[b]thiophen-2-ylcarbamoyl]-5,6-dihydro-2H-pyran-3-carboxylic acid: Light yellow solid (32%) MS (ESI): m/z=452.1090 [M+H]+.

Intermediate

Ethyl 5-[[3-(3-cyclopropyl-1,2,4-oxadiazol-5-yl)-6,6-difluoro-5,7-dihydro-4H-benzothiophen-2-yl]carbamoyl]-3,6-dihydro-2H-pyran-4-carboxylate The title compound was prepared in analogy to example 112, from 3-(3-cyclopropyl-[1,2,4]oxadiazol-5-yl)-6,6-difluoro-4,5,6,7-tetrahydro-benzo[b]-thiophen-2-ylamine (example 144, intermediate) and ethyl 5-chlorocarbonyl-3,6-dihydro-2H-pyran-4-carboxylate (prepared in analogy to example 112, from 4-(ethoxycarbonyl)-5,6-dihydro-2H-pyran-3-carboxylic acid(examples 246247, intermediate b). The compound was purified by silica gel chromatography on a 20 g column using an MPLC system eluting with a gradient of n-heptane:EtOAc (100:0 to 60:40). Light yellow waxy solid (16%). MS (ESI): m/z=480.1406 [M+H]$^+$.

Examples 253 and 254

4-[6,6-Difluoro-3-(4-methyl-thiazol-2-yl)-4,5,6,7-tetrahydro-benzo[b]thiophen-2-ylcarbamoyl]-5,6-dihydro-2H-pyran-3-carboxylic acid and 5-[6,6-Difluoro-3-(4-methyl-thiazol-2-yl)-4,5,6,7-tetrahydro-benzo[b]thiophen-2-ylcarbamoyl]-3,6-dihydro-2H-pyran-4-carboxylic acid

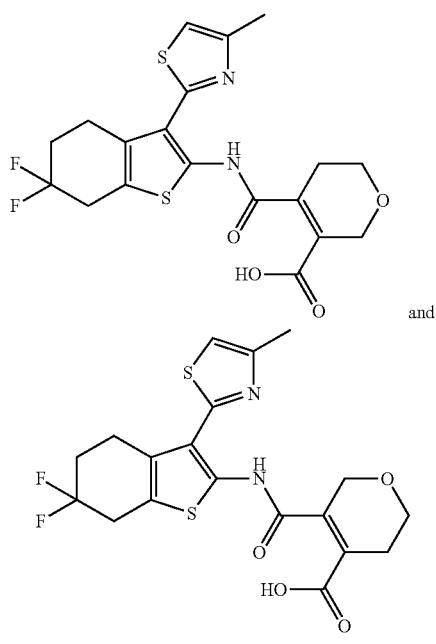

and

The title compounds were prepared in analogy to example 113, from ethyl 4-[[6,6-difluoro-3-(4-methylthiazol-2-yl)-5,7-dihydro-4H-benzothiophen-2-yl]carbamoyl]-3,6-dihydro-2H-pyran-5-carboxylate and subsequent separation of the position isomers preparative Chiralpak-AD chiral column using a isocratic mixture of EtOH (+0.5% formic acid):n-heptane (3:7). The structures of the position isomers were tentatively assigned.

4-[6,6-Difluoro-3-(4-methyl-thiazol-2-yl)-4,5,6,7-tetrahydro-benzo[b]thiophen-2-ylcarbamoyl]-5,6-dihydro-2H-pyran-3-carboxylic acid. Light yellow solid (35%). MS (ESI): m/z=441.0756 [M+H]$^+$.

5-[6,6-Difluoro-3-(4-methyl-thiazol-2-yl)-4,5,6,7-tetrahydro-benzo[b]thiophen-2-ylcarbamoyl]-3,6-dihydro-2H-pyran-4-carboxylic acid. Yellow solid (31%). MS (ESI): m/z=441.0754 [M+H]$^+$.

Intermediate

Ethyl 4-[[6,6-difluoro-3-(4-methylthiazol-2-yl)-5,7-dihydro-4H-benzothiophen-2-yl]carbamoyl]-3,6-dihydro-2H-pyran-5-carboxylate The title compound was prepared in analogy to example 112, from 6,6-difluoro-3-(4-methylthiazol-2-yl)-5,7-dihydro-4H-benzothiophen-2-amine (example 150, intermediate a) and ethyl 5-chlorocarbonyl-3,6-dihydro-2H-pyran-4-carboxylate (prepared in analogy to example 112, from 4-(ethoxycarbonyl)-5,6-dihydro-2H-pyran-3-carboxylic acid (examples 245/246, intermediate b)). The compound was purified by silica gel chromatography on a 20 g column using an MPLC system eluting with a gradient of n-heptane:EtOAc (100:0 to 60:40). Yellow solid (70%). MS (ESI): m/z=469.1067[M+H]$^+$.

Example 255

(R)-1-[[3-(3-methyl-1,2,4-oxadiazol-5-yl)-5,6,7,8-tetrahydro-4H-cyclohepta[b]thiophen-2-yl]carbamoyl] pyrrolidine-2-carboxylic acid

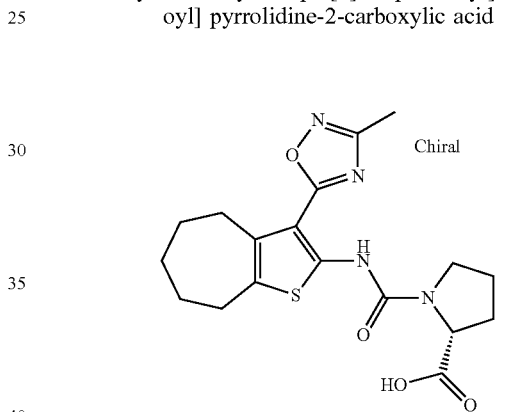

The title compound was prepared in analogy to example 27, from 5-(2-isocyanato-5,6,7,8-tetrahydro-4H-cyclohepta[b]thiophen-3-yl)-3-methyl-[1,2,4]oxadiazole and D-proline, using a gradient of CH$_2$Cl$_2$:MeOH (98:2 to 95:5) for the chromatographic purification, followed by crystallization from CH$_2$Cl$_2$/n-hexane. Off-white solid (53%). MS (ESI): m/z=391.2 [M+H]$^+$.

Intermediate 5-(2-Isocyanato-5,6,7,8-tetrahydro-4H-cyclohepta[b]thiophen-3-yl)-3-methyl-1,2,4-oxadiazole The title compound was prepared in analogy to example 27, intermediate a, from 3-(3-methyl-1,2,4-oxadiazol-5-yl)-5,6,7,8-tetrahydro-4H-cyclohepta[b]thiophen-2-amine (example 120, intermediate) after a reaction time of 2 h at RT. Brown solid (99%) which was used in the next step without further purification.

Example 256

(R)-1-[[3-[3-(trifluoromethyl)-1,2,4-oxadiazol-5-yl]-5,6,7,8-tetrahydro-4H-cyclohepta[b]thiophen-2-yl]carbamoyl]pyrrolidine-2-carboxylic acid

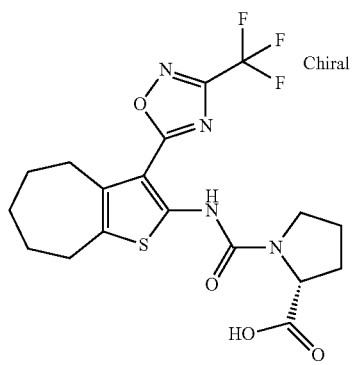 [SMILES: O=C(O)[C@H]1CCCN1C(=O)Nc1sc2c(c1-c1nc(C(F)(F)F)no1)CCCCC2]

The title compound was prepared in analogy to example 27, from 5-(2-isocyanato-5,6,7,8-tetrahydro-4H-cyclohepta[b]thiophen-3-yl)-3-trifluoromethyl-[1,2,4]oxadiazole and D-proline and using a gradient of $CH_2Cl_2$:MeOH (98:2 to 95:5), followed by crystallization from $CH_2Cl_2$/n-hexane. Off-white solid (49%). MS (ESI): m/z=443.4 [M–H]⁻.

Intermediate 5-(2-Isocyanato-5,6,7,8-tetrahydro-4H-cyclohepta[b]thiophen-3-yl)-3-trifluoromethyl-[1,2,4]oxadiazole The title compound was prepared in analogy to example 27, intermediate a, from 3-(3-trifluoromethyl-[1,2,4]oxadiazol-5-yl)-5,6,7,8-tetrahydro-4H-cyclohepta[b]-thiophen-2-ylamine (example 126, intermediate) after a reaction time of 2 h at 25° C. Brown solid (98%) which was used in the next step without further purification.

Example 257

(R)-1-[[3-[3-(trifluoromethyl)-1,2,4-oxadiazol-5-yl]-4,5,6,7-tetrahydrobenzothiophen-2-yl]carbamoyl]pyrrolidine-2-carboxylic acid

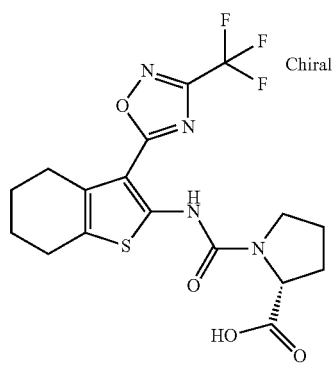 [SMILES: O=C(O)[C@H]1CCCN1C(=O)Nc1sc2c(c1-c1nc(C(F)(F)F)no1)CCCC2]

The title compound was prepared in analogy to example 27, from 5-(2-isocyanato-4,5,6,7-tetrahydro-benzo[b]thiophen-3-yl)-3-trifluoromethyl-[1,2,4]oxadiazole and D-proline, using a gradient of $CH_2Cl_2$:MeOH (98:2 to 95:5) followed by crystallization from $CH_2Cl_2$/n-hexane. Off-white solid (23%). MS (ESI): m/z=429.4 [M–H]⁻.

Intermediate 5-(2-Isocyanato-4,5,6,7-tetrahydro-benzo[b]thiophen-3-yl)-3-trifluoromethyl-[1,2,4]oxadiazole The title compound was prepared in analogy to example 27, intermediate, from 3-(3-trifluoromethyl-[1,2,4]oxadiazol-5-yl)-4,5,6,7-tetrahydro-benzo[b]-thiophen-2-ylamine (example 61, intermediate a) after a reaction time of 2 h at 25° C. Brown solid (94%) which was used in the next step without further purification.

Example 258

(S)-1-[[3-(3-cyclopropyl-1,2,4-oxadiazol-5-yl)-5,6,7,8-tetrahydro-4H-cyclohepta[b]thiophen-2-yl]carbamoyl]pyrrolidine-2-carboxylic acid

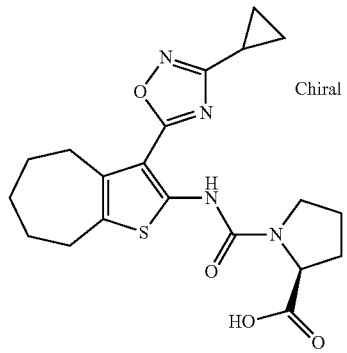 [SMILES: O=C(O)[C@@H]1CCCN1C(=O)Nc1sc2c(c1-c1nc(C3CC3)no1)CCCCC2]

To a solution of 3-(3-cyclopropyl-1,2,4-oxadiazol-5-yl)-5,6,7,8-tetrahydro-4H-cyclohepta[b]thiophen-2-amine (0.1 g, 363 µmol; example 123, intermediate) in THF (2 mL) at 0° C. was added dropwise a solution of phenyl chloroformate (59.7 mg, 47.8 µL, 381 µmol) in THF (1 mL). The clear, colorless solution was stirred at reflux for 1.5 h and then allowed to cool to RT. L-Prolin (41.8 mg, 363 µmol), $H_2O$ (2 mL) and $K_2CO_3$ (100 mg, 726 µmol) were added and stirring was continued at RT for 24 h. The reaction mixture was poured on 1M aqueous HCl solution and EtOAc and the layers were separated. The aqueous layer was extracted twice with EtOAc. The organic layers were washed with brine, dried over $MgSO_4$, filtered, treated with silica gel and evaporated. The compound was purified by silica gel chromatography on a 10 g column using an MPLC system eluting with a gradient of $CH_2Cl_2$:MeOH (100:0 to 85:15). Light brown foam (0.094 g; 62.1%). MS (ESI): m/z=417.16 [M+H]⁺.

Example A

A compound of formula (I) can be used in a manner known per se as the active ingredient for the production of tablets of the following composition:

| Per tablet | |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula (I) can be used in a manner known per se as the active ingredient for the production of capsules of the following composition:

| Per capsule | |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

The invention claimed is:

1. A compound of formula (I)

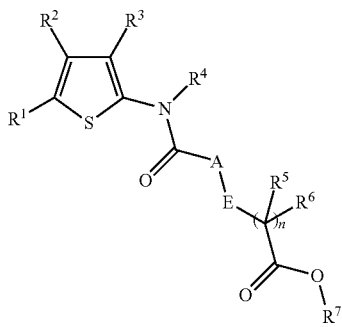

(I)

wherein
R$^1$ and R$^2$ together form —CR$^{14}$=CR$^{15}$—CR$^{16}$=CR$^{17}$—, —CR$^{14}$R$^{15}$—O—(CR$^{16}$R$^{17}$)$_m$—CR$^{18}$R$^{19}$—, —CR$^{14}$R$^{15}$—(CR$^{16}$R$^{17}$)$_m$—O—CR$^{18}$R$^{19}$—, —O—CR$^{14}$R$^{15}$—(CR$^{16}$R$^{17}$)$_m$—CR$^{18}$R$^{19}$—, —CR$^{14}$R$^{15}$—NR$^{22}$—CR$^{16}$R$^{17}$—CR$^{18}$R$^{19}$—, CR$^{14}$R$^{15}$—S(O)$_2$—CR$^{16}$R$^{17}$—CR$^{18}$R$^{19}$—, —CR$^{14}$R$^{15}$—CR$^{20}$R$^{21}$— or —CR$^{14}$R$^{15}$—CR$^{16}$R$^{17}$—(CR$^{18}$R$^{19}$)$_p$—CR$^{20}$R$^{21}$—;

R$^3$ is a substituted phenyl, substituted 4,5-dihydro-oxazolyl, pyrrolidinyl, substituted [1,2,4]-oxadiazolyl, oxazolyl, substituted [1,2,4]-thiadiazolyl, thiazolyl, pyridinyl or pyrimidinyl, wherein substituted phenyl, substituted 4,5-dihydro-oxazolyl, substituted [1,2,4]-thiadiazolyl, and substituted [1,2,4]-oxadiazolyl are substituted with R$^{23}$ and can be further substituted with R$^{24}$ and/or R$^{25}$;

R$^4$ is H or alkyl;
R$^5$ and R$^6$ are independently selected from H, alkyl and cycloalkyl;
R$^7$ is H, alkyl or cycloalkyl;
A is NR$^8$ or CR$^9$R$^{10}$;
E is NR$^{11}$ or CR$^{12}$R$^{13}$;
R$^8$ and R$^{11}$ are independently selected from H, alkyl or cycloalkyl;
R$^9$, R$^{10}$, R$^{12}$ and R$^{13}$ are independently selected from H, halogen, alkyl, haloalkyl or cycloalkyl;
or R$^5$ and R$^{12}$ together with the carbon atoms to which they are attached form a substituted cycloalkyl, substituted heterocycloalkyl or substituted heteroaryl, wherein substituted cycloalkyl, substituted heterocycloalkyl and substituted heteroaryl are substituted with R$^{26}$ and can be further substituted with R$^{27}$ and/or R$^{28}$, wherein in case R$^5$ and R$^{12}$ together with the carbon atoms to which they are attached form a substituted heteroaryl, then R$^6$ and R$^{13}$ are absent;
or R$^8$ and R$^{12}$ together with the nitrogen and carbon atoms to which they are attached form a substituted heterocycloalkyl or substituted heteroaryl, wherein substituted heterocycloalkyl and substituted heteroaryl are substituted with R$^{26}$ and can be further substituted with R$^{27}$ and/or R$^{28}$, wherein in case R$^8$ and R$^{12}$ together with the carbon atoms to which they are attached form a substituted heteroaryl, then R$^{13}$ is absent;
or R$^9$ and R$^{11}$ together with the nitrogen and carbon atoms to which they are attached form a substituted heterocycloalkyl or substituted heteroaryl, wherein substituted heterocycloalkyl and substituted heteroaryl are substituted with R$^{26}$ and can be further substituted with R$^{27}$ and/or R$^{28}$, wherein in case R$^9$ and R$^{11}$ together with the carbon atoms to which they are attached form a substituted heteroaryl, then R$^{10}$ is absent;
or R$^9$ and R$^{12}$ together with the carbon atoms to which they are attached form a substituted cycloalkyl,- substituted heterocycloalkyl or substituted heteroaryl, wherein substituted cycloalkyl, substituted heterocycloalkyl and substituted heteroaryl are substituted with R$^{26}$ and can be further substituted with R$^{27}$ and/or R$^{28}$, wherein in case R$^9$ and R$^{12}$ together with the carbon atoms to which they are attached form a substituted heteroaryl, then R$^{10}$ and R$^{13}$ are absent;
or R$^{10}$ and R$^{13}$ together with the carbon atoms to which they are attached form a substituted cycloalkyl, substituted heterocycloalkyl or substituted heteroaryl, wherein substituted cycloalkyl, substituted heterocycloalkyl and substituted heteroaryl are substituted with R$^{29}$ and can be further substituted with R$^{30}$ and/or R$^{31}$, wherein in case R$^{10}$ and R$^{13}$ together with the carbon atoms to which they are attached form a substituted heteroaryl, then R$^9$ and R$^{12}$ are absent;
or R$^{10}$ and R$^{13}$ together with the carbon atoms to which they are attached form a double bond;
R$^{14}$, R$^{15}$, R$^{16}$, R$^{17}$, R$^{18}$, R$^{19}$, R$^{20}$, R$^{21}$, R$^{23}$, R$^{24}$, R$^{25}$, R$^{26}$, R$^{27}$, R$^{28}$, R$^{29}$, R$^{30}$ and R$^{31}$ are independently selected from H, oxo, hydroxy, halogen, alkyl, cycloalkyl, haloalkyl, alkoxy, alkoxyalkyl, alkoxycarbonyl or carboxy;
or R$^{16}$ and R$^{17}$ together with the carbon atoms to which they are attached form a cycloalkyl or heterocycloalkyl;
or R$^{14}$ and R$^{20}$together with the carbon atoms to which they are attached form —CH$_2$— or —CH$_2$—CH$_2$—;
R$^{22}$ is H, alkyl, cycloalkyl or alkoxycarbonyl;
m is zero or 1;
n is zero or 1;
p is zero, 1 or 2;
or a pharmaceutically acceptable salt thereof.

2. The compound of claim 1, wherein
R$^1$ and R$^2$ together form —CR$^{14}$=CR$^{15}$—CR$^{16}$=CR$^{17}$—, —CR$^{14}$R$^{15}$—O—(CR$^{16}$R$^{17}$)$_m$—

$CR^{18}R^{19}$—, —O—$CR^{14}R^{15}$—$(CR^{16}R^{17})_m CR^{18}R^{19}$—, —$CR^{14}R^{15}$—$NR^{22}$—$CR^{16}R^{17}$—$CR^{18}R^{19}$—, —$CR^{14}R^{18}$—$S(O)_2$—$CR^{16}R^{17}$—$CR^{18}R^{19}$— or —$CR^{14}R^{15}$—$CR^{16}R^{17}$—$(CR^{18}R^{19})_p$—$CR^{20}R^{21}$—;

$R^3$ is a substituted phenyl, substituted 4,5-dihydro-oxazolyl, pyrrolidinyl, substituted [1,2,4]-oxadiazolyl, oxazolyl, substituted [1,2,4]-thiadiazolyl, thiazolyl, pyridinyl or pyrimidinyl, wherein substituted phenyl, substituted 4,5-dihydro-oxazolyl, substituted [1,2,4]-thiadiazolyl, and substituted [1,2,4]-oxadiazolyl are substituted with $R^{23}$ and can be further substituted with $R^{24}$ and/or $R^{25}$;

$R^4$ is H or alkyl;

$R^5$ and $R^6$ are independently selected from H, alkyl and cycloalkyl;

$R^7$ is H, alkyl or cycloalkyl;

A is $NR^8$ or $CR^9R^{10}$;

E is $NR^{11}$ or $CR^{12}R^{13}$;

$R^8$ and $R^{11}$ are independently selected from H, alkyl or cycloalkyl;

$R^9$, $R^{10}$, $R^{12}$ and $R^{13}$ are independently selected from H, halogen, alkyl, haloalkyl or cycloalkyl;

or $R^5$ and $R^{12}$ together with the carbon atoms to which they are attached form a substituted cycloalkyl, substituted heterocycloalkyl or substituted heteroaryl, wherein substituted cycloalkyl, substituted heterocycloalkyl and substituted heteroaryl are substituted with $R^{26}$ and can be further substituted with $R^{27}$ and/or $R^{28}$, wherein in case $R^5$ and $R^{12}$ together with the carbon atoms to which they are attached form a substituted heteroaryl, then $R^6$ and $R^{13}$ are absent;

or $R^8$ and $R^{12}$ together with the nitrogen and carbon atoms to which they are attached form a substituted heterocycloalkyl or substituted heteroaryl, wherein substituted heterocycloalkyl and substituted heteroaryl are substituted with $R^{26}$ and can be further substituted with $R^{27}$ and/or $R^{28}$, wherein in case $R^8$ and $R^{12}$ together with the carbon atoms to which they are attached form a substituted heteroaryl, then $R^{13}$ is absent;

or $R^9$ and $R^{11}$ together with the nitrogen and carbon atoms to which they are attached form a substituted heterocycloalkyl or substituted heteroaryl, wherein substituted heterocycloalkyl and substituted heteroaryl are substituted with $R^{26}$ and can be further substituted with $R^{27}$ and/or $R^{28}$, wherein in case $R^9$ and $R^{11}$ together with the carbon atoms to which they are attached form a substituted heteroaryl, then $R^{10}$ is absent;

or $R^9$ and $R^{12}$ together with the carbon atoms to which they are attached form a substituted cycloalkyl, substituted heterocycloalkyl or substituted heteroaryl, wherein substituted cycloalkyl, substituted heterocycloalkyl and substituted heteroaryl are substituted with $R^{26}$ and can be further substituted with $R^{27}$ and/or $R^{28}$, wherein in case $R^9$ and $R^{12}$ together with the carbon atoms to which they are attached form a substituted heteroaryl, then $R^{10}$ and $R^{13}$ are absent;

or $R^{10}$ and $R^{13}$ together with the carbon atoms to which they are attached form a substituted cycloalkyl, substituted heterocycloalkyl or substituted heteroaryl, wherein substituted cycloalkyl, substituted heterocycloalkyl and substituted heteroaryl are substituted with $R^{29}$ and can be further substituted with $R^{30}$ and/or $R^{31}$, wherein in case $R^{10}$ and $R^{13}$ together with the carbon atoms to which they are attached form a substituted heteroaryl, then $R^9$ and $R^{12}$ are absent;

or $R^{10}$ and $R^{13}$ together with the carbon atoms to which they are attached form a double bond;

$R^{14}$, $R^{15}$, $R^{16}$, $R^{17}$, $R^{18}$, $R^{19}$, $R^{20}$, $R^{21}$, $R^{23}$, $R^{24}$, $R^{25}$, $R^{26}$, $R^{27}$, $R^{28}$, $R^{29}$, $R^{30}$ and $R^{31}$ are independently selected from H, oxo, halogen, alkyl, cycloalkyl, haloalkyl, alkoxy, alkoxyalkyl, alkoxycarbonyl or carboxy;

or $R^{16}$ and $R^{17}$ together with the carbon atoms to which they are attached form a cycloalkyl or heterocycloalkyl;

or $R^{14}$ and $R^{20}$ together with the carbon atoms to which they are attached form —$CH_2$— or —$CH_2$—$CH_2$—;

$R^{22}$ is H, alkyl, cycloalkyl or alkoxycarbonyl;

m is zero or 1;

n is zero or 1;

p is zero, 1 or 2;

or a pharmaceutically acceptable salt thereof.

3. The compound of claim 1, wherein $R^1$ and $R^2$ together form —$CR^{14}R^{15}$—O—$(CR^{16}R^{17})_m$—$CR^{18}R^{19}$—, —$CR^{14}R^{15}$—O—$(CR^{16}R^{17})_m$—$CR^{18}R^{19}$— or —$CR^{14}R^{15}$—$CR^{16}R^{17}$—$(CR^{18}R^{19})_p$—$CR^{20}R^{21}$—.

4. The compound of claim 1, wherein $R^1$ and $R^2$ together form —$CR^{14}R^{15}$—O—$(CR^{16}R^{17})_m$—$CR^{18}R^{19}$—.

5. The compound of claim 1, wherein $R^1$ and $R^2$ together form —$CR^{14}R^{15}$—$CR^{16}R^{17}$—$(CR^{18}R^{19})_p$—$CR^{20}R^{21}$—.

6. The compound of claim 1, wherein $R^3$ is substituted [1,2,4]-oxadiazolyl, oxazolyl, substituted [1,2,4]-thiadiazolyl or thiazolyl, wherein substituted [1,2,4]-oxadiazolyl and substituted [1,2,4]-thiadiazolyl are substituted with $R^{23}$ and can be further substituted with $R^{24}$ and/or $R^{25}$.

7. The compound of claim 1, wherein $R^7$ is H.

8. The compound of claim 1, wherein A is $CR^9R^{10}$.

9. The compound of claim 1, wherein E is $CR^{12}R^{13}$.

10. The compound of claim 1, wherein $R^{10}$ and $R^{13}$ together with the carbon atoms to which they are attached form a double bond.

11. The compound of claim 1, wherein $R^9$ and $R^{12}$ together with the carbon atoms to which they are attached form a substituted cycloalkyl, -or substituted heteroaryl, wherein substituted cycloalkyl, and substituted heteroaryl are substituted with $R^{26}$ and can be further substituted with $R^{27}$ and/or $R^{28}$, wherein in case $R^9$ and $R^{12}$ together with the carbon atoms to which they are attached form a substituted heteroaryl, then $R^{10}$ and $R^{13}$ are absent.

12. The compound of claim 1, wherein $R^9$ and $R^{12}$ together with the carbon atoms to which they are attached form a substituted cycloalkyl or substituted heterocycloalkyl, wherein substituted cycloalkyl and substituted heterocycloalkyl are substituted with $R^{26}$ and can be further substituted with $R^{27}$ and/or $R^{28}$.

13. The compound of claim 1, wherein $R^9$ and $R^{12}$ together with the carbon atoms to which they are attached form a cycloalkyl which is substituted with $R^{26}$ and can be further substituted with $R^{27}$ and/or $R^{28}$.

14. The compound of claim 1, wherein $R^9$ and $R^{12}$ together with the carbon atoms to which they are attached form cyclohexyl substituted with $R^{26}$ and can be further substituted with $R^{27}$ and/or $R^{28}$.

15. The compound of claim 1, wherein $R^9$ and $R^{12}$ together with the carbon atoms to which they are attached form a substituted pyrazinyl, wherein substituted pyrazinyl are substituted with $R^{26}$ and can be further substituted with $R^{27}$ and/or $R^{28}$, and $R^{10}$ and $R^{13}$ are absent.

16. The compound of claim 1, wherein $R^{14}$, $R^{15}$, $R^{16}$, $R^{17}$, $R^{18}$, $R^{19}$, $R^{20}$, $R^{21}$, $R^{23}$, $R^{24}$, $R^{25}$, $R^{26}$, $R^{27}$, $R^{28}$, $R^{29}$, $R^{30}$ and $R^{31}$ are independently selected from H, halogen, alkyl, cycloalkyl, haloalkyl, alkoxy or alkoxyalkyl.

17. A compound selected from
2-(3-Phenyl-benzo[b]thiophen-2-ylcarbamoyl)-cyclopent-1-enecarboxylic acid;
2-[3-(3-Methyl-[1,2,4]oxadiazol-5-yl)-4,5,6,7-tetrahydro-benzo[b]thiophen-2-ylcarbamoyl]-cyclopent-1-enecarboxylic acid;
2-[3-(3-Methyl-[1,2,4]oxadiazol-5-yl)-4,5,6,7-tetrahydro-benzo[b]thiophen-2-ylcarbamoyl]-cyclohex-1-enecarboxylic acid;
(Z)-3-[3-(3-Methyl -[1,2,4]oxadiazol-5-yl)-4,5,6,7-tetrahydro-benzo[b]thiophen-2-ylcarbamoyl]-acrylic acid;
2-[3-(3-Cyclopropyl-[1,2,4]oxadiazol-5-yl)-4,5,6,7-tetrahydro-benzo[b]thiophen-2-ylcarbamoyl]-cyclopent-1-enecarboxylic acid;
2-[3-(3-Cyclopropyl-[1,2,4]oxadiazol-5-yl)-benzo[b]thiophen-2-ylcarbamoyl]-cyclopent-1-enecarboxylic acid;
(1RS,2SR)-2-[3-(3-Methyl-[1,2,4]oxadiazol-5-yl)-4,5,6,7-tetrahydro-benzo[b]thiophen-2-ylcarbamoyl]-cyclopentanecarboxylic acid;
2-[3-(4-Methyl-thiazol-2-yl)-4,5,6,7-tetrahydro-benzo[b]thiophen-2-ylcarbamoyl]-cyclopent-1-enecarboxylic acid;
3-[3-(3-Methyl-[1,2,4]oxadiazol-5-yl)-4,5,6,7-tetrahydro-benzo[b]thiophen-2-ylcarbamoyl]-pyrazine-2-carboxylic acid;
(1RS,3SR)-2,2-Dimethyl-3-[3-(3-methyl-[1,2,4]oxadiazol-5-yl)-4,5,6,7-tetrahydro-benzo[b]thiophen-2-ylcarbamoyl]-cyclopropanecarboxylic acid;
3-[3-(3-Methyl-[1,2,4]oxadiazol-5-yl)-4,5,6,7-tetrahydro-benzo[b]thiophen-2-ylcarbamoyl]-bicyclo[2.2.2]oct-2-ene-2-carboxylic acid;
(1RS,2SR)-2-[3-(3-Methyl-[1,2,4]oxadiazol-5-yl)-4,5,6,7-tetrahydro-benzo[b]thiophen-2-ylcarbamoyl]-cyclohexanecarboxylic acid;
2-[3-(4,4-Dimethyl-4,5-dihydro-oxazol-2-yl)-4,5,6,7-tetrahydro-benzo[b]thiophen-2-ylcarbamoyl]-cyclopent-1-enecarboxylic acid;
2-(3-Pyrimidin-2-yl-4,5,6,7-tetrahydro-benzo[b]thiophen-2-ylcarbamoyl)-cyclopent-1-enecarboxylic acid;
2-(3-[1,2,4]Oxadiazol-3-yl-4,5,6,7-tetrahydro-benzo[b]thiophen-2-ylcarbamoyl)-cyclopent-1-enecarboxylic acid;
2-(3-Pyrimidin-2-yl-4,5,6,7-tetrahydro-benzo[b]thiophen-2-ylcarbamoyl)-cyclohex-1-enecarboxylic acid;
3-(3-Pyrimidin-2-yl-4,5,6,7-tetrahydro-benzo[b]thiophen-2-ylcarbamoyl)-pyrazine-2-carboxylic acid,
(1RS,6SR)-6-[3-(3-Methyl-[1,2,4]oxadiazol-5-yl)-4,5,6,7-tetrahydro-benzo[b]thiophen-2-ylcarbamoyl]-cyclohex-3-enecarboxylic acid;
3-(3-Pyrimidin-2-yl-4,5,6,7-tetrahydro-benzo[b]thiophen-2-ylcarbamoyl)-bicyclo[2.2.2]oct-2-ene-2-carboxylic acid;
3-(3-[1,2,4]Oxadiazol-3-yl-4,5,6,7-tetrahydro-benzo[b]thiophen-2-ylcarbamoyl)-bicyclo[2.2.2]oct-2-ene-2-carboxylic acid;
2,2,3,3-Tetrafluoro-N-[3-(3-methyl-[1,2,4]oxadiazol-5-yl)-4,5,6,7-tetrahydro-benzo[b]thiophen-2-yl]-succinamic acid;
(R)-1-[3-(3-Methyl-[1,2,4]oxadiazol-5-yl)-4,5,6,7-tetrahydro-benzo[b]thiophen-2-ylcarbamoyl]-pyrrolidine-2-carboxylic acid;
3-[3-(5-tert-Butyl-[1,2,4]oxadiazol-3-yl)-4,5,6,7-tetrahydro-benzo[b]thiophen-2-ylcarbamoyl]-bicyclo[2.2.2]oct-2-ene-2-carboxylic acid;
2-[3-(5-tert-Butyl-[1,2,4]oxadiazol-3-yl)-4,5,6,7-tetrahydro-benzo[b]thiophen-2-ylcarbamoyl]-cyclopent-1-enecarboxylic acid;
2-(5,5-Dimethyl-3-pyrimidin-2-yl-4,5,6,7-tetrahydro-benzo[b]thiophen-2-ylcarbamoyl)-cyclopent-1-enecarboxylic acid;
2-[5,5-Dimethyl-3-(4-methyl-thiazol-2-yl)-4,5,6,7-tetrahydro-benzo[b]thiophen-2-ylcarbamoyl]-cyclopent-1-enecarboxylic acid;
(R)-1-[3-(3-Cyclopropyl-[1,2,4]oxadiazol-5-yl)-4,5,6,7-tetrahydro-benzo[b]thiophen-2-ylcarbamoyl]-pyrrolidine-2-carboxylic acid;
(1RS,6SR)-6-[6,6-Dimethyl-3-(4-methyl-thiazol-2-yl)-4,5,6,7-tetrahydro-benzo[b]thiophen-2-ylcarbamoyl]-cyclohex-3-enecarboxylic acid;
2-[6,6-Dimethyl-3-(4-methyl-thiazol-2-yl)-4,5,6,7-tetrahydro-benzo[b]thiophen-2-ylcarbamoyl]-cyclopent-1-enecarboxylic acid;
{1-[3-(3-Cyclopropyl-[1,2,4]oxadiazol-5-yl)-4,5,6,7-tetrahydro-benzo[b]thiophen-2-ylcarbamoyl]-pyrrolidin-2-yl}-acetic acid;
(R)-1-[3-(3-Cyclopropyl-[1,2,4]oxadiazol-5-yl)-4,5,6,7-tetrahydro-benzo[b]thiophen-2-ylcarbamoyl]-piperidine-2-carboxylic acid;
(R)-1-[3-(3-Cyclopropyl-[1,2,4]oxadiazol-5-yl)-4,5,6,7-tetrahydro-benzo[b]thiophen-2-ylcarbamoyl]-azetidine-2-carboxylic acid;
3-[3-(3-Cyclopropyl-[1,2,4]oxadiazol-5-yl)-4,5,6,7-tetrahydro-benzo[b]thiophen-2-ylcarbamoyl]-bicyclo[2.2.2]oct-2-ene-2-carboxylic acid;
(1RS,2SR)-2-[3-(3-Cyclopropyl-[1,2,4]oxadiazol-5-yl)-4,5,6,7-tetrahydro-benzo[b]thiophen-2-ylcarbamoyl]-cyclohexanecarboxylic acid;
3-[6,6-Dimethyl-3-(4-methyl-thiazol-2-yl)-4,5,6,7-tetrahydro-benzo[b]thiophen-2-ylcarbamoyl]-bicyclo[2.2.2]oct-5-ene-2-carboxylic acid;
(1SR,2SR)-2-[6,6-Dimethyl-3-(4-methyl-thiazol-2-yl)-4,5,6,7-tetrahydro-benzo[b]thiophen-2-ylcarbamoyl]-cyclohexanecarboxylic acid;
(1SR,2SR)-2-[3-(3-Methyl-[1,2,4]oxadiazol-5-yl)-4,5,6,7-tetrahydro-benzo[b]thiophen-2-ylcarbamoyl]-cyclohexanecarboxylic acid;
N-[3-(3-Methyl-[1,2,4]oxadiazol-5-yl)-4,5,6,7-tetrahydro-benzo[b]thiophen-2-yl]-phthalamic acid;
(1RS,6SR)-6-[6-Methoxy-3-(4-methyl-thiazol-2-yl)-4,5,6,7-tetrahydro-benzo[b]thiophen-2-ylcarbamoyl]-cyclohex-3-enecarboxylic acid;
2-[3-(4-Methyl-thiazol-2-yl)-5,6,7,8-tetrahydro-4H-cyclohepta[b]thiophen-2-ylcarbamoyl]-cyclopent-1-enecarboxylic acid;
3-[3-(3-Methyl-[1,2,4]oxadiazol-5-yl)-4,5,6,7-tetrahydro-benzo[b]thiophen-2-ylcarbamoyl]-bicyclo[2.2.2]oct-5-ene-2-carboxylic acid;
2-[3-(3-Ethyl-[1,2,4]oxadiazol-5-yl)-4,5,6,7-tetrahydro-benzo[b]thiophen-2-ylcarbamoyl]-cyclopent-1-enecarboxylic acid;
N-[6,6-Dimethyl-3-(4-methyl-thiazol-2-yl)-4,5,6,7-tetrahydro-benzo[b]thiophen-2-yl]-phthalamic acid;
2-{3-[3-(3-Cyclopropyl-[1,2,4]oxadiazol-5-yl)-4,5,6,7-tetrahydro-benzo[b]thiophen-2-yl]-ureido}-nicotinic acid;
4-{3-[3-(3-Cyclopropyl-[1,2,4]oxadiazol-5-yl)-4,5,6,7-tetrahydro-benzo[b]thiophen-2-yl]-ureido}-2-methyl-2H-pyrazole-3-carboxylic acid;
(1RS,6SR)-6-[3-(4-Methyl-thiazol-2-yl)-5,6,7,8-tetrahydro-4H-cyclohepta[b]thiophen-2-ylcarbamoyl]-cyclohex-3-enecarboxylic acid;

3-[6,6-Dimethyl-3-(4-methyl-thiazol-2-yl)-4,5,6,7-tetrahydro-benzo[b]thiophen-2-ylcarbamoyl]-bicyclo[2.2.2]oct-2-ene-2-carboxylic acid;

(1SR,2SR)-2-[3-(4-Methyl-thiazol-2-yl)-4,5,6,7-tetrahydro-benzo[b]thiophen-2-ylcarbamoyl]-cyclohexanecarboxylic acid;

3-[3-(4-Methyl-thiazol-2-yl)-4,5,6,7-tetrahydro-benzo[b]thiophen-2-ylcarbamoyl]-bicyclo[2.2.2]oct-2-ene-2-carboxylic acid;

2-[6-Methoxy-3-(4-methyl-thiazol-2-yl)-4,5,6,7-tetrahydro-benzo[b]thiophen-2-ylcarbamoyl]-cyclohexanecarboxylic acid;

3-[3-(4-Methyl-thiazol-2-yl)-5,6,7,8-tetrahydro-4H-cyclohepta[b]thiophen-2-ylcarbamoyl]-bicyclo[2.2.2]oct-2-ene-2-carboxylic acid;

(1SR,2SR)-2-{[3-(4-methyl-1,3-thiazol-2-yl)-4,7-dihydro-5H-spiro[1-benzothiophene-6,1'-cyclopropan]-2-yl]carbamoyl}cyclohexanecarb oxylic acid;

(S)-1-[3-(3-Cyclopropyl-[1,2,4]oxadiazol-5-yl)-4,5,6,7-tetrahydro-benzo[b]thiophen-2-ylcarbamoyl]-pyrrolidine-2-carboxylic acid;

(1SR,2SR)-2-[3-(4-Methyl-thiazol-2-yl)-5,6,7,8-tetrahydro-4H-cyclohepta[b]thiophen-2-ylcarbamoyl]-cyclohexanecarboxylic acid;

2-[3-(3-Cyclopropyl-[1,2,4]oxadiazol-5-yl)-4,7-dihydro-5H-thieno[2,3-c]pyran-2-ylcarbamoyl]-cyclopent-1-enecarboxylic acid;

3-[3-(4-Methyl-thiazol-2-yl)-4,7-dihydro-5H-thieno[2,3-c]pyran-2-ylcarbamoyl]-bicyclo[2.2.2]oct-2-ene-2-carboxylic acid;

2-[3-(4, 5-Dimethyl-oxazol-2-yl)-4,7-dihydro-5H-thieno[2,3-c]pyran-2-ylcarbamoyl]-cyclopent-1-enecarboxylic acid;

2-[3-(3-Cyclopropyl-[1,2,4]oxadiazol-5-yl)-4,4,6,6-tetramethyl-4,6-dihydro-thieno[2,3-c]furan-2-ylcarbamoyl]-cyclopent-1-enecarboxylic acid;

2-[3-(4-Methyl-thiazol-2-yl)-4,7-dihydro-5H-thieno[2,3-c]pyran-2-ylcarbamoyl]-cyclopent-1-enecarboxylic acid;

2-[(2-Carboxy-cyclopent-1-enecarbonyl)-amino]-3-(4-methyl-thiazol-2-yl)-4,7-dihydro-5H-thieno[2,3-c]pyridine-6-carboxylic acid tert-butyl ester;

2-[3-(3-Trifluoromethyl-[1,2,4]oxadiazol-5-yl)-4,5,6,7-tetrahydro-benzo[b]thiophen-2-ylcarbamoyl]-cyclopent-1-enecarboxylic acid;

3-[3-(3-Trifluoromethyl-[1,2,4]oxadiazol-5-yl)-4,5,6,7-tetrahydro-benzo[b]thiophen-2-ylcarbamoyl]-bicyclo[2.2.2]oct-2-ene-2-carboxylic acid;

(RS)-{2-[3-(4-Methyl-thiazol-2-yl)-4,5,6,7-tetrahydro-benzo[b]thiophen-2-ylcarbamoyl]-pyrrolidin-1-yl}-acetic acid;

3-[3-(3-Cyclopropyl-[1,2,4]oxadiazol-5-yl)-4,7-dihydro-5H-thieno[2,3-c]pyran-2-ylcarbamoyl]-bicyclo[2.2.2]oct-2-ene-2-carboxylic acid;

2-[3-(4-Methyl-thiazol-2-yl)-6,6-dioxo-4,5,6,7-tetrahydro-6λ6-thieno[2,3-c]thiopyran-2-ylcarbamoyl]-cyclopent-1-enecarboxylic acid;

2-[3-(4-Methyl-thiazol-2-yl)-4,7-dihydro-5H-thieno[2,3-c]pyran-2-ylcarbamoyl]-cyclohex-1-enecarboxylic acid;

2-[3-(3-Isopropyl-[1,2,4]oxadiazol-5-yl)-4,5,6,7-tetrahydro-benzo[b]thiophen-2-ylcarbamoyl]-cyclopent-1-enecarboxylic acid;

3-[3-(3-Isopropyl-[1,2,4]oxadiazol-5-yl)-4,5,6,7-tetrahydro-benzo[b]thiophen-2-ylcarbamoyl]-bicyclo[2.2.2]oct-2-ene-2-carboxylic acid;

2-[3-(3-Isopropyl-[1,2,4]oxadiazol-5-yl)-4,7-dihydro-5H-thieno[2,3-c]pyran-2-ylcarbamoyl]-cyclopent-1-enecarboxylic acid;

3-[3-(3-Isopropyl-[1,2,4]oxadiazol-5-yl)-4,7-dihydro-5H-thieno[2,3-c]pyran-2-ylcarbamoyl]-bicyclo[2.2.2]oct-2-ene-2-carboxylic acid;

2-[3-(3-Trifluoromethyl-[1,2,4]oxadiazol-5-yl)-4,7-dihydro-5H-thieno[2,3-c]pyran-2-ylcarbamoyl]-cyclopent-1-enecarboxylic acid;

2-(3-(3-Methyl-1,2,4-oxadiazol-5-yl)-5 ,7-dihydro-4H-spiro[benzo[b]thiophene-6,3'-oxetane]-2-ylcarbamoyl)cyclopent-1-enecarboxylic acid;

3-(3-(3-methyl-1,2,4-oxadiazol-5-yl)-5,7-dihydro-4H-spiro[benzo[b]thiophene-6,3'-oxetane]-2-ylcarbamoyl)bicyclo[2.2.2]oct-2-ene-2-carboxylic acid;

2-(3-(4-methylthiazol-2-yl)-5,7-dihydro-4H-spiro[benzo[b]thiophene-6,3'-oxetane]-2-ylcarbamoyl)cyclopent-1-enecarboxylic acid;

(1SR,2SR)-2-[3-(3-Isopropyl-[1,2,4]oxadiazol-5-yl)-4,7-dihydro-5H-thieno[2,3-c]pyran-2-ylcarbamoyl]-cyclohexanecarboxylic acid;

(1RS,2SR)-2-[3-(3-Isopropyl-[1,2,4]oxadiazol-5-yl)-4,7-dihydro-5H-thieno[2,3-c]pyran-2-ylcarbamoyl]-cyclohexanecarboxylic acid;

2-[4,4-Dimethyl-3-(3-methyl-[1,2,4]oxadiazol-5-yl)-5,6-dihydro-4H-cyclopenta[b]thiophen-2-ylcarbamoyl]-cyclopent-1-enecarboxylic acid;

2-[3-(4-Methyl-oxazol-2-yl)-4,7-dihydro-5H-thieno[2,3-c]pyran-2-ylcarbamoyl]-cyclopent-1-enecarboxylic acid;

3-[3-(4-Methyl-oxazol-2-yl)-4,7-dihydro-5H-thieno[2,3-c]pyran-2-ylcarbamoyl]-bicyclo[2.2.2]oct-2-ene-2-carboxylic acid;

3-[3-(3-Cyclopropyl-[1,2,4]oxadiazol-5-yl)-benzo[b]thiophen-2-ylcarbamoyl]-bicyclo[2.2.2]oct-2-ene-2-carboxylic acid;

2-[6,6-Dioxo-3-(3-trifluoromethyl-[1,2,4]oxadiazol-5-yl)-4,5,6,7-tetrahydro-6λ6-thieno[2,3-c]thiopyran-2-ylcarbamoyl]-cyclopent-1-enecarboxylic acid;

2,2-Dimethyl-N-[3-(3-methyl-[1,2,4]oxadiazol-5-yl)-4,5,6,7-tetrahydro-benzo[b]thiophen-2-yl]-succinamic acid;

2-[3-(3-Cyclopropyl-[1,2,4]oxadiazol-5-yl)-5,5-dimethyl-4,7-dihydro-5H-thieno[2,3-c]pyran-2-ylcarbamoyl]-cyclopent-1-enecarboxylic acid;

2-[3-(3-Cyclopropyl-[1,2,4]oxadiazol-5-yl)-5,5-dimethyl-4,7-dihydro-5H-thieno[2,3-c]pyran-2-ylcarbamoyl]-cyclohex-1-enecarboxylic acid;

2-[3-(4-Trifluoromethyl-thiazol-2-yl)-4,5,6,7-tetrahydro-benzo[b]thiophen-2-ylcarbamoyl]-cyclopent-1-enecarboxylic acid;

2-[3-(4-Trifluoromethyl-thiazol-2-yl)-4,5,6,7-tetrahydro-benzo[b]thiophen-2-ylcarbamoyl]-cyclohex-1-enecarboxylic acid;

3-[3-(4-Trifluoromethyl-thiazol-2-yl)-4,5,6,7-tetrahydro-benzo[b]thiophen-2-ylcarbamoyl]-bicyclo[2.2.2]oct-2-ene-2-carboxylic acid;

(RS)-2-[3-(3-Cyclopropyl-[1,2,4]oxadiazol-5-yl)-6-methyl-4,5,6,7-tetrahydro-benzo[b]thiophen-2-ylcarbamoyl]-cyclopent-1-enecarboxylic acid;

2-[3-(4-Trifluoromethyl-thiazol-2-yl)-4,7-dihydro-5H-thieno[2,3-c]pyran-2-ylcarbamoyl]-cyclopent-1-enecarboxylic acid;

2-[3-(4-Trifluoromethyl-thiazol-2-yl)-4,7-dihydro-5H-thieno[2,3-c]pyran-2-ylcarbamoyl]-cyclohex-1-enecarboxylic acid;

3-[3-(4-Trifluoromethyl-thiazol-2-yl)-4,7-dihydro-5H-thieno[2,3-c]pyran-2-ylcarbamoyl]-bicyclo[2.2.2]oct-2-ene-2-carboxylic acid;

(RS)-2-[3-(3-Cyclopropyl-[1,2,4]oxadiazol-5-yl)-6-methyl-4,5,6,7-tetrahydro-benzo[b]thiophen-2-ylcarbamoyl]-cyclohex-1-enecarboxylic acid;

(RS)-3-[3-(3-Cyclopropyl-[1,2,4]oxadiazol-5-yl)-6-methyl-4,5,6,7-tetrahydro-benzo[b]thiophen-2-ylcarbamoyl]-bicyclo[2.2.2]oct-2-ene-2-carboxylic acid;

2-[4,4-Dimethyl-3-(3-methyl-[1,2,4]oxadiazol-5-yl)-5,6-dihydro-4H-cyclopenta[b]thiophen-2-ylcarbamoyl]-cyclohex-1-enecarboxylic acid;

3-[4,4-Dimethyl-3-(3-methyl-[1,2,4]oxadiazol-5-yl)-5,6-dihydro-4H-cyclopenta[b]thiophen-2-ylcarbamoyl]-bicyclo[2.2.2]oct-2-ene-2-carboxylic acid;

2-[3-(4-Cyclopropyl-thiazol-2-yl)-4,7-dihydro-5H-thieno[2,3-c]pyran-2-ylcarbamoyl]-cyclopent-1-enecarboxylic acid;

3-[3-(4-Cyclopropyl-thiazol-2-yl)-4,7-dihydro-5H-thieno[2,3-c]pyran-2-ylcarbamoyl]-bicyclo[2.2.2]oct-2-ene-2-carboxylic acid;

3-[3-(3-Cyclopropyl-[1,2,4]oxadiazol-5-yl)-5,5-dimethyl-4,7-dihydro-5H-thieno[2,3-c]pyran-2-ylcarbamoyl]-bicyclo[2.2.2]oct-2-ene-2-carboxylic acid;

3,3-Dimethyl-4-[3-(3-methyl-[1,2,4]oxadiazol-5-yl)-4,5,6,7-tetrahydro-benzo[b]thiophen-2-ylcarbamoyl]-butyric acid;

2-[3-(3-Methyl-[1,2,4]oxadiazol-5-yl)-4,7-dihydro-5H-thieno[2,3-c]pyran-2-ylcarbamoyl]-cyclohex-1-enecarboxylic acid;

2-[3-(4, 5-Dimethyl-thiazol-2-yl)-4,7-dihydro-5H-thieno[2,3-c]pyran-2-ylcarbamoyl]-cyclopent-1-enecarboxylic acid;

2-[3-(3-Cyclopropyl-[1,2,4]oxadiazol-5-yl)-4,4-dimethyl-4,5,6,7-tetrahydro-benzo[b]thiophen-2-ylcarbamoyl]-cyclopent-1-enecarboxylic acid;

3-[3-(3-Cyclopropyl-[1,2,4]oxadiazol-5-yl)-4,4-dimethyl-4,5,6,7-tetrahydro-benzo[b]thiophen-2-ylcarbamoyl]-bicyclo[2.2.2]oct-2-ene-2-carboxylic acid;

3-[3-(3-Methyl-[1,2,4]oxadiazol-5-yl)-4,7-dihydro-5H-thieno[2,3-c]pyran-2-ylcarbamoyl]-bicyclo[2.2.2]oct-2-ene-2-carboxylic acid;

2-[3-(3-Methyl-[1,2,4]oxadiazol-5-yl)-4,7-dihydro-5H-thieno[2,3-c]pyran-2-ylcarbamoyl]-cyclopent-1-enecarboxylic acid;

(1RS,2SR)-2-[3-(3-Trifluoromethyl-[1,2,4]oxadiazol-5-yl)-4,7-dihydro-5H-thieno[2,3-c]pyran-2-ylcarbamoyl]-cyclohexanecarboxylic acid;

2-[3-(4-Cyclopropyl-thiazol-2-yl)-4,7-dihydro-5H-thieno[2,3-c]pyran-2-ylcarbamoyl]-cyclohex-1-enecarboxylic acid;

(+)-2-[3-(3-Cyclopropyl-[1,2,4]oxadiazol-5-yl)-6-methyl-4,5,6,7-tetrahydro-benzo[b]thiophen-2-ylcarbamoyl]-cyclohex-1-enecarboxylic acid;

(−)-2-[3-(3-Cyclopropyl-[1,2,4]oxadiazol-5-yl)-6-methyl-4,5,6,7-tetrahydro-benzo[b]thiophen-2-ylcarbamoyl]-cyclohex-1-enecarboxylic acid;

2-{3-[3-(2-Methoxy-ethyl)-[1,2,4]oxadiazol-5-yl]-4,7-dihydro-5H-thieno[2,3-c]pyran-2-ylcarbamoyl}-cyclohex-1-enecarboxylic acid;

3-{3-[3-(2-Methoxy-ethyl)-[1,2,4]oxadiazol-5-yl]-4,7-dihydro-5H-thieno[2,3-c]pyran-2-ylcarbamoyl}-bicyclo[2.2.2]oct-2-ene-2-carboxylic acid;

(1RS,5SR)-5-[3-(3-Methyl -[1,2,4]ox adi azol-5-yl)-4,5,6,7-tetrahydro-benzo[b]thiophen-2-ylcarbamoyl]-bicyclo[3.1.0]hexane-1-carboxylic acid methyl ester;

(1RS,5SR)-5-[3-(3-Methyl-[1,2,4]oxadiazol-5-yl)-4,5,6,7-tetrahydro-benzo[b]thiophen-2-ylcarbamoyl]-bicyclo[3.1.0]hexane-1-carboxylic acid;

(1SR,2SR)-2-[3-(3-Trifluoromethyl-[1,2,4]oxadiazol-5-yl)-4,7-dihydro-5H-thieno[2,3-c]pyran-2-ylcarbamoyl]-cyclohexanecarboxylic acid;

(1SR,2SR)-2-[3-(3-Trifluoromethyl-[1,2,4]oxadiazol-5-yl)-4,7-dihydro-5H-thieno[2,3-c]pyran-2-ylcarbamoyl]-cyclohexanecarboxylic acid;

(1RS,2SR)-2-[3-(3-Trifluoromethyl-[1,2,4]oxadiazol-5-yl)-4,7-dihydro-5H-thieno[2,3-c]pyran-2-ylcarbamoyl]-cyclohexanecarboxylic acid;

(1RS,2SR)-2-[3-(3-Trifluoromethyl-[1,2,4]oxadiazol-5-yl)-4,7-dihydro-5H-thieno[2,3-c]pyran-2-ylcarbamoyl]-cyclohexanecarboxylic acid;

2-[5-(3-Cyclopropyl-[1,2,4]oxadiazol-5-yl)-3-thia-tricyclo[5.2.1.0²,⁶]deca-2(6),4-dien-4-ylcarbamoyl]-cyclopent-1-enecarboxylic acid;

2-{3-[3-(2-Methoxy-ethyl)-[1,2,4]oxadiazol-5-yl]-4,7-dihydro-5H-thieno[2,3-c]pyran-2-ylcarbamoyl}-cyclopent-1-enecarboxylic acid;

2-[3-(3-Methyl-[1,2,4]oxadiazol-5-yl)-5,6,7,8-tetrahydro-4H-cyclohepta[b]thiophen-2-ylcarbamoyl]-cyclopent-1-enecarboxylic acid;

2-[3-(3-Methyl-[1,2,4]oxadiazol-5-yl)-5,6,7,8-tetrahydro-4H-cyclohepta[b]thiophen-2-ylcarbamoyl]-cyclohex-1-enecarboxylic acid;

3-[3-(3-Methyl-[1,2,4]oxadiazol-5-yl)-5,6,7,8-tetrahydro-4H-cyclohepta[b]thiophen-2-ylcarbamoyl]-bicyclo[2.2.2]oct-2-ene-2-carboxylic acid;

2-[3-(3-Cyclopropyl-[1,2,4]oxadiazol-5-yl)-5,6,7,8-tetrahydro-4H-cyclohepta[b]thiophen-2-ylcarbamoyl]-cyclopent-1-enecarboxylic acid;

2-[3-(3-Cyclopropyl-[1,2,4]oxadiazol-5-yl)-5,6,7,8-tetrahydro-4H-cyclohepta[b]thiophen-2-ylcarbamoyl]-cyclohex-1-enecarboxylic acid;

3-[3-(3-Cyclopropyl-[1,2,4]oxadiazol-5-yl)-5,6,7,8-tetrahydro-4H-cyclohepta[b]thiophen-2-ylcarbamoyl]-bicyclo[2.2.2]oct-2-ene-2-carboxylic acid;

2-[3-(3-Trifluoromethyl-[1,2,4]oxadiazol-5-yl)-5,6,7,8-tetrahydro-4H-cyclohepta[b]thiophen-2-ylcarbamoyl]-cyclopent-1-enecarboxylic acid;

2-[3-(3-Trifluoromethyl-[1,2,4]oxadiazol-5-yl)-5,6,7,8-tetrahydro-4H-cyclohepta[b]thiophen-2-ylcarbamoyl]-cyclohex-1-enecarboxylic acid;

3-[3-(3-Trifluoromethyl-[1,2,4]oxadiazol-5-yl)-5,6,7,8-tetrahydro-4H-cyclohepta[b]thiophen-2-ylcarbamoyl]-bicyclo[2.2.2]oct-2-ene-2-carboxylic acid;

2-[3-(3-Methyl-[1,2,4]oxadiazol-5-yl)-5,6-dihydro-4H-cyclopenta[b]thiophen-2-ylcarbamoyl]-cyclopent-1-enecarboxylic acid;

2-[3-(3-Methyl-[1,2,4]oxadiazol-5-yl)-5,6-dihydro-4H-cyclopenta[b]thiophen-2-ylcarbamoyl]-cyclohex-1-enecarboxylic acid;

3-[3-(3-Methyl-[1,2,4]oxadiazol-5-yl)-5,6-dihydro-4H-cyclopenta[b]thiophen-2-ylcarbamoyl]-bicyclo[2.2.2]oct-2-ene-2-carboxylic acid;

2-[3-(3-Cyclopropyl-[1,2,4]oxadiazol-5-yl)-5,6-dihydro-4H-cyclopenta[b]thiophen-2-ylcarbamoyl]-cyclopent-1-enecarboxylic acid;

2-[3-(3-Cyclopropyl-[1,2,4]oxadiazol-5-yl)-5,6-dihydro-4H-cyclopenta[b]thiophen-2-ylcarbamoyl]-cyclohex-1-enecarboxylic acid;

3-[3-(3-Cyclopropyl-[1,2,4]oxadiazol-5-yl)-5,6-dihydro-4H-cyclopenta[b]thiophen-2-ylcarbamoyl]-bicyclo[2.2.2]oct-2-ene-2-carboxylic acid;

2-[3-(3-Trifluoromethyl-[1,2,4]oxadiazol-5-yl)-5,6-dihydro-4H-cyclopenta[b]thiophen-2-ylcarbamoyl]-cyclopent-1-enecarboxylic acid;
2-[3-(3-Trifluoromethyl-[1,2,4]oxadiazol-5-yl)-5,6-dihydro-4H-cyclopenta[b]thiophen-2-ylcarbamoyl]-cyclohex-1-enecarboxylic acid;
3-[3-(3-Trifluoromethyl-[1,2,4]oxadiazol-5-yl)-5,6-dihydro-4H-cyclopenta[b]thiophen-2-ylcarbamoyl]-bicyclo[2.2.2]oct-2-ene-2-carboxylic acid;
2-[3-(4-Methyl-thiazol-2-yl)-5,6-dihydro-4H-cyclopenta[b]thiophen-2-ylcarbamoyl]-cyclopent-1-enecarboxylic acid;
2-[3-(4-Methyl-thiazol-2-yl)-5,6-dihydro-4H-cyclopenta[b]thiophen-2-ylcarbamoyl]-cyclohex-1-enecarboxylic acid;
3-[3-(4-Methyl-thiazol-2-yl)-5,6-dihydro-4H-cyclopenta[b]thiophen-2-ylcarbamoyl]-bicyclo[2.2.2]oct-2-ene-2-carboxylic acid;
2-[6,6-Difluoro-3-(3-methyl-[1,2,4]oxadiazol-5-yl)-4,5,6,7-tetrahydro-benzo[b]thiophen-2-ylcarbamoyl]-cyclopent-1-enecarboxylic acid;
2-[6,6-Difluoro-3-(3-methyl-[1,2,4]oxadiazol-5-yl)-4,5,6,7-tetrahydro-benzo[b]thiophen-2-ylcarbamoyl]-cyclohex-1-enecarboxylic acid;
3-[6,6-Difluoro-3-(3-methyl-[1,2,4]oxadiazol-5-yl)-4,5,6,7-tetrahydro-benzo[b]thiophen-2-ylcarbamoyl]-bicyclo[2.2.2]oct-2-ene-2-carboxylic acid;
2-[3-(3-Cyclopropyl-[1,2,4]oxadiazol-5-yl)-6,6-difluoro-4,5,6,7-tetrahydro-benzo[b]thiophen-2-ylcarbamoyl]-cyclopent-1-enecarboxylic acid;
2-[3-(3-Cyclopropyl-[1,2,4]oxadiazol-5-yl)-6,6-difluoro-4,5,6,7-tetrahydro-benzo[b]thiophen-2-ylcarbamoyl]-cyclohex-1-enecarboxylic acid;
3-[3-(3-Cyclopropyl-[1,2,4]oxadiazol-5-yl)-6,6-difluoro-4,5,6,7-tetrahydro-benzo[b]thiophen-2-ylcarbamoyl]-bicyclo[2.2.2]oct-2-ene-2-carboxylic acid;
2-[6,6-Difluoro-3-(3-trifluoromethyl-[1,2,4]oxadiazol-5-yl)-4,5,6,7-tetrahydro-benzo[b]thiophen-2-ylcarbamoyl]-cyclopent-1-enecarboxylic acid;
2-[6,6-Difluoro-3-(3-trifluoromethyl-[1,2,4]oxadiazol-5-yl)-4,5,6,7-tetrahydro-benzo[b]thiophen-2-ylcarbamoyl]-cyclohex-1-enecarboxylic acid;
3-[6,6-Difluoro-3-(3-trifluoromethyl-[1,2,4]oxadiazol-5-yl)-4,5,6,7-tetrahydro-benzo[b]thiophen-2-ylcarbamoyl]-bicyclo[2.2.2]oct-2-ene-2-carb oxylic acid;
2-[6,6-Difluoro-3-(4-methyl-thiazol-2-yl)-4,5,6,7-tetrahydro-benzo[b]thiophen-2-ylcarbamoyl]-cyclopent-1-enecarboxylic acid;
2-[6,6-Difluoro-3-(4-methyl-thiazol-2-yl)-4,5,6,7-tetrahydro-benzo[b]thiophen-2-ylcarbamoyl]-cyclohex-1-enecarboxylic acid;
3-[6,6-Difluoro-3-(4-methyl-thiazol-2-yl)-4,5,6,7-tetrahydro-benzo[b]thiophen-2-ylcarbamoyl]-bicyclo[2.2.2]oct-2-ene-2-carboxylic acid,
(1RS,2SR)-2-[3-(3-Cyclopropyl-[1,2,4]oxadiazol-5-yl)-6,6-difluoro-4,5,6,7-tetrahydro-benzo[b]thiophen-2-ylcarbamoyl]-cyclohexanecarboxylic acid;
(1SR,2SR)-2-[3-(3-Cyclopropyl-[1,2,4]oxadiazol-5-yl)-6,6-difluoro-4,5,6,7-tetrahydro-benzo[b]thiophen-2-ylcarbamoyl]-cyclohexanecarboxylic acid;
(1RS,2SR)-2-[6,6-Difluoro-3-(4-methyl-thiazol-2-yl)-4,5,6,7-tetrahydro-benzo[b]thiophen-2-ylcarbamoyl]-cyclohexanecarboxylic acid;
(1SR,2SR)-2-[6,6-Difluoro-3-(4-methyl-thiazol-2-yl)-4,5,6,7-tetrahydro-benzo[b]thiophen-2-ylcarbamoyl]-cyclohexanecarboxylic acid;
(1RS,2SR)-2-[3-(3-Cyclopropyl-[1,2,4]oxadiazol-5-yl)-5,6,7,8-tetrahydro-4H-cyclohepta[b]thiophen-2-ylcarbamoyl]-cyclohexanecarboxylic acid;
(1SR,2SR)-2-[3-(3-Cyclopropyl-[1,2,4]oxadiazol-5-yl)-5,6,7,8-tetrahydro-4H-cyclohepta[b]thiophen-2-ylcarbamoyl]-cyclohexanecarboxylic acid;
(1RS,2SR)-2-[3-(4-Methyl-thiazol-2-yl)-5,6,7,8-tetrahydro-4H-cyclohepta[b]thiophen-2-ylcarbamoyl]-cyclohexanecarboxylic acid;
(1SR,2SR)-2-[3-(4-Methyl-thiazol-2-yl)-5,6,7,8-tetrahydro-4H-cyclohepta[b]thiophen-2-ylcarbamoyl]-cyclohexanecarboxylic acid;
(1RS,2SR)-2-[3-(3-Cyclopropyl-[1,2,4]oxadiazol-5-yl)-5,6-dihydro-4H-cyclopenta[b]thiophen-2-ylcarbamoyl]-cyclohexanecarboxylic acid;
(1SR,2SR)-2-[3-(3-Cyclopropyl-[1,2,4]oxadiazol-5-yl)-5,6-dihydro-4H-cyclopenta[b]thiophen-2-ylcarbamoyl]-cyclohexanecarboxylic acid;
(1RS,2SR)-2-[3-(4-Methyl-thiazol-2-yl)-5,6-dihydro-4H-cyclopenta[b]thiophen-2-ylcarbamoyl]-cyclohexanecarboxylic acid;
(1SR,2SR)-2-[3-(4-Methyl-thiazol-2-yl)-5,6-dihydro-4H-cyclopenta[b]thiophen-2-ylcarbamoyl]-cyclohexanecarboxylic acid;
and pharmaceutically acceptable salts thereof.

18. A compound selected from
(1RS,2SR)-2-[3-(3-Cyclopropyl-[1,2,4]oxadiazol-5-yl)-5,6,7,8-tetrahydro-4H-cyclohepta[b]thiophen-2-ylcarbamoyl]-cyclohexanecarboxylic acid;
2-[3-(3-Cyclopropyl-[1,2,4]oxadiazol-5-yl)-6-ethyl-4,5,6,7-tetrahydro-benzo[b]thiophen-2-ylcarbamoyl]-cyclopent-1-enecarboxylic acid;
2-[(S)-3-(3-Cyclopropyl-[1,2,4]oxadiazol-5-yl)-6-ethyl-4,5,6,7-tetrahydro-benzo[b]thiophen-2-ylcarbamoyl]-cyclopent-1-enecarboxylic acid;
2-[(R)-3-(3-Cyclopropyl-[1,2,4]oxadiazol-5-yl)-6-ethyl-4,5,6,7-tetrahydro-benzo[b]thiophen-2-ylcarbamoyl]-cyclopent-1-enecarboxylic acid;
3-[3-(3-Cyclopropyl-[1,2,4]oxadiazol-5-yl)-6-ethyl-4,5,6,7-tetrahydro-benzo[b]thiophen-2-ylcarbamoyl]-bicyclo[2.2.2]oct-2-ene-2-carboxylic acid;
3-[(S)-3-(3-Cyclopropyl-[1,2,4]oxadiazol-5-yl)-6-ethyl-4,5,6,7-tetrahydro-benzo[b]thiophen-2-ylcarbamoyl]-bicyclo[2.2.2]oct-2-ene-2-carboxylic acid;
3-[(R)-3-(3-Cyclopropyl-[1,2,4]oxadiazol-5-yl)-6-ethyl-4,5,6,7-tetrahydro-benzo[b]thiophen-2-ylcarbamoyl]-bicyclo[2.2.2]oct-2-ene-2-carboxylic acid;
2-[3-(3-Cyclopropyl-[1,2,4]oxadiazol-5-yl)-6-trifluoromethyl-4,5,6,7-tetrahydro-benzo[b]thiophen-2-ylcarbamoyl]-cyclopent-1-enecarboxylic acid;
2-[(S)-3-(3-Cyclopropyl-[1,2,4]oxadiazol-5-yl)-6-trifluoromethyl-4,5,6,7-tetrahydro-benzo[b]thiophen-2-ylcarbamoyl]-cyclopent-1-enecarboxylic acid;
2-[(R)-3-(3-Cyclopropyl-[1,2,4]oxadiazol-5-yl)-6-trifluoromethyl-4,5,6,7-tetrahydro-benzo[b]thiophen-2-ylcarbamoyl]-cyclopent-1-enecarboxylic acid;
2-[3-(3-Cyclopropyl-[1,2,4]oxadiazol-5-yl)-6-trifluoromethyl-4,5,6,7-tetrahydro-benzo[b]thiophen-2-ylcarbamoyl]-cyclohex-1-enecarboxylic acid;
3-[3-(3-Cyclopropyl-[1,2,4]oxadiazol-5-yl)-6-trifluoromethyl-4,5,6,7-tetrahydro-benzo[b]thiophen-2-ylcarbamoyl]-bicyclo[2.2.2]oct-2-ene-2-carboxylic acid;
3-[(S)-3-(3-Cyclopropyl-[1,2,4]oxadiazol-5-yl)-6-trifluoromethyl -4,5,6,7-tetrahydro-benzo[b ]thiophen-2-ylcarbamoyl]-bicyclo[2.2.2]oct-2-ene-2-carboxylic acid;

3-[(R)-3-(3-Cyclopropyl -[1,2,4]oxadiazol-5-yl)-6-trifluorom ethyl-4,5,6,7-tetrahydro-benzo[b ]thiophen-2-ylcarbamoyl]-bicyclo[2.2.2]oct-2-ene-2-carboxylic acid;

3-[6-Ethyl-3-(4-methyl-thiazol-2-yl)-4,5,6,7-tetrahydro-benzo[b]thiophen-2-ylcarbamoyl]-bicyclo[2.2.2]oct-2-ene-2-carboxylic acid;

3-[(S)-6-Ethyl-3-(4-methyl-thiazol-2-yl)-4,5,6,7-tetrahydro-benzo[b]thiophen-2-ylcarbamoyl]-bicyclo[2.2.2]oct-2-ene-2-carboxylic acid;

3-[(R)-6-Ethyl-3-(4-methyl-thiazol-2-yl)-4,5,6,7-tetrahydro-benzo[b]thiophen-2-ylcarbamoyl]-bicyclo[2.2.2]oct-2-ene-2-carboxylic acid;

2-[6-Ethyl-3-(4-methyl-thiazol-2-yl)-4,5,6,7-tetrahydro-benzo[b]thiophen-2-ylcarbamoyl]-cyclopent-1-enecarboxylic acid;

2-[(S)-6-Ethyl-3-(4-methyl-thiazol-2-yl)-4,5,6,7-tetrahydro-benzo[b]thiophen-2-ylcarbamoyl]-cyclopent-1-enecarboxylic acid;

2-[(R)-6-Ethyl-3-(4-methyl-thiazol-2-yl)-4,5,6,7-tetrahydro-benzo[b]thiophen-2-ylcarbamoyl]-cyclopent-1-enecarboxylic acid;

3-[3-(4-Methyl-thiazol-2-yl)-6-trifluoromethyl-4,5,6,7-tetrahydro-benzo[b]thiophen-2-ylcarbamoyl]-bicyclo[2.2.2]oct-2-ene-2-carboxylic acid;

3-[(S)-3-(4-Methyl-thiazol-2-yl)-6-trifluoromethyl-4,5,6,7-tetrahydro-benzo[b]thiophen-2-ylcarbamoyl]-bicyclo[2.2.2]oct-2-ene-2-carboxylic acid;

3-[(R)-3-(4-Methyl-thiazol-2-yl)-6-trifluoromethyl-4,5,6,7-tetrahydro-benzo[b]thiophen-2-ylcarbamoyl]-bicyclo[2.2.2]oct-2-ene-2-carboxylic acid;

2-[3-(4-Methyl-thiazol-2-yl)-6-trifluoromethyl-4,5,6,7-tetrahydro-benzo[b]thiophen-2-ylcarbamoyl]-cyclopent-1-enecarboxylic acid;

2-[(S)-3-(4-Methyl-thiazol-2-yl)-6-trifluoromethyl-4,5,6,7-tetrahydro-benzo[b]thiophen-2-ylcarbamoyl]-cyclopent-1-enecarboxylic acid;

2-[(R)-3-(4-Methyl-thiazol-2-yl)-6-trifluoromethyl-4,5,6,7-tetrahydro-benzo[b]thiophen-2-ylcarbamoyl]-cyclopent-1-enecarboxylic acid;

2-[3-(4-Methyl-thiazol-2-yl)-6-trifluoromethyl-4,5,6,7-tetrahydro-benzo[b]thiophen-2-ylcarbamoyl]-cyclohex-1-enecarboxylic acid;

2-[3-(3-Cyclopropyl-[1,2,4]oxadiazol-5-yl)-6-ethyl-4,5,6,7-tetrahydro-benzo[b]thiophen-2-ylcarbamoyl]-cyclohex-1-enecarboxylic acid;

2[6-Ethyl-3-(4-methyl-thiazol-2-yl)-4,5,6,7-tetrahydro-benzo[b]thiophen-2-ylcarbamoyl]-cyclohex-1-enecarboxylic acid;

3-[3-(3-Cyclopropyl-[1,2,4]oxadiazol-5-yl)-4,7-dihydro-5H-thieno[2,3-c]pyran-2-ylcarbamoyl]-isonicotinic acid;

3-[3-(3-Cyclopropyl-[1,2,4]oxadiazol-5-yl)-4,5,6,7-tetrahydro-benzo[b]thiophen-2-ylcarbamoyl]-isonicotinic acid;

2-[6,6-Difluoro-3-(3-methyl-[1,2,4]thiadiazol-5-yl)-4,5,6,7-tetrahydro-benzo[b]thiophen-2-ylcarbamoyl]-cyclopent-1-enecarboxylic acid;

2-[6,6-Difluoro-3-(3-methyl-[1,2,4]thiadiazol-5-yl)-4,5,6,7-tetrahydro-benzo[b]thiophen-2-ylcarbamoyl]-cyclohex-1-enecarboxylic acid;

2-[3-(3-Cyclopropyl-[1,2,4]thiadiazol-5-yl)-6,6-difluoro-4,5,6,7-tetrahydro-benzo[b]thiophen-2-ylcarbamoyl]-cyclopent-1-enecarboxylic acid;

2-[3-(3-Cyclopropyl-[1,2,4]thiadiazol-5-yl)-6,6-difluoro-4,5,6,7-tetrahydro-benzo[b]thiophen-2-ylcarbamoyl]-cyclohex-1-enecarboxylic acid;

2-[3-(3-Cyclopropyl-[1,2,4]oxadiazol-5-yl)-6-fluoro-4,5,6,7-tetrahydro-benzo[b]thiophen-2-ylcarbamoyl]-cyclopent-1-enecarboxylic acid;

2-[3-(3-Methyl-[1,2,4]thiadiazol-5-yl)-4,5,6,7-tetrahydro-benzo[b]thiophen-2-ylcarbamoyl]-cyclopent-1-enecarboxylic acid;

2-[3-(3-Methyl-[1,2,4]thiadiazol-5-yl)-4,5,6,7-tetrahydro-benzo[b]thiophen-2-ylcarbamoyl]-cyclohex-1-enecarboxylic acid;

2-[3-(3-Cyclopropyl-[1,2,4]oxadiazol-5-yl)-6-fluoro-4,5,6,7-tetrahydro-benzo[b]thiophen-2-ylcarbamoyl]-cyclohex-1-enecarboxylic acid;

3-[3-(3-Methyl-[1,2,4]thiadiazol-5-yl)-4,5,6,7-tetrahydro-benzo[b]thiophen-2-ylcarbamoyl]-bicyclo[2.2.2]oct-2-ene-2-carboxylic acid;

3-[6,6-Difluoro-3-(3-methyl-[1,2,4]thiadiazol-5-yl)-4,5,6,7-tetrahydro-benzo[b]thiophen-2-ylcarbamoyl]-bicyclo[2.2.2]oct-2-ene-2-carboxylic acid;

2-[3-(3-Cyclopropyl-[1,2,4]thiadiazol-5-yl)-4,5,6,7-tetrahydro-benzo[b]thiophen-2-ylcarbamoyl]-cyclopent-1-enecarboxylic acid;

2-[3-(3-Cyclopropyl-[1,2,4]thiadiazol-5-yl)-4,5,6,7-tetrahydro-benzo[b]thiophen-2-ylcarbamoyl]-cyclohex-1-enecarboxylic acid;

(R)-1-[3-(3-Cyclopropyl-[1,2,4]oxadiazol-5-yl)-6,6-difluoro-4,5,6,7-tetrahydro-benzo[b]thiophen-2-ylcarbamoyl]-pyrrolidine-2-carboxylic acid;

(R)-1-[3-(3-Cyclopropyl-[1,2,4]oxadiazol-5-yl)-5,6-dihydro-4H-cyclopenta[b]thiophen-2-ylcarbamoyl]-pyrrolidine-2-carboxylic acid;

2-[4-(3-Cyclopropyl-[1,2,4]oxadiazol-5-yl)-2-thia-bicyclo[3.2.0]hepta-1(5),3-dien-3-ylcarbamoyl]-cyclopent-1-enecarboxylic acid;

3-[3-(3-Cyclopropyl-[1,2,4]thiadiazol-5-yl)-4,5,6,7-tetrahydro-benzo[b]thiophen-2-ylcarbamoyl]-bicyclo[2.2.2]oct-2-ene-2-carboxylic acid;

3-[3-(3-Cyclopropyl-[1,2,4]thiadiazol-5-yl)-6,6-difluoro-4,5,6,7-tetrahydro-benzo[b]thiophen-2-ylcarbamoyl]-bicyclo[2.2.2]oct-2-ene-2-carb oxylic acid;

(R)-1-[3-(3-Cyclopropyl-[1,2,4]oxadiazol-5-yl)-5,6,7,8-tetrahydro-4H-cyclohepta[b]thiophen-2-ylcarbamoyl]-pyrrolidine-2-carboxylic acid;

(2R,4S)-1-[3-(3-Cyclopropyl-[1,2,4]oxadiazol-5-yl)-4,5,6,7-tetrahydro-benzo[b]thiophen-2-ylcarbamoyl]-4-hydroxy-pyrrolidine-2-carboxylic acid;

(2R,4R)-1-[3-(3-Cyclopropyl-[1,2,4]oxadiazol-5-yl)-4,5,6,7-tetrahydro-benzo[b]thiophen-2-ylcarbamoyl]-4-hydroxy-pyrrolidine-2-carboxylic acid;

2-[5-(3-Cyclopropyl-[1,2,4]oxadiazol-5-yl)-3,4-dihydro-2H-thieno[2,3-b]pyran-6-ylcarbamoyl]-cyclohex-1-enecarboxylic acid;

2-[5-(3-Cyclopropyl-[1,2,4]oxadiazol-5-yl)-3,4-dihydro-2H-thieno[2,3-b]pyran-6-ylcarbamoyl]-cyclopent-1-enecarboxylic acid;

2-[3-(3-Cyclopropyl-[1,2,4]oxadiazol-5-yl)-4,5,6,7-tetrahydro-benzo[b]thiophen-2-ylcarbamoyl]-4,4-dimethyl-cyclopent-1-enecarb oxylic acid;

2-[3-(3-Cyclopropyl-[1,2,4]oxadiazol-5-yl)-6,7-dihydro-4H-thieno[3,2-c]pyran-2-ylcarbamoyl]-cyclopent-1-enecarboxylic acid;

2-[3-(3-Cyclopropyl-[1,2,4]oxadiazol-5-yl)-6,7-dihydro-4H-thieno[3,2-c]pyran-2-ylcarbamoyl]-cyclohex-1-enecarboxylic acid;

3-[3-(3-Cyclopropyl-[1,2,4]oxadiazol-5-yl)-4,7-dihydro-5H-thieno[2,3-c]pyran-2-ylcarbamoyl]-5-methyl-1H-pyrazole-4-carboxylic acid;

2-[3-(3-Cyclopropyl-[1,2,4]oxadiazol-5-yl)-6-hydroxy-6-methyl-4,5,6,7-tetrahydro-benzo[b]thiophen-2-ylcarbamoyl]-cyclopent-1-enecarboxylic acid;
3-[3-(3-Cyclopropyl-[1,2,4]oxadiazol-5-yl)-6-hydroxy-6-methyl-4,5,6,7-tetrahydro-benzo[b]thiophen-2-ylcarbamoyl]-bicyclo[2.2.2]oct-2-ene-2-carboxylic acid;
2-[3-(3-Cyclopropyl-[1,2,4]oxadiazol-5-yl)-6-hydroxy-6-methyl-4,5,6,7-tetrahydro-benzo[b]thiophen-2-ylcarbamoyl]-cyclohex-1-enecarboxylic acid;
3-[3-(3-Cyclopropyl-[1,2,4]oxadiazol-5-yl)-4,7-dihydro-5H-thieno[2,3-c]pyran-2-ylcarbamoyl]-pyridine-2-carboxylic acid;
2-[3-(3-Cyclopropyl-[1,2,4]oxadiazol-5-yl)-4,7-dihydro-5H-thieno[2,3-c]pyran-2-ylcarbamoyl]-nicotinic acid;
(1S,5R)-5-[3-(3-Cyclopropyl-[1,2,4]oxadiazol-5-yl)-4,7-dihydro-5H-thieno[2,3-c]pyran-2-ylcarbamoyl]-bicyclo[3.1.0]hexane-1-carboxylic acid;
3-[3-(3-Cyclopropyl-[1,2,4]oxadiazol-5-yl)-4,7-dihydro-5H-thieno[2,3-c]pyran-2-ylcarbamoyl]-1,5-dimethyl-1H-pyrazole-4-carboxylic acid;
2-[3-(6-Chloro-pyridin-2-yl)-4,5,6,7-tetrahydro-benzo[b]thiophen-2-ylcarbamoyl]-cyclopent-1-enecarboxylic acid;
2-[3-(5-Chloro-pyridin-2-yl)-4,5,6,7-tetrahydro-benzo[b]thiophen-2-ylcarbamoyl]-cyclopent-1-enecarboxylic acid;
2-[6,6-Difluoro-3-(4-isopropyl-thiazol-2-yl)-4,5,6,7-tetrahydro-benzo[b]thiophen-2-ylcarbamoyl]-cyclopent-1-enecarboxylic acid;
3-[6,6-Difluoro-3-(4-isopropyl-thiazol-2-yl)-4,5,6,7-tetrahydro-benzo[b]thiophen-2-ylcarbamoyl]-bicyclo[2.2.2]oct-2-ene-2-carboxylic acid;
2-[6,6-Difluoro-3-(4-isopropyl-thiazol-2-yl)-4,5,6,7-tetrahydro-benzo[b]thiophen-2-ylcarbamoyl]-cyclohex-1-enecarboxylic acid;
2-[3-(4-Methyl-thiazol-2-yl)-4,5,6,7-tetrahydro-benzo[b]thiophen-2-ylcarbamoyl]-nicotinic acid;
2-[6,6-Difluoro-3-(4-methyl-thiazol-2-yl)-4,5,6,7-tetrahydro-benzo[b]thiophen-2-ylcarbamoyl]-nicotinic acid;
2-[3-(3-Cyclopropyl-[1,2,4]oxadiazol-5-yl)-5,5-dimethyl-4,5,6,7-tetrahydro-benzo[b]thiophen-2-ylcarbamoyl]-cyclopent-1-enecarboxylic acid;
2-[3-(3-Cyclopropyl-[1,2,4]oxadiazol-5-yl)-5,5-dimethyl-4,5,6,7-tetrahydro-benzo[b]thiophen-2-ylcarbamoyl]-cyclohex-1-enecarboxylic acid;
3-[3-(3-Cyclopropyl-[1,2,4]oxadiazol-5-yl)-5,5-dimethyl-4,5,6,7-tetrahydro-benzo[b]thiophen-2-ylcarbamoyl]-bicyclo[2.2.2]oct-2-ene-2-carboxylic acid;
2-[3-(3-Cyclopropyl-[1,2,4]oxadiazol-5-yl)-4,5,6,7-tetrahydro-benzo[b]thiophen-2-ylcarbamoyl]-cyclohex-1-enecarboxylic acid;
2-[3-(3-Cyclopropyl-[1,2,4]oxadiazol-5-yl)-6-methoxy-6-methyl-4,5,6,7-tetrahydro-benzo[b]thiophen-2-ylcarbamoyl]-cyclopent-1-enecarboxylic acid;
2-[6,6-Difluoro-3-(3-trifluoromethyl-[1,2,4]oxadiazol-5-yl)-4,5,6,7-tetrahydro-benzo[b]thiophen-2-ylcarbamoyl]-nicotinic acid;
2-[3-(3-Trifluoromethyl-[1,2,4]oxadiazol-5-yl)-4,5,6,7-tetrahydro-benzo[b]thiophen-2-ylcarbamoyl]-nicotinic acid;
2-[(R)-3-(3-Cyclopropyl-[1,2,4]oxadiazol-5-yl)-6-methoxy-6-methyl-4,5,6,7-tetrahydro-benzo[b]thiophen-2-ylcarbamoyl]-cyclopent-1-enecarboxylic acid;
2-[(S)-3-(3-Cyclopropyl-[1,2,4]oxadiazol-5-yl)-6-methoxy-6-methyl-4,5,6,7-tetrahydro-benzo[b]thiophen-2-ylcarbamoyl]-cyclopent-1-enecarboxylic acid;
5-[3-(3-Cyclopropyl-[1,2,4]oxadiazol-5-yl)-4,5,6,7-tetrahydro-benzo[b]thiophen-2-ylcarbamoyl]-3,6-dihydro-2H-pyran-4-carboxylic acid;
4-[3-(3-Cyclopropyl-[1,2,4]oxadiazol-5-yl)-4,5,6,7-tetrahydro-benzo[b]thiophen-2-ylcarbamoyl]-5,6-dihydro-2H-pyran-3-carboxylic acid;
2-[3-(3-Cyclopropyl-[1,2,4]oxadiazol-5-yl)-6,6-dioxo-4,5,6,7-tetrahydro-6λ6-thieno[2,3-c]thiopyran-2-ylcarbamoyl]-cyclopent-1-enecarboxylic acid;
2-{2-[(2-Carboxy-cyclopent-1-enecarbonyl)-amino]-6,6-difluoro-4,5,6,7-tetrahydro-benzo[b]thiophen-3-yl}-thiazole-4-carboxylic acid ethyl ester;
2-[(S)-3-(3-Cyclopropyl-[1,2,4]oxadiazol-5-yl)-6-fluoro-4,5,6,7-tetrahydro-benzo[b]thiophen-2-ylcarbamoyl]-cyclohex-1-enecarboxylic acid;
2-[(R)-3-(3-Cyclopropyl-[1,2,4]oxadiazol-5-yl)-6-fluoro-4,5,6,7-tetrahydro-benzo[b]thiophen-2-ylcarbamoyl]-cyclohex-1-enecarboxylic acid;
5-[3-(3-Cyclopropyl-[1,2,4]oxadiazol-5-yl)-6,6-difluoro-4,5,6,7-tetrahydro-benzo[b]thiophen-2-ylcarbamoyl]-3,6-dihydro-2H-pyran-4-carboxylic acid;
4-[3-(3-Cyclopropyl-[1,2,4]oxadiazol-5-yl)-6,6-difluoro-4,5,6,7-tetrahydro-benzo[b]thiophen-2-ylcarbamoyl]-5,6-dihydro-2H-pyran-3-carboxylic acid;
4-[6,6-Difluoro-3-(4-methyl-thiazol-2-yl)-4,5,6,7-tetrahydro-benzo[b]thiophen-2-ylcarbamoyl]-5,6-dihydro-2H-pyran-3-carboxylic acid;
5-[6,6-Difluoro-3-(4-methyl-thiazol-2-yl)-4,5,6,7-tetrahydro-benzo[b]thiophen-2-ylcarbamoyl]-3,6-dihydro-2H-pyran-4-carboxylic acid;
(2R)-1-[[3-(3-methyl-1,2,4-oxadiazol-5-yl)-5,6,7,8-tetrahydro-4H-cyclohepta[b]thiophen-2-yl]carbamoyl]pyrrolidine-2-carboxylic acid;
(2R)-1-[[3-[3-(trifluoromethyl)-1,2,4-oxadiazol-5-yl]-5,6,7,8-tetrahydro-4H-cyclohepta[b]thiophen-2-yl]carbamoyl]pyrrolidine-2-carboxylic acid;
(2R)-1-[[3-[3-(trifluoromethyl)-1,2,4-oxadiazol-5-yl]-4,5,6,7-tetrahydrobenzothiophen-2-yl]carbamoyl]pyrrolidine-2-carboxylic acid;
(2S)-1-[[3-(3-cyclopropyl-1,2,4-oxadiazol-5-yl)-5,6,7,8-tetrahydro-4H-cyclohepta[b]thiophen-2-yl]carbamoyl]pyrrolidine-2-carboxylic acid;
and pharmaceutically acceptable salts thereof.

19. A compound selected from
2-[3-(3-Methyl-[1,2,4]oxadiazol-5-yl)-4,5,6,7-tetrahydro-benzo[b]thiophen-2-ylcarbamoyl]-cyclopent-1-enecarboxylic acid;
2-[3-(3-Methyl-[1,2,4]oxadiazol-5-yl)-4,5,6,7-tetrahydro-benzo[b]thiophen-2-ylcarbamoyl]-cyclohex-1-enecarboxylic acid;
2-[3-(3-Cyclopropyl-[1,2,4]oxadiazol-5-yl)-4,7-dihydro-5H-thieno[2,3-c]pyran-2-ylcarbamoyl]-cyclopent-1-enecarboxylic acid;
3-[3-(3-Trifluoromethyl-[1,2,4]oxadiazol-5-yl)-4,5,6,7-tetrahydro-benzo[b]thiophen-2-ylcarbamoyl]-bicyclo[2.2.2]oct-2-ene-2-carboxylic acid;
3-[3-(3-Cyclopropyl-[1,2,4]oxadiazol-5-yl)-4,7-dihydro-5H-thieno[2,3-c]pyran-2-ylcarbamoyl]-bicyclo[2.2.2]oct-2-ene-2-carboxylic acid;
2-[3-(3-Isopropyl-[1,2,4]oxadiazol-5-yl)-4,5,6,7-tetrahydro-benzo[b]thiophen-2-ylcarbamoyl]-cyclopent-1-enecarboxylic acid;
3-[3-(3-Isopropyl-[1,2,4]oxadiazol-5-yl)-4,5,6,7-tetrahydro-benzo[b]thiophen-2-ylcarbamoyl]-bicyclo[2.2.2]oct-2-ene-2-carboxylic acid;

2-[3-(4-Methyl-oxazol-2-yl)-4,7-dihydro-5H-thieno[2,3-c]pyran-2-ylcarbamoyl]-cyclopent-1-enecarboxylic acid;

2-[3-(4-Trifluoromethyl-thiazol-2-yl)-4,7-dihydro-5H-thieno[2,3-c]pyran-2-ylcarbamoyl]-cyclohex-1-enecarboxylic acid;

(+)-2-[3-(3-Cyclopropyl-[1,2,4]oxadiazol-5-yl)-6-methyl-4,5,6,7-tetrahydro-benzo[b]thiophen-2-ylcarbamoyl]-cyclohex-1-enecarboxylic acid;

2-[3-(3-Cyclopropyl-[1,2,4]oxadiazol-5-yl)-5,6,7,8-tetrahydro-4H-cyclohepta[b]thiophen-2-ylcarbamoyl]-cyclohex-1-enecarboxylic acid;

3-[3-(3-Cyclopropyl-[1,2,4]oxadiazol-5-yl)-5,6,7,8-tetrahydro-4H-cyclohepta[b]thiophen-2-ylcarbamoyl]-bicyclo[2.2.2]oct-2-ene-2-carboxylic acid;

3-[3-(3-Trifluoromethyl-[1,2,4]oxadiazol-5-yl)-5,6,7,8-tetrahydro-4H-cyclohepta[b]thiophen-2-ylcarbamoyl]-bicyclo[2.2.2]oct-2-ene-2-carboxylic acid;

3-[3-(3-Cyclopropyl-[1,2,4]oxadiazol-5-yl)-5,6-dihydro-4H-cyclopenta[b]thiophen-2-ylcarbamoyl]-bicyclo[2.2.2]oct-2-ene-2-carboxylic acid;

2-[3-(3-Cyclopropyl-[1,2,4]oxadiazol-5-yl)-6,6-difluoro-4,5,6,7-tetrahydro-benzo[b]thiophen-2-ylcarbamoyl]-cyclopent-1-enecarboxylic acid;

2-[6,6-Difluoro-3-(3-trifluoromethyl-[1,2,4]oxadiazol-5-yl)-4,5,6,7-tetrahydro-benzo[b]thiophen-2-ylcarbamoyl]-cyclopent-1-enecarboxylic acid;

3-[6,6-Difluoro-3-(3-trifluoromethyl-[1,2,4]oxadiazol-5-yl)-4,5,6,7-tetrahydro-benzo[b]thiophen-2-ylcarbamoyl]-bicyclo[2.2.2]oct-2-ene-2-carboxylic acid;

2-[6,6-Difluoro-3-(4-methyl-thiazol-2-yl)-4,5,6,7-tetrahydro-benzo[b]thiophen-2-ylcarbamoyl]-cyclohex-1-enecarboxylic acid;

and pharmaceutically acceptable salts thereof.

20. A compound selected from

2-[3-(3-Cyclopropyl-[1,2,4]thiadiazol-5-yl)-6,6-difluoro-4,5,6,7-tetrahydro-benzo[b]thiophen-2-ylcarbamoyl]-cyclopent-1-enecarboxylic acid;

2-[3-(3-Cyclopropyl-[1,2,4]thiadiazol-5-yl)-6,6-difluoro-4,5,6,7-tetrahydro-benzo[b]thiophen-2-ylcarbamoyl]-cyclohex-1-enecarboxylic acid;

2-[3-(3-Cyclopropyl-[1,2,4]oxadiazol-5-yl)-6-fluoro-4,5,6,7-tetrahydro-benzo[b]thiophen-2-ylcarbamoyl]-cyclopent-1-enecarboxylic acid;

(R)-1-[3-(3-Cyclopropyl-[1,2,4]oxadiazol-5-yl)-5,6,7,8-tetrahydro-4H-cyclohepta[b]thiophen-2-ylcarbamoyl]-pyrrolidine-2-carboxylic acid;

2-[3-(3-Cyclopropyl-[1,2,4]oxadiazol-5-yl)-6,7-dihydro-4H-thieno[3,2-c]pyran-2-ylcarbamoyl]-cyclohex-1-enecarboxylic acid;

2-[3-(3-Cyclopropyl-[1,2,4]oxadiazol-5-yl)-4,7-dihydro-5H-thieno[2,3-c]pyran-2-ylcarbamoyl]-nicotinic acid;

2-[3-(3-Cyclopropyl-[1,2,4]oxadiazol-5-yl)-4,5,6,7-tetrahydro-benzo[b]thiophen-2-ylcarbamoyl]-cyclohex-1-enecarboxylic acid;

5-[3-(3-Cyclopropyl-[1,2,4]oxadiazol-5-yl)-4,5,6,7-tetrahydro-benzo[b]thiophen-2-ylcarbamoyl]-3,6-dihydro-2H-pyran-4-carboxylic acid;

4-[3-(3-Cyclopropyl-[1,2,4]oxadiazol-5-yl)-4,5,6,7-tetrahydro-benzo[b]thiophen-2-ylcarbamoyl]-5,6-dihydro-2H-pyran-3-carboxylic acid;

4-[3-(3-Cyclopropyl-[1,2,4]oxadiazol-5-yl)-6,6-difluoro-4,5,6,7-tetrahydro-benzo[b]thiophen-2-ylcarbamoyl]-5,6-dihydro-2H-pyran-3-carboxylic acid;

5-[6,6-Difluoro-3-(4-methyl-thiazol-2-yl)-4,5,6,7-tetrahydro-benzo[b]thiophen-2-ylcarbamoyl]-3,6-dihydro-2H-pyran-4-carboxylic acid;

(2R)-1-[[3-[3-(trifluoromethyl)-1,2,4-oxadiazol-5-yl]-5,6,7,8-tetrahydro-4H-cyclohepta[b]thiophen-2-yl]carbamoyl]pyrrolidine-2-carboxylic acid;

(2R)-1-[[3-[3-(trifluoromethyl)-1,2,4-oxadiazol-5-yl]-4,5,6,7-tetrahydrobenzothiophen-2-yl]carbamoyl]pyrrolidine-2-carboxylic acid;

and pharmaceutically acceptable salts thereof.

21. A pharmaceutical composition comprising a compound of claim 1 and a therapeutically inert carrier.

* * * * *